United States Patent
Cook et al.

(10) Patent No.: US 10,906,909 B2
(45) Date of Patent: Feb. 2, 2021

(54) TREATMENT OF COGNITIVE AND MOOD SYMPTOMS IN NEURODEGENERATIVE AND NEUROPSYCHIATRIC DISORDERS WITH ALPHA5-CONTAINING GABAA RECEPTOR AGONISTS

(71) Applicants: UWM Research Foundation, Inc., Milwaukee, WI (US); Centre for Addiction and Mental Health, Toronto (CA); University of Belgrade—Faculty of Pharmacy, Belgrade (RS)

(72) Inventors: James M. Cook, Milwaukee, WI (US); Guanguan Li, Milwaukee, WI (US); Michael Ming-Jin Poe, Vernon, CT (US); Miroslav M. Savic, Belgrade (RS); Etienne Sibille, Toronto (CA)

(73) Assignees: UWM Research Foundation, Inc., Milwaukee, WI (US); Centre for Addiction and Mental Health, Toronto (CA); University of Belgrade—Faculty of Pharmacy, Belgrade (RS)

( * ) Notice: Subject to any disclaimer, the term of this patent is extended or adjusted under 35 U.S.C. 154(b) by 32 days.

(21) Appl. No.: 16/086,053

(22) PCT Filed: Mar. 20, 2017

(86) PCT No.: PCT/US2017/023206
§ 371 (c)(1),
(2) Date: Sep. 18, 2018

(87) PCT Pub. No.: WO2017/161370
PCT Pub. Date: Sep. 21, 2017

(65) Prior Publication Data
US 2020/0181146 A1    Jun. 11, 2020

Related U.S. Application Data

(60) Provisional application No. 62/310,409, filed on Mar. 18, 2016.

(51) Int. Cl.
| | | |
|---|---|---|
| *A61K 31/5517* | (2006.01) | |
| *A61P 25/00* | (2006.01) | |
| *C07D 487/04* | (2006.01) | |
| *A61P 25/22* | (2006.01) | |

(52) U.S. Cl.
CPC ............ *C07D 487/04* (2013.01); *A61P 25/22* (2018.01)

(58) Field of Classification Search
CPC .... A61K 31/5517; A61P 25/00; C07D 487/04
See application file for complete search history.

(56) References Cited

U.S. PATENT DOCUMENTS

| | | |
|---|---|---|
| 4,226,768 A | 10/1980 | Walser |
| 7,119,196 B2 | 10/2006 | Cook et al. |
| 7,235,656 B2 | 6/2007 | Cook et al. |
| 8,835,424 B2 | 9/2014 | Cook et al. |
| 9,006,233 B2 | 4/2015 | Cook et al. |
| 9,597,342 B2 | 3/2017 | Cook et al. |
| 10,259,815 B2 | 4/2019 | Cook et al. |
| RE47,475 E | 7/2019 | Cook et al. |
| 2003/0176456 A1 | 9/2003 | June et al. |
| 2004/0082573 A1 | 4/2004 | Cook et al. |
| 2006/0003995 A1 | 1/2006 | Cook et al. |
| 2006/0258643 A1 | 11/2006 | Cook et al. |
| 2009/0093466 A1 | 4/2009 | Mattson |
| 2009/0183566 A1 | 6/2009 | Brown et al. |
| 2010/0004226 A1 | 1/2010 | Cook et al. |
| 2010/0130479 A1 | 5/2010 | Cook et al. |
| 2010/0261711 A1 | 10/2010 | Cook et al. |
| 2010/0317619 A1 | 12/2010 | Cook et al. |
| 2012/0295892 A1 | 11/2012 | Cook et al. |
| 2015/0258128 A1 | 9/2015 | Cook et al. |

FOREIGN PATENT DOCUMENTS

| | | |
|---|---|---|
| GB | 1527131 A | 10/1978 |
| WO | WO2007018660 A2 | 2/2007 |
| WO | WO2009046004 A1 | 4/2009 |
| WO | WO2014047413 A1 | 3/2014 |
| WO | WO2016154031 A1 | 9/2016 |

OTHER PUBLICATIONS

Cai, et al., "Sample Reduction Strategies in Discovery Bioanalysis," Future Science, 2013, 5, 1691-701.
Castagne, et al., "Rodent Models of Depression: Forced Swim and Tail Suspension Behavioral Despair Tests in Rats and Mice," Current Protocols in Neuroscience, 2011, Chapter 8.
Chestnut, et al, "Selective isolation of transiently transfected cells from a mammalian cell population with vectors expressing a membrane anchored single-chain antibody," 1996, J. Immunol. Methods 193, 17-27.
Choudhary, M.S. et al. "Identification of receptor domains that modify ligand binding to 5-hydroxy-tryptamine2 and 5-hydroxytryptamine1c serotonin receptors," Molecular Pharmacology, Oct. 1992, p. 627-633, vol. 42; issue 4.
Crawley, "Exploratory behavior models of anxiety in mice," Neuroscience Biobehavioral Reviews, 1985, 9, 37-44.
Cryan, et al, "In search of a depressed mouse: utility of models for studying depression-related behavior in genetically modified mice," Molecular Psychiatry, 2004, 9, 326.
Deacon, "Digging and marble burying in mice: simple methods for in vivo identification of biological impacts," Nature Protocols, 2006, 1, 122.
Del Pozo, et al., "Reactions of 1,4 Benzodiazepinic N-Nitrosoamidines with Tosylmethyl Isocyanide: A Novel Synthesis of Midazolam", Department of Organic and Inorganic Chemistry, University of Oviedo, Apr. 14, 2004, p. 2697-2703.

(Continued)

*Primary Examiner* — Brenda L Coleman
(74) *Attorney, Agent, or Firm* — Michael Best & Friedrich LLP

(57) ABSTRACT

Provided herein are alpha5-containing $GABA_A$ receptor agonists and pharmaceutical compositions and methods of treatment of cognitive and mood symptoms in neurodegenerative and neuropsychiatric disorders using them.

7 Claims, 78 Drawing Sheets

(56) References Cited

OTHER PUBLICATIONS

DI_LIO_"HZ-166, A Novel GABAA Receptor Subtype-Selective Benzodiazepine Site Ligand, Is Antihyperalgesic in Mouse Models of Inflammatory and Neuropathic Pain," Neuropharmacology, 60, 626-632, 2011.
Filizola et al., "Benzodiazepine-Induced Hyperphagia: Development and Assessment of a 3D Pharmacophore by Computational Methods," Journal of Biomolecular Structure & Dynamics, 2000, 17(5):769-778.
Fischell, et al, "Rapid Antidepressant Action and Restoration of Excitatory Synaptic Strength After Chronic Stress by Negative Modulators of Alpha5-Containing GABAA Receptors," Neuropsychopharmacology, 2015, 40, 2499-2509.
Fischer, "Effects of Hz-166, A Novel $\alpha 2$ and $\alpha 3$ Subunit-containing GABA(A) Receptor Agonist, on Inflammatory Pain and Operant Behavior in Mice," Abstracts Drug and Alcohol Dependence, 146, e278 (2015).
Fischer, et al, "Anxiolytic-like Effects of 8-Acetylene Imidazobenzodiazepines in Rhesus Monkey Conflict Procedure," Neuropharmacology, 59, 612-618, (2010).
Fisher, et al., "The Role of $\alpha 1$ and $\alpha 6$ Subtype Amino-Terminal Domains in Allosteric Regulation of $\gamma$-Aminobutyric Acida Receptors," Molecular Pharmacology, 1997, 52, 714-724.
Forkuo, et al., "Development of GABAA Receptor Subtype-Selective Imidazobenzodiazepines as Novel Asthma Treatments", Molecular Pharmaceutics, (ACS), 13, 2026-2038 (2016).
Gallagher, et al, "Severity of Spatial Learning Impairment in Aging: Development of a Learning Index for Performance in the Morris Water Maze," Behavioral Neuroscience, 1993, 107,618-626.
Gallos, et al, "Selective targeting of the alpha5-subunit of GABAA receptors relaxes airway smooth muscle and inhibits cellular calcium handling," Am J Physiol Lung Cell Mol Physiol 2015, 308, (9), L931-42.
Guilloux, et al, "Molecular evidence for BDNF- and GABA-related dysfunctions in the amygdala of female subjects with major depression," Molecular Psychiatry, 2012, 17, 1134-1142.
Janus, et al, "A$\beta$ peptide immunization reduces behavioural impairment and plaques in a model of Alzheimer's disease," Nature, 2000, 408:979-982.
Kinsey, et al., "Inhibition of endocannabinoid catabolic enzymes elicits anxiolytic-like effects in the marble burying assay," Pharmacology Biochemical Behaviors, 2011, 98, 21.
Lalonde, "The neurobiological basis of spontaneous alternation," Neuroscience & Biobehavioral Reviews; 2002, 26, 91-104.
Li, et al, "Development of Selective Ligands for Benzodiazepine Receptor Subtypes by Manipulating the Substituents at Positions -3 and -7 of Optically Active BzR Ligands," Medicinal Chemistry Research, 13, 259-281 (2004).
Li, et al, "Studies in search of diazepam-insensitive subtype selective agents for GABA(A)/Bz receptors," Med Chem Res 2002, 11, (9), 504-537.
Millan, et al, "Towards improved animal models for evaluating social cognition and its disruption in schizophrenia: The CNTRICS initiative," Neurosciences & Biobehavioral Reviews, 2013, 37, 2166-2180.
Morici, et al, "Medial prefrontal cortex role in recognition memory in rodents," Behavioural Brain Research, 2015, 292, 241-251.
Namjoshi et al., "Search for $\alpha 3\beta 2/3\gamma 2$ Subtype Selective Ligands That are Stable on Human Liver Microsomes," Bioorg Med Chem, 2013, 21(1):93-101.
Nollet, et al, "Models of Depression: Unpredictable Chronic Mild Stress in Mice," Current Protocols Neuroscience, 2013, Chapter 5.
Northoff, et al, "Why are cortical GABA neurons relevant to internal focus in depression? A cross-level model linking cellular, biochemical and neural network findings," Molecular Psychiatry; 2014, 19, 966-977.
Obradovic, et al., "SH-I-048A, an in vitro non-selective superagonist at the benzodiazepine site of GABAA receptors: The approximated activation of receptor subtypes may explain behavioral effects," Brain Research, 2014, 1554, 36-48.

Pham, et al., "Automated scoring of fear-related behavior using EthoVision software," J Neuroscience Methods, 2009, 178, 323-326.
Phillips, et al, "Differential Contribution of Amygdala and Hippocampus to Cued and Contextual Fear Conditioning," Behavioral Neuroscience, 1992, 106, 274-285.
Piantadosi, et al, "Sex-Dependent Anti-Stress Effect of an $\alpha 5$ Subunit Containing GABAA Receptor Positive Allosteric Modulator," Frontiers in Pharmacology, 2016, 7, 446.
Richetto et al., "Behavioral Effects of the Benzodiazepine-Positive Modulator SH-053-2'F-S-CH3 in an Immune-Mediated Neurodevelopmental Disruption Model," Int J. of Neuropsychopharmacology, 1-11 (2015).
Poe, et al, "Synthesis and Characterization of a Novel $\gamma$-Aminobutyric Acid Type A (GABAA) Receptor Ligand that Combines Outstanding Metabolic Stability, Pharmacokinetics, and Anxiolytic Efficacy", J. Med. Chem, 59, (2016).
Soumier et al, "Opposing Effects of Acute versus Chronic Blockade of Frontal Cortex Somatostatin-Positive Inhibitory Neurons on Behavioral Emotionality in Mice," Neuropsychopharmacology, 2014, 39:9, 2252-62.
Savic, et al, "Novel Positive Allosteric Modulators of GABA(A) Receptors: Do Subtle Differences in Activity at Alpha 1 Plus Alpha 5 Versus Alpha 2 Plus Alpha 3 Subunits Account for Dissimilarities in Behavioral Effects in Rats", Progress in Neuro-Psychopharmacology and Behavioral Psychiatry, 34, 376-386 (2010).
Savic; et al., "The differential role of $\alpha 1$- and $\alpha 5$-containing GABAA receptors in mediating diazepam effects on spontaneous locomotor activity and water-maze learning and memory in rats," Int. J. Neuropsychopharmacology, 2009, 12, 1179-1193.
Schwabe, et al., "Memory formation under stress: Quantity and quality," Neuroscience & Biobehavioral review, 2010, 34, 584-591.
Stamenic, et al., "Ester to amide substitution improves selectivity, efficacy and kinetic behavior of a benzodiazepine positive modulator of GABAA receptors containing the $\alpha 5$ subunit," Eur. J. Pharmacology 2016, 791, 433-443.
Swinyard, E. A, et al., "Comparative assays of antiepileptic drugs in mice and rats, in the Journal of pharmacology and experimental therapeutics," Levy, R.H. M., et al., Eds.; Raven Press: New York, 1952; pp. 319-330.
Swinyard, et al. "Studies on the mechanism of amphetamine toxicity in aggregated mice," J. Physiology 1961, 132, 97-102.
Tang et al. "Home cage activity and behavioral performance in inbred and hybrid mice," Behavioral Brain Research, 2002, 136, 555-569.
Tripp, et al, "Brain-Derived Neurotrophic Factor Signaling and Subgenual Anterior Cingulate Cortex Dysfunction in Major Depressive Disorder," Am J Psychiatry, 2012, 169, 1194-1202.
Vinkers, et al, "GABAA Receptor $\alpha$ Subunits Differentially Contribute to Diazepam Tolerance after Chronic Treatment," PLOS ONE, 7 (8) e43054, 1-11 (2012).
Vorhees, et al, "Assessing Spatial Learning and Memory in Rodents," ILAR J, 2014, 55,310-332.
Voss, et al. "Rotarod studies in the rat of the GABAA receptor agonist gaboxadol: lack of ethanol potentiation and benzodiazepine cross-tolerance," European Journal of Pharmacology, 2003, 482, 215-222.
Walser, et al., "Quinazolines and 1, 4 Benzodiazepines. XCV [1]. Synthesis of 1, 4 Benzodiazepines sby Ring Expansion of 2-Chloromethylquinazolines with Carbanions", Roche Research Center, Hoffman-La Roche Inc, Jan. 27, 1986, p. 1303-1314.
Watjen et al., "Novel Benzodiazepine Receptor Partial Agonists: Oxadiazolylimidazobenzodiazepines", J. Med. Chem., 1989, 32, p. 2282-2291.
White, et al, "Pharmacokinetic Theory of Cassette Dosing in Drug Discovery Screening," Drug Metabolism and Disposition, 2001, 29, 957-66.
White, H. S., et al., "Experimental selection, quantification, and evaluation of antiepileptic drugs," in Antiepileptic Drugs, Levy, R.H. M., Meldrum, B. S., Eds.; Raven Press: New York, pp. 99-110, 1995.

(56) References Cited

OTHER PUBLICATIONS

White, H. S., et al., "The early identifcation of anticonvulsant activity: role of the maximal electroshock and subcutaneous pentylenetetrazol seizure models," Ital J Neural Sci. 1995a 16, 73-77.

Willner, "Chronic Mild Stress (CMS) Revisited: Consistency and Behavioural-Neurobiological Concordance in the Effects of CMS," Neuropsychobiology, 2005, 52, 90-110.

Yang, et al, "An Improved Process for the Synthesis of 4-H-Imidazo-[1,5—a][1,4] benzodiazepines," Synthesis, 6, 1036-1040 (2009).

Yocum, et al, "Targeting the gamma-Aminobutyric Acid A Receptor alpha4 Subunit in Airway Smooth Muscle to Alleviate Bronchoconstriction," Am J Respir Cell Mol Biol 2016, 54, (4), 546-53.

Co-pending U.S. Appl. No. 16/325,080, filed Feb. 12, 2019 by Cook et al.

European Patent Office Extended Search Report for Application No. 17767701.0 dated Oct. 25, 2019 (9 pages).

International Search Report and Written Opinion for Application No. PCT/US2017/023206 dated Jun. 22, 2017 (13 pages).

United States Patent Office Action for U.S. Appl. No. 15/267,953 dated Oct. 9, 2018 (16 pages).

United States Patent Office Action for U.S. Appl. No. 15/267,953 dated Dec. 22, 2017 (15 pages).

United States Patent Office Action for U.S. Appl. No. 15/267,953 dated Jul. 26, 2017 (22 pages).

United States Patent Office Action Response by Applicant for U.S. Appl. No. 15/267,953 dated Nov. 21, 2017 (13 pages).

United States Patent Office Action Response by Applicant for U.S. Appl. No. 15/267,953 dated May 29, 2018 (14 pages).

United States Patent Office Action Response by Applicant for U.S. Appl. No. 15/267,953 dated Dec. 13, 2018 (13 pages).

United States Patent Office Action Supplemental Response by Applicant for U.S. Appl. No. 15/267,953 dated Jan. 18, 2019 (15 pages).

Savic et al., "Are GABAA Receptors Containing alpha5 Subunits Contributing to the Sedative Properties of Benzodiazepine Site Agonist", Neuropsychopharmacology, 33, pp. 332-339, 2008.

Patani et al., "Bioisoterism: A Rational Approach in Drug Design", Chem. Rev. 96, pp. 3147-3176, 1996.

Rivas et al., "Antiseizure Activity of Novel gamma-Aminobutyric acid (A) Receptor Subtype-Selective Benzodiaepine Analogues in Mice and Rat Models", J. Med. Chem. 52, pp. 1795-1798, 2009.

Rudoph et al., "Benzodiazepine actions mediated by specific γ-aminobutyric acidA receptor subtypes," Nature, Oct. 1999, vol. 401, pp. 796-800.

Low et al., "Molecular and Neuronal Substrate for the Selective Attenuation of Anxiety," Science, Oct. 2000, vol. 290, pp. 131-134.

McKernan et al., "Sedative but not anxiolytic properties of benzodiazepines are mediated by the GABAA receptor α1 subtype," Nature Neuroscience, Jun. 2000, vol. 3, No. 6, pp. 587-592.

Crestani et al., "Trace Fear Conditioning Involves Hippocampal GABAA Receptors," Institute of Pharmacology, Jun. 2002, vol. 99, No. 13, pp. 8980-8985.

Chambers et al., "Identification of a Novel, Selective GABAA a5 Receptor Inverse Agonist Which Enhances Cognition," J. Med. Chem 2003, 46, pp. 2227-2240.

Knabl et al., "Reversal of Pathological Pain Through Specific Spinal GABAA Receptor Subtypes," Nature, Jan. 2008, vol. 451(7176), pp. 330-335.

Knabl et a., "Genuine Antihyperalgesia by Sysemic Diazepam Revealed by Experiments in GABAA Receptor Point-Mutated Mice," Pain 141, 2009, Int'l Assoc for the Study of Pain, pp. 233-238.

Kontinen et al., "Effect of Midazolam in the Spinal Nerve Ligation Model of Neuropathic Pain in Rats," Pain 85, 2009, Int'l Assoc for the Study of Pain, pp. 425-431.

Tucker et al., "Intrathecal Midazolam II: Combination with Intrathecal Fentanyl for Labor Pain," Anesth Analg International Anesthesia Research Society 2004, pp. 1521-1527.

Wieland et al., "A Single Histidine in GABAA Receptors is Essential for Benzodiazepine Agonist Binding," J. of Biological Chemistry, vol. 267, No. 3, Jan. 1992, pp. 1426-1429.

Barnard et al., "International Union of Pharmacology, XV Subtypes of γ-aminobutyric acidA receptors: Classification on the Basis of Subunit Structure and Receptor Function," Pharmacological Reviews, vol. 50, No. 21, 1998, pp. 291-313.

Scott-Stevens et al., Rodent Pharmacokinetics and Receptor Occupancy of the GABAA Receptor Subtype Selective Benzodiazepine Site Ligand L-838417; Biopharmaceutics & Drug Disposition, 26:.2005. pp. 13-20.

Barnard, The Molecular Architecture of GABAA Receptors. Pharmacology of GBA and Glyci, 2001, vol. 150, pp. 77-99.

United States Patent Office Preliminary Amendment for U.S. Appl. No. 15/267,953 dated Sep. 16, 2016 (11 pages).

| Genus # | Genus Structure | Compound Structure | Chemical Name | Code # | Formula | M.W. (g/mol) |
|---|---|---|---|---|---|---|
| II | | | (R)-8-ethynyl-6-(2-fluorophenyl)-N,4-dimethyl-4H-benzo[f]imidazo[1,5-a][1,4]diazepine-3-carboxamide | MP-III-022 | C22H17FN4O | 372.39 |
| II | | | (R)-8-ethynyl-6-(2-fluorophenyl)-N,N,4-trimethyl-4H-benzo[f]imidazo[1,5-a][1,4]diazepine-3-carboxam | GL-II-73 | C23H19FN4O | 386.42 |
| II | | | (R)-N-ethyl-8-ethynyl-6-(2-fluorophenyl)-4-methyl-4H-benzo[f]imidazo[1,5-a][1,4]diazepine-3-carboxamide | GL-II-74 | C23H19FN4O | 386.42 |
| II | | | (R)-N-cyclopropyl-8-ethynyl-6-(2-fluorophenyl)-4-methyl-4H-benzo[f]imidazo[1,5-a][1,4]diazepine-3-carboxamide | GL-II-75 | C24H19FN4O | 398.43 |
| II | | | (R)-(8-ethynyl-6-(2-fluorophenyl)-4-methyl-4H-benzo[f]imidazo[1,5-a][1,4]diazepin-3-yl)(pyrrolidin-1-yl)methanone | GL-II-76 | C25H21FN4O | 412.46 |

FIG. 1

| Genus # | Genus Structure | Compound Structure | Chemical Name | Code # | Formula | M.W. (g/mol) |
|---|---|---|---|---|---|---|
| I | 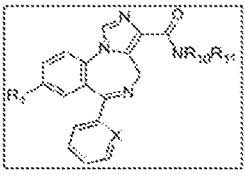 | 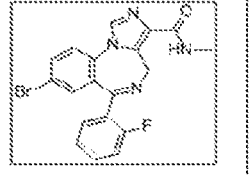 | 8-bromo-6-(2-fluorophenyl)-N-methyl-4H-benzo[f]imidazo[1,5-a][1,4]diazepine-3-carboxamide | RV-II-04 | C18H14BrFN4O | 413.24 |
| II | 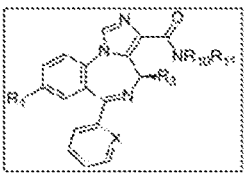 | 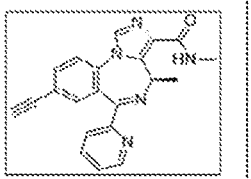 | (R)-8-ethynyl-N,4-dimethyl-6-(pyridin-2-yl)-4H-benzo[f]imidazo[1,5-a][1,4]diazepine-3-carboxamide | GL-II-31 | C21H17N5O | 355.39 |
| III | 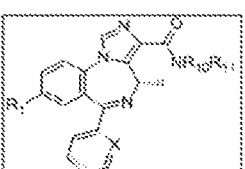 | 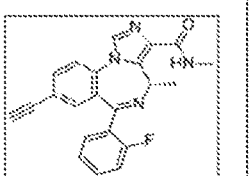 | (S)-8-ethynyl-6-(2-fluorophenyl)-N,4-dimethyl-4H-benzo[f]imidazo[1,5-a][1,4]diazepine-3-carboxamide | MP-III-022 | C22H17FN4O | 372.39 |
| III | 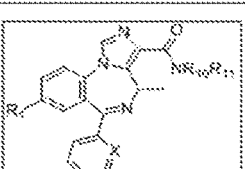 | 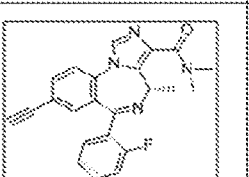 | (S)-8-ethynyl-6-(2-fluorophenyl)-N,N,4-trimethyl-4H-benzo[f]imidazo[1,5-a][1,4]diazepine-3-carboxamide | GL-I-54 | C23H19FN4O | 386.42 |
| IV | 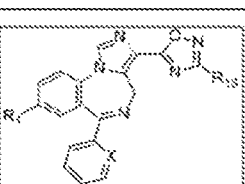 | 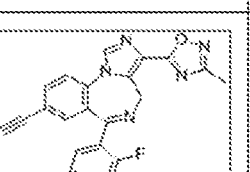 | 5-(8-ethynyl-6-(2-fluorophenyl)-4H-benzo[f]imidazo[1,5-a][1,4]diazepin-3-yl)-3-methyl-1,2,4-oxadiazole | GL-III-23 | C22H14FN5O | 383.38 |
| V | 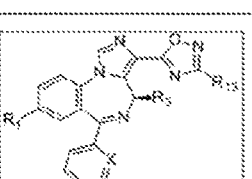 | 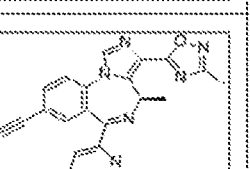 | (R)-5-(8-ethynyl-4-methyl-6-(pyridin-2-yl)-4H-benzo[f]imidazo[1,5-a][1,4]diazepin-3-yl)-3-methyl-1,2,4-oxadiazole | GL-II-33 | C22H16N6O | 380.4 |
| V | 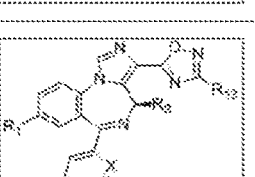 | 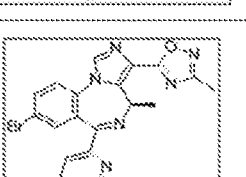 | (R)-5-(8-bromo-4-methyl-6-(pyridin-2-yl)-4H-benzo[f]imidazo[1,5-a][1,4]diazepin-3-yl)-3-methyl-1,2,4-oxadiazole | GL-II-54 | C20H15BrN6O | 435.28 |
| VI | 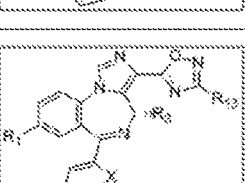 | 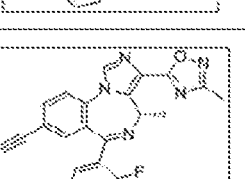 | (S)-5-(8-ethynyl-6-(2-fluorophenyl)-4-methyl-4H-benzo[f]imidazo[1,5-a][1,4]diazepin-3-yl)-3-methyl-1,2,4-oxadiazole | GL-I-65 | C23H16FN5O | 397.4 |

FIG. 2

| Compound | Animal species and dosing | Tissue | Route of administration | $C_{max}$ (Mean ± SEM, ng/ml – plasma, ng/g - brain) | $T_{max}$ (Mean ± SEM, h) | $AUC_{0-12}$ (Mean ± SEM, ng*h/ml – plasma, ng*h/g – brain) | $AUC_{0-\infty}$ (Mean ± SEM, ng*h/ml – plasma, ng*h/g – brain) | $T_{1/2}$ (Mean ± SEM, h) | $\beta$ (Mean ± SEM, 1/h) |
|---|---|---|---|---|---|---|---|---|---|
| RV-II-04 | Mouse 3 mg/kg | Plasma | IV | 1910.44 ± 190.95 | 0.00 ± 0.00 | 2974.93 ± 429.88 | 2981.44 ± 436.01 | 1.13 ± 0.24 | 0.66 ± 0.12 |
| | | | PO | 528.54 ± 129.42 | 1.78 ± 1.13 | 3573.79 ± 667.43 | 3714.70 ± 642.36 | 2.76 ± 0.41 | 0.26 ± 0.04 |
| | | | IP | 1412.33 ± 152.97 | 0.25 ± 0.08 | 4876.15 ± 503.26 | 4883.35 ± 502.87 | 1.13 ± 0.24 | 0.67 ± 0.12 |
| | | Brain | IV | 1816.24 ± 227.80 | 0.25 ± 0.08 | 3414.70 ± 815.13 | 3416.05 ± 815.27 | 1.10 ± 0.06 | 0.63 ± 0.03 |
| | | | PO | 554.17 ± 51.12 | 0.55 ± 0.22 | 2897.87 ± 765.81 | 2902.37 ± 764.41 | 2.11 ± 0.86 | 0.43 ± 0.13 |

FIG. 27

| | | | | | | | | |
|---|---|---|---|---|---|---|---|---|
| | | | IP | 1626.66 ± 22.20 | 0.33 ± 0.00 | 5631.75 ± 644.15 | 5632.10 ± 644.27 | 0.91 ± 0.03 | 0.76 ± 0.02 |
| Rat 3 mg/kg | Plasma | IV | 981.66 ± 184.23 | 0.00 ± 0.00 | 450.49 ± 46.77 | 456.25 ± 45.97 | 1.61 ± 0.15 | 0.42 ± 0.04 |
| | | PO | 13.27 ± 5.27 | 2.33 ± 0.67 | 75.76 ± 32.18 | 94.28 ± 21.19 | 5.67 ± 3.02 | 0.20 ± 0.08 |
| | | IP | 452.21 ± 36.63 | 0.17 ± 0.08 | 976.30 ± 353.51 | 979.41 ± 354.60 | 1.40 ± 0.07 | 0.46 ± 0.01 |
| | Brain | IV | 3343.61 ± 463.84 | 0.08 ± 0.00 | 1761.11 ± 143.44 | 1788.35 ± 139.97 | 1.78 ± 0.07 | 0.39 ± 0.01 |
| | | PO | 136.34 ± 61.97 | 1.44 ± 0.80 | 631.71 ± 298.55 | 649.36 ± 294.93 | 3.13 ± 1.26 | 0.29 ± 0.08 |
| | | IP | 959.19 ± 162.83 | 0.25 ± 0.08 | 4745.20 ± 1385.08 | 5368.98 ± 786.53 | 3.79 ± 2.64 | 0.43 ± 0.18 |

FIG. 27 continued

| | | | | | | | | |
|---|---|---|---|---|---|---|---|---|
| GL-II-31 | Mouse 3 mg/kg | Plasma | IV | 340.07 ± 73.23 | 0.00 ± 0.00 | 630.86 ± 297.47 | 631.16 ± 297.52 | 1.12 ± 0.01 | 0.62 ± 0.01 |
| | | | PO | 195.40 ± 41.41 | 1.00 ± 0.00 | 894.63 ± 187.36 | 902.16 ± 190.71 | 1.42 ± 0.35 | 0.54 ± 0.11 |
| | | | IP | 381.96 ± 45.02 | 0.78 ± 0.22 | 1143.66 ± 67.30 | 1145.95 ± 65.82 | 1.30 ± 0.21 | 0.56 ± 0.09 |
| | | Brain | IV | 418.68 ± 24.31 | 0.25 ± 0.08 | 389.02 ± 179.73 | 389.33 ± 179.66 | 1.26 ± 0.12 | 0.56 ± 0.06 |
| | | | PO | 47.74 ± 10.09 | 0.69 ± 0.31 | 122.77 ± 64.36 | 123.31 ± 64.13 | 1.87 ± 0.54 | 0.43 ± 0.11 |
| | | | IP | 168.60 ± 5.83 | 0.33 ± 0.00 | 382.88 ± 78.33 | 383.20 ± 78.42 | 1.20 ± 0.07 | 0.58 ± 0.04 |
| | Rat 3 mg/kg | Plasma | IV | 639.33 ± 204.62 | 0.00 ± 0.00 | 620.61 ± 36.43 | 635.33 ± 37.88 | 2.04 ± 0.04 | 0.34 ± 0.01 |
| | | | PO | 58.33 ± 13.71 | 3.00 ± 0.00 | 386.97 ± 81.52 | 394.82 ± 80.48 | 2.08 ± 0.20 | 0.34 ± 0.03 |
| | | | IP | 180.44 ± 7.76 | 0.33 ± 0.00 | 819.66 ± 147.89 | 849.45 ± 149.74 | 2.38 ± 0.38 | 0.31 ± 0.04 |

FIG. 27 continued

| | | | | 708.92 | 0.08 | 732.82 | 795.57 | 2.67 | 0.28 |
| --- | --- | --- | --- | --- | --- | --- | --- | --- | --- |
| | | | IV | ± 167.01 | ± 0.00 | ± 145.63 | ± 120.25 | ± 0.45 | ± 0.06 |
| | | Brain | PO | 25.20 ± 9.18 | 6.00 ± 3.00 | 184.38 ± 48.92 | 234.32 ± 29.38 | 4.55 ± 0.96 | 0.17 ± 0.04 |
| | | | IP | 116.40 ± 12.71 | 0.25 ± 0.08 | 501.55 ± 65.11 | 595.01 ± 114.54 | 2.71 ± 0.39 | 0.27 ± 0.04 |
| MP-III-023 | Mouse 3 mg/kg | Plasma | IV | 1053.42 ± 178.15 | 0.00 ± 0.00 | 1324.67 ± 72.10 | 1325.81 ± 72.41 | 1.10 ± 0.12 | 0.64 ± 0.06 |
| | | | PO | 495.79 ± 92.02 | 1.00 ± 0.00 | 1419.40 ± 288.19 | 1431.44 ± 286.06 | 1.73 ± 0.16 | 0.41 ± 0.04 |
| | | | IP | 914.38 ± 54.14 | 0.08 ± 0.00 | 1069.20 ± 141.30 | 1073.74 ± 143.84 | 1.50 ± 0.15 | 0.47 ± 0.04 |
| | | Brain | IV | 1041.87 ± 204.05 | 0.08 ± 0.00 | 936.37 ± 81.20 | 936.41 ± 81.20 | 0.85 ± 0.01 | 0.81 ± 0.01 |
| | | | PO | 163.97 ± 21.32 | 0.25 ± 0.08 | 364.60 ± 108.18 | 364.89 ± 108.25 | 1.18 ± 0.08 | 0.59 ± 0.04 |
| | | | IP | 708.50 ± 23.43 | 0.25 ± 0.08 | 1236.64 ± 127.71 | 1236.78 ± 127.67 | 0.85 ± 0.10 | 0.84 ± 0.10 |

FIG. 27 continued

| | | | | | | | | |
|---|---|---|---|---|---|---|---|---|
| | Rat 3 mg/kg | Plasma | IV | 740.38 ± 132.13 | 0.00 ± 0.00 | 487.30 ± 42.55 | 500.45 ± 47.09 | 1.81 ± 0.30 | 0.40 ± 0.06 |
| | | | PO | 17.77 ± 7.92 | 1.44 ± 0.80 | 69.63 ± 18.64 | 91.31 ± 6.23 | 6.60 ± 4.06 | 0.22 ± 0.11 |
| | | | IP | 256.08 ± 43.26 | 0.17 ± 0.08 | 240.18 ± 8.63 | 250.65 ± 7.25 | 2.37 ± 0.37 | 0.31 ± 0.06 |
| | | Brain | IV | 2720.98 ± 356.62 | 0.08 ± 0.00 | 1404.13 ± 60.66 | 1430.22 ± 58.02 | 1.82 ± 0.09 | 0.38 ± 0.02 |
| | | | PO | 45.62 ± 32.85 | 5.11 ± 3.53 | 100.93 ± 30.80 | 142.39 ± 46.10 | 5.54 ± 2.66 | 0.20 ± 0.09 |
| | | | IP | 502.48 ± 168.89 | 0.25 ± 0.08 | 553.60 ± 192.31 | 568.40 ± 189.21 | 1.74 ± 0.65 | 0.63 ± 0.32 |
| GL-I-54 | Mouse 3 mg/kg | Plasma | IV | 1390.42 ± 222.26 | 0.00 ± 0.00 | 2039.56 ± 50.53 | 2039.68 ± 50.56 | 0.88 ± 0.02 | 0.79 ± 0.02 |
| | | | PO | 339.70 ± 29.77 | 0.55 ± 0.22 | 1511.09 ± 287.14 | 1511.18 ± 187.17 | 0.90 ± 0.06 | 0.78 ± 0.05 |
| | | | IP | 1283.79 ± 46.18 | 0.08 ± 0.00 | 2445.94 ± 401.30 | 2445.96 ± 401.30 | 0.74 ± 0.01 | 0.94 ± 0.01 |

FIG. 27 continued

| | | | | | | | | |
|---|---|---|---|---|---|---|---|---|
| | | Brain | IV | 464.81 ± 117.94 | 0.08 ± 0.00 | 400.91 ± 21.65 | 400.95 ± 21.65 | 0.91 ± 0.04 | 0.77 ± 0.04 |
| | | | PO | 83.43 ± 6.75 | 0.33 ± 0.00 | 199.71 ± 38.48 | 199.77 ± 38.47 | 1.00 ± 0.05 | 0.70 ± 0.04 |
| | | | IP | 320.13 ± 2.22 | 0.25 ± 0.08 | 467.03 ± 36.06 | 467.05 ± 36.06 | 0.82 ± 0.03 | 0.84 ± 0.03 |
| Rat 3 mg/kg | | Plasma | IV | 1389.45 ± 257.98 | 0.00 ± 0.00 | 537.21 ± 70.83 | 578.24 ± 70.22 | 1.62 ± 0.06 | 0.43 ± 0.02 |
| | | | PO | 77.48 ± 35.02 | 0.33 ± 0.00 | 142.98 ± 43.91 | 149.82 ± 44.25 | 3.05 ± 0.42 | 0.24 ± 0.04 |
| | | | IP | 979.87 ± 196.66 | 0.17 ± 0.08 | 487.07 ± 27.52 | 490.08 ± 28.49 | 1.72 ± 0.03 | 0.40 ± 0.01 |
| | | Brain | IV | 916.08 ± 196.67 | 0.08 ± 0.00 | 458.63 ± 64.25 | 485.71 ± 59.34 | 2.34 ± 0.17 | 0.30 ± 0.02 |
| | | | PO | 114.97 ± 55.53 | 0.33 ± 0.00 | 322.24 ± 30.29 | 347.25 ± 29.89 | 0.37 ± 0.01 | 1.90 ± 0.05 |
| | | | IP | 186.50 ± 65.09 | 0.17 ± 0.08 | 406.85 ± 69.29 | 444.70 ± 79.70 | 0.40 ± 0.02 | 1.76 ± 0.09 |

FIG. 27 continued

| | | | | | | | | | |
|---|---|---|---|---|---|---|---|---|---|
| GL-III-23 | Mouse 3 mg/kg | Plasma | IV | 164.27 ± 32.71 | 0.00 ± 0.00 | 392.05 ± 56.38 | 457.81 ± 86.29 | 3.37 ± 1.09 | 0.29 ± 0.14 |
| | | | PO | 109.84 ± 30.55 | 3.00 ± 1.00 | 827.77 ± 263.74 | 1317.38 ± 626.00 | 5.91 ± 2.59 | 0.34 ± 0.25 |
| | | | IP | 242.45 ± 30.57 | 0.78 ± 0.22 | 1199.56 ± 142.88 | 1386.94 ± 158.65 | 4.14 ± 0.12 | 0.17 ± 0.01 |
| | | Brain | IV | 524.04 ± 102.71 | 0.08 ± 0.00 | 931.76 ± 192.73 | 974.14 ± 191.48 | 2.50 ± 0.58 | 0.31 ± 0.07 |
| | | | PO | 191.42 ± 60.45 | 3.00 ± 1.00 | 1170.40 ± 340.95 | 1285.24 ± 263.90 | 3.61 ± 1.97 | 0.32 ± 0.12 |
| | | | IP | 479.03 ± 7.53 | 2.00 ± 1.00 | 3056.79 ± 274.84 | 3284.04 ± 342.75 | 2.67 ± 1.00 | 0.47 ± 0.28 |
| | Rat 3 mg/kg | Plasma | IV | 195.59 ± 42.20 | 0.00 ± 0.00 | 215.37 ± 23.64 | 216.19 ± 23.64 | 1.48 ± 0.02 | 0.47 ± 0.01 |
| | | | PO | 103.65 ± 34.15 | 0.78 ± 0.22 | 245.99 ± 119.30 | 246.85 ± 119.21 | 1.56 ± 0.17 | 0.45 ± 0.05 |
| | | | IP | 63.62 ± 7.85 | 0.39 ± 0.31 | 281.37 ± 32.48 | 334.37 ± 17.65 | 4.42 ± 0.77 | 0.17 ± 0.03 |

FIG. 27 continued

|  |  |  |  | 356.14 ± 72.29 | 0.40 ± 0.31 | 783.91 ± 117.03 | 872.52 ± 99.94 | 3.38 ± 0.64 | 0.22 ± 0.05 |
|---|---|---|---|---|---|---|---|---|---|
|  |  | Brain | IV |  |  |  |  |  |  |
|  |  |  | PO | 128.73 ± 24.94 | 5.33 ± 3.38 | 822.11 ± 147.77 | 1276.76 ± 260.35 | 5.00 ± 1.73 | 0.18 ± 0.07 |
|  |  |  | IP | 175.58 ± 3.40 | 0.08 ± 0.00 | 952.11 ± 129.97 | 1213.43 ± 65.82 | 5.19 ± 1.31 | 0.15 ± 0.03 |
| GL-II-33 | Mouse 3 mg/kg | Plasma | IV | 111.24 ± 34.45 | 0.00 ± 0.00 | 175.30 ± 34.25 | 212.91 ± 35.01 | 4.40 ± 0.41 | 0.16 ± 0.01 |
|  |  |  | PO | 59.54 ± 15.91 | 3.00 ± 1.00 | 442.50 ± 88.97 | 803.70 ± 180.17 | 10.73 ± 6.96 | 0.30 ± 0.23 |
|  |  |  | IP | 134.63 ± 3.29 | 0.78 ± 0.22 | 701.76 ± 51.78 | 1019.78 ± 126.91 | 7.61 ± 2.16 | 0.10 ± 0.02 |
|  |  | Brain | IV | 298.17 ± 67.12 | 0.08 ± 0.00 | 372.27 ± 189.23 | 550.31 ± 263.79 | 5.46 ± 2.13 | 0.21 ± 0.12 |
|  |  |  | PO | 85.81 ± 25.49 | 3.00 ± 1.00 | 508.42 ± 207.87 | 631.34 ± 307.79 | 3.11 ± 1.37 | 0.36 ± 0.18 |

FIG. 27 continued

| Compound | Species/Dose | Matrix | Route | | | | | | |
|---|---|---|---|---|---|---|---|---|---|
| | | | IP | 240.73 ± 49.80 | 2.00 ± 1.00 | 1386.97 ± 270.11 | 1487.33 ± 266.22 | 3.01 ± 0.08 | 0.23 ± 0.01 |
| | Rat 3 mg/kg | Plasma | IV | 104.15 ± 42.00 | 0.00 ± 0.00 | 50.61 ± 10.03 | 51.77 ± 10.00 | 2.12 ± 0.07 | 0.33 ± 0.011 |
| | | | PO | 39.24 ± 21.86 | 1.67 ± 0.67 | 58.27 ± 27.70 | 59.87 ± 27.34 | 2.91 ± 0.73 | 0.27 ± 0.05 |
| | | | IP | 4.75 ± 1.50 | 0.17 ± 0.08 | 9.50 ± 1.11 | 12.70 ± 1.32 | 5.83 ± 0.40 | 0.12 ± 0.01 |
| | | Brain | IV | 172.47 ± 28.89 | 0.17 ± 0.08 | 613.23 ± 55.69 | 1944.91 ± 688.72 | 17.95 ± 6.41 | 0.05 ± 0.02 |
| | | | PO | 68.56 ± 21.58 | 0.69 ± 0.31 | 296.85 ± 18.10 | 1361.21 ± 985.70 | 25.35 ± 22.02 | 0.20 ± 0.14 |
| | | | IP | 97.18 ± 19.76 | 0.17 ± 0.08 | 422.85 ± 28.86 | 1003.05 ± 415.06 | 15.00 ± 10.05 | 0.20 ± 0.15 |
| GL-II-54 | Mouse 3 mg/kg | Plasma | IV | 954.60 | 0.00 | 738.85 | 798.85 | 3.23 | 0.22 |
| | | | PO | 137.05 | 3.00 | 872.15 | 993.08 | 3.61 | 0.23 |
| | | | IP | 370.78 | 0.78 | 1672.11 | 1811.11 | 3.30 | 0.21 |
| | | Brain | IV | 877.97 | 0.08 | 1458.62 | 1459.02 | 1.07 | 0.65 |
| | | | PO | 107.05 | 3.00 | 538.84 | 539.88 | 1.31 | 0.63 |
| | | | IP | 352.86 | 2.00 | 2105.67 | 2119.37 | 1.53 | 0.49 |

FIG. 27 continued

|  |  |  |  |  |  |  |  |  |
|---|---|---|---|---|---|---|---|---|
| | | Plasma | IV | 592.56 | 0.00 | 884.99 | 885.77 | 1.25 | 0.56 |
| | | | PO | 230.93 | 1.67 | 939.87 | 947.33 | 1.58 | 0.51 |
| | | | IP | 146.92 ± 3.71 | 0.56 ± 0.22 | 867.00 ± 101.00 | 1021.54 ± 77.54 | 4.46 ± 1.13 | 0.18 ± 0.04 |
| | Rat 3 mg/kg | Brain | IV | 290.14 ± 36.86 | 0.17 ± 0.08 | 859.22 ± 60.61 | 1284.87 ± 17.83 | 6.51 ± 0.57 | 0.11 ± 0.01 |
| | | | PO | 105.66 ± 13.92 | 1.67 ± 0.67 | 859.69 ± 97.79 | 1600.41 ± 348.96 | 9.13 ± 4.23 | 0.17 ± 0.11 |
| | | | IP | 118.75 ± 5.80 | 0.56 ± 0.22 | 799.87 ± 48.21 | 1988.85 ± 484.63 | 14.49 ± 4.13 | 0.06 ± 0.02 |
| GL-I-65 | Mouse 3 mg/kg | Plasma | IV | 101.89 ± 34.49 | 0.00 ± 0.00 | 156.09 ± 29.81 | 181.70 ± 37.05 | 3.69 ± 0.87 | 0.21 ± 0.04 |
| | | | PO | 51.35 ± 10.68 | 3.00 ± 1.00 | 363.06 ± 84.22 | 575.32 ± 140.25 | 7.20 ± 3.80 | 0.32 ± 0.24 |
| | | | IP | 151.10 ± 8.67 | 0.78 ± 0.22 | 619.41 ± 46.29 | 871.09 ± 34.30 | 6.25 ± 0.65 | 0.11 ± 0.01 |

FIG. 27 continued

| | | | | | | | | |
|---|---|---|---|---|---|---|---|---|
| | | Brain | IV | 230.63 ± 50.40 | 0.08 ± 0.00 | 286.56 ± 174.85 | 288.39 ± 175.90 | 1.65 ± 0.09 | 0.42 ± 0.02 |
| | | | PO | 65.51 ± 11.60 | 3.00 ± 1.00 | 304.52 ± 106.53 | 312.22 ± 99.28 | 1.74 ± 0.85 | 0.57 ± 0.19 |
| | | | IP | 182.58 ± 37.57 | 2.00 ± 1.00 | 1029.72 ± 192.47 | 1126.95 ± 203.15 | 3.16 ± 0.44 | 0.23 ± 0.03 |
| Rat 3 mg/kg | Plasma | | IV | 116.77 ± 40.89 | 0.00 ± 0.00 | 150.23 ± 15.11 | 151.23 ± 15.11 | 1.74 ± 0.03 | 0.40 ± 0.01 |
| | | | PO | 46.81 ± 20.78 | 1.67 ± 0.67 | 105.25 ± 20.10 | 106.25 ± 20.07 | 1.74 ± 0.06 | 0.40 ± 0.01 |
| | | | IP | 24.71 ± 1.36 | 0.33 ± 0.00 | 76.83 ± 8.40 | 78.03 ± 8.38 | 2.09 ± 0.02 | 0.33 ± 0.00 |
| | Brain | | IV | 152.07 ± 29.08 | 0.08 ± 0.00 | 530.05 ± 83.18 | 2031.38 ± 1099.74 | 20.31 ± 10.35 | 0.06 ± 0.03 |
| | | | PO | 62.10 ± 18.05 | 1.67 ± 0.67 | 310.43 ± 16.93 | 531.37 ± 110.46 | 7.93 ± 2.74 | 0.11 ± 0.03 |
| | | | IP | 92.43 ± 19.98 | 0.17 ± 0.08 | 447.07 ± 79.99 | 730.43 ± 100.40 | 8.46 ± 1.48 | 0.09 ± 0.02 |

FIG. 27 continued

| | | | | | | | | | |
|---|---|---|---|---|---|---|---|---|---|
| GL-II-73 | Mouse 10 mg/kg | Plasma | IP | 5384.54 ± 838.04 | 0.08 ± 0.00 | 4620.09 ± 323.21 | 4626.35 ± 322.80 | 1.20 ± 0.02 | 0.58 ± 0.01 |
| | | Brain | IP | 1195.94 ± 51.75 | 0.17 ± 0.08 | 1311.86 ± 85.86 | 1397.47 ± 119.30 | 2.44 ± 0.20 | 0.29 ± 0.02 |
| | Rat 3 mg/kg | Plasma | IV | 777.76 ± 31.34 | 0.00 ± 0.00 | 434.48 ± 63.02 | 435.03 ± 62.92 | 1.21 ± 0.07 | 0.58 ± 0.03 |
| | | | PO | 79.43 ± 50.72 | 0.25 ± 0.08 | 68.54 ± 19.28 | 144.52 ± 65.73 | 7.16 ± 1.82 | 2.70 ± 2.58 |
| | | Brain | IV | 239.70 ± 11.83 | 0.08 ± 0.00 | 103.79 ± 7.18 | 110.44 ± 7.05 | 2.35 ± 0.26 | 0.30 ± 0.03 |
| | | | PO | 20.50 ± 13.49 | 1.22 ± 0.89 | 54.09 ± 8.58 | 68.79 ± 13.69 | 7.20 ± 3.94 | 0.16 ± 0.06 |
| GL-II-74 | Mouse 10 mg/kg | Plasma | IP | 2840.74 ± 404.87 | 0.08 ± 0.00 | 2053.17 ± 297.11 | 2102.62 ± 298.38 | 1.84 ± 0.17 | 0.38 ± 0.03 |
| | | Brain | IP | 3246.23 ± 184.90 | 0.08 ± 0.00 | 2218.83 ± 177.52 | 2231.34 ± 177.69 | 1.47 ± 0.07 | 0.48 ± 0.02 |

FIG. 27 continued

|  | Rat 3 mg/kg | Plasma | IV | 426.55 ± 77.06 | 0.00 ± 0.00 | 292.69 ± 4.72 | 294.25 ± 4.15 | 1.50 ± 0.13 | 0.47 ± 0.04 |
|---|---|---|---|---|---|---|---|---|---|
|  |  | Brain | IV | 690.92 ± 23.66 | 0.08 ± 0.00 | 339.54 ± 11.53 | 344.94 ± 11.28 | 1.75 ± 0.09 | 0.40 ± 0.02 |
| GL-II-75 | Mouse 10 mg/kg | Plasma | IP | 2151.323 ± 81.07 | 0.25 ± 0.08 | 4845.31 ± 118.92 | 4856.48 ± 111.76 | 0.53 ± 0.06 | 0.16 ± 0.06 |
|  |  | Brain | IP | 1410.23 ± 136.71 | 0.33 ± 0.00 | 3895.80 ± 114.08 | 3907.26 ± 112.51 | 1.43 ± 0.09 | 0.49 ± 0.03 |

FIG. 27 continued

TREATMENT OF COGNITIVE AND MOOD SYMPTOMS IN NEURODEGENERATIVE AND NEUROPSYCHIATRIC DISORDERS WITH ALPHA5-CONTAINING GABAA RECEPTOR AGONISTS

CROSS-REFERENCE TO RELATED APPLICATION

This patent application is the U.S. national stage entry, under 35 U.S.C. § 371, of international application number PCT/US2017/023206, filed Mar. 20, 2017, which claims the benefit of U.S. Provisional Application No. 62/310,409 filed on Mar. 18, 2016, the entire contents of each being incorporated by reference in their entirety.

STATEMENT REGARDING FEDERALLY SPONSORED RESEARCH OR DEVELOPMENT

This invention was made with government support under R01 MH096463 awarded by the National Institutes of Health. The government has certain rights to the invention.

BACKGROUND

According to the World Health Organization, major depressive disorder (MDD) is a leading cause of disability, affecting 350 million people worldwide. It is a complex disorder with symptoms that include low affect, anhedonia, anxiety, rumination, appetite changes, sleep disturbances, and cognitive impairments. Its early onset and chronic nature have serious consequences for lost education and unemployment. It has an estimated annual and lifelong prevalence of 5.3% and 13.2% respectively, with a high rate of recurrence, higher prevalence in women, and a 37% rate of heritability. MDD is the leading cause of years lost due to disability both in developing and developed countries, and in both women and men. The burden of depression is growing. Treatment-resistant depression, a severe and chronic form of the illness, has an estimated prevalence of 1-3% of the population at any given time, a proportion that is greater than schizophrenia and bipolar disorder cases combined. Despite an unacceptable burden on affected individuals, their family and society, pharmaceutical companies have mostly withdrawn from developing new antidepressant drugs. Cognitive impairments are part of the comorbid symptoms that develop alongside anxiety, anhedonia, sleep disturbance and other deficits. Cognitive dysfunction refers to deficits in attention, visual and auditory processing, short term and working memory, motor function, learning and memory processes. Despite overwhelming consensus on the importance of cognitive impairment in depression, there is no conclusion regarding the full profile of cognitive impairment in depression. Cognitive impairments may be a primary dysfunction in MDD and several other core symptoms may act as mediators of cognitive dysfunction. Current antidepressant medications are all derived from approaches and modes of action that were discovered by chance over 50 years ago. These drugs act predominantly on the monoamine (serotonin and norepinephrine) systems. They often take weeks to achieve therapeutic effects, and subjects experience poor response, low remission rate (~50%) and considerable side-effects. Moreover, available antidepressant are not designed to treat cognitive impairment, and in some case (like some benzodiazepine), their positive effects on some dimensions of the illness (anxiety, anhedonia) are counterbalanced by negative side effects affecting cognition. Furthermore, clinical studies have demonstrated that cognitive deficits are still detected even in periods of remission from mood symptoms. Hence, developing antidepressants that can potentially rescue the cognitive dysfunction as well as the emotional and motivational symptoms seem critical for future treatment of MDD.

The barriers to new antidepressant drug development are multiple, starting with a paucity of knowledge on disease mechanisms and of targets that are informed by the primary pathology of the illness. Accordingly, there is currently little effort made toward rational drug design or for developing biological diagnostic and therapeutic markers for personalized treatments.

SUMMARY

In one embodiment, the disclosure provides a compound according to any one of formulas (II) or (III):

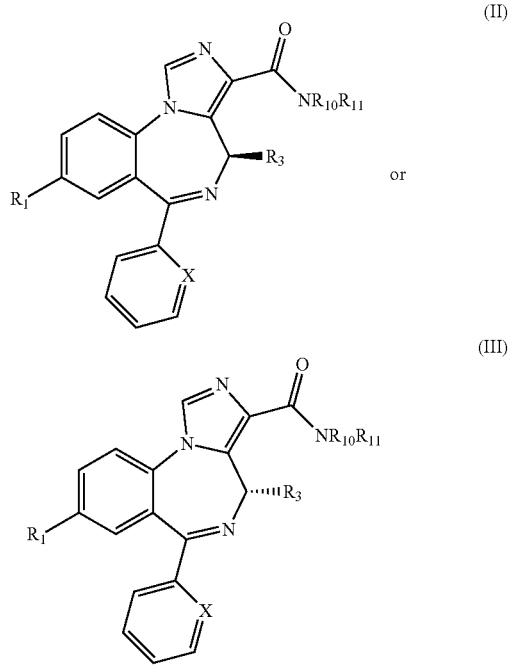

or a pharmaceutically acceptable salt thereof.

In another embodiment the disclosure provides a compound according to any one of formulas (V) or (VI):

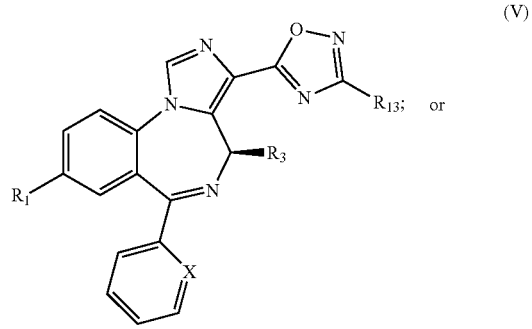

-continued

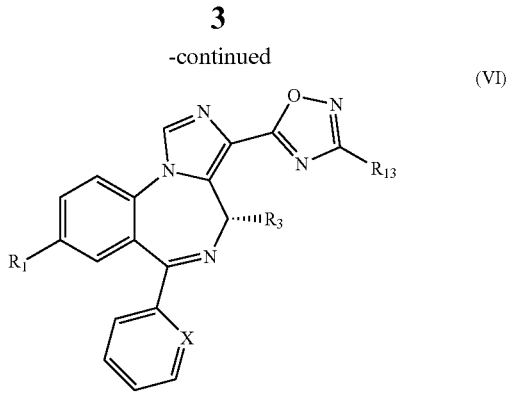

(VI)

or a pharmaceutically acceptable salt thereof.

In an embodiment, the disclosure provides a pharmaceutical composition comprising a compound according to the disclosure and a pharmaceutically acceptable excipient.

In an embodiment, the disclosure provides a method of treating cognitive and/or mood symptoms comprising administering a compound according to the disclosure to a subject in need thereof.

Other aspects of the disclosure will become apparent by consideration of the detailed description and accompanying drawings.

BRIEF DESCRIPTION OF THE DRAWINGS

FIG. 1 shows various compounds useful in the methods of the disclosure.

FIG. 2 shows various compounds useful in the methods of the disclosure.

path efficiency during acquisition trials in the water maze. ***$p<0.001$ compared to solvent (SOL) group; +$p<0.05$, +++$p<0.001$ compared to 2 mg/kg diazepam (DZP 2) group; #$p<0.05$, ###$p<0.001$ compared to 1 mg/kg (MP-III-022 1) group. Animals per treatment group were 6-7. SOL=solvent, DZP 2=2 mg/kg diazepam, MP-III-022 1=1 mg/kg MP-III-022, MP-III-022 2.5=2.5 mg/kg MP-III-022, MP-III-022 10=10 mg/kg MP-III-022.

FIG. 12 shows the effects of 2 mg/kg diazepam and 1, 2 and 10 mg/kg MP-III-022 on (a) distance in the target zone (meters) and (b) distance in the peripheral ring (%) during probe trial in the water maze. *$p<0.05$, **$p<0.01$ compared to solvent (SOL) group; +$p<0.05$, ++$p<0.01$ compared to 2 mg/kg diazepam (DZP 2) group; #$p<0.05$ compared to 1 mg/kg MP-III-022 (MP-III-022 1) group. Animals per treatment group were 6-7. SOL=solvent, DZP 2=2 mg/kg diazepam, MP-III-022 1=1 mg/kg MP-III-022, MP-III-022 2.5=2.5 mg/kg MP-III-022, MP-III-022 10=10 mg/kg MP-III-022.

Figure 13:
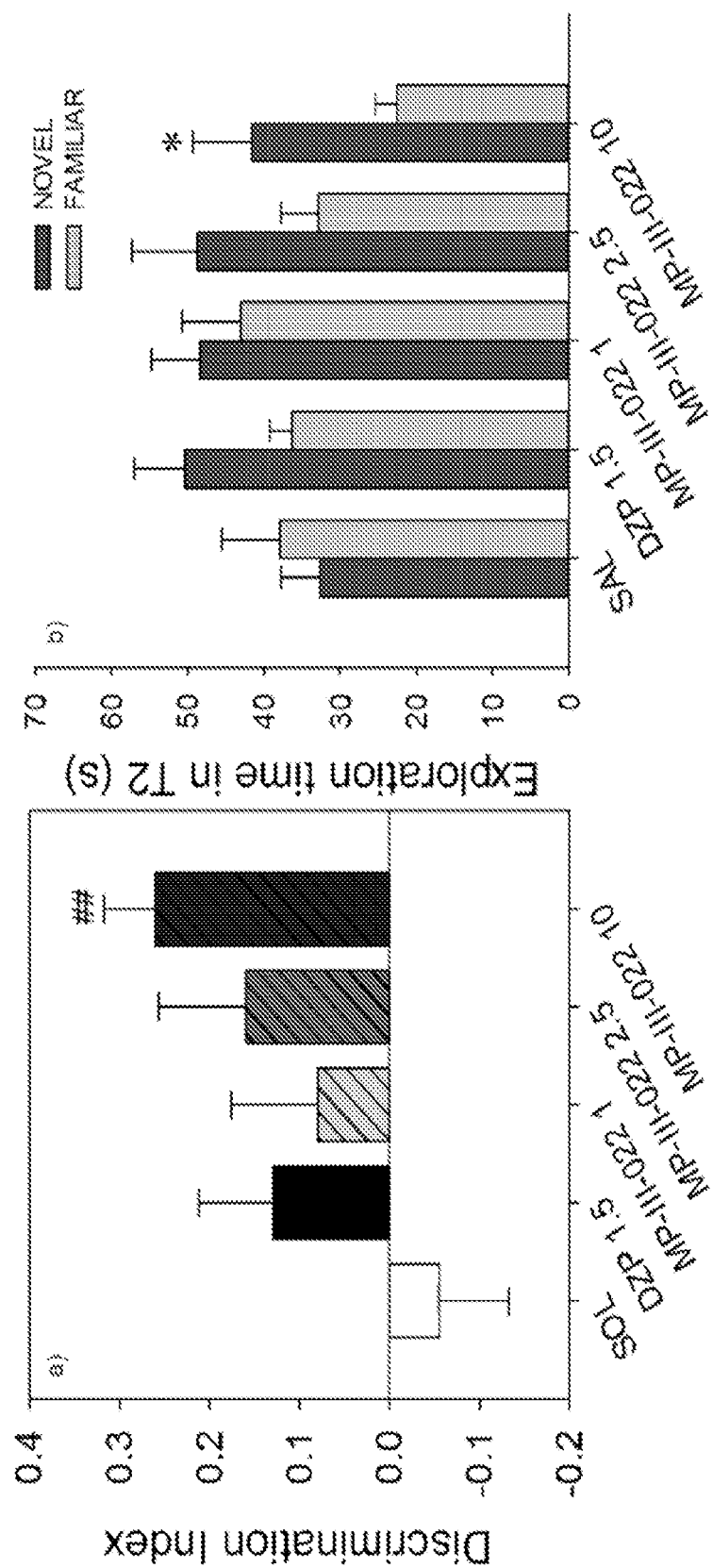

FIG. 13 shows the effects of 1.5 mg/kg diazepam (DZP 1.5) and 1, 2.5 and 10 mg/kg MP-III-022 on discrimination index (a) and the time exploring the familiar and the novel juvenile rat in P2 (b) in social novelty discrimination procedure. A significant difference from zero for discrimination index is indicated with # (one sample t-test, ##$p<0.01$). *$p<0.05$ for the familiar vs. novel exploration times (paired-samples t-test). Data are represented as mean+SEM. Number of animals per treatment group was 8. SOL=solvent, DZP 1.5=1.5 mg/kg diazepam, MP-III-022 1=1 mg/kg MP-III-022, MP-III-022 2.5=2.5 mg/kg MP-III-022, MP-III-022 10=10 mg/kg MP-III-022.

Figure 14:
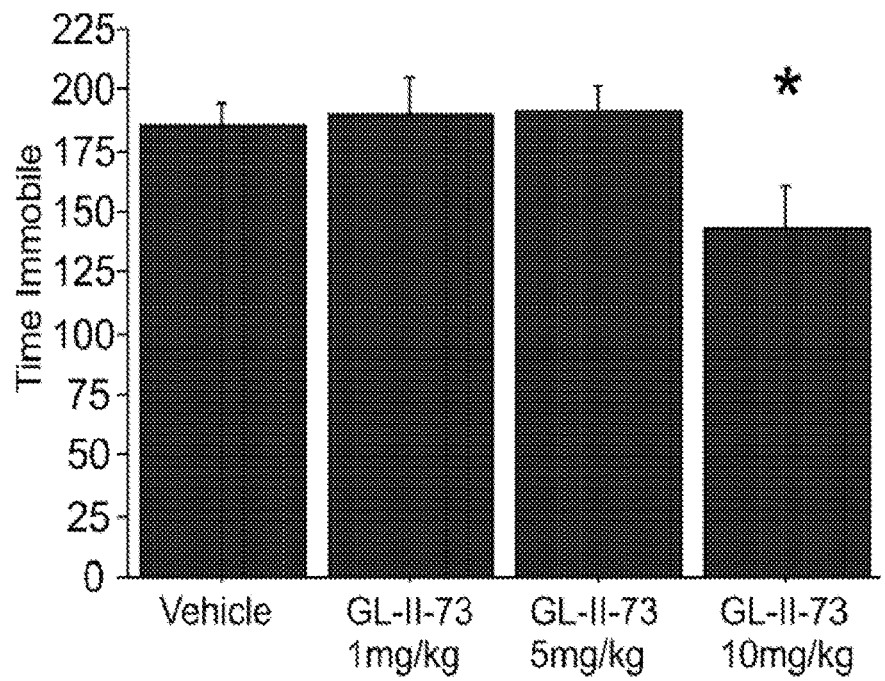

FIG. 14 shows the effects of GL-II-73 on time spent immobile in the FST. Dose response for GL-II-73 at 0, 1, 5 or 10 mg/kg administered i.p. (24, 20, 1 hour before testing). Number of animals tested (n), n=16, 8, 6 and 15/group respectively. ANOVA and post hoc analysis revealed a significant antidepressant-like efficacy at 10 mg/kg as compared to the vehicle group. *$p<0.05$ when compared to vehicle group.

Figure 15:
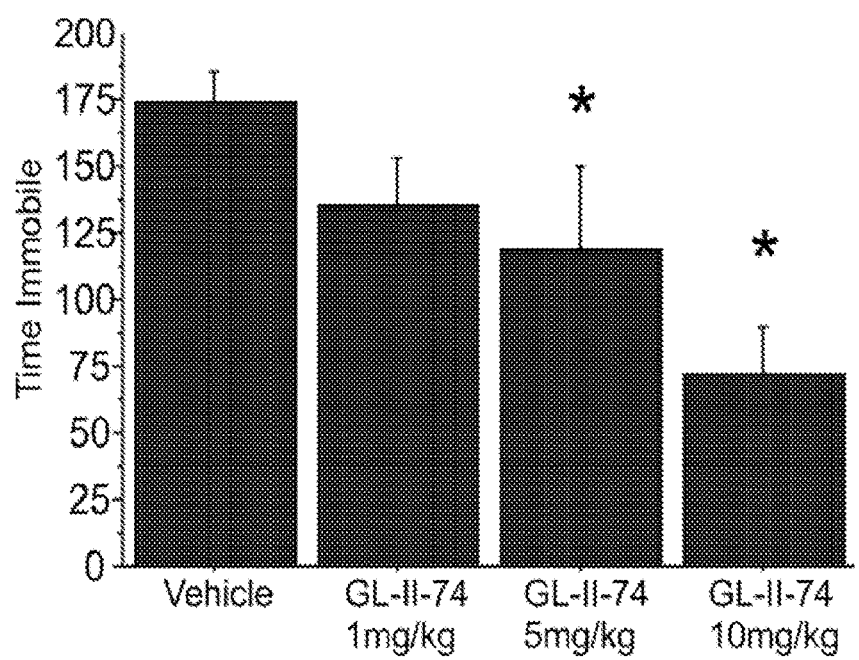

FIG. 15 shows the effects of GL-II-74 on time spent immobile in the FST. Dose response for GL-II-74 at 0, 1, 5 or 10 mg/kg administered i.p. (24, 20, 1 hour before testing). Number of animals tested (n), n=16, 8, 8 and 15/group respectively. ANOVA and post hoc analysis revealed a significant antidepressant-like efficacy at 5 and 10 mg/kg as compared to the vehicle group. *$p<0.05$ when compared to vehicle group.

Figure 16:
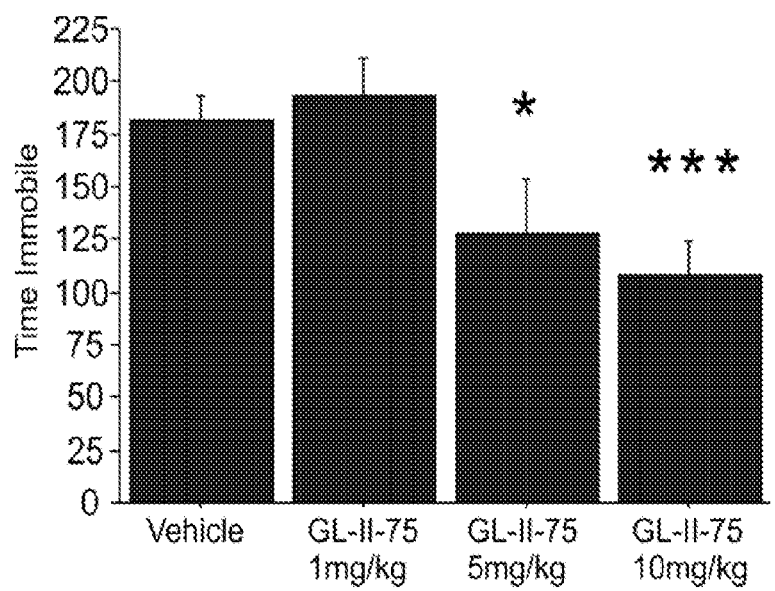

FIG. 16 shows the effects of GL-II-75 on time spent immobile in the FST. Dose response for GL-II-75 at 0, 1, 5 or 10 mg/kg administered i.p. (24, 20, 1 hour before testing). Number of animals tested (n), n=16, 8, 8 and 16/group respectively ANOVA and post hoc analysis revealed a significant antidepressant-like efficacy at 5 and 10 mg/kg as compared to the vehicle group. *$p<0.05$ and ***$p<0.001$ when compared to vehicle group.

Figure 17:
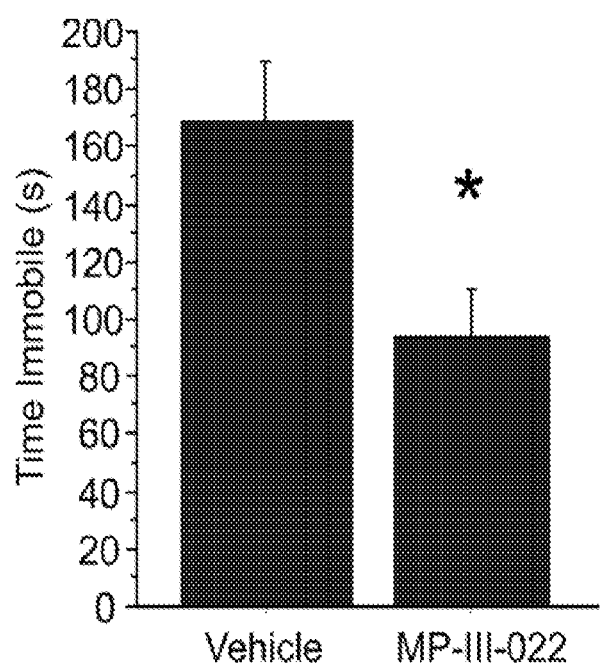

FIG. 17 shows the effects of MP-III-022 on time spent immobile in the FST. MP-III-022 10 mg/kg administered i.p. (24, 20, 1 hour before testing) induced a significant antidepressant-like action when compared to the vehicle group. *$p<0.05$ when compared to vehicle group. Number of animals tested (n), n=8/group.

Figure 18:
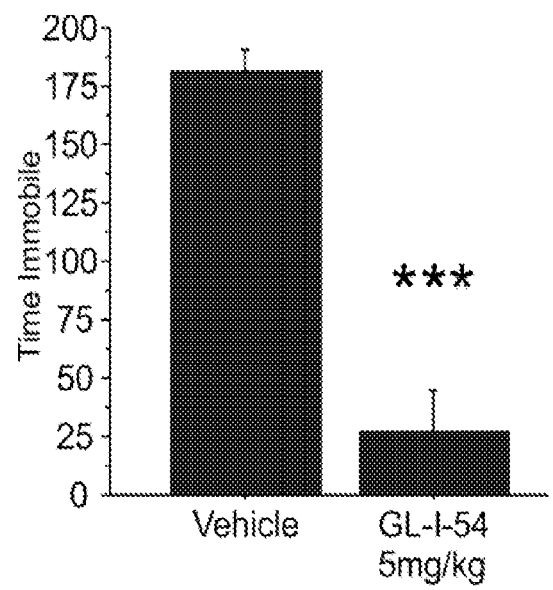

FIG. 18 shows the effects of GL-I-54 on time spent immobile in the FST. GL-I-54 at 5 mg/kg administered i.p. (24, 20, 1 hour before testing) induced a significant antidepressant-like action when compared to the vehicle group. ***$p<0.001$ when compared to vehicle group. Number of animals tested (n), n=10 and 9/group respectively.

Figure 19:
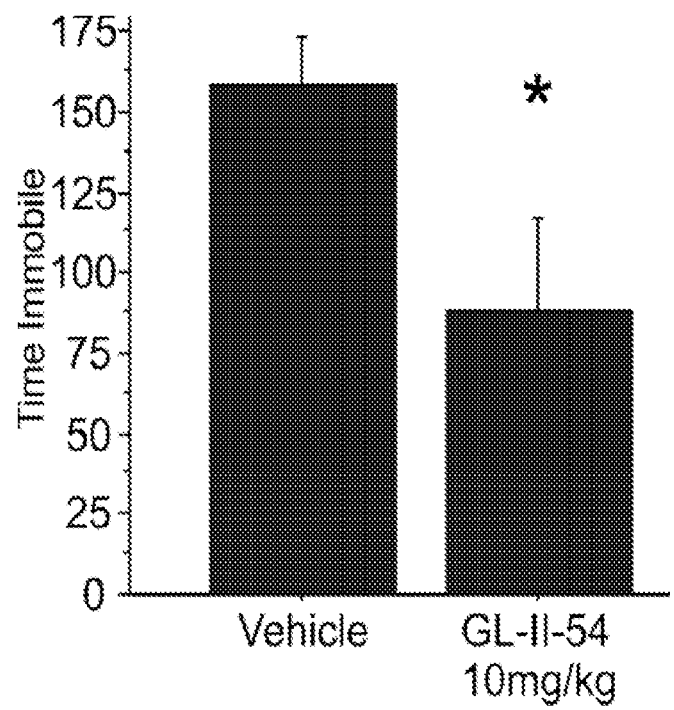

FIG. 19 shows the effects of GL-II-54 on time spent immobile in the FST. GL-II-54 at 10 mg/kg administered i.p. (24, 20, 1 hour before testing) induced a significant antidepressant-like action when compared to the vehicle group. *$p<0.05$ when compared to vehicle group. Number of animals tested (n), n=10 and 9/group respectively.

Figure 20:
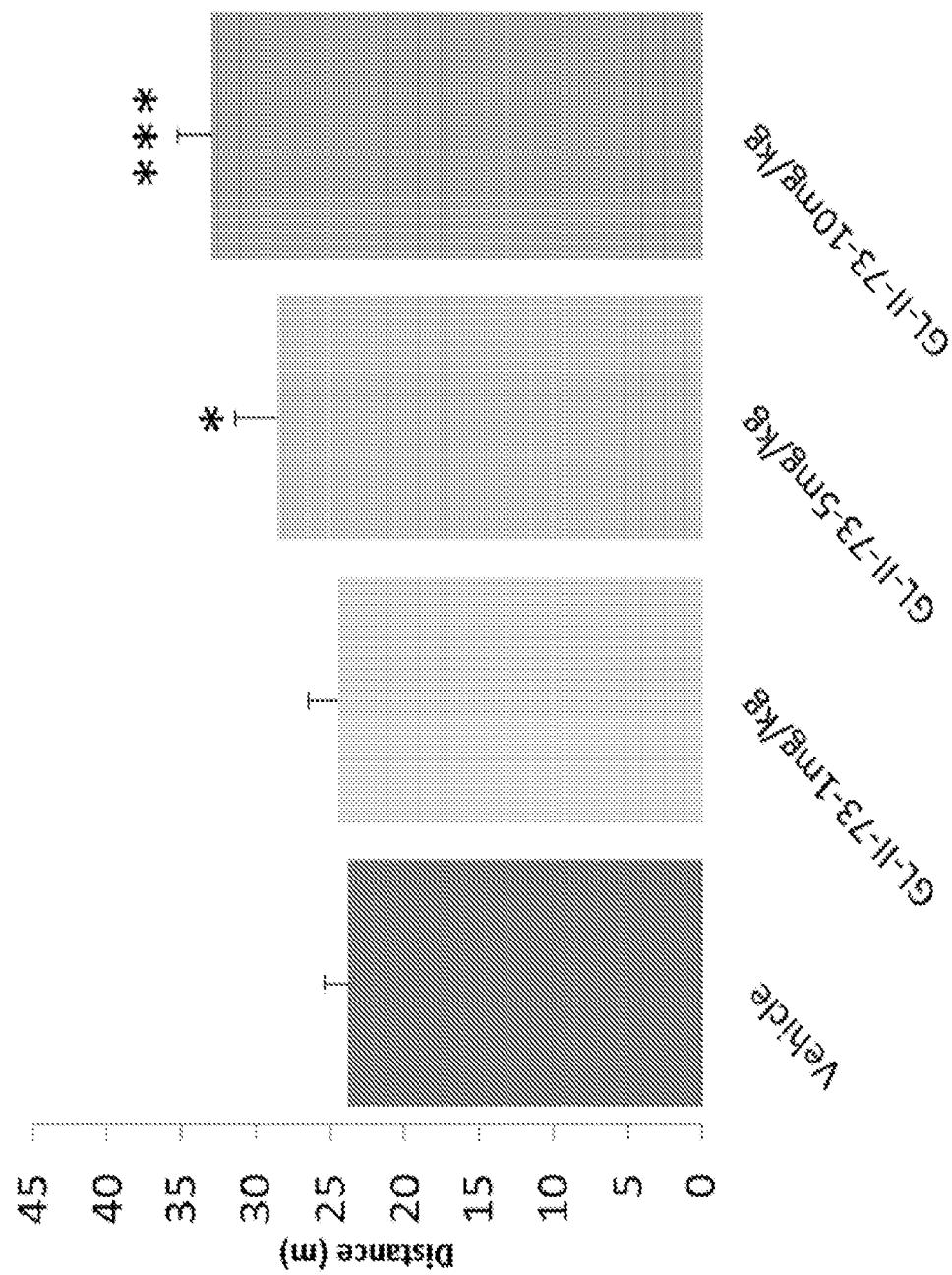

FIG. 20 shows the effects of GL-II-73 on locomotor activity. Data are expressed in meter of distance travelled (30 min session). The animals were injected i.p. 60 minutes before testing. Number of animals tested (n), n=16,8,8,6/group respectively. ANOVA revealed statistical significance on the overall effect of treatment. Post hoc analysis showed GL-II-73 has no effect on locomotor activity at 1 mg/kg, but induced a significant increase in distance traveled at 5 and 10 mg/kg. Differences between groups were tested using the PLSD post-hoc test (*$p<0.05$ and ***$p<0.001$ compared to the "Vehicle" group).

Figure 21:
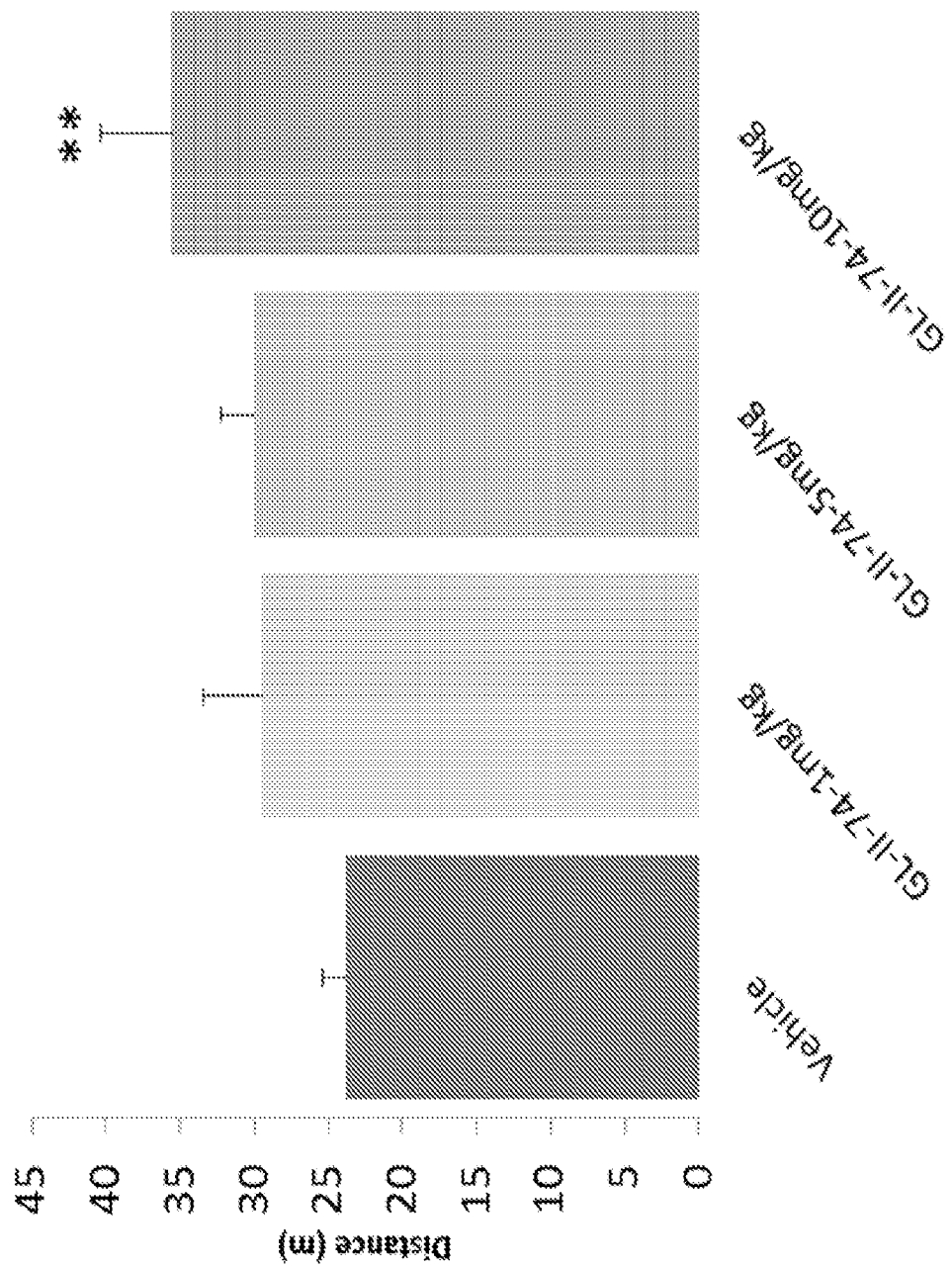

FIG. 21 shows the effects of GL-II-74 on locomotor activity. Data are expressed in meter of distance travelled (30 min session). The animals were injected i.p. 60 minutes before testing. Number of animals tested (n), n=16,8,8,6/group respectively. ANOVA revealed statistical significance on the overall effect of treatment. Post hoc analysis showed GL-II-74 has no effect on locomotor activity at 1 or 5 mg/kg, but induced a significant increase in distance traveled at 10 mg/kg. Differences between groups were tested using the PLSD post-hoc test (**$p<0.01$ compared to the "Vehicle" group).

Figure 22:
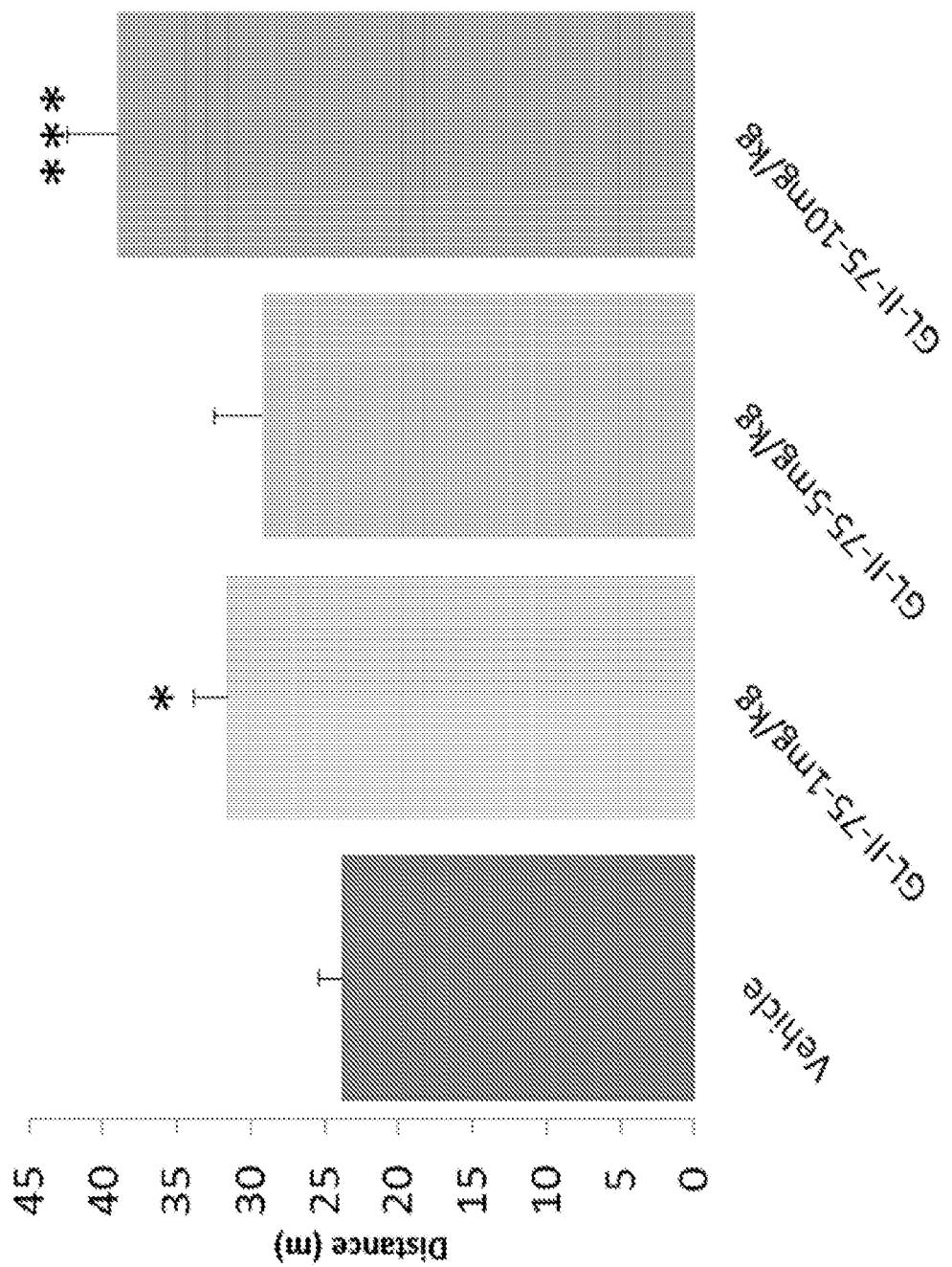

FIG. 22 shows the effects of GL-II-75 on locomotor activity. Data are expressed in meter of distance travelled (30 min session). The animals were injected i.p. 60 minutes before testing. Number of animals tested (n), n=16,8,8,8/group respectively. ANOVA revealed statistical significance on the overall effect of treatment. Post hoc analysis showed GL-II-75 has no effect on locomotor activity at 5 mg/kg, but induced a significant increase in distance traveled at 1 and 10 mg/kg. Differences between groups were tested using the PLSD post-hoc test (*$p<0.05$ and ***$p<0.001$ compared to the "Vehicle" group).

Figure 23:
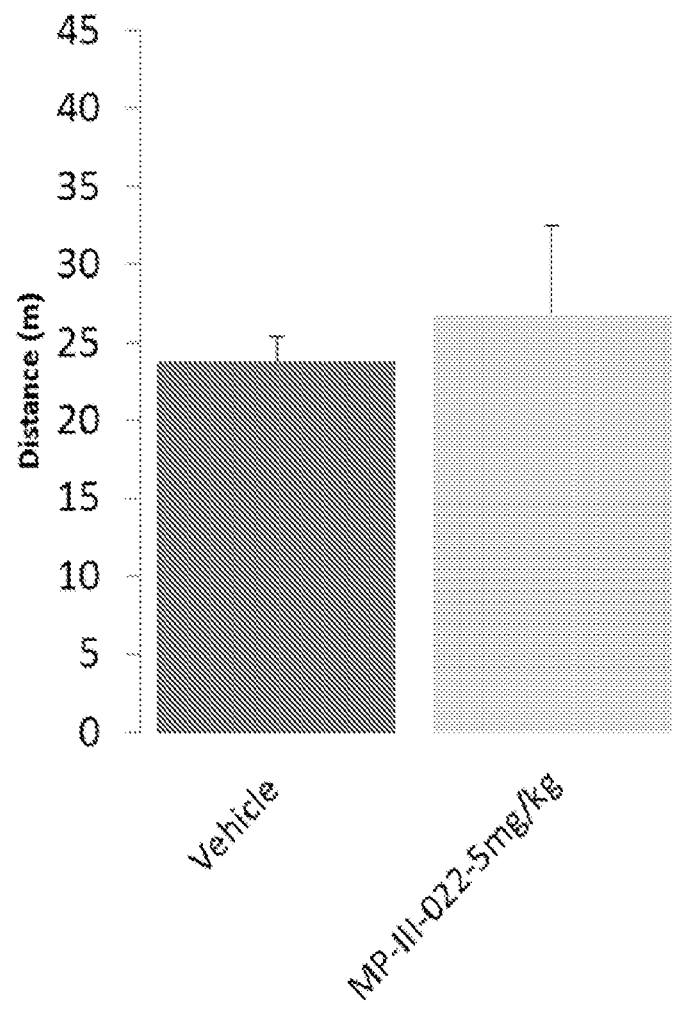

FIG. 23 shows the effects of MP-III-022 on locomotor activity. Data are expressed in meter of distance travelled (30 min session). The animals were injected i.p. 60 minutes before testing. Number of animals tested (n), n=16 and 8/group respectively. Statistical analysis revealed no effect of MP-III-022 on locomotor activity.

Figure 24A:
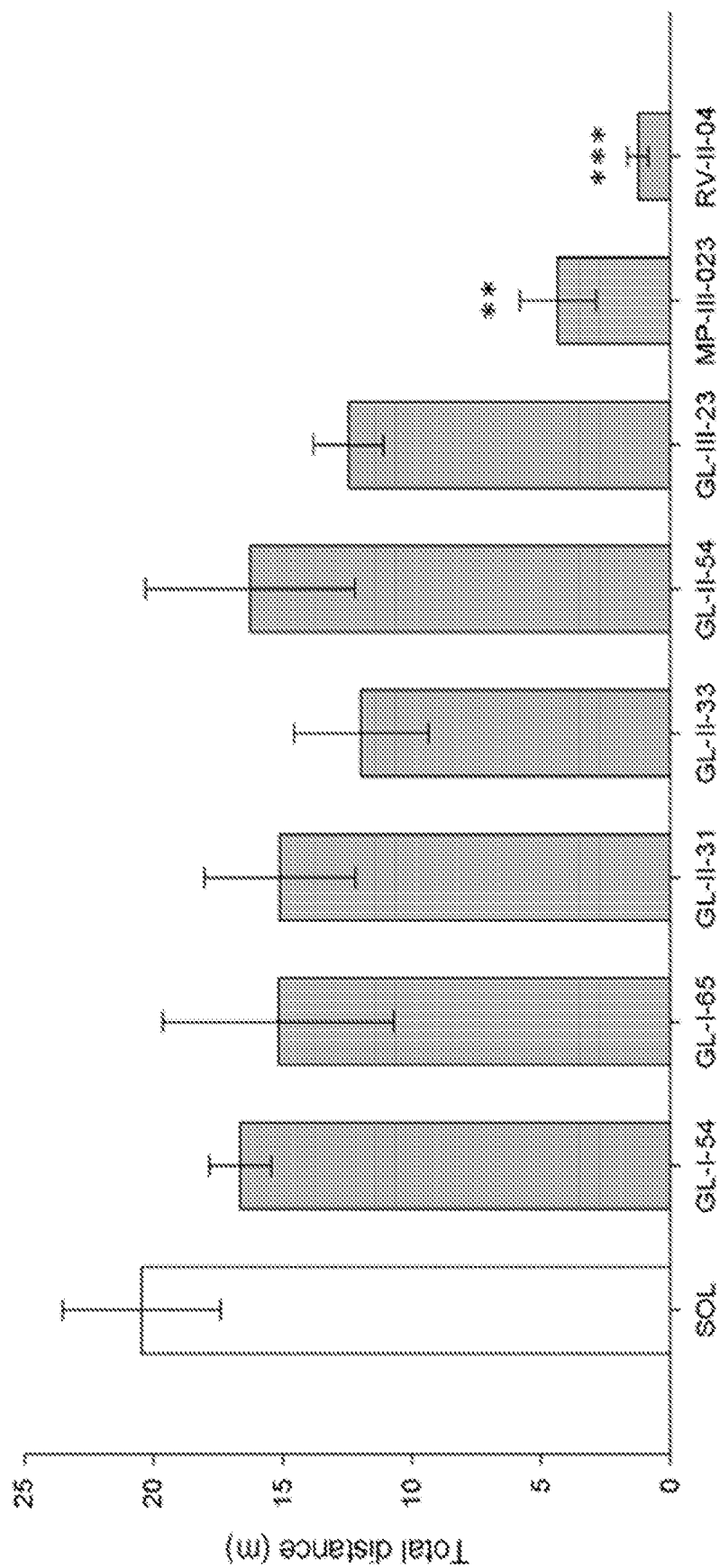

FIG. 24 shows (a) the effects of GL-I-54, GL-I-65, GL-II-31, GL-II-33, GL-II-54, GL-III-23, MP-III-023, and RV-II-04, all dosed i.p. at 10 mg/kg, on spontaneous locomotor activity during 60 min of recording in rats. All data are presented as the mean±S.E.M. Number of animals per treatment group were 5, with exception of GL-II-33, GL-II-54, GL-III-23 and SOL (n=6). $P<0.01$ and *$P<0.001$ versus SOL group. Other differences were not presented; in general, the animals treated with RV-II-04 were sedated when compared to all other groups, with exception of MP-III-023. (b) The graph represents the data split by 5 minute intervals.

Figure 25:
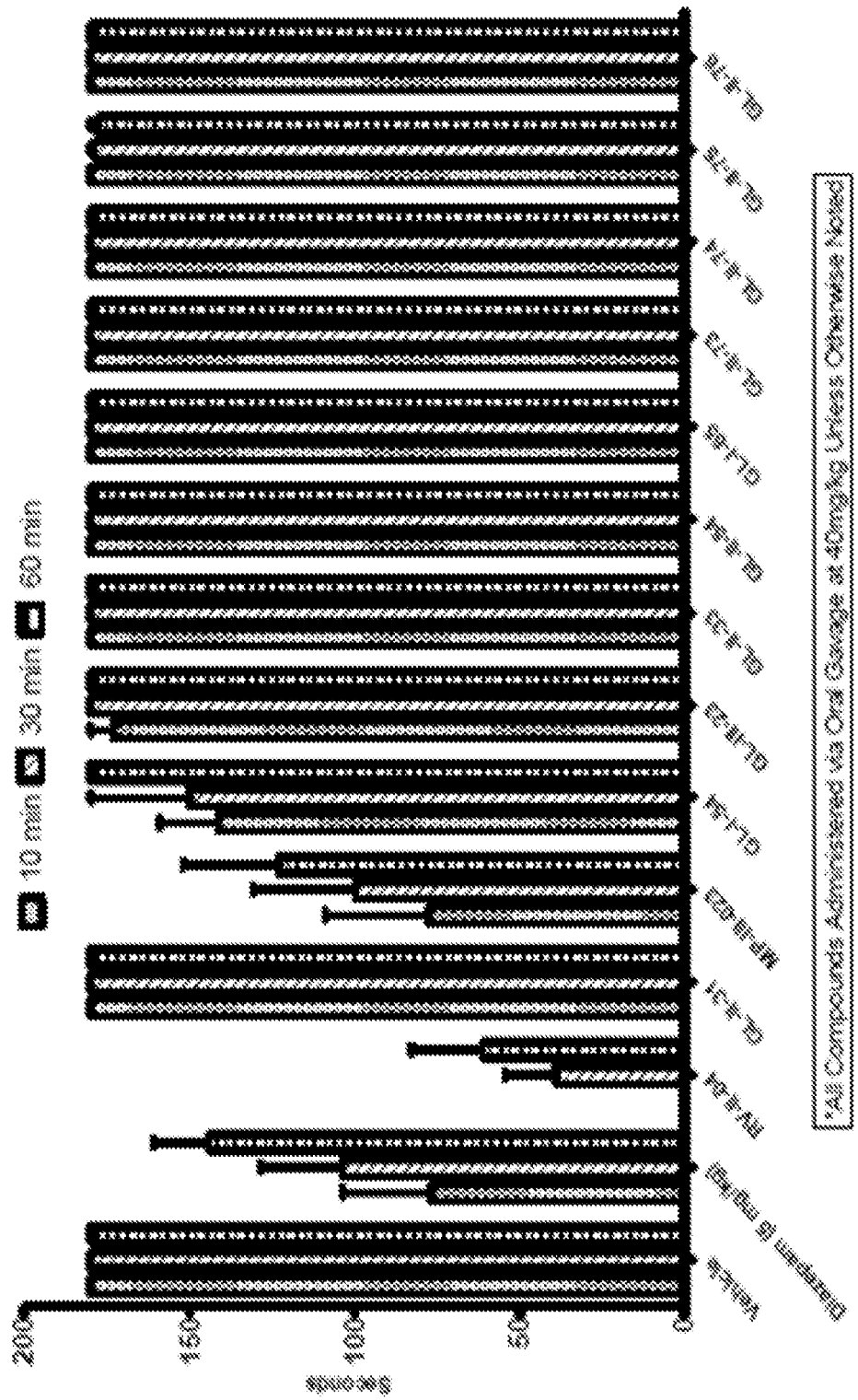

FIG. 25 shows the effects of compounds on sensorimotor coordination. Female Swiss Webster mice were tested on a rotarod at 15 rpm for 3 min at 10, 30, and 60 min following compound exposure. Mice (N=10) received a single oral injection via oral gavage of test compound (40 mg/kg), diazepam (5 mg/kg), or vehicle. The time of fall was recorded if it occurred prior to 3 min. Data are expressed as mean±SEM (N=10). $p<0.01$ or *$p<0.001$ significance compared to vehicle-treated mice. All compounds presented herein were able to be dissolved in the oral vehicle.

Figure 26:
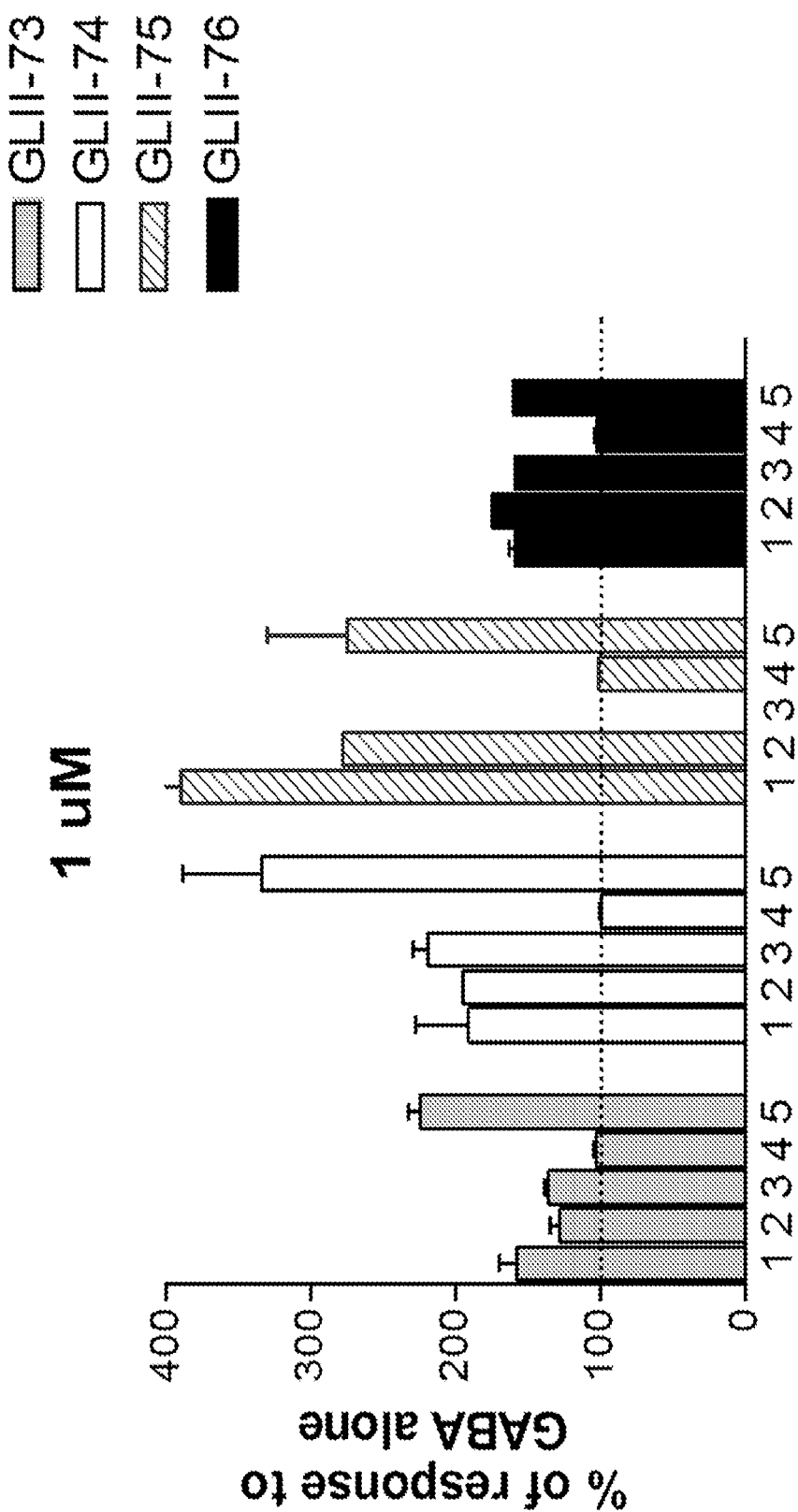

FIG. 26 shows the percent response to GABA in presence of GL-II-73,74,75,76 in human embryonic kidney cell line HEK-293T transfected with plasmids expressing alpha1, 2, 3, 4, or 5 GABA receptor subtypes.

FIG. 27 shows the pharmacokinetic parameters in mice and rats for 12 novel αPAMs compounds, with different doses and routes of administration.

Figure 28A:
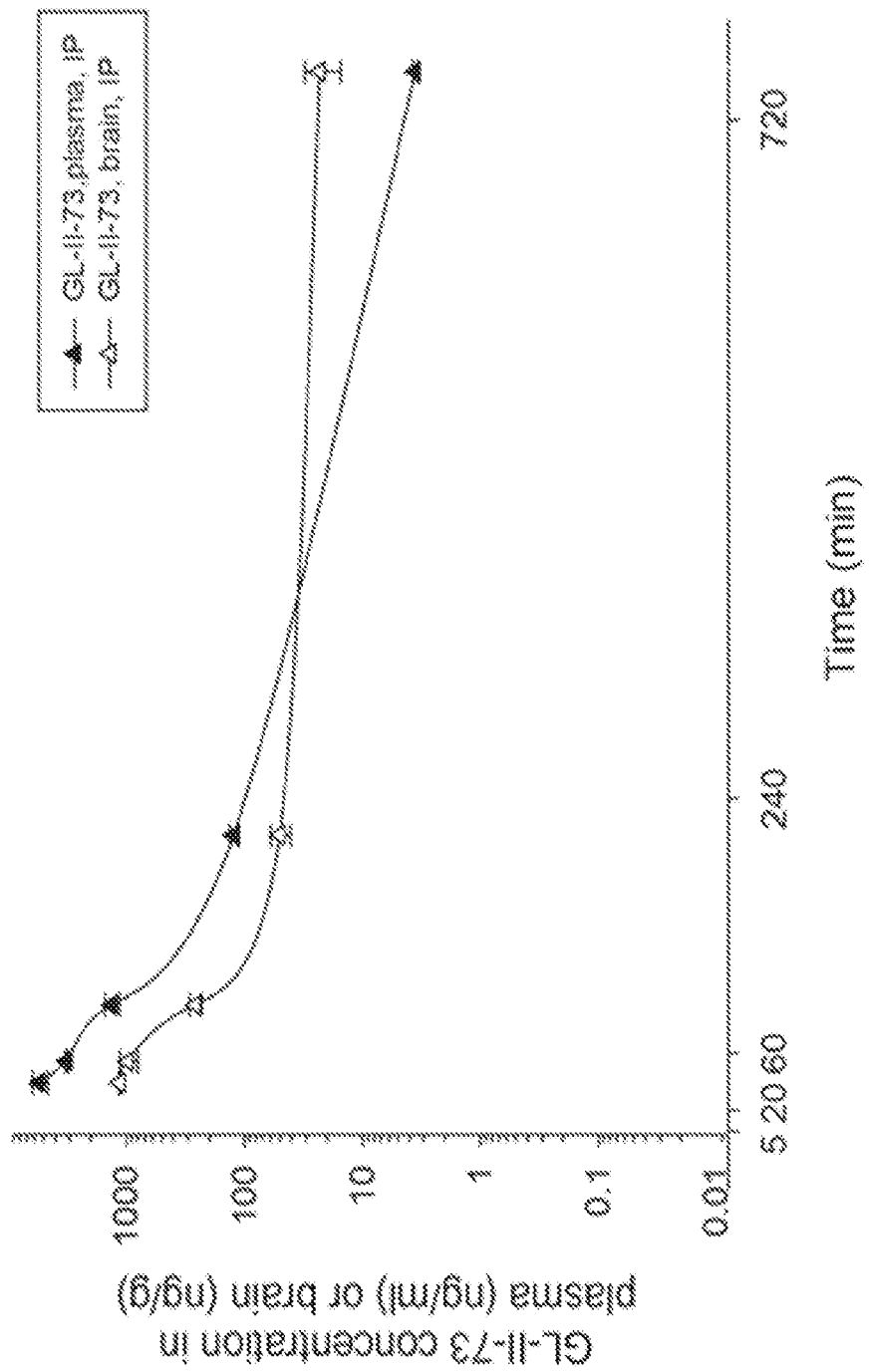
Figure 28B:
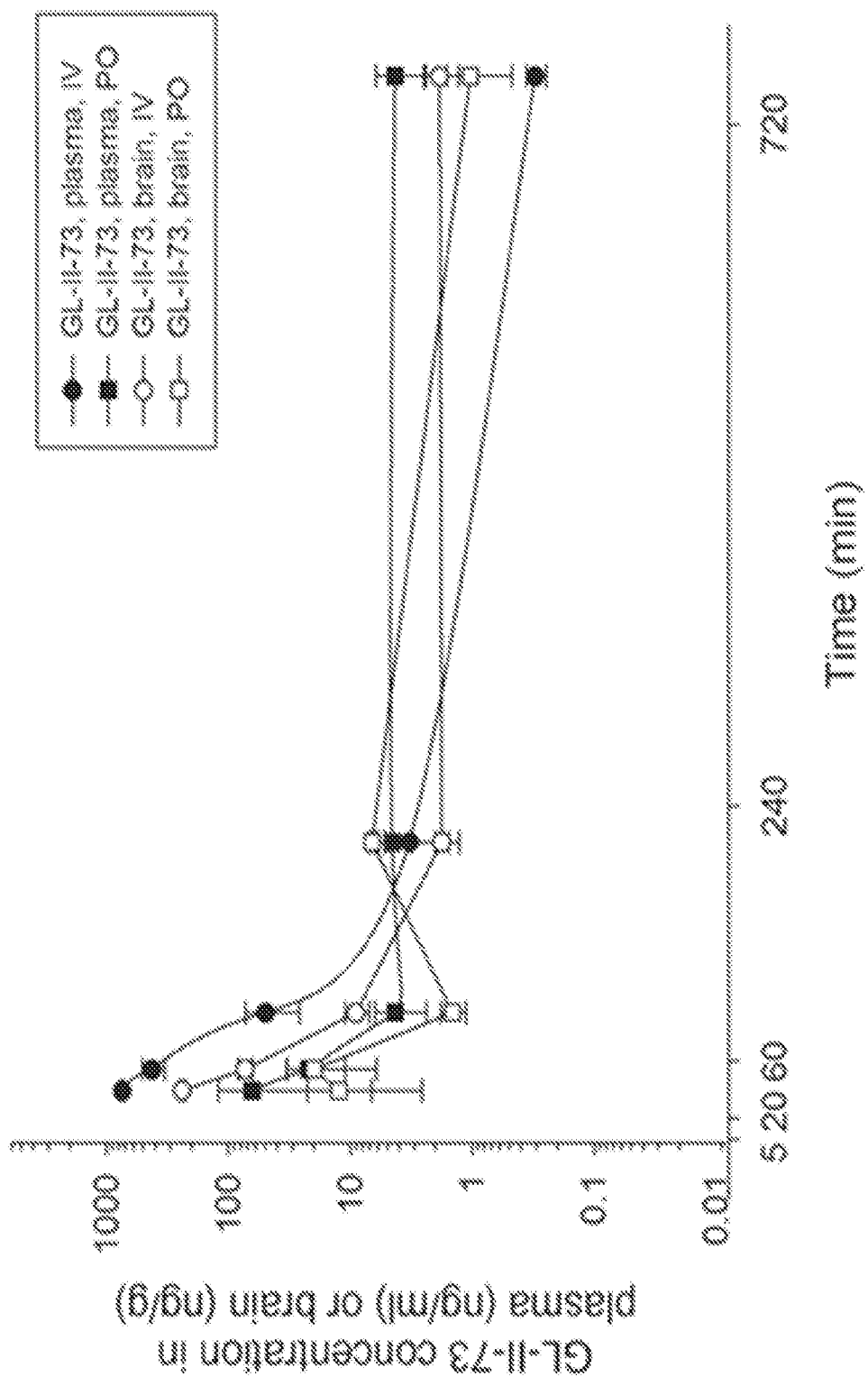

FIG. 28 shows the concentration-time profile of GL-II-73 after intraperitoneal (IP) administration of the 10 mg/kg dose in mouse plasma and brain (a) and after intravenous (IV) and peroral (PO) administration of the 3 mg/kg dose in rat plasma and brain (b). n=3 per time point.

Figure 29A:
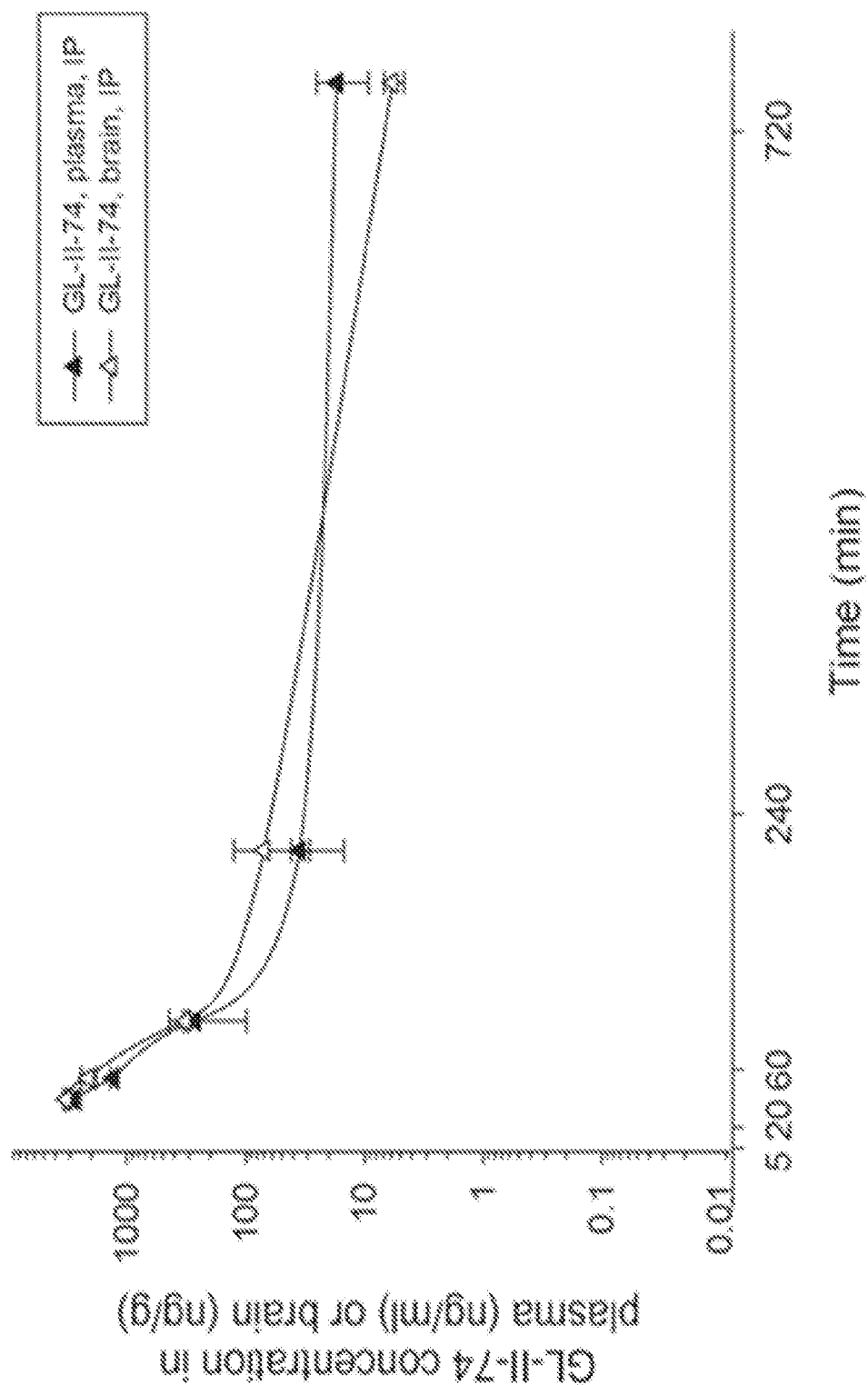
Figure 29B:
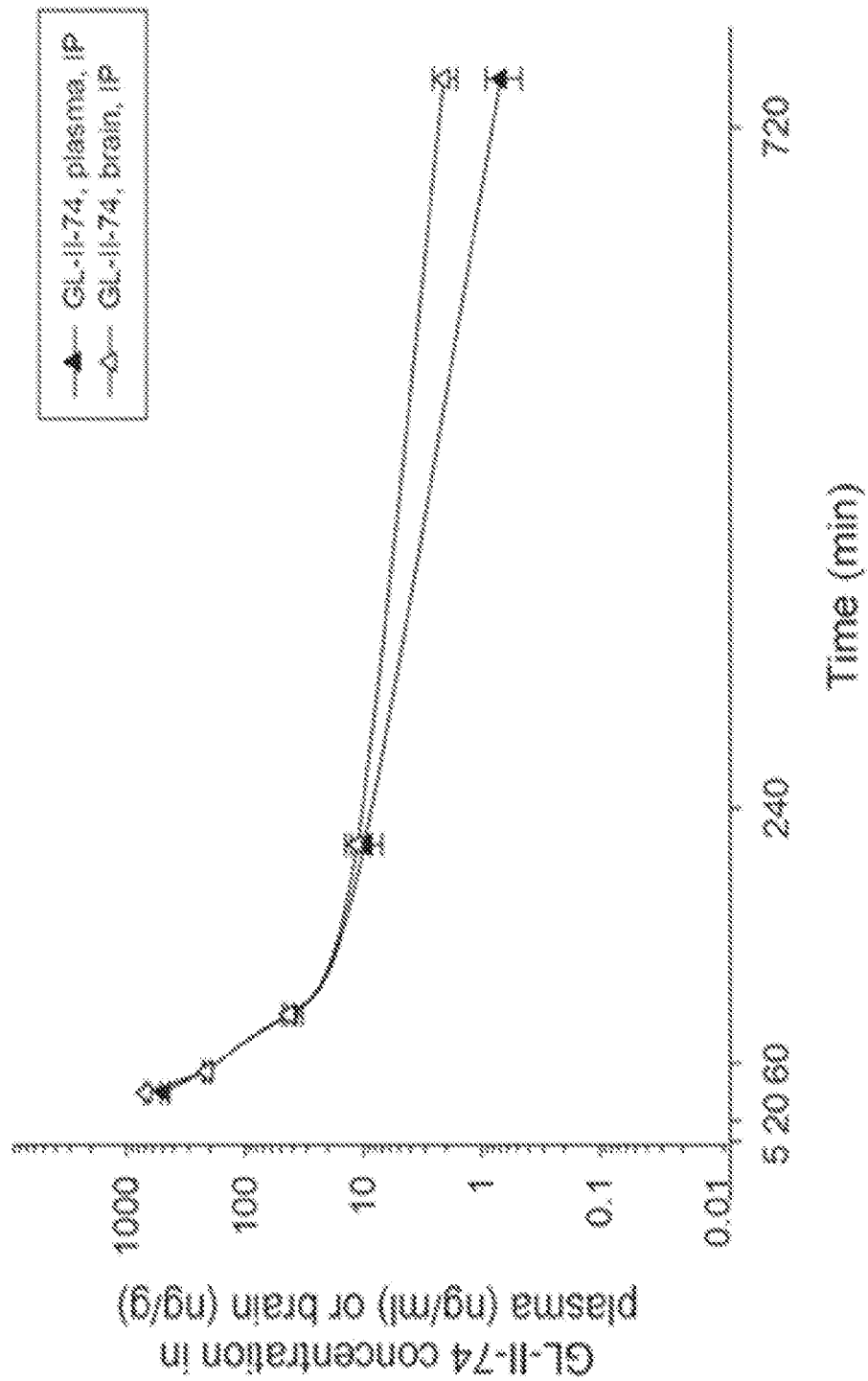

FIG. 29 shows the concentration-time profile of GL-II-74 after intraperitoneal (IP) administration of the 10 mg/kg dose in mouse plasma and brain (a) and after intravenous (IV) administration of the 3 mg/kg dose in rat plasma and brain (b). n=3 per time point.

Figure 30:
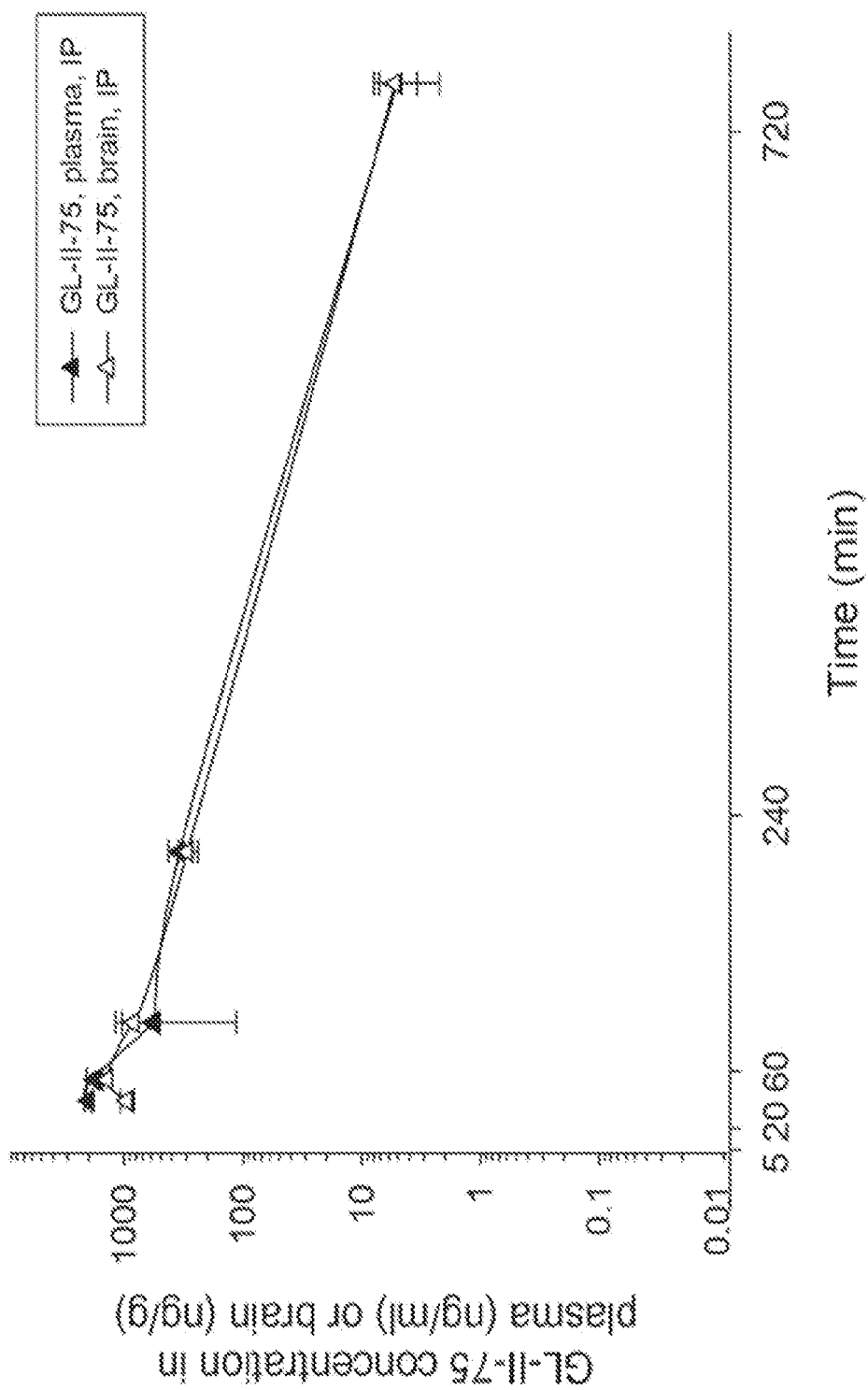
Figure 31A:
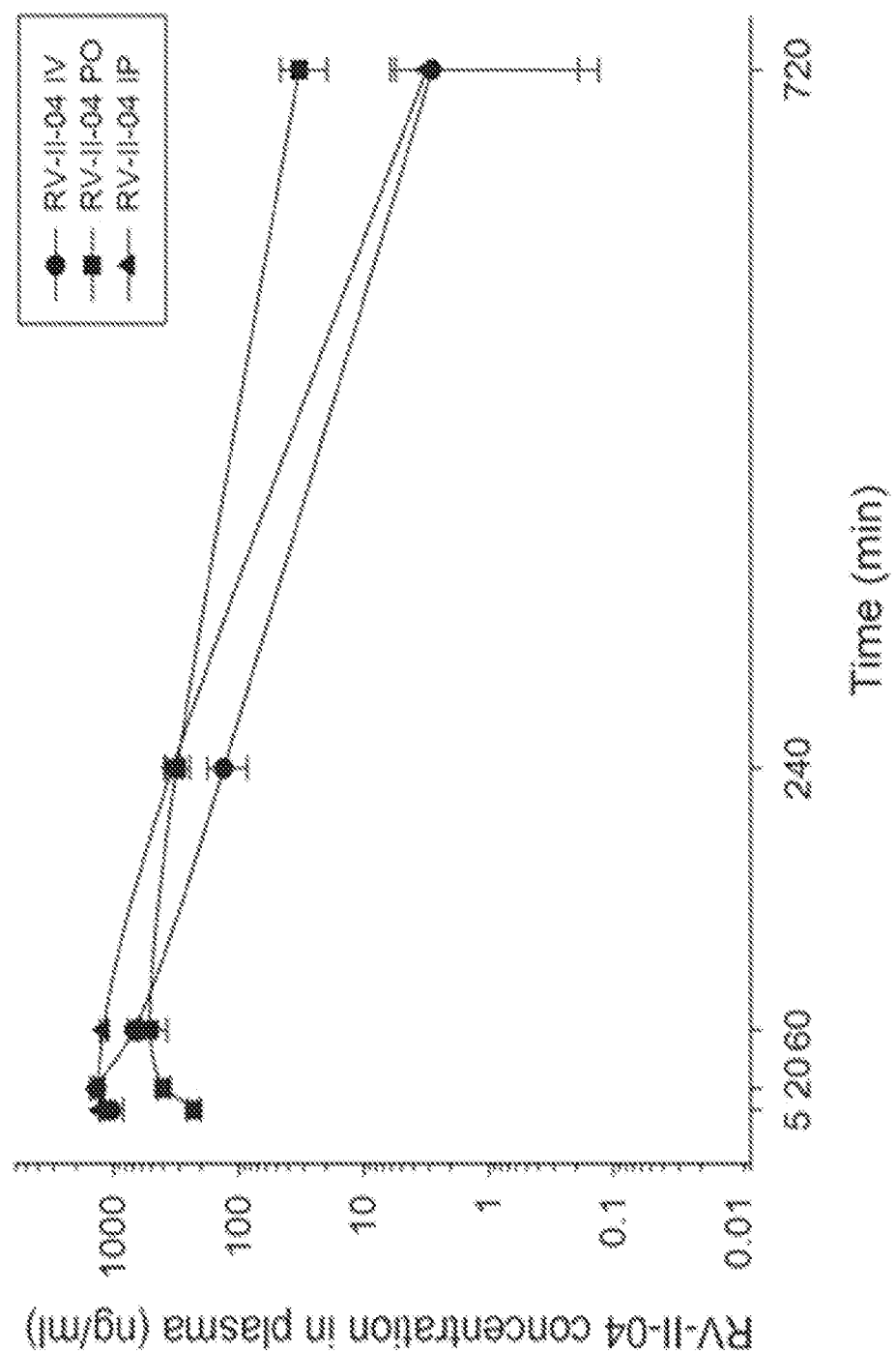
Figure 31B:
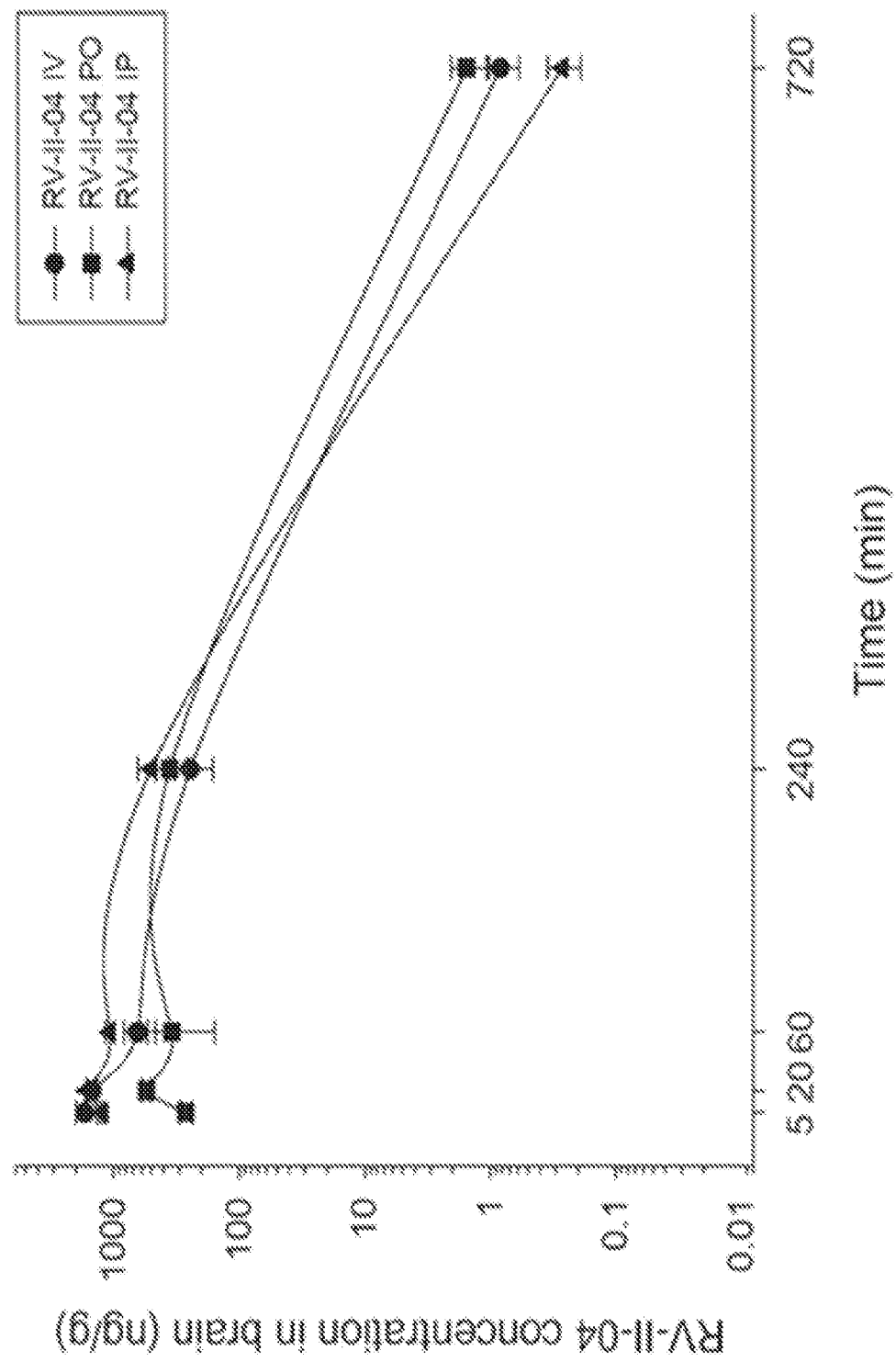
Figure 31C:
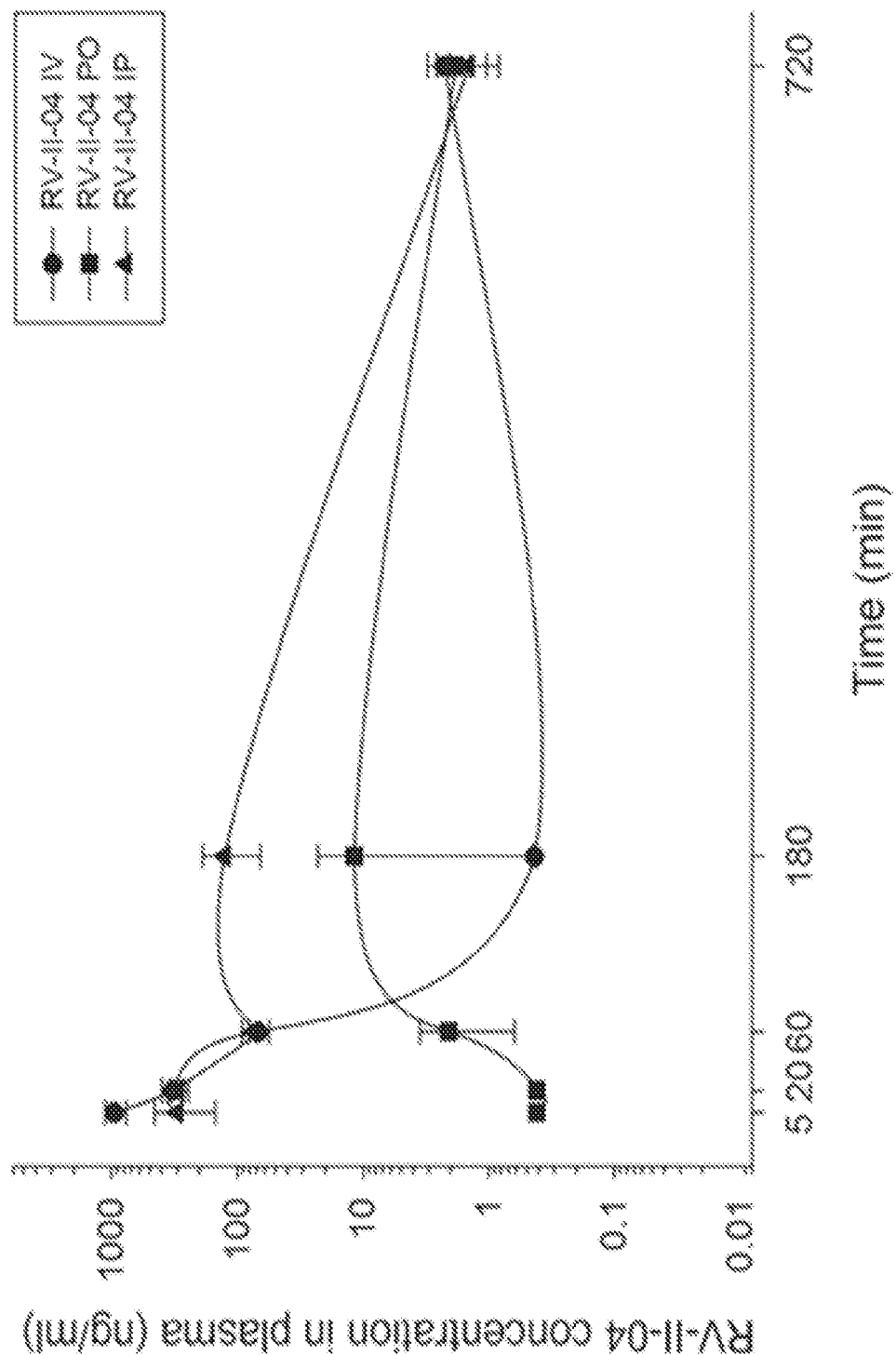
Figure 31D:
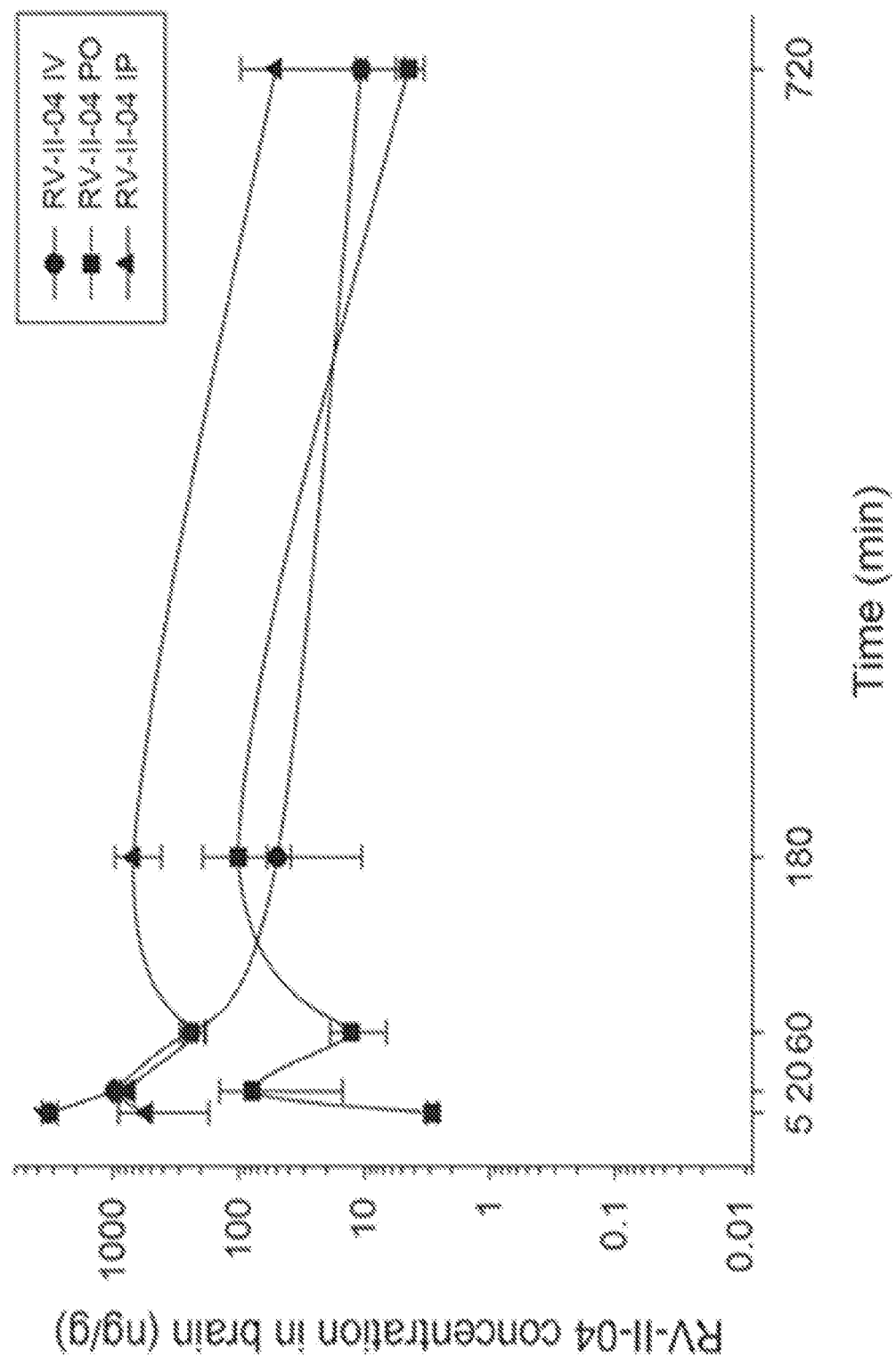
Figure 32A:
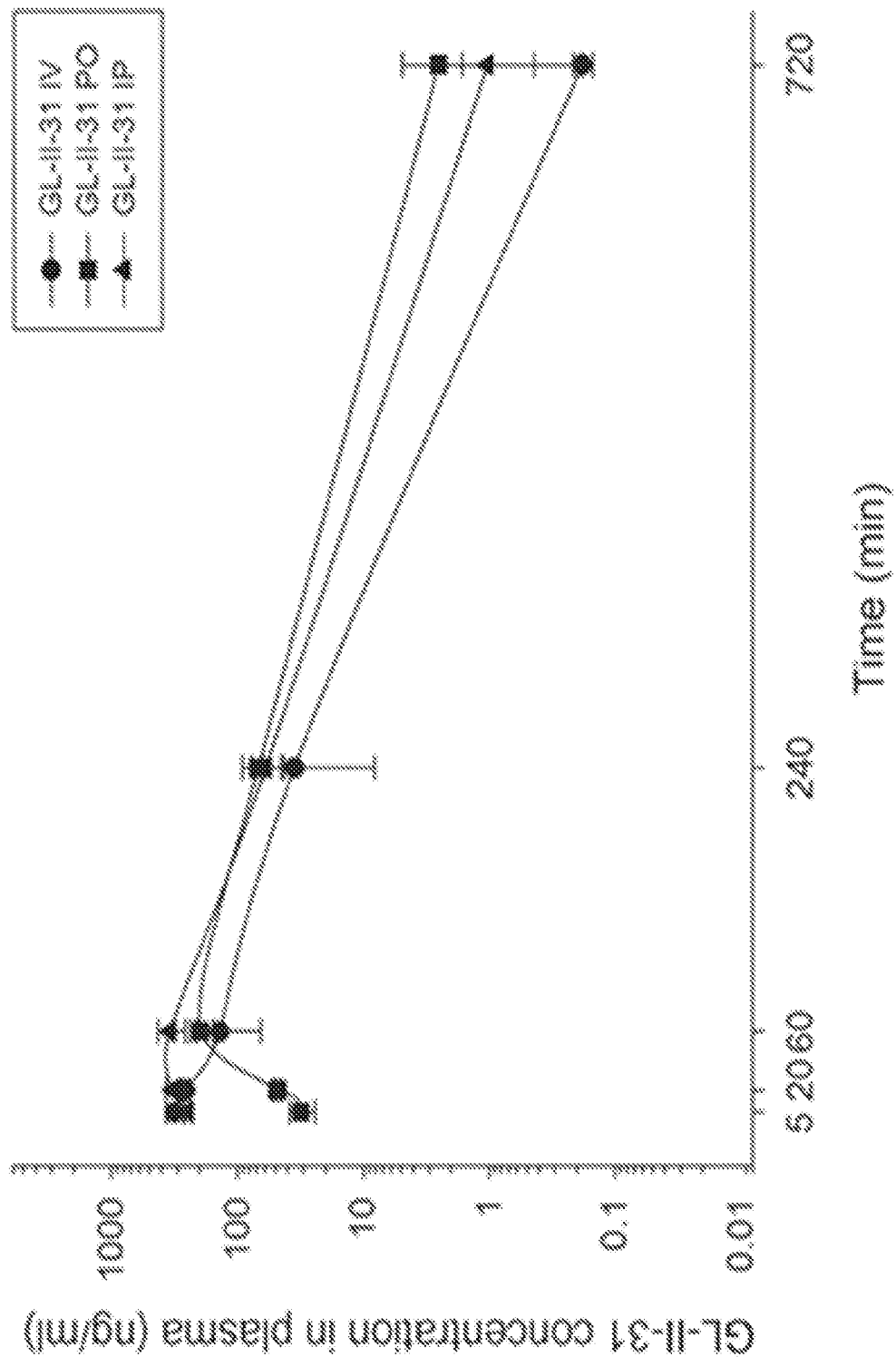
Figure 32B:
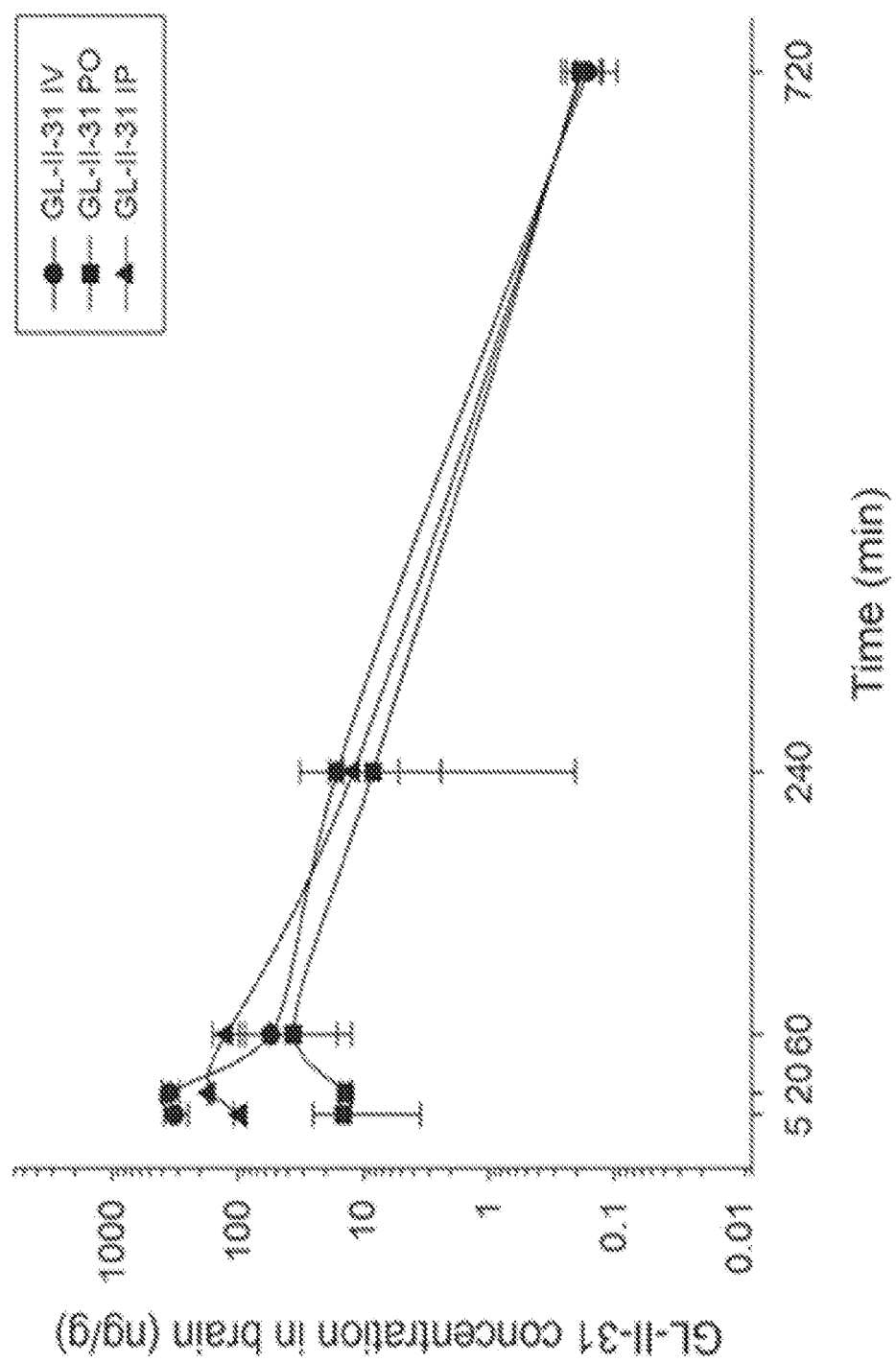
Figure 32C:
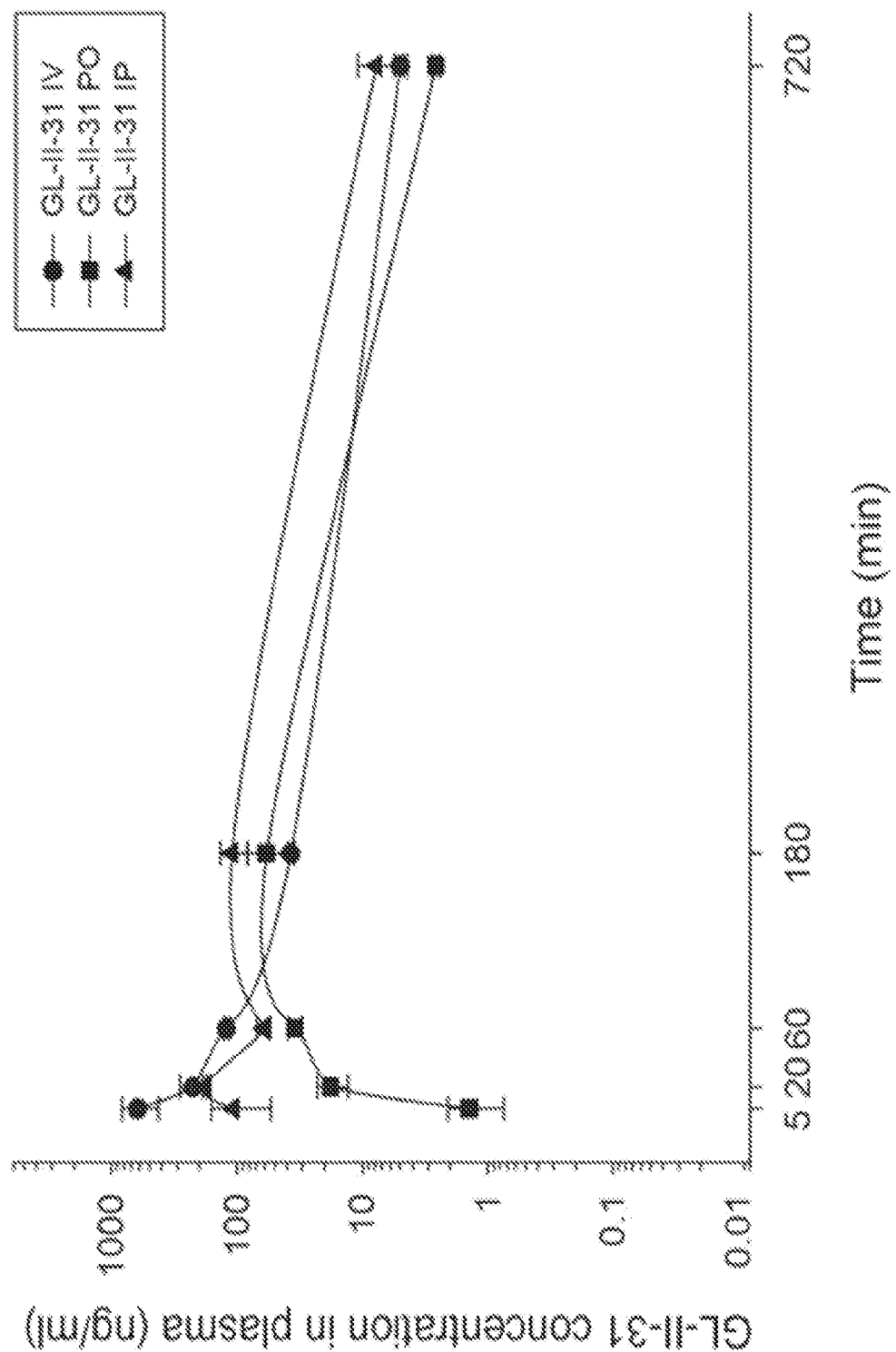
Figure 32D:
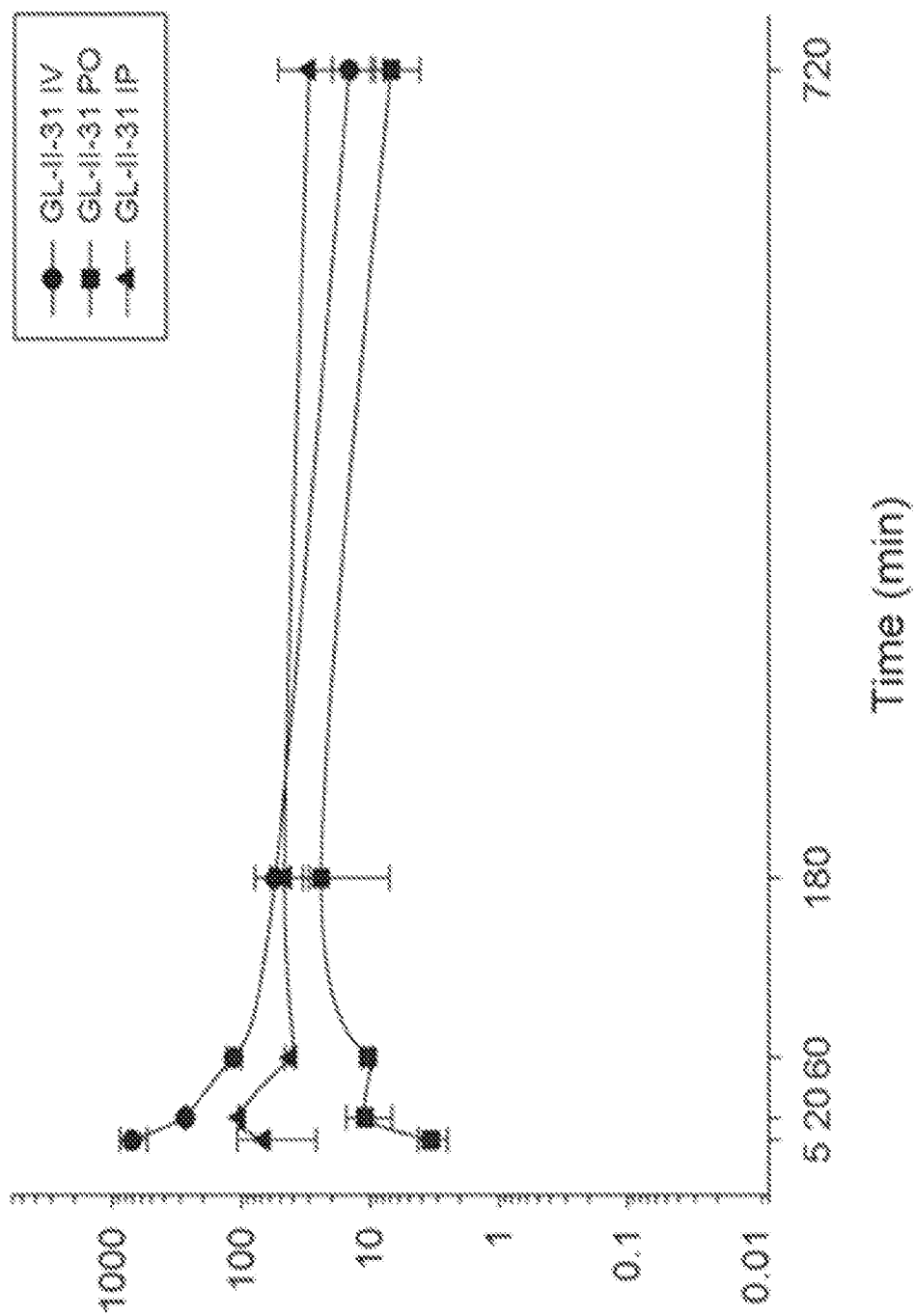
Figure 33A:
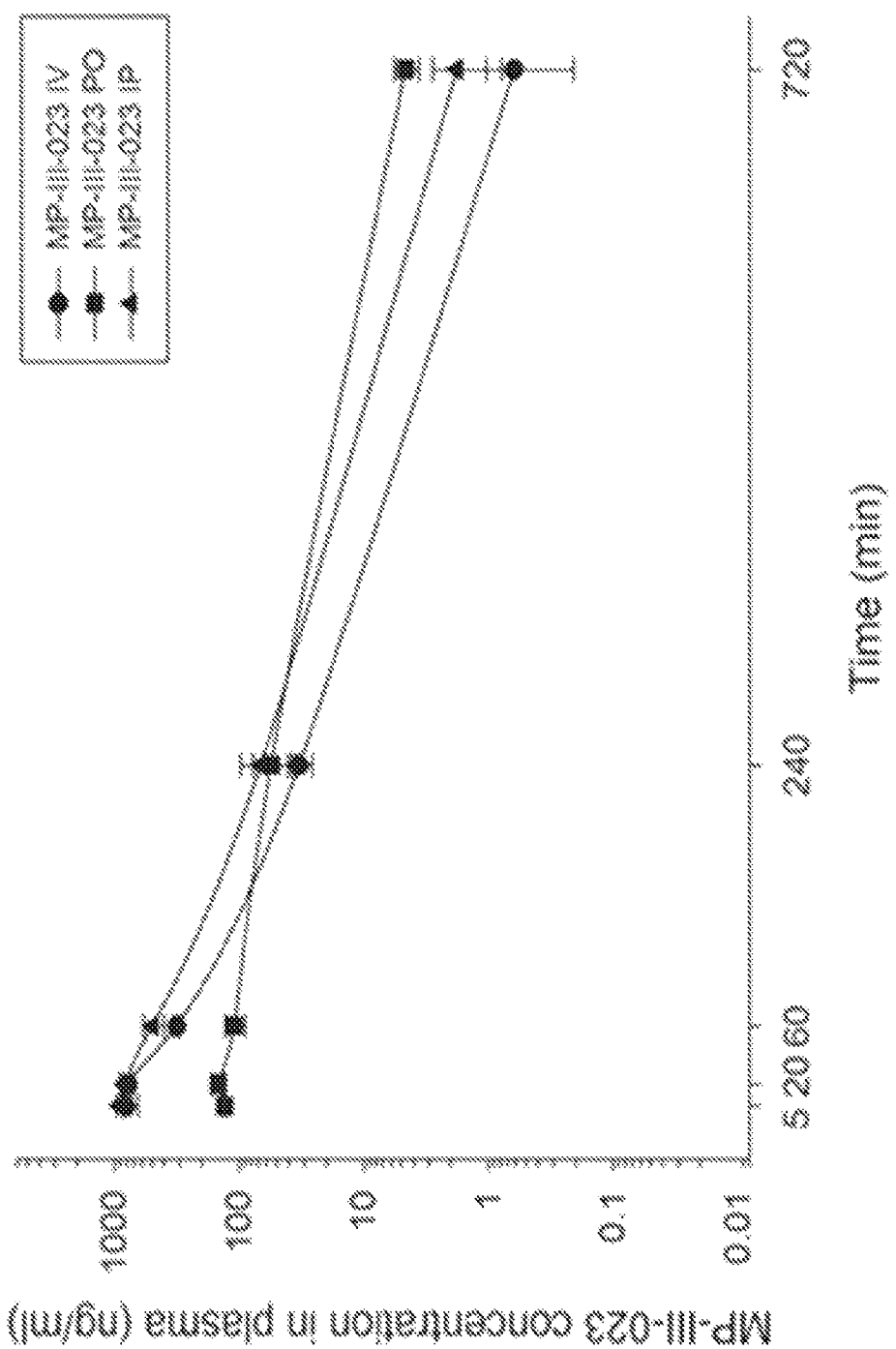
Figure 33B:
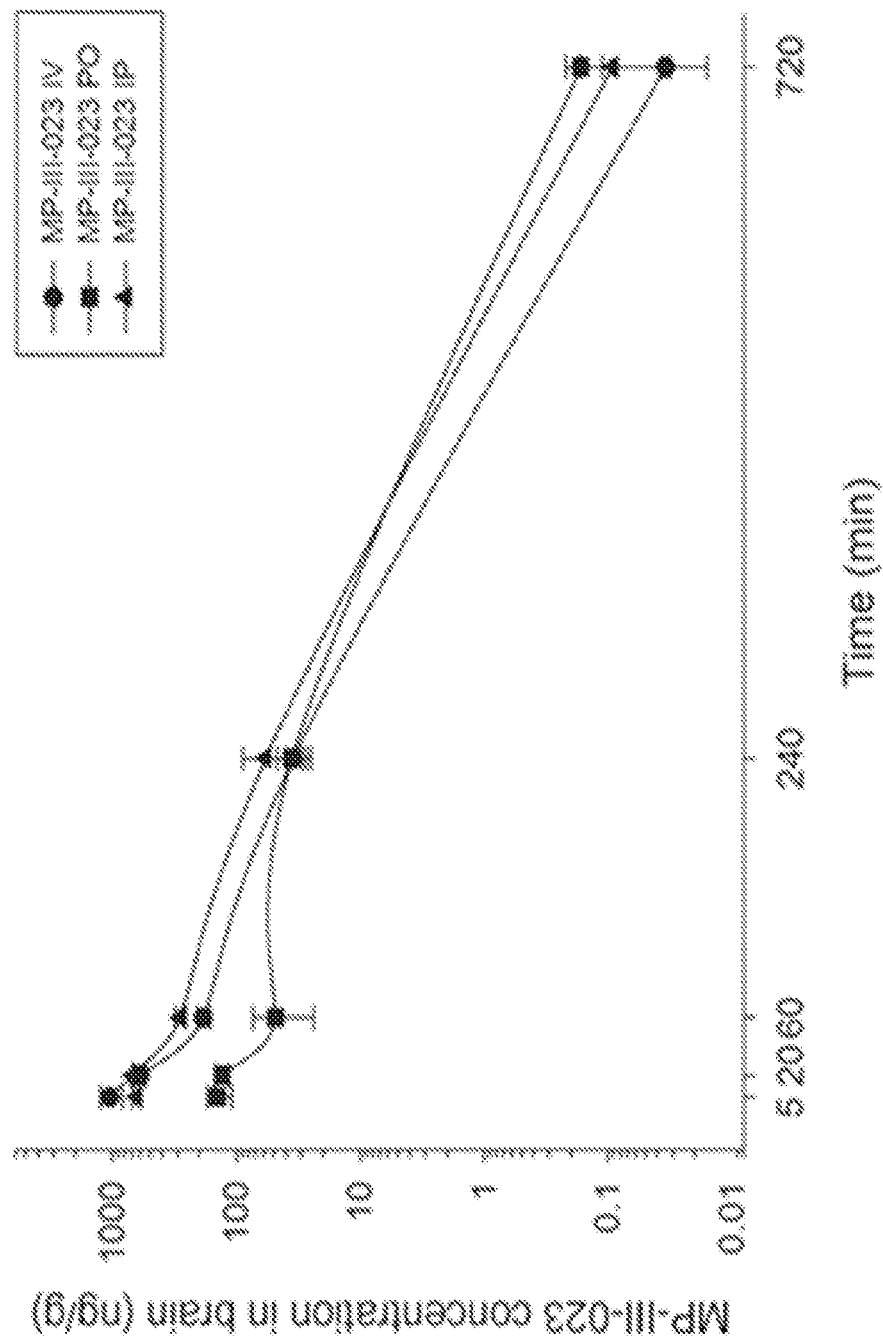
Figure 33C:
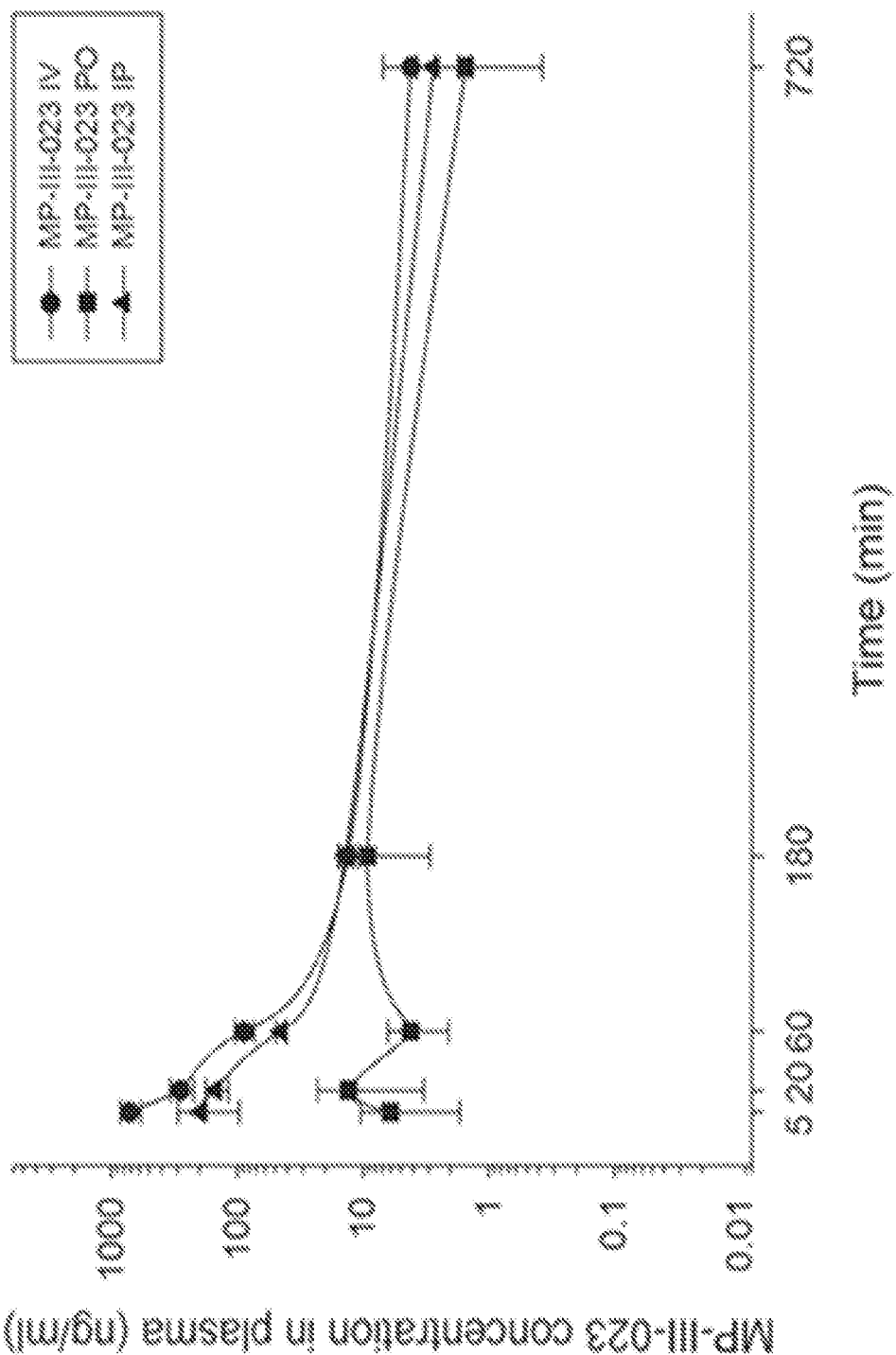
Figure 33D:
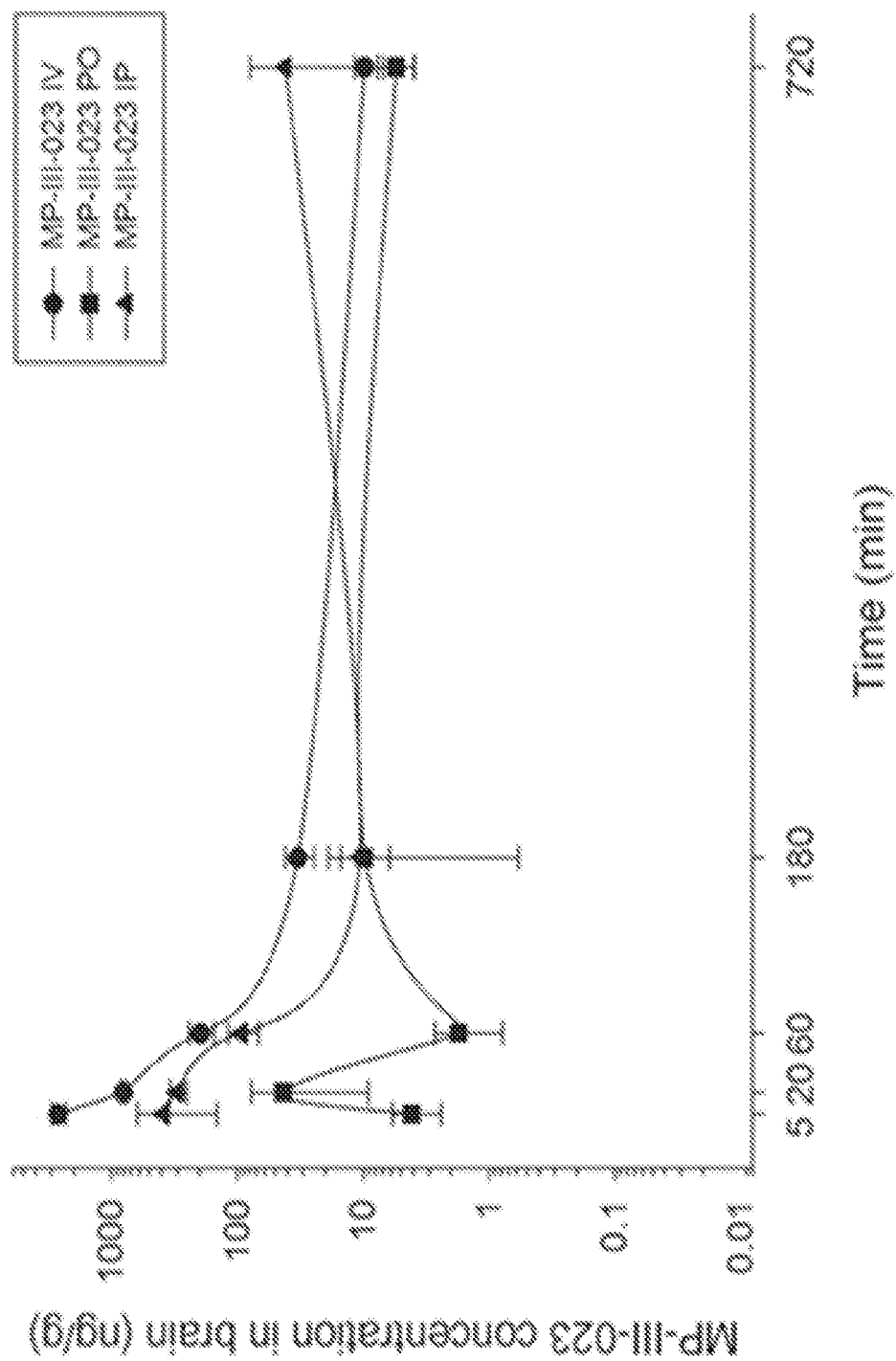
Figure 34A:
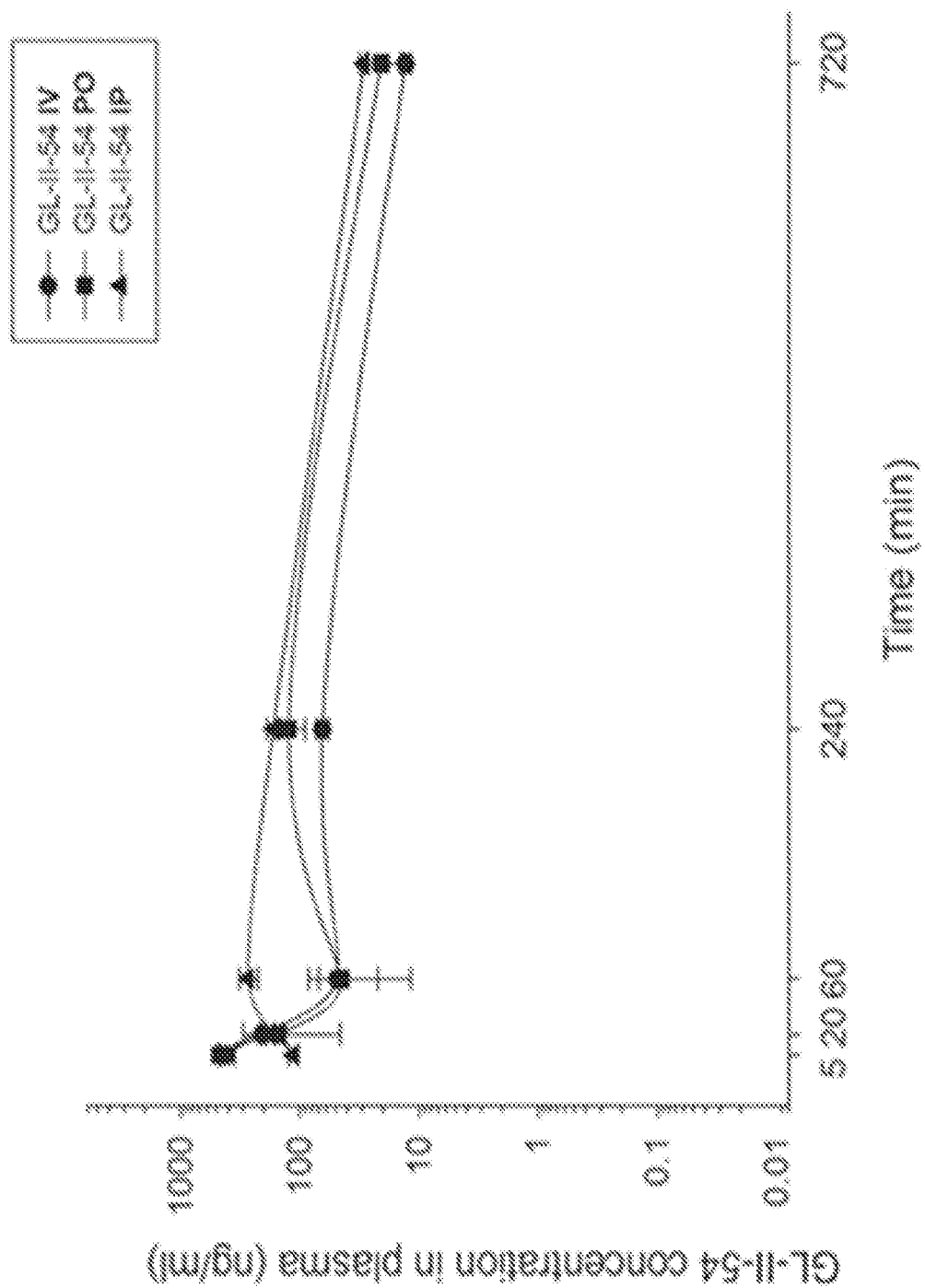
Figure 34B:
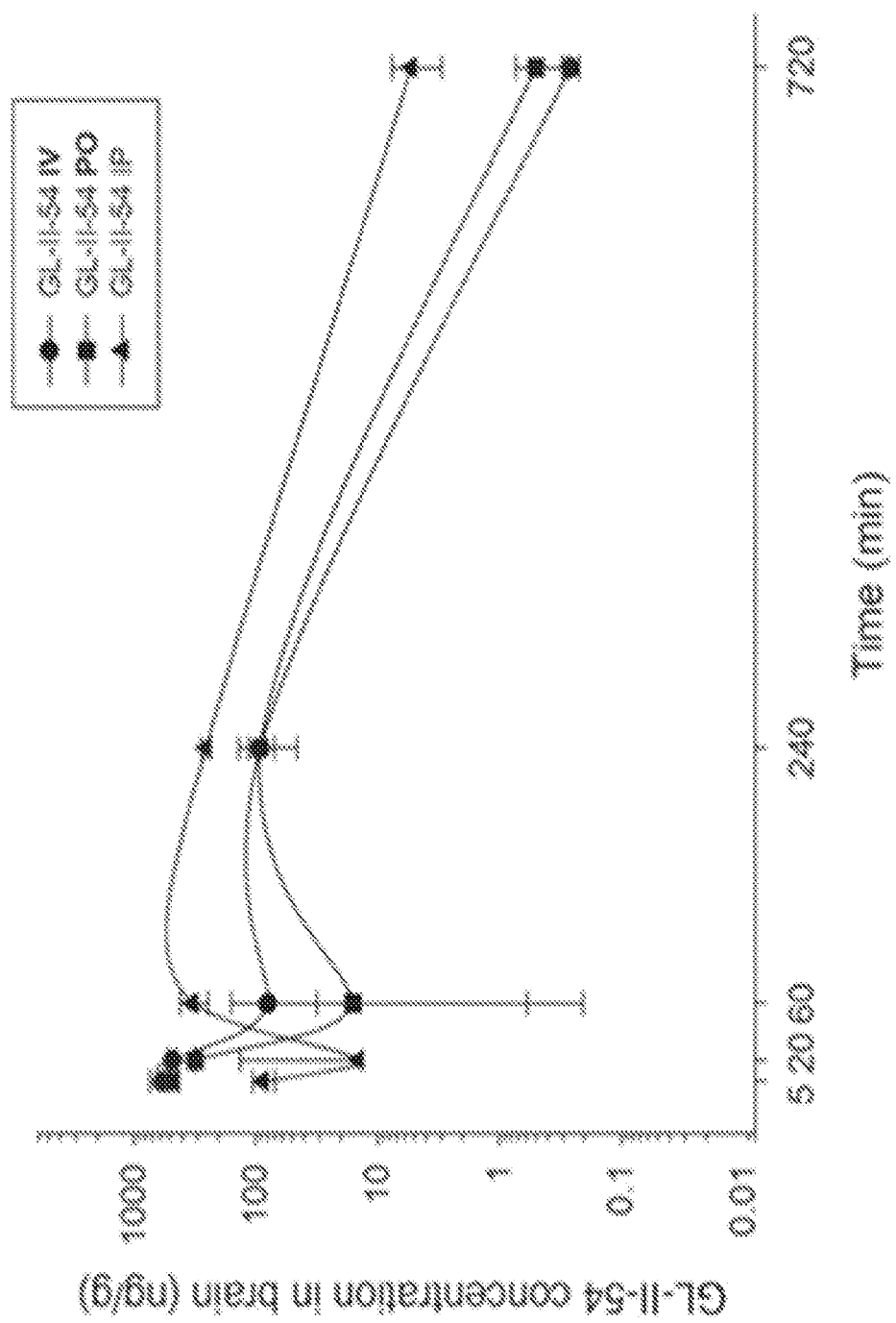
Figure 34C:
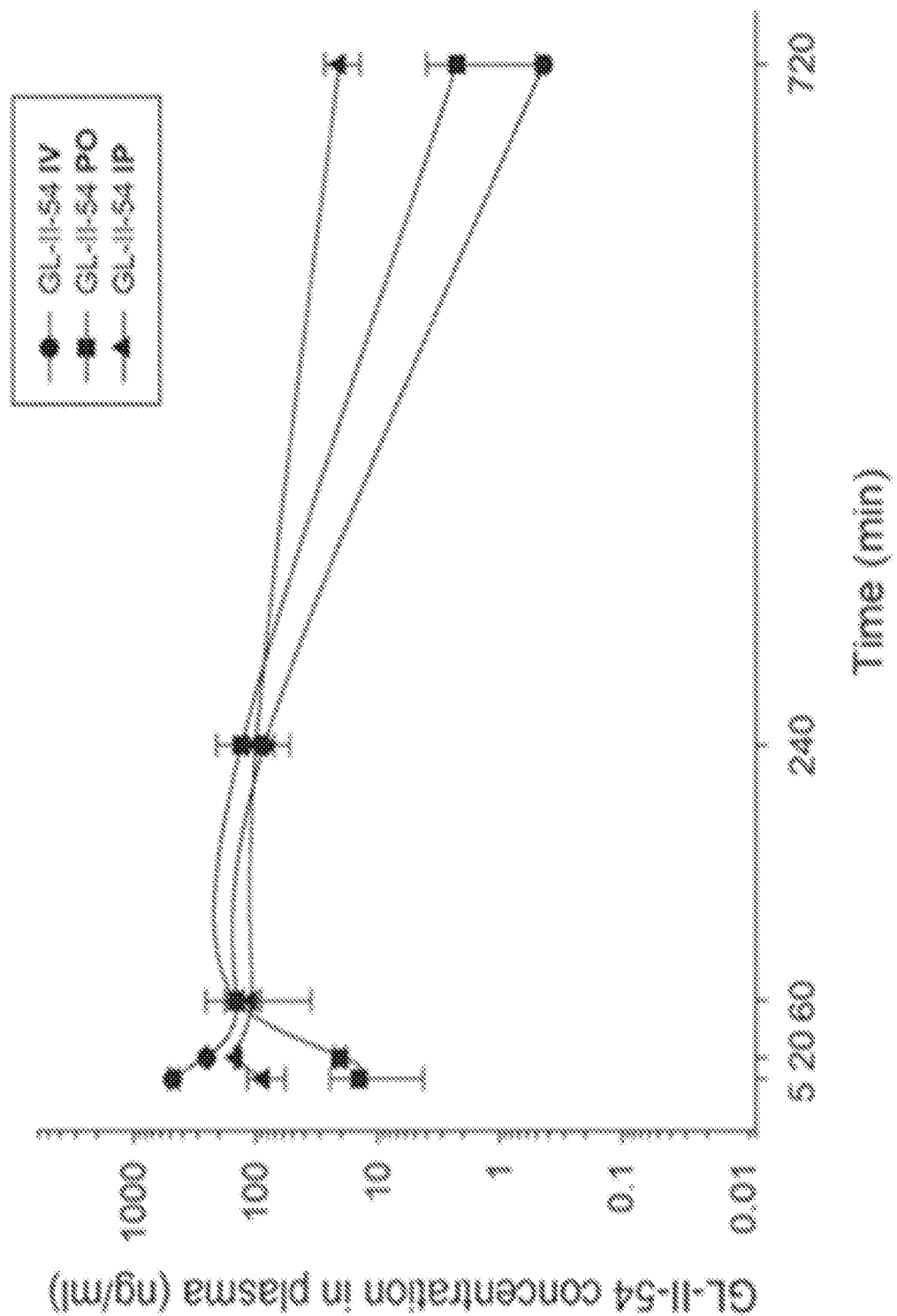
Figure 34D:
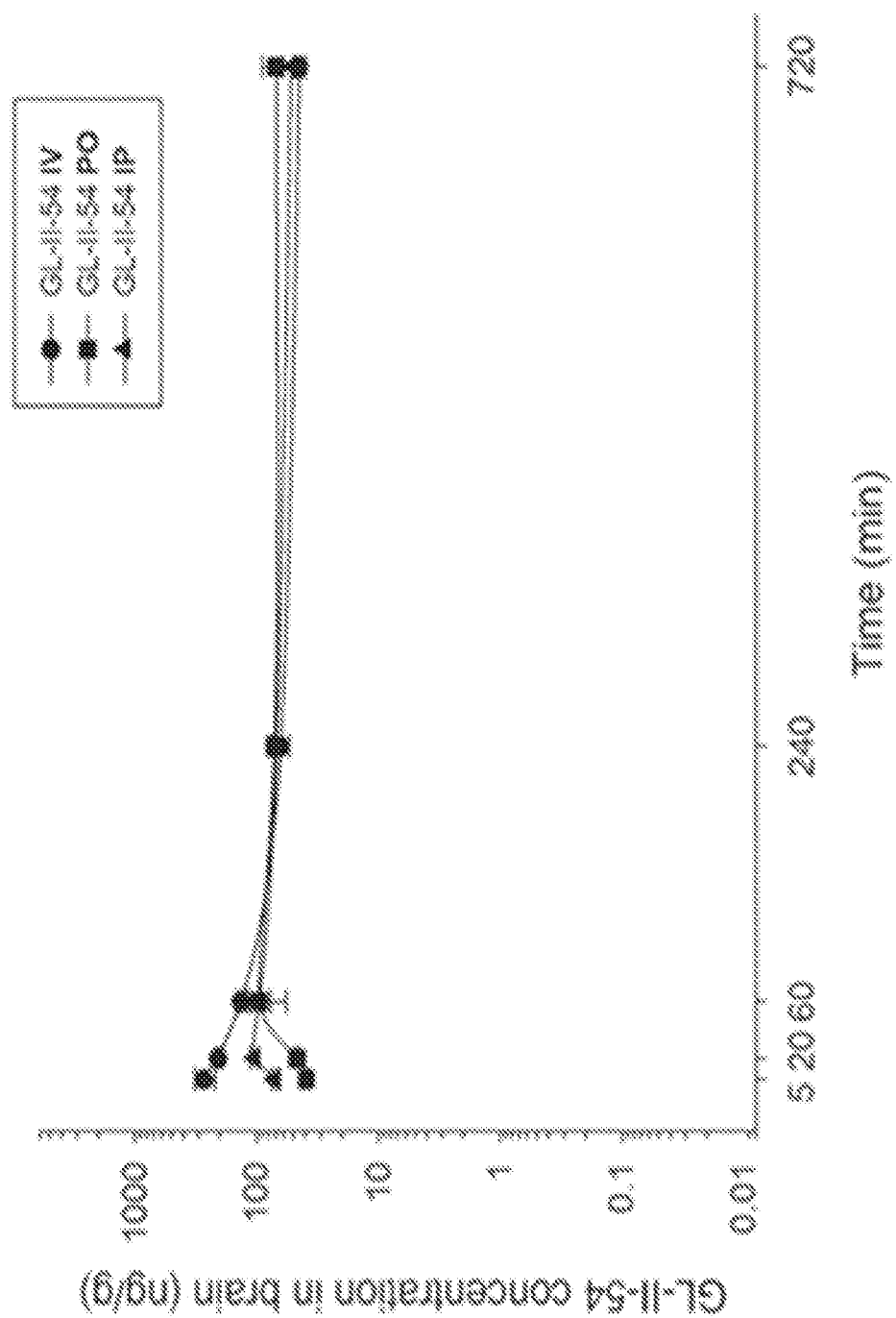
Figure 35A:
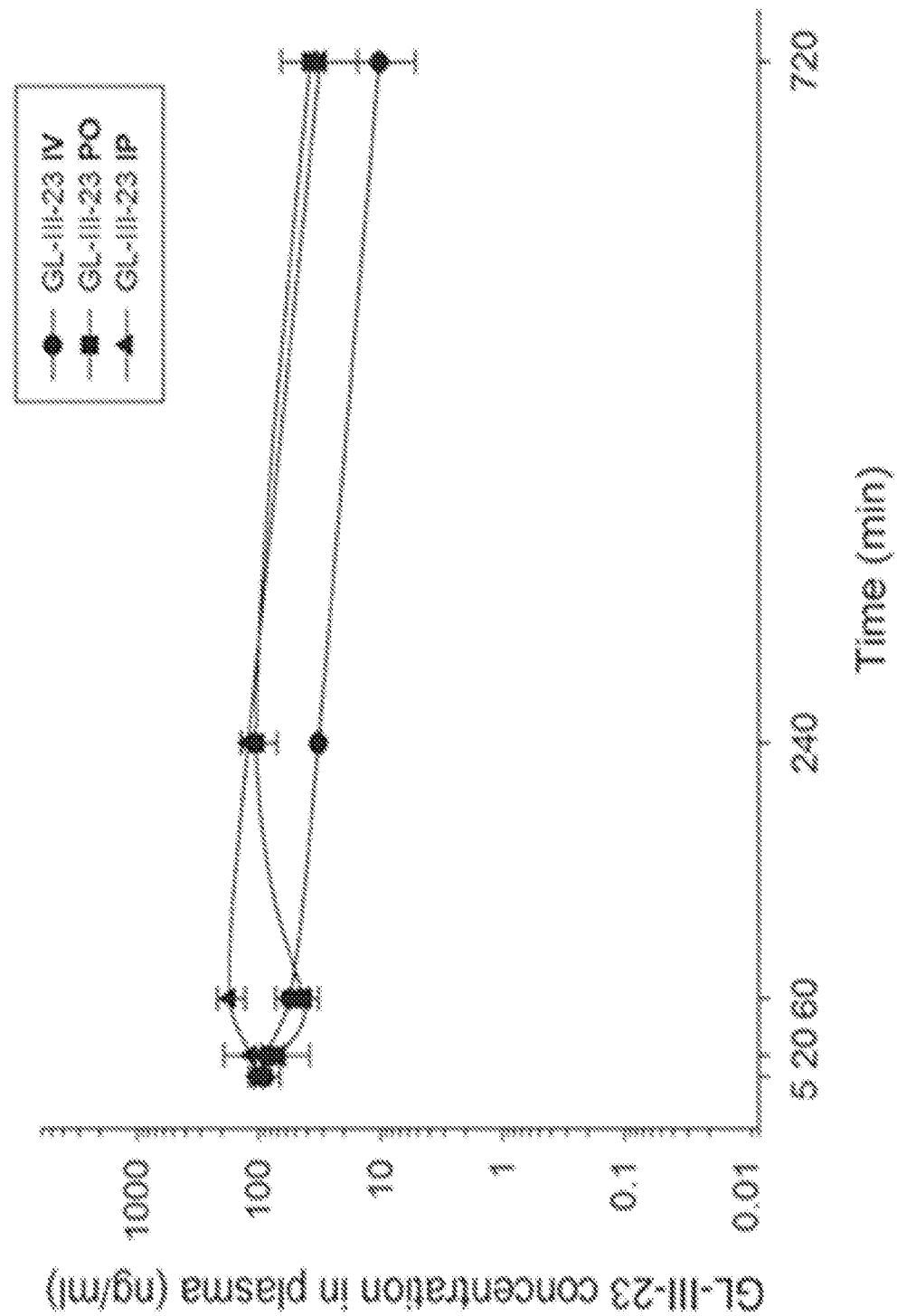
Figure 35B:
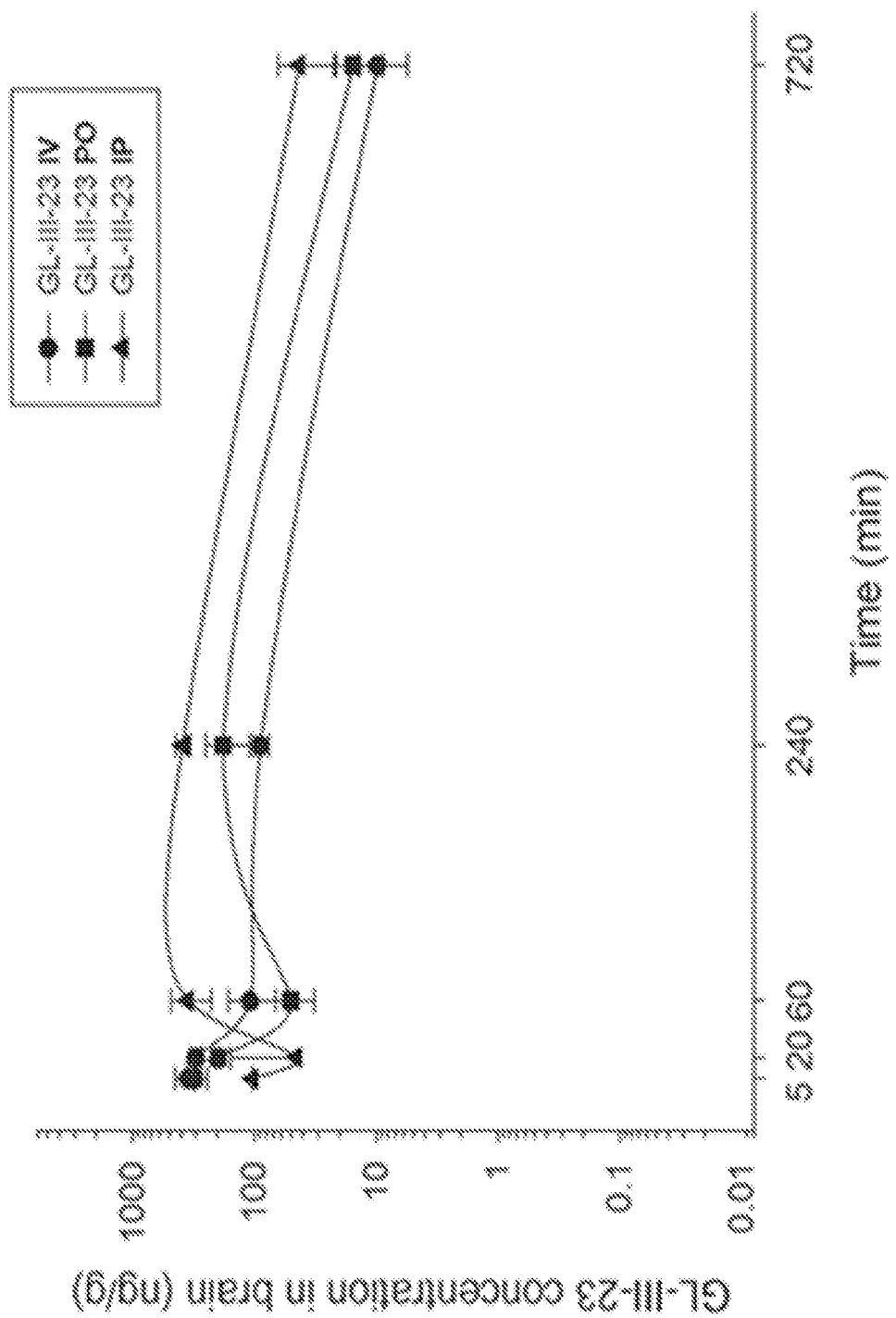
Figure 35C:
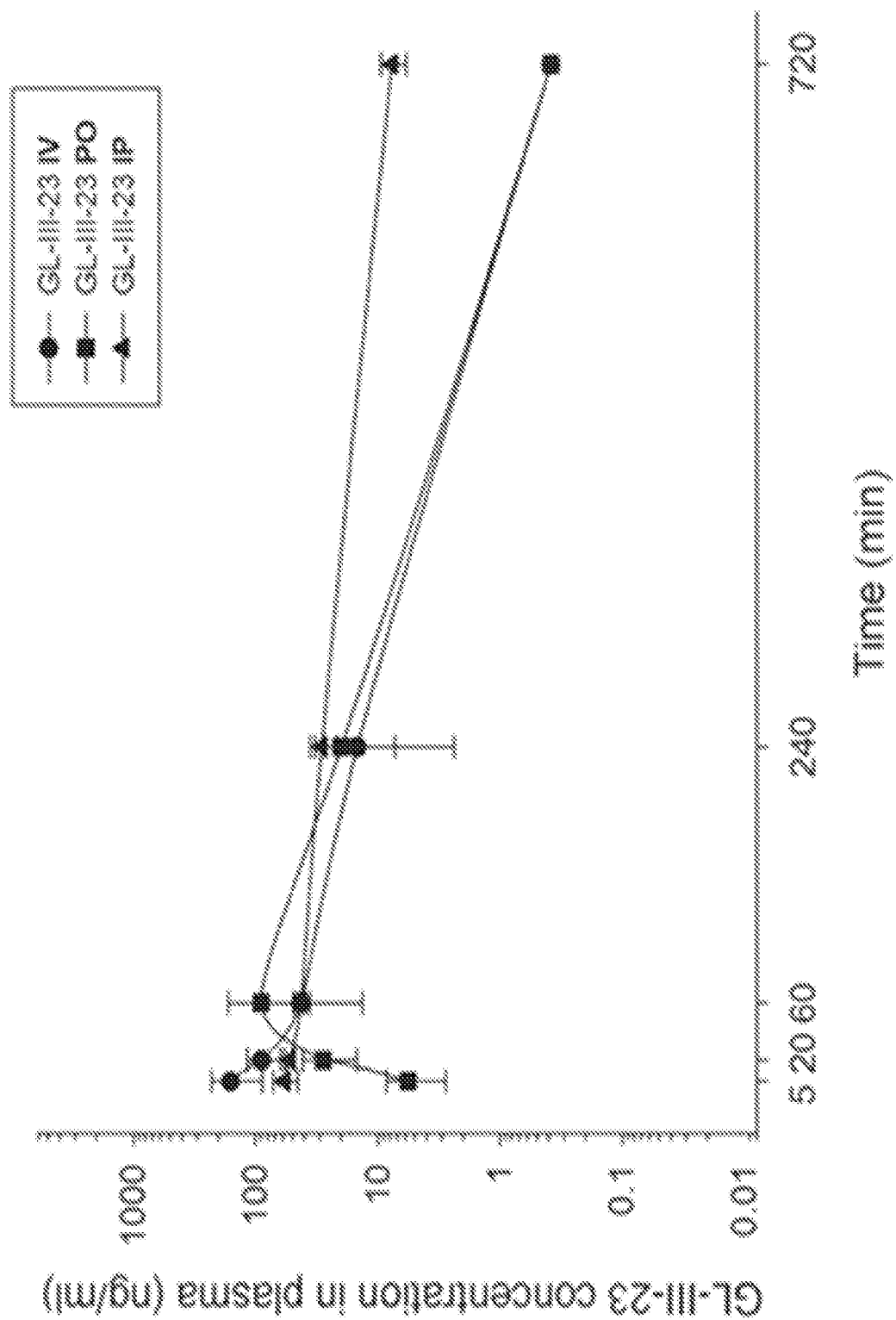
Figure 35D:
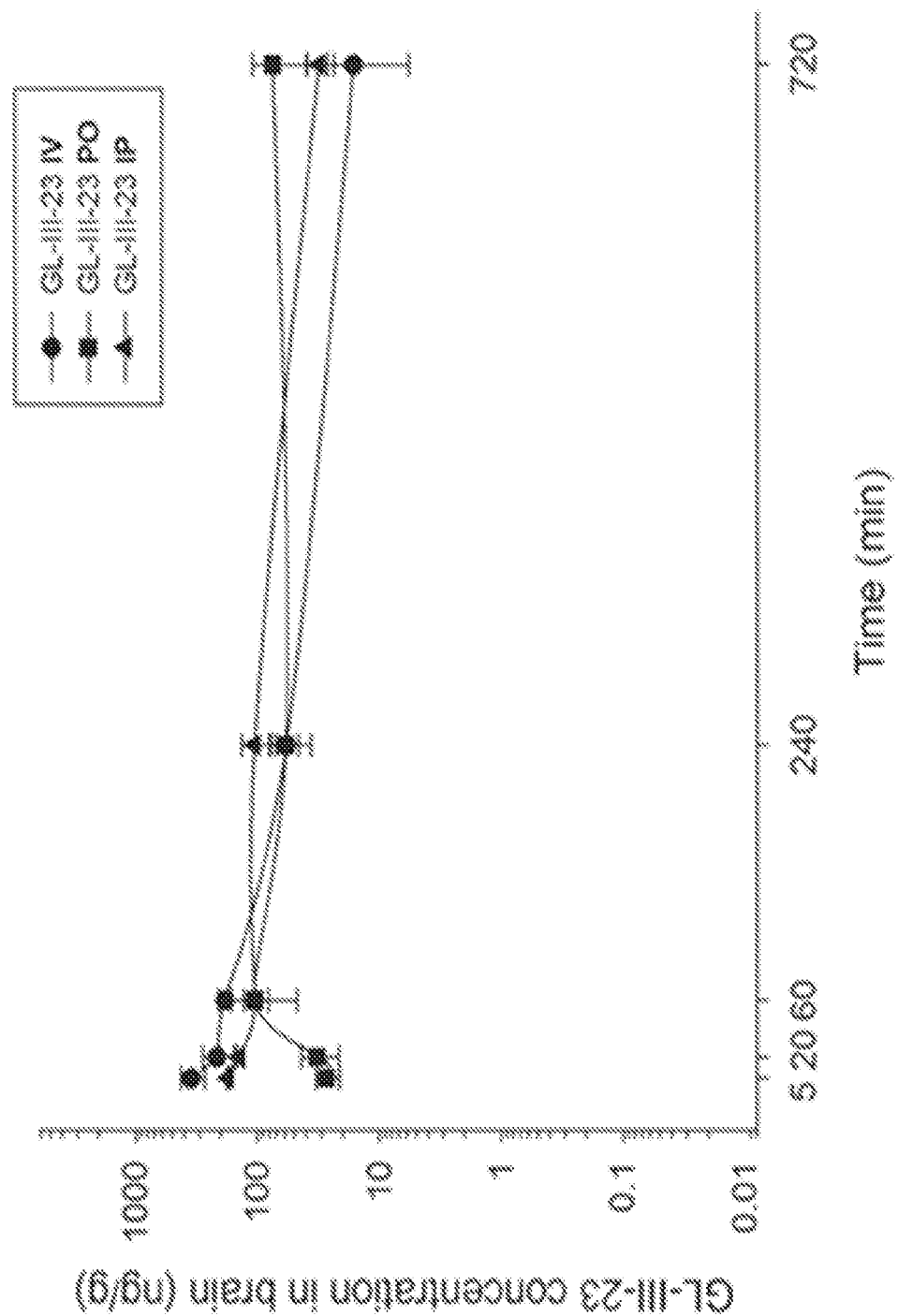
Figure 36A:
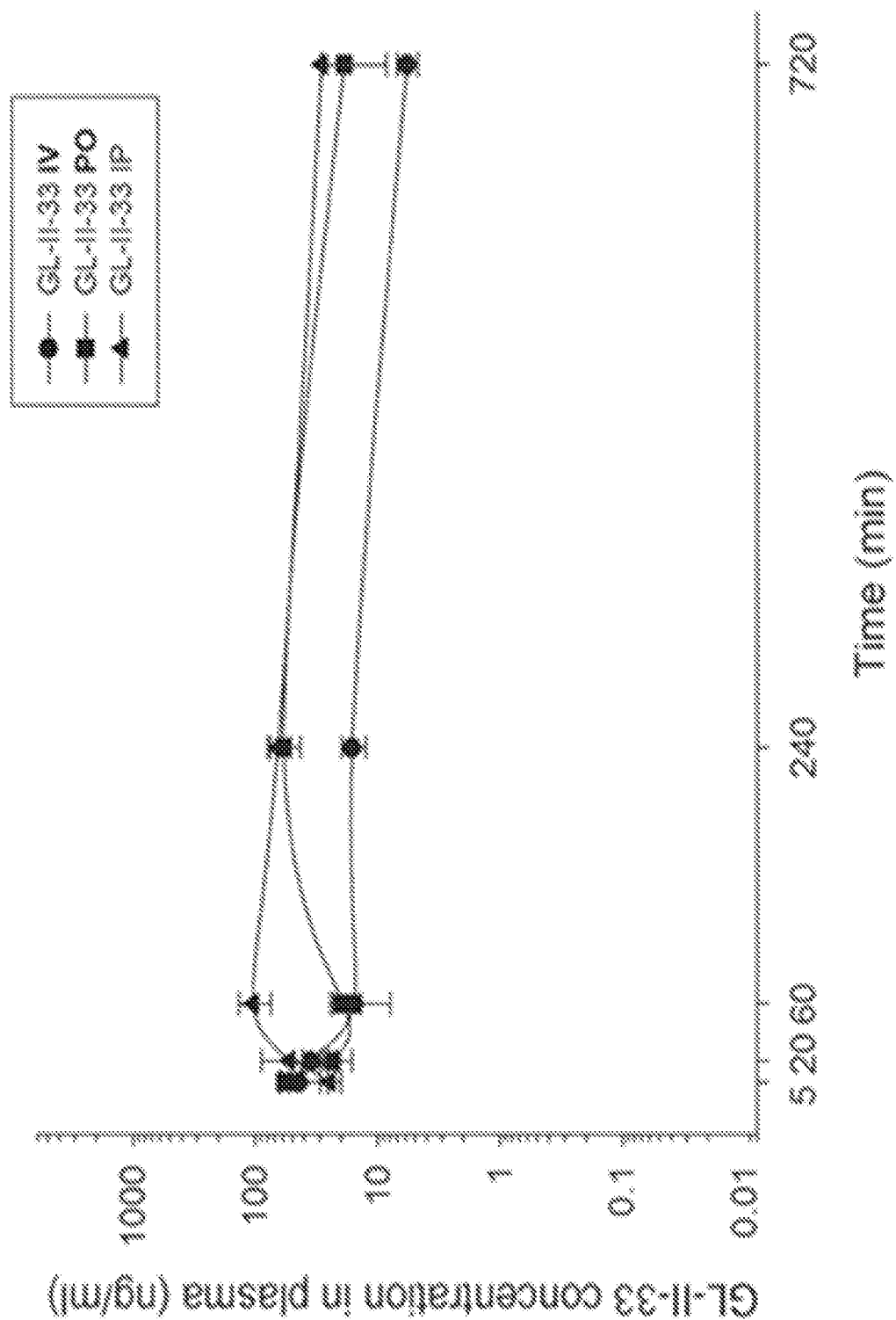
Figure 36B:
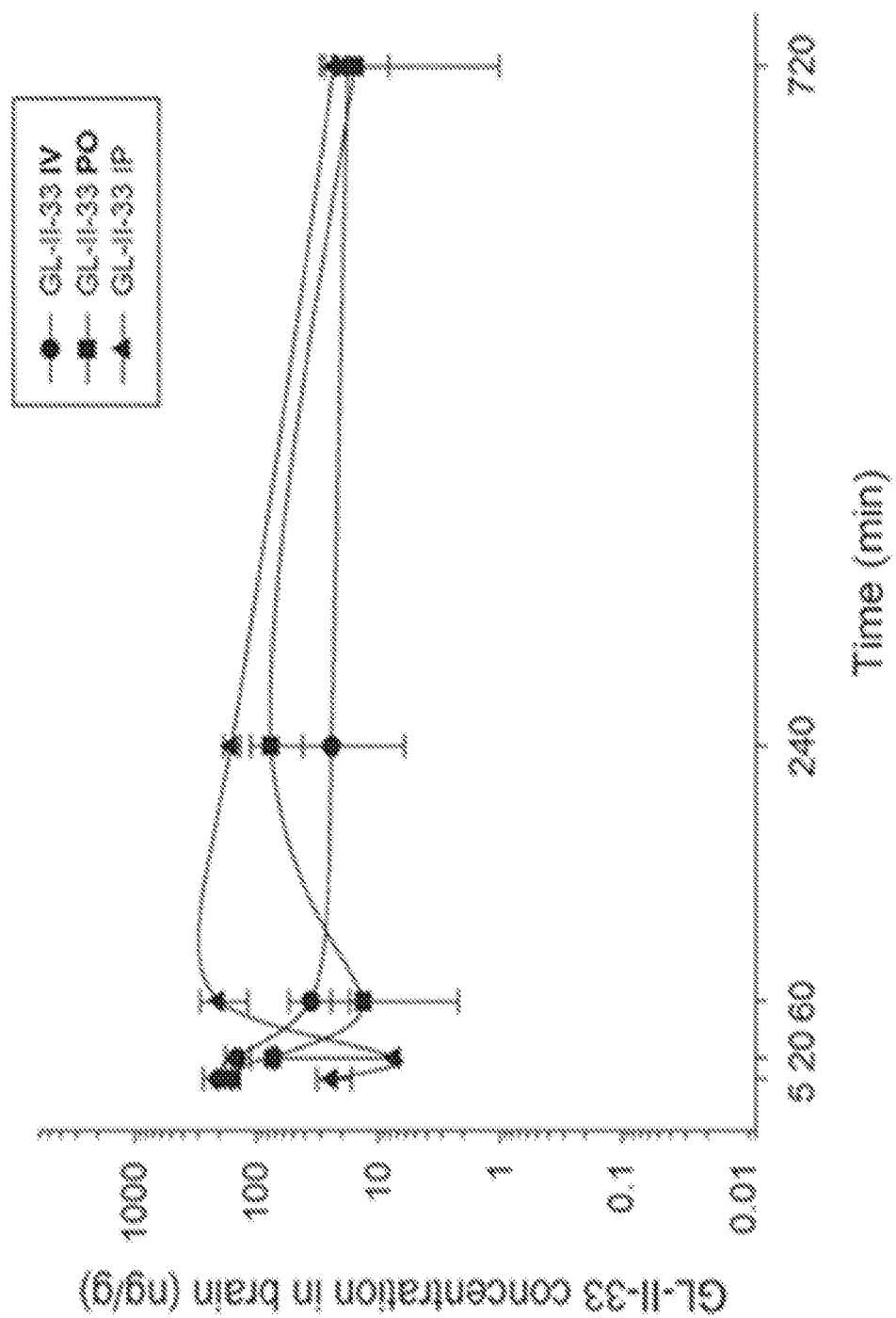
Figure 36C:
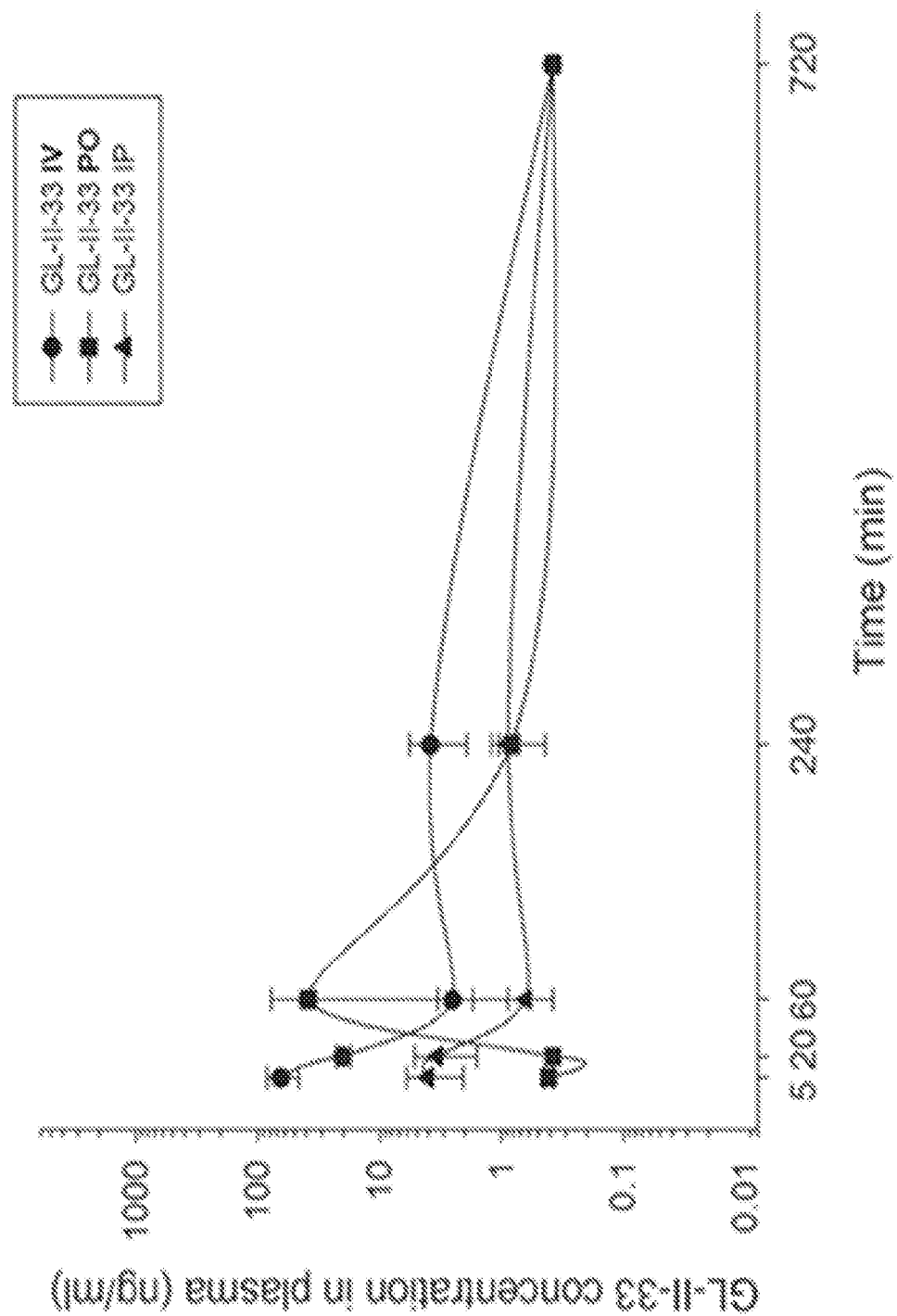
Figure 36D:
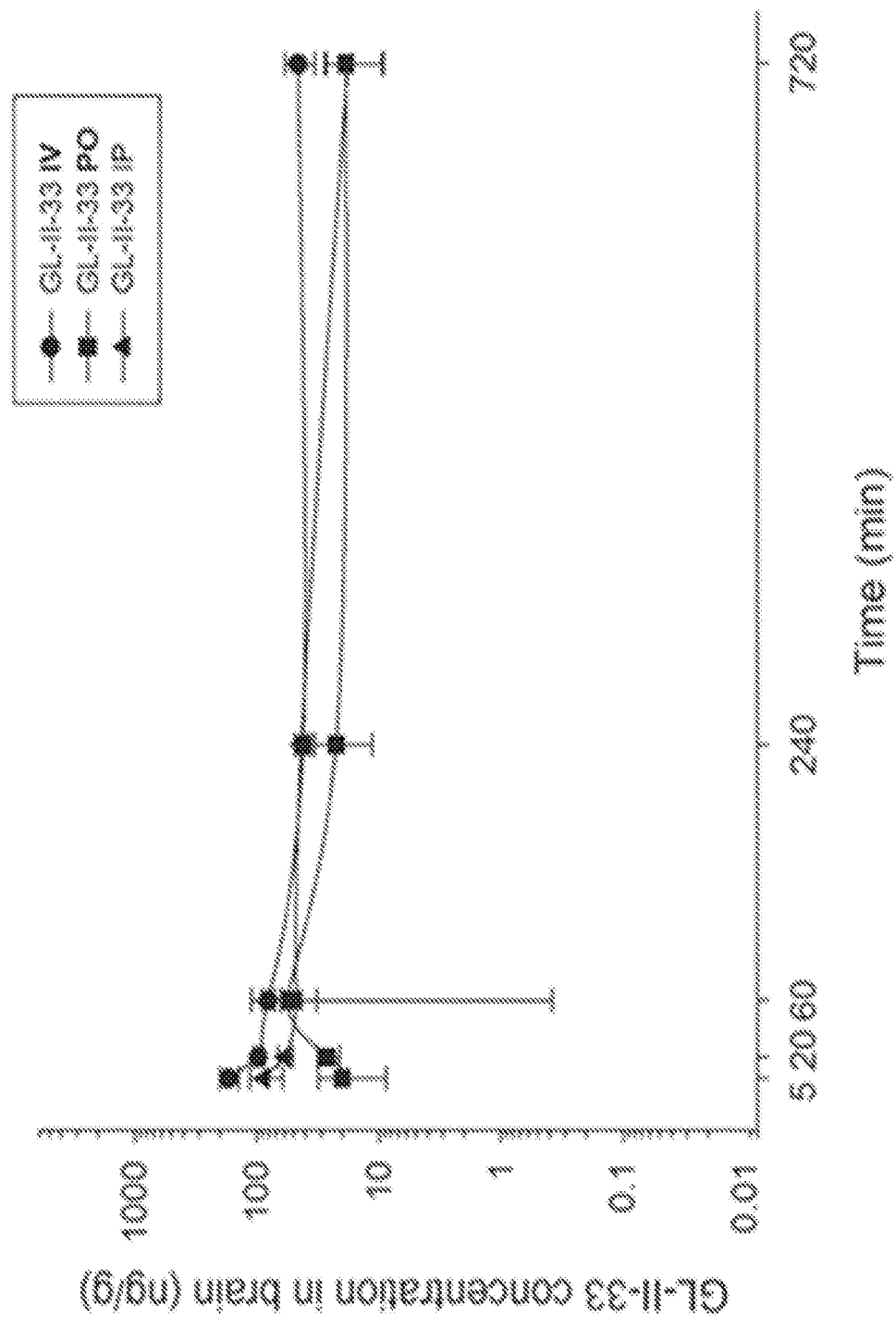
Figure 37A:
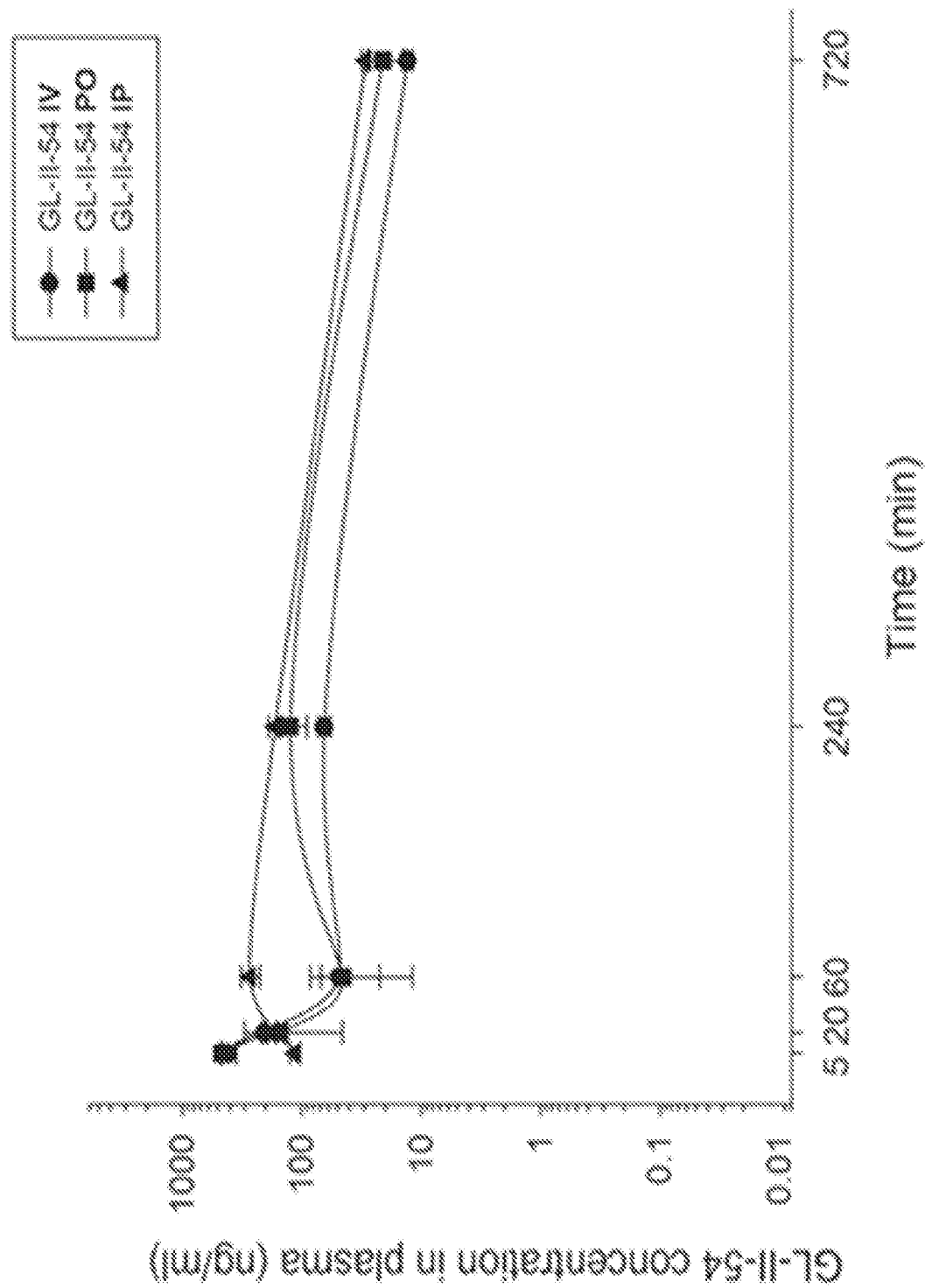
Figure 37B:
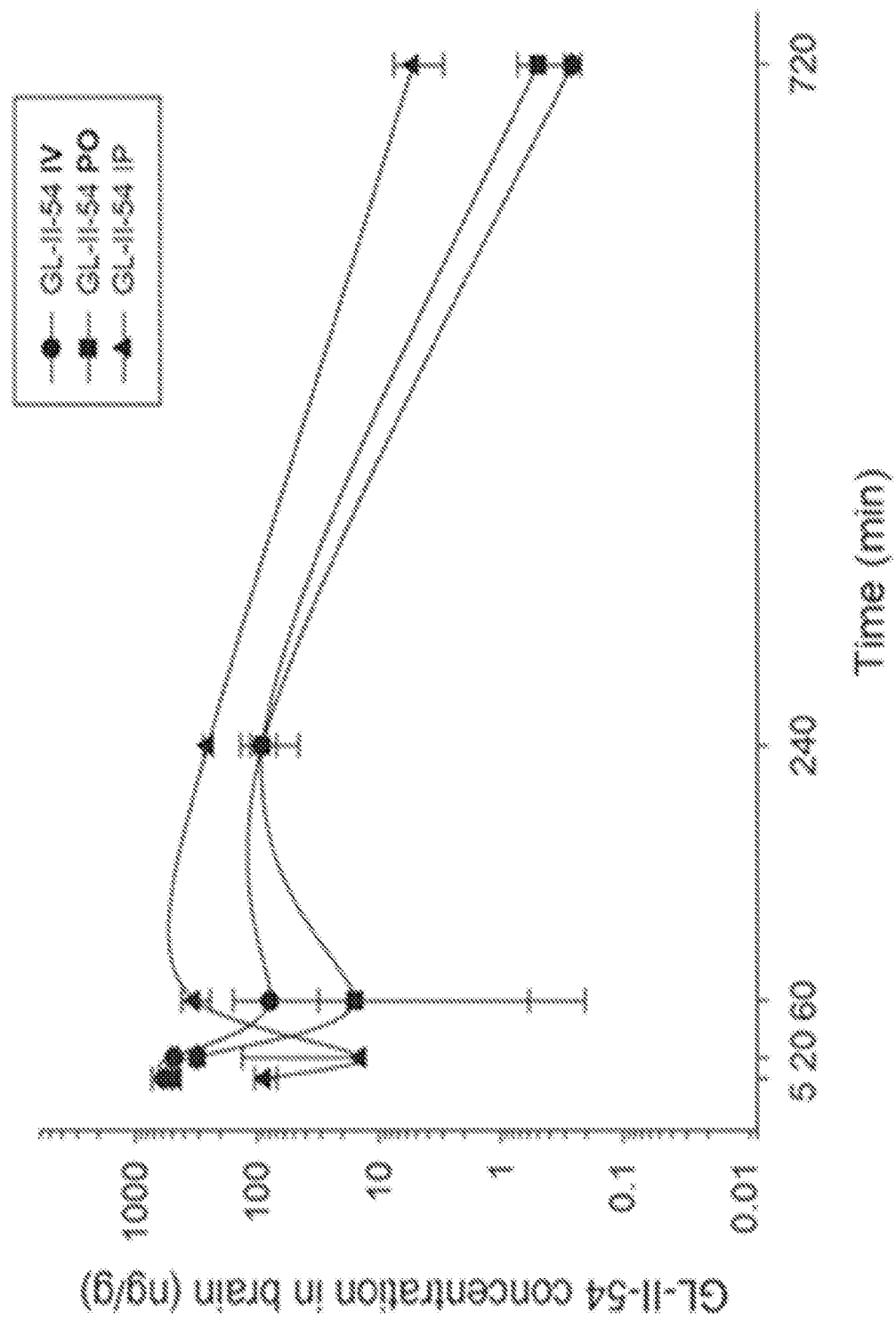
Figure 37C:
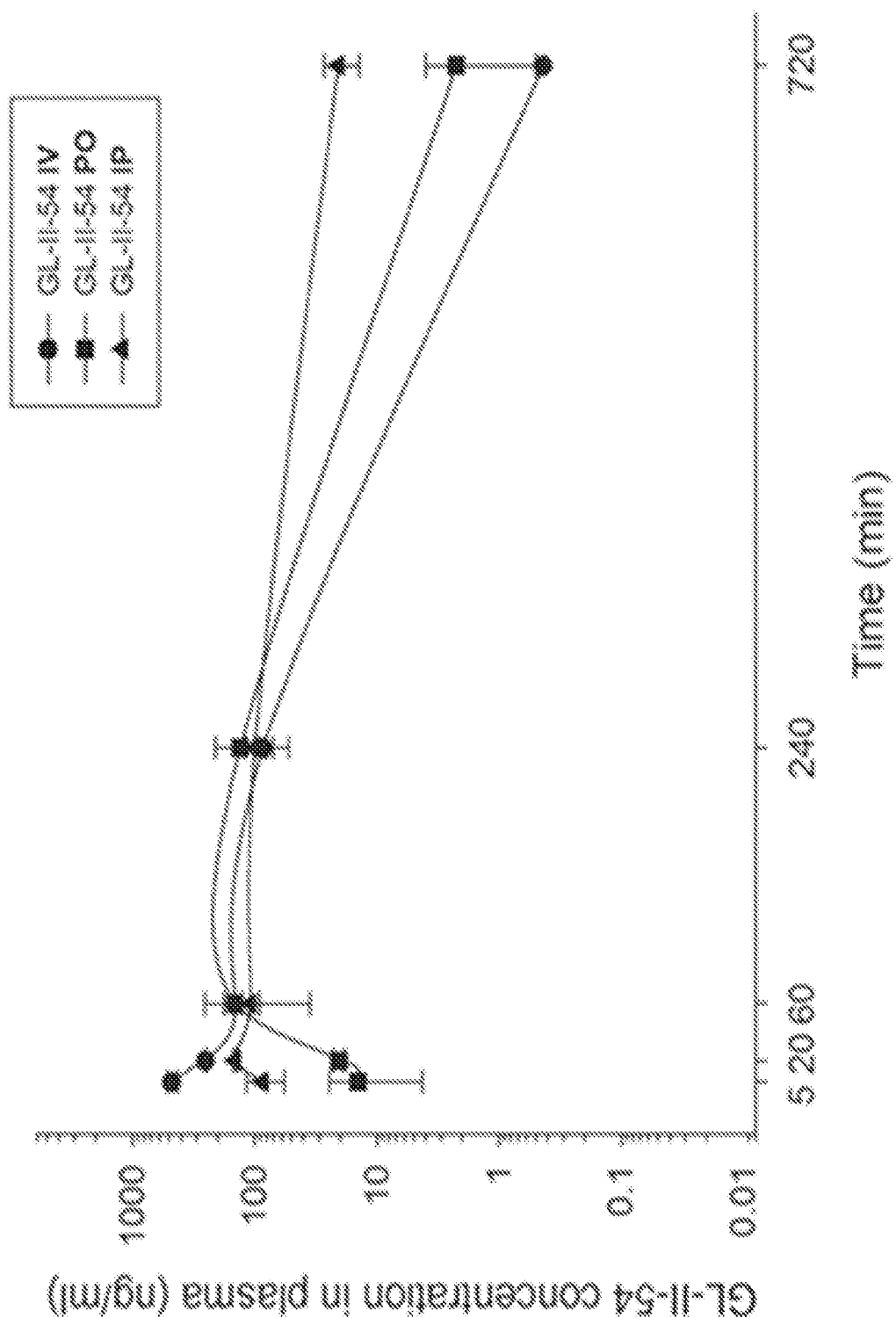
Figure 37D:
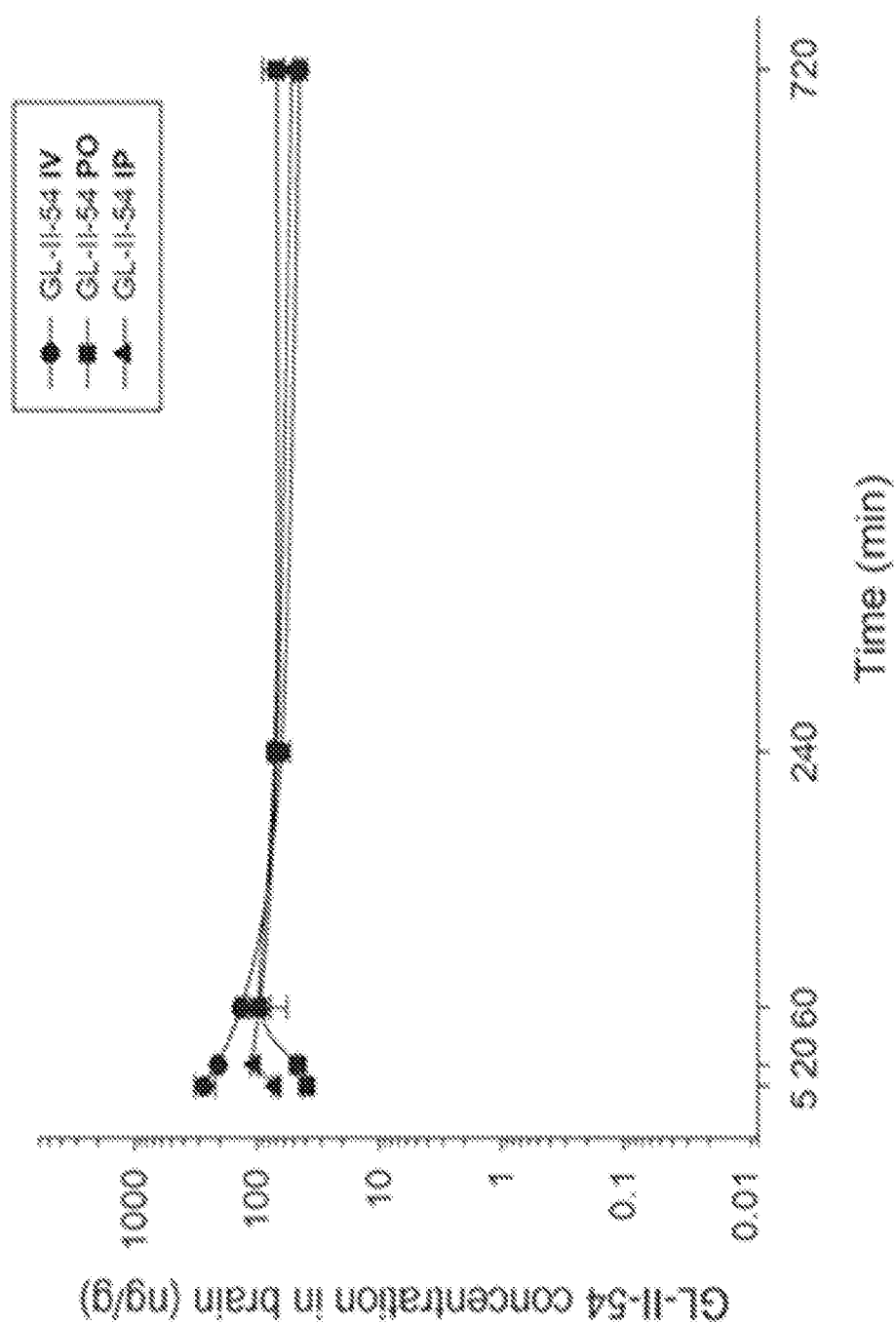
Figure 38A:
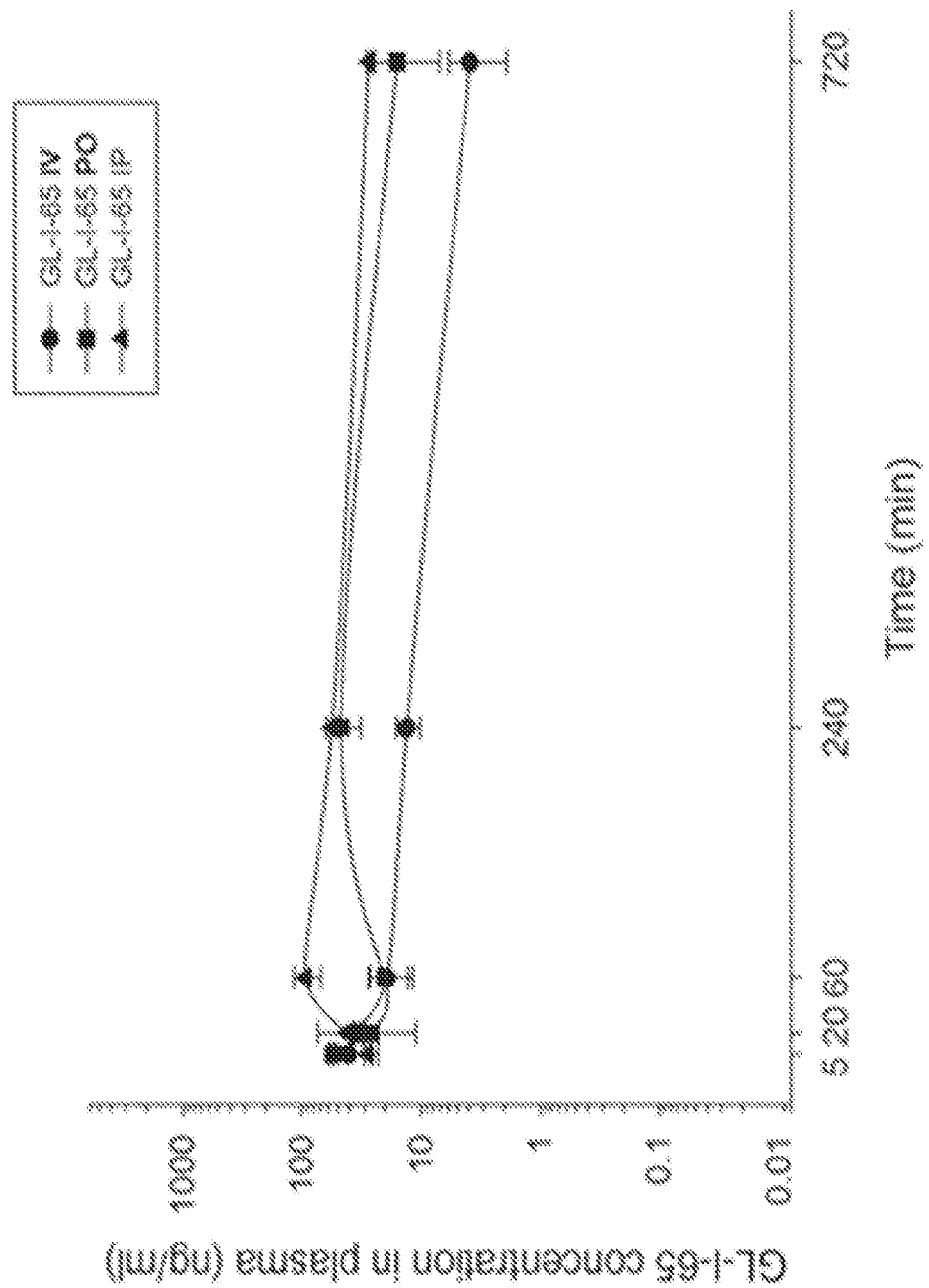
Figure 38B:
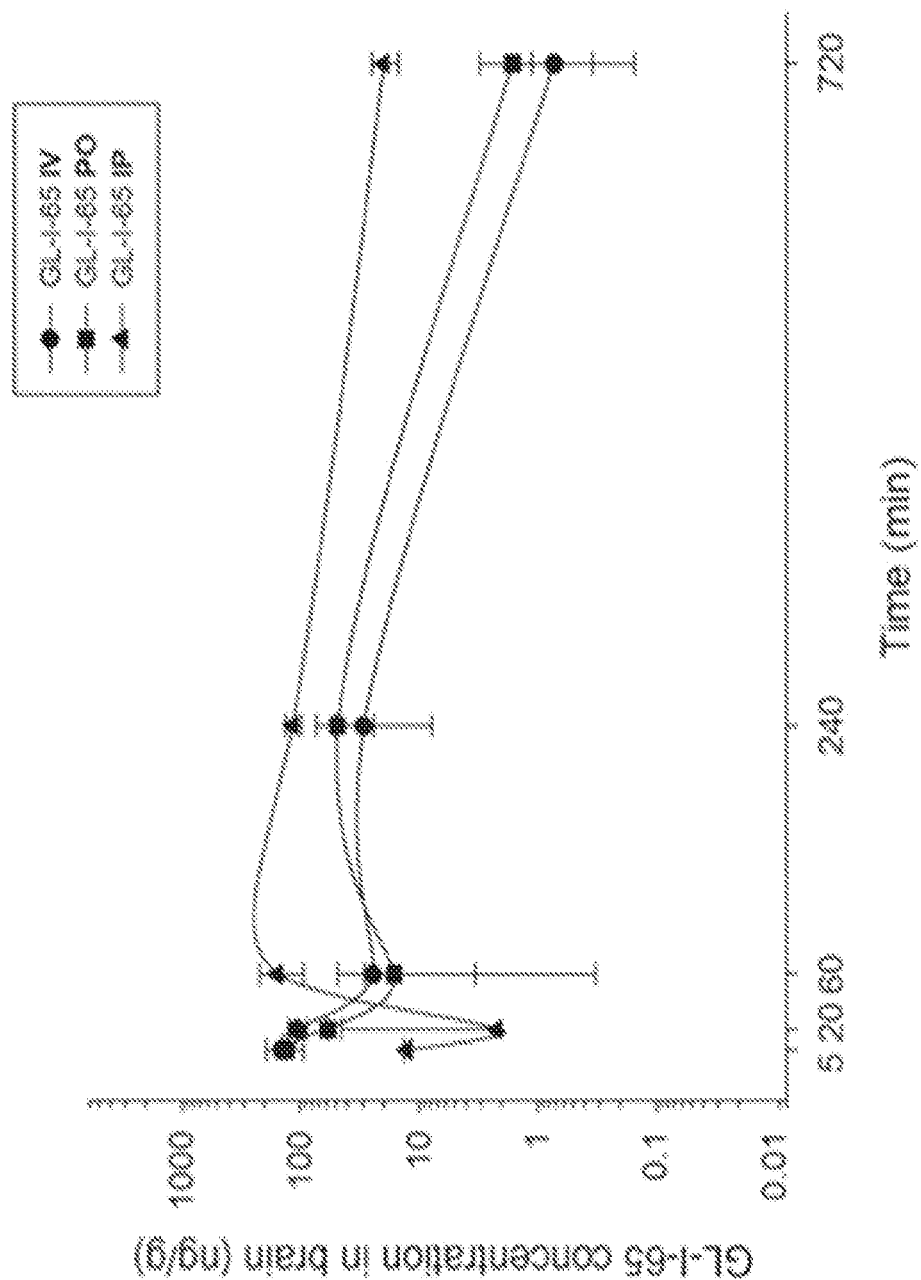
Figure 38C:
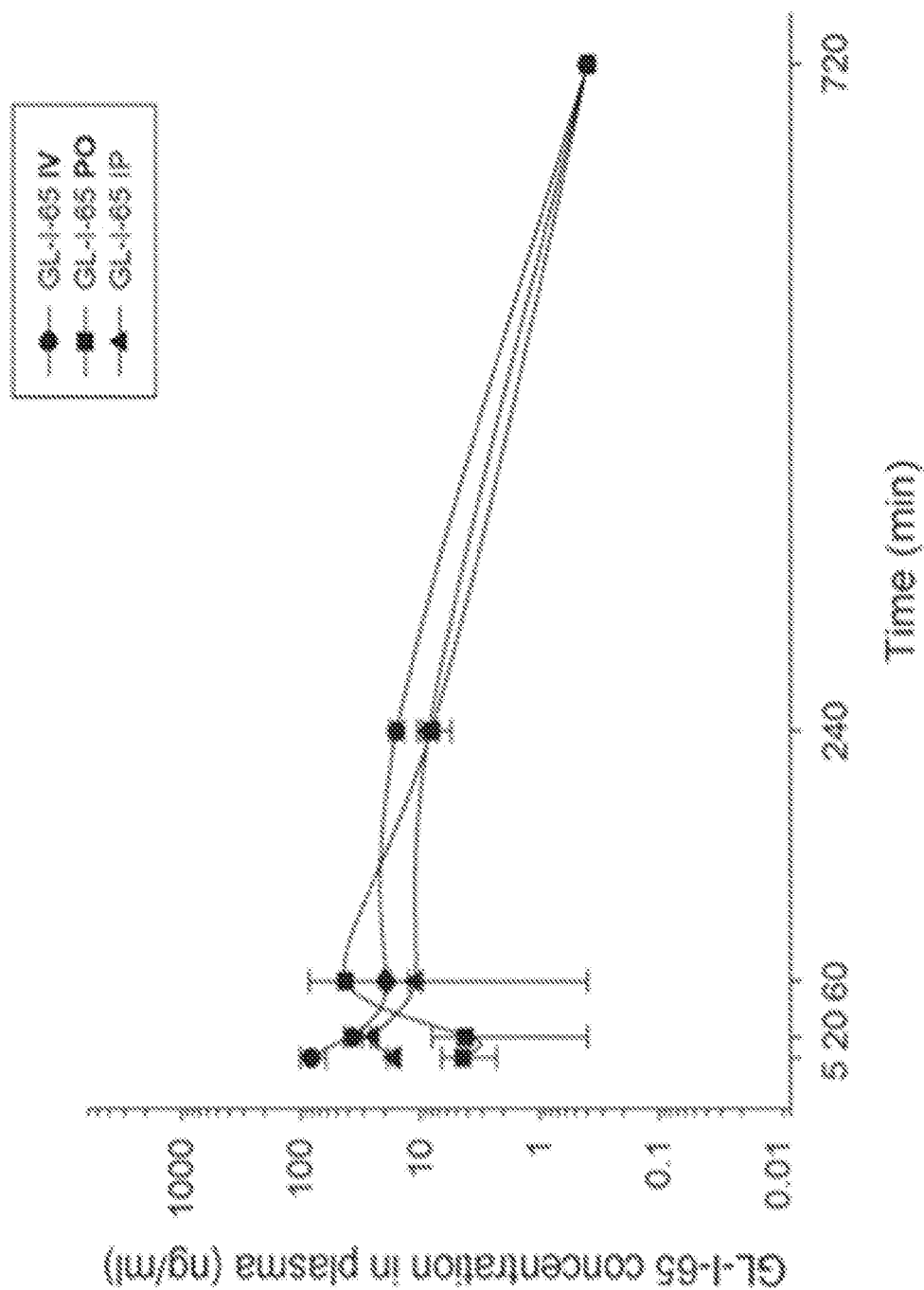
Figure 38D:
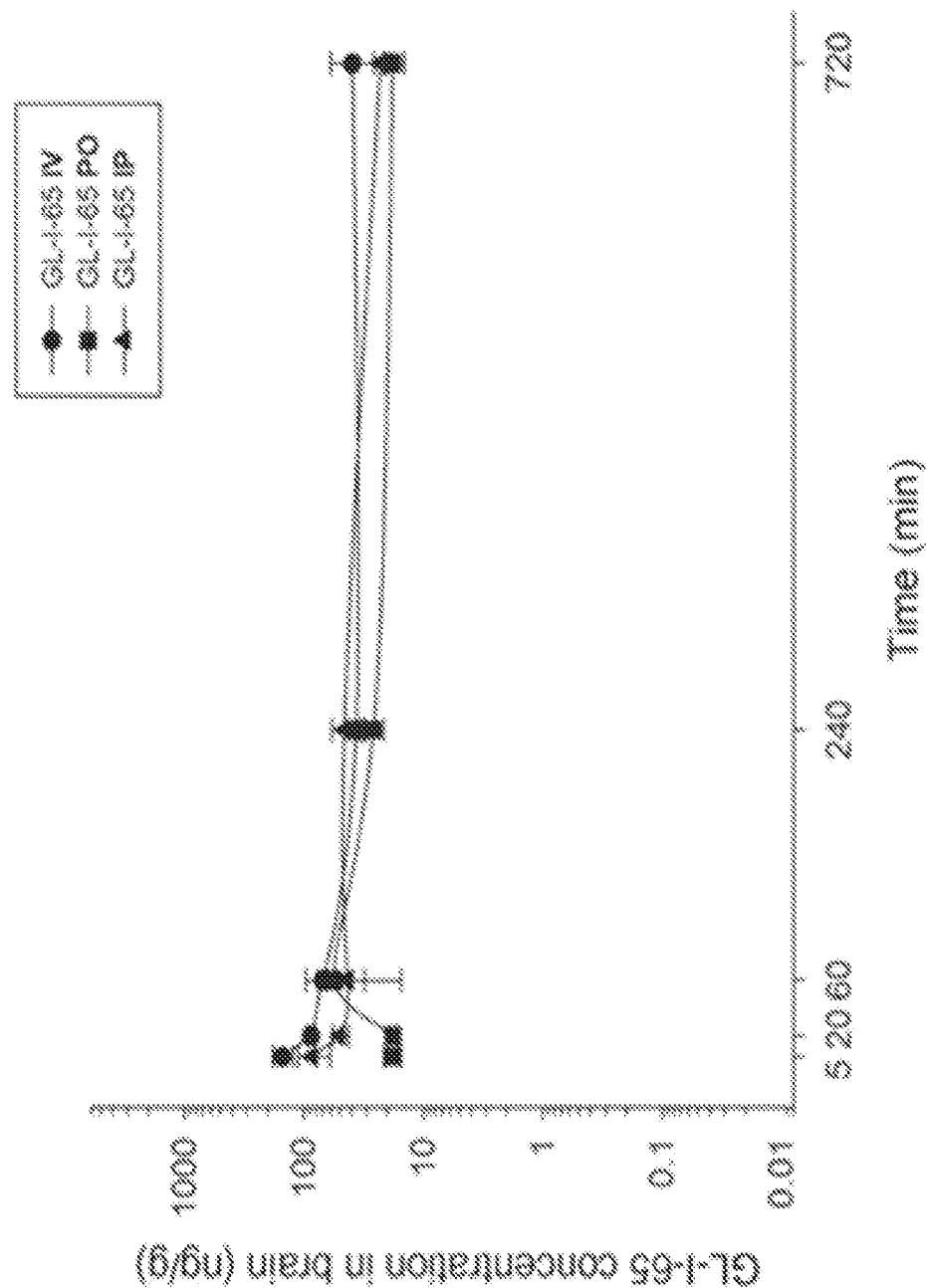

FIG. 30 shows the concentration-time profile of GL-II-75 after intraperitoneal (IP) administration of the 10 mg/kg dose (n=3 per time point) in mouse plasma and brain.

FIG. 31 shows the concentration-time profile of RV-II-04 after intravenous (IV), peroral (PO) or intraperitoneal (IP) administration of the 3 mg/kg dose (n=3 per time point) in mouse plasma (a) and brain (b), as well as in rat plasma (c) and brain (d).

FIG. 32 shows the concentration-time profile of GL-II-31 after intravenous (IV), peroral (PO) or intraperitoneal (IP) administration of the 3 mg/kg dose (n=3 per time point) in mouse plasma (a) and brain (b), as well as in rat plasma (c) and brain (d).

FIG. 33 shows the concentration-time profile of MP-III-023 after intravenous (IV), peroral (PO) or intraperitoneal (IP) administration of the 3 mg/kg dose (n=3 per time point) in mouse plasma (a) and brain (b), as well as in rat plasma (c) and brain (d).

FIG. 34 shows the concentration-time profile of GL-I-54 after intravenous (IV), peroral (PO) or intraperitoneal (IP) administration of the 3 mg/kg dose (n=3 per time point) in mouse plasma (a) and brain (b), as well as in rat plasma (c) and brain (d).

FIG. 35 shows the concentration-time profile of GL-III-23 after intravenous (IV), peroral (PO) or intraperitoneal (IP) administration of the 3 mg/kg dose (n=3 per time point) in mouse plasma (a) and brain (b), as well as in rat plasma (c) and brain (d).

FIG. 36 shows the concentration-time profile of GL-II-33 after intravenous (IV), peroral (PO) or intraperitoneal (IP) administration of the 3 mg/kg dose (n=3 per time point) in mouse plasma (a) and brain (b), as well as in rat plasma (c) and brain (d).

FIG. 37 shows the concentration-time profile of GL-II-54 after intravenous (IV), peroral (PO) or intraperitoneal (IP) administration of the 3 mg/kg dose (n=3 per time point) in mouse plasma (a) and brain (b), as well as in rat plasma (c) and brain (d).

FIG. 38 shows the concentration-time profile of GL-I-65 after intravenous (IV), peroral (PO) or intraperitoneal (IP) administration of the 3 mg/kg dose (n=3 per time point) in mouse plasma (a) and brain (b), as well as in rat plasma (c) and brain (d).

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways.

Improvement in medical interventions and living conditions have dramatically increased the average human lifespan. As a result, a growing number of people are suffering from neurodegenerative diseases, including dementia. 46.8 million people worldwide lived with dementia in 2015 and this number is expected to double every 20 years, reaching 74.7 million in 2030 and 131.5 million in 2050. A majority of people with dementia suffer from Alzheimer's disease (AD). AD is a fatal disease that affects cognitive, emotional and behavioral aspects of a person's life. Cognitive symptoms include negative effects on a person's ability to make decisions, perform simple tasks, or follow a conversation. Anticholinergic drugs are used for the cognitive deficits in AD but with very limited success. Mood symptoms in AD include apathy, loss of interest, low affect, anxiety and withdrawal. AD is exerting an increasing personal, societal and economic burden of AD, namely $604 billion in 2013, predicted to surpass $2 trillion in 2050, not counting the burden of prodromal (mild cognitive impairment) and high risk factor (aging and depression) states. This burden is compounded by the recent failures of clinical trials aimed at the classical neuropathologies of AD (i.e. amyloid plaques and tangles).

Recent progress in uncovering the biological bases of brain disorders demonstrates a significant sharing and continuum of cellular and molecular pathologies across the classical categorical diagnostics of diseases. Accordingly the GABA-related pathology that is described in this document and that is targeted by compounds with agonist or positive allosteric activities at alpha5-containing $GABA_A$ receptors has been reported across brain disorders from neuropsychiatric (e.g., depression, schizophrenia) to neurodegenerative (e.g. AD) disorders. Hence the novel therapeutic strategies could be directed at specific disorders as well as symptom dimensions (e.g. cognition, mood) across disorders, from neuropsychiatric (e.g., depression, schizophrenia) to neurodegenerative (e.g. AD) disorders.

The molecular and cellular pathology of brain disorders has been investigated using unbiased genomic approaches in human postmortem brains; genetic and environmental mouse models have been used to investigate causal links between the pathologies identified in the human brain and mood and cognitive regulatory mechanisms in rodents; targets have been identified within those causal pathological modules and have performed preliminary preclinical studies to support the value of these targets as novel therapeutic strategies. This has led to the GABA system and to the alpha5 subunit containing $GABA_A$ receptor as a novel target for cognitive remediation antidepressant/anxiolytic treatment.

More specifically, converging evidence has long suggested a role for the inhibitory GABA system in depression. Recent evidence suggests a specific cellular origin for those changes (Guilloux et al, Molecular Psychiatry, 2012, 17, 1130-1142; Tripp et al, Am J Psychiatry, 2012, 169, 1194-1202). These findings have been integrated into a model, linking GABA-related biochemical, cellular and brain region findings with psychological concepts and symptom dimensions in depression (Northoff & Sibille, Molecular Psychiatry, 2014, 19, 966-977). In this model, deficits in somatostatin-positive (SST+) GABA neurons that regulate excitatory input onto the dendrites of pyramidal cells translate into altered information processing by local cell circuits, and result in altered activity of key brain regions (frontal and cingulate cortices) and neural networks (default-mode and executive networks). In turn these integrated biological deficits surface as anhedonia (lack of experiencing pleasure) and increased negative self-focus (rumination, suicidality), two central features of depression.

Based on the inspection of the molecular components of the cell-specific link between SST+GABA and pyramidal neurons, it is proposed that the alpha 5 subunit of the $GABA_A$ receptor is a logical target to remediate the molecular pathology of depression and to potentially exert pro-cognitive and antidepressant-like activity. The different alpha subunits of $GABA_A$ receptors determine the localization of these receptors across cellular compartments. Alpha 5-containing $GABA_A$ receptors are located on dendrites of pyramidal cells, opposite from SST+GABA neuronal terminals; hence they mediate the function of SST+GABA neurons. The $GABA_A$ receptor alpha subunits are the main targets of benzodiazepine-like compounds. These compounds have sedative, anxiolytic and anticonvulsant effects. This broad activity is due to their non-specific targeting of several alpha subunits. This pan-alpha subunit activity has considerably limited their therapeutic potential, due to sedation, tolerance and cognitive side-effects. Recent anatomical, genetic and functional characterization of the various $GABA_AR$ alpha subunits has raised hopes that the selective targeting of specific subunits will uncover novel therapeutic opportunities for neuropsychiatric disorders.

Here a novel pro-cognitive and antidepressant modality is proposed which is informed by the primary molecular pathology of depression. The primary target is the inhibitory $GABA_A$ receptor Alpha5 subunit, the pharmacological effect is positive allosteric modulation (Alpha5-PAM), and the therapeutic indication is for depression and other disorders that share mood and cognitive deficits, potentially focusing on the cognitive and rumination core symptoms. The rationale for choosing this target is based on (1) the findings using human postmortem brain samples suggesting reduced function at the $GABA_A$-Alpha5-containing synapse in depression, (2) a large body of research suggesting altered GABA function in depression, and (3) the preclinical rodent studies showing antidepressant effects of Alpha5-PAM (Piantodosi et al, Frontiers in Pharmacology, 2016, 7, 446; See also included figures and results) and pro-cognitive effects (See included figure and results). Note that recent findings also suggest that reducing the function of alpha5-containing $GABA_A$ receptors may exert antidepressant activity (Fischell et al, Neuropsychopharmacology, 2015, 40, 2499-2509). This suggests a putative inverted U-shape effect for alpha5-$GABA_A$ receptor function, where both high and low function may have therapeutic potential. However reducing the function of alpha5-containing $GABA_A$ receptors is notably predicted to worsen the primary pathology observed in brain disorders (i.e. reduced SST cell function), hence it is potentially associated with higher risk for long-term detrimental effects.

There is strong evidence of reduced expression and function of somatostatin (SST)-positive inhibitory GABA neurons in neurological disorders, including AD, schizophrenia, bipolar depression, and major depression (Lin and Sibille, Frontiers Pharmacology, 2013, 4, 110). SST-positive GABA neurons are a subtype of inhibitory neurons which are characterized by inhibiting the dendritic compartment of glutamatergic pyramidal neurons, the main excitatory cells in the brain. Signaling through SST neurons regulate information and neural processes and has been specifically implicated in regulating cognition and mood. The main function of SST-positive neurons is mediated by the neurotransmitter GABA and by a specific subtype of $GABA_A$ receptors which contain the alpha5 subunit. Alpha5-containing $GABA_A$ receptors are localized on the dendrites of pyramidal cells, the cellular compartment targeted by SST-positive neurons. Hence, the deficits in SST positive cells that is observed across neurological disorders is postulated to result in reduced signaling though Alpha5-containing $GABA_A$ receptors. Increasing Alpha5-containing $GABA_A$ receptor signaling may therefore have therapeutic value for cognitive and mood symptoms across brain disorders, and specifically in AD and MDD.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl and tert-butyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to nonaromatic, saturated or partially unsaturated cyclic, bicyclic, tricyclic or polycyclic hydrocarbon groups having 3 to 12 carbons (e.g., 3, 4, 5, 6 or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "halo" or "halogen" as used herein refers to any radical of fluorine, chlorine, bromine or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocyclyl" as used herein refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O— alkyl radical. The term "aryloxy" refers to an —O-aryl radical. The term "haloalkoxy" refers to an —O-haloalkyl radical.

The term "substituent" refers to a group "substituted" on an alkyl, alkenyl, alkynyl, cycloalkyl, heterocyclyl, aryl, arylalkyl or heteroaryl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C═O), phosphonate, sulfinyl, sulfonyl, sulfonate, sulfonamino, sulfonamido, thioamido, thiol, thioxo (e.g., C═S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et and Ph represent methyl, ethyl and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH2O— optionally also recites —OCH2-.

In accordance with a convention used in the art, the group:

is used in structural formulas herein to depict the bond that is the point of attachment of the moiety or substituent to the core or backbone structure.

In the context of treating a disorder, the term "effective amount" as used herein refers to an amount of the compound or a composition comprising the compound which is effective, upon single or multiple dose administrations to a subject, in treating a cell, or curing, alleviating, relieving or improving a symptom of the disorder in a subject. An effective amount of the compound or composition may vary according to the application. In the context of treating a disorder, an effective amount may depend on factors such as the disease state, age, sex, and weight of the individual, and the ability of the compound to elicit a desired response in the individual. In an example, an effective amount of a compound is an amount that produces a statistically significant change in a given parameter as compared to a control, such as in cells (e.g., a culture of cells) or a subject not treated with the compound.

The term "subject" as used herein refers to mammals, such as humans, cats, dogs, horses, cattle, etc.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

Compounds

Provided herein are novel compounds. The compounds may include modulators of the GABA$_A$ receptor Alpha5 subunit. The compounds may include positive allosteric modulators of GABA$_A$ receptor Alpha5 subunit.

Compounds may be of the following formula (I):

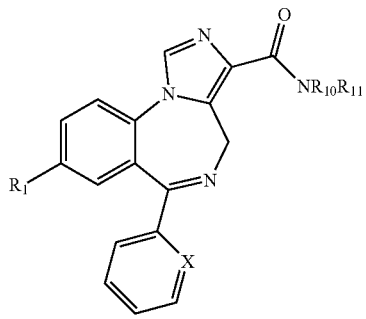

(I)

or a salt thereof, wherein:
X is selected from the group consisting of N, C—H, C—F, C—Cl, C—Br, C—I, and C—NO$_2$;
R$^1$ is selected from the group consisting of —Br, C≡CH, —C≡C—Si(CH$_3$)$_3$, -cyclopropyl, and bicycle[1.1.1]pentane

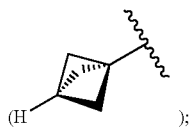

and
R$^{10}$ and R$^{11}$ are independently selected from H, C$_{1-6}$ alkyl, cycloalkyl, or together may form a cycloalkyl ring.

In some embodiments, X is N. In some embodiments, X is CH. In some embodiments, X is CF. In some embodiments, X is CCl. In some embodiments, X is CBr. In some embodiments, X is CI. In some embodiments, R$^1$ is —Br. In some embodiments, R$^1$ is —C≡CH. In some embodiments, R$^1$ is —C≡C—Si(CH$_3$)$_3$. In some embodiments, R$^1$ is -cyclopropyl. In some embodiments, R$^1$ is bicycle[1.1.1]pentane.

Compounds may be of the following formula (II):

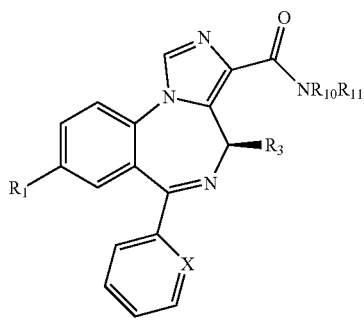

(II)

or a salt thereof, wherein:
X is selected from the group consisting of N, C—H, C—F, C—Cl, C—Br, C—I, and C—NO$^2$;
R$^1$ is selected from the group consisting of —Br, —C≡CH, —C≡C—Si(CH$_3$)$_3$, -cyclopropyl, and bicycle[1.1.1]pentane

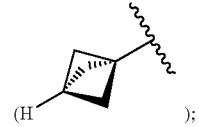

R$_3$ is selected from the group consisting of —CH$_3$, —CH$_2$CH$_3$, —CH(CH$_3$)$_2$, —CD$_3$, —OH, —F, —Cl, —CF$_3$, and —CCl$_3$; and
R$^{10}$ and R$^{11}$ are independently selected from H, C$_{1-6}$ alkyl, cycloalkyl, or together may form a cycloalkyl ring.

In some embodiments, X is N. In some embodiments, X is CH. In some embodiments, X is CF. In some embodiments, X is CCl. In some embodiments, X is CBr. In some embodiments, X is Cl. In some embodiments, R$^1$ is —Br. In some embodiments, R$^1$ is —C≡CH. In some embodiments, R$^1$ is —C≡C—Si(CH$_3$)$_3$. In some embodiments, R$^1$ is -cyclopropyl. In some embodiments, R$^1$ is bicycle[1.1.1]pentane. In some embodiments, R$^3$ is —H. In some embodiments, R$^3$ is —CH$_3$. In some embodiments, R$^3$ is —CH$_2$CH$_3$. In some embodiments, R$^3$ is —CH(CH$_3$)$_2$. In some embodiments, R$^3$ is F. In some embodiments, R$^3$ is Cl. In some embodiments, R$^3$ is —CF$_3$. In some embodiments, R$^3$ is —CCl$_3$.

Compounds may be of the following formula (III):

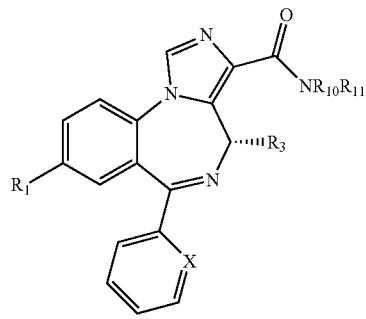

(III)

or a salt thereof, wherein:
X is selected from the group consisting of N, C—H, C—F, C—Cl, C—Br, C—I, and C—NO$_2$;
R$^1$ is selected from the group consisting of —Br, —C≡CH, —C≡C—Si(CH$_3$)$_3$, -cyclopropyl, and bicycle[1.1.1]pentane

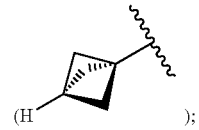

R$_3$ is selected from the group consisting of —CH$_3$, —CH$_2$CH$_3$, —CH(CH$_3$)$_2$, —CD$_3$, —OH, —F, —Cl, —CF$_3$, and —CCl$_3$; and
R$^{10}$ and R$^{11}$ are independently selected from H, C$_{1-6}$ alkyl, cycloalkyl, or together may form a cycloalkyl ring.

In some embodiments, X is N. In some embodiments, X is CH. In some embodiments, X is CF. In some embodiments, X is CCl. In some embodiments, X is CBr. In some embodiments, X is Cl. In some embodiments, R¹ is —Br. In some embodiments, R¹ is —C≡CH. In some embodiments, R¹ is —C≡C—Si(CH₃)₃. In some embodiments, R¹ is -cyclopropyl. In some embodiments, R¹ is bicycle[1.1.1]pentane. In some embodiments, R³ is —H. In some embodiments, R³ is —CH₃. In some embodiments, R³ is —CH₂CH₃. In some embodiments, R³ is —CH(CH₃)₂. In some embodiments, R³ is F. In some embodiments, R³ is Cl. In some embodiments, R³ is —CF₃. In some embodiments, R³ is —CCl₃.

Compounds may be of the following formula (IV):

(IV)

or a pharmaceutically acceptable salt thereof, wherein:

X is selected from the group consisting of N, C—H, C—F, C—Cl, C—Br, C—I, and C—NO₂;

R₁ is selected from the group consisting of —Br, —C≡CH, —C≡C—Si(CH₃)₃, -cyclopropyl, and bicycle[1.1.1]pentane

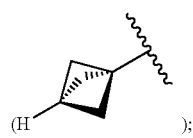

and

R₁₃ is selected from the group consisting of —H, —CD₃, C₁₋₆ alkyl, and cycloalkyl;

In some embodiments, X is N. In some embodiments, X is CH. In some embodiments, X is CF. In some embodiments, X is CCl. In some embodiments, X is CBr. In some embodiments, X is Cl. In some embodiments, R¹ is —Br. In some embodiments, R¹ is —C≡CH. In some embodiments, R¹ is —C≡C—Si(CH₃)₃. In some embodiments, R¹ is -cyclopropyl. In some embodiments, R¹ is bicycle[1.1.1]pentane. In some embodiments, R¹³ is —CH₃, —CH₂CH₃, or CH(CH₃)₂.

In some embodiments, the compound of Formula (IV) is not

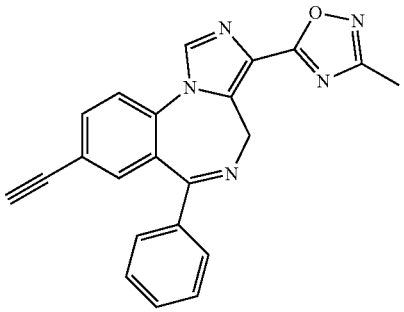

,

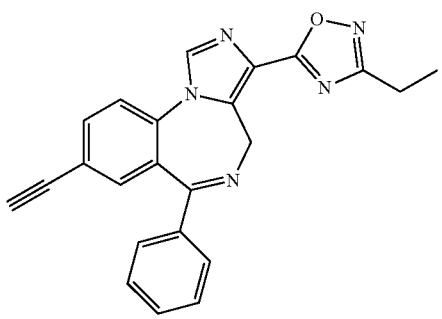

,

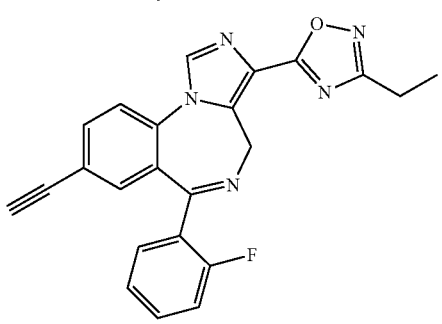

,

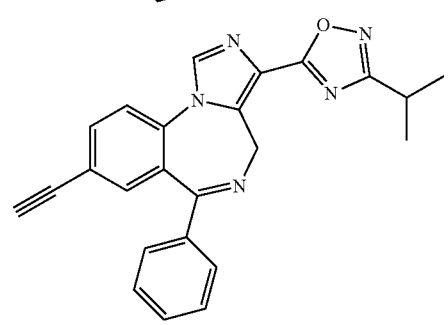

, or

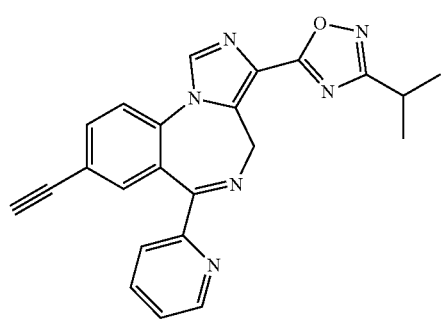

-continued

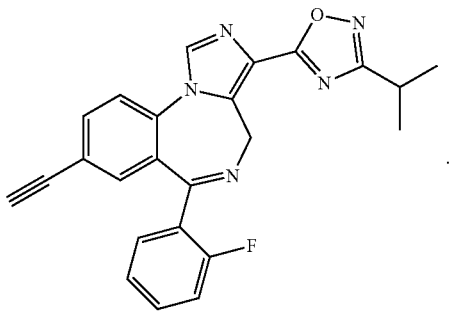

Compounds may be of the following formula (V):

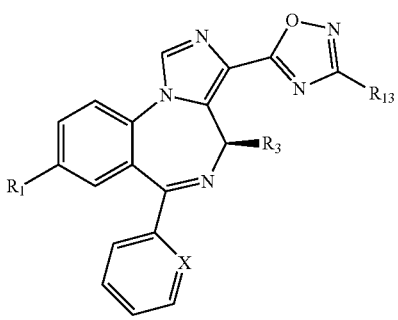
(V)

or a salt thereof, wherein:
X is selected from the group consisting of N, C—H, C—F, C—Cl, C—Br, C—I, and C—$NO_2$;
$R^1$ is selected from the group consisting of —Br, —C≡CH, —C≡C—Si$(CH_3)_3$, -cyclopropyl, and bicycle[1.1.1]pentane

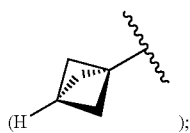

$R_3$ is selected from the group consisting of —$CH_3$, —$CH_2CH_3$, —CH$(CH_3)_2$, —$CD_3$, —OH, —F, —Cl, —$CF_3$, and —$CCl_3$; and
$R^{13}$ is selected from the group consisting of —H, —$CD_3$, $C_{1-6}$ alkyl, and cycloalkyl.

In some embodiments, X is N. In some embodiments, X is CH. In some embodiments, X is CF. In some embodiments, X is CCl. In some embodiments, X is CBr. In some embodiments, X is Cl. In some embodiments, $R^1$ is —Br. In some embodiments, $R^1$ is —C≡CH. In some embodiments, $R^1$ is —C≡C—Si$(CH_3)_3$. In some embodiments, $R^1$ is -cyclopropyl. In some embodiments, $R^1$ is bicycle[1.1.1]pentane. In some embodiments, $R^3$ is —H. In some embodiments, $R^3$ is —$CH^3$. In some embodiments, $R^3$ is —$CH_2CH_3$. In some embodiments, $R^3$ is —CH$(CH_3)_2$. In some embodiments, $R^3$ is F. In some embodiments, $R^3$ is Cl. In some embodiments, $R^3$ is —$CF_3$. In some embodiments, $R^3$ is —$CCl_3$. In some embodiments, $R^{13}$ is —$CH_3$, —$CH_2CH_3$, or CH$(CH_3)_2$.

Compounds may be of the following formula (VI):

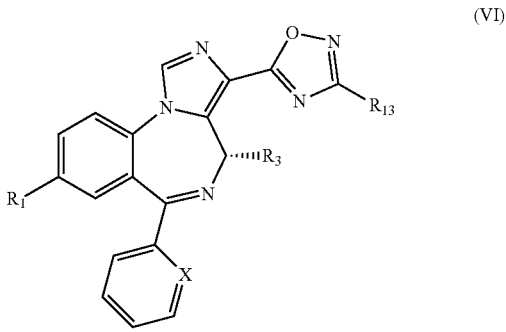
(VI)

or a salt thereof, wherein:
X is selected from the group consisting of N, C—H, C—F, C—Cl, C—Br, C—I, and C—$NO_2$;
$R^1$ is selected from the group consisting of —Br, —C≡CH, —C≡C—Si$(CH_3)_3$, -cyclopropyl, and bicycle[1.1.1]pentane

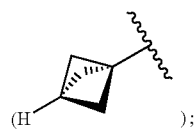

$R_3$ is selected from the group consisting of —$CH_3$, —$CH_2CH_3$, —CH$(CH_3)_2$, —$CD_3$, —OH, —F, —Cl, —$CF_3$, and —$CCl_3$; and
$R^{13}$ is selected from the group consisting of —H, —$CD_3$, $C_{1-6}$ alkyl, and cycloalkyl.

In some embodiments, X is N. In some embodiments, X is CH. In some embodiments, X is CF. In some embodiments, X is CCl. In some embodiments, X is CBr. In some embodiments, X is Cl. In some embodiments, $R^1$ is —Br. In some embodiments, $R^1$ is —C≡CH. In some embodiments, $R^1$ is —C≡C—Si$(CH_3)_3$. In some embodiments, $R^1$ is -cyclopropyl. In some embodiments, $R^1$ is bicycle[1.1.1]pentane. In some embodiments, $R^3$ is —H. In some embodiments, $R^3$ is —$CH_3$. In some embodiments, $R^3$ is —$CH_2CH_3$. In some embodiments, $R^3$ is —CH$(CH_3)_2$. In some embodiments, $R^3$ is F. In some embodiments, $R^3$ is Cl. In some embodiments, $R^3$ is —$CF_3$. In some embodiments, $R^3$ is —$CCl_3$. In some embodiments, $R^{13}$ is —$CH_3$, —$CH_2CH_3$, or CH$(CH_3)_2$.

In some embodiments, for formulas (IV)-(VI), $R^{13}$ is not $C_{1-6}$ alkyl, particularly ethyl. In some embodiments for formulas (I)-(III), the compound is not one or more of:

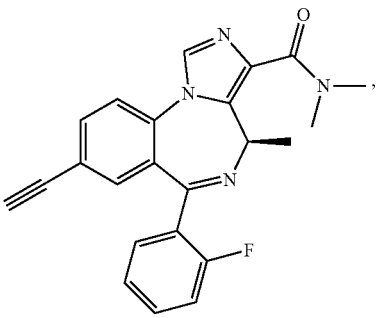 [SMILES: C#Cc1ccc2c(c1)C(c1ccccc1F)=N[C@H](C)c1c(C(=O)N(C)C)ncn1-2]

In some embodiments, compounds may be selected from the following:
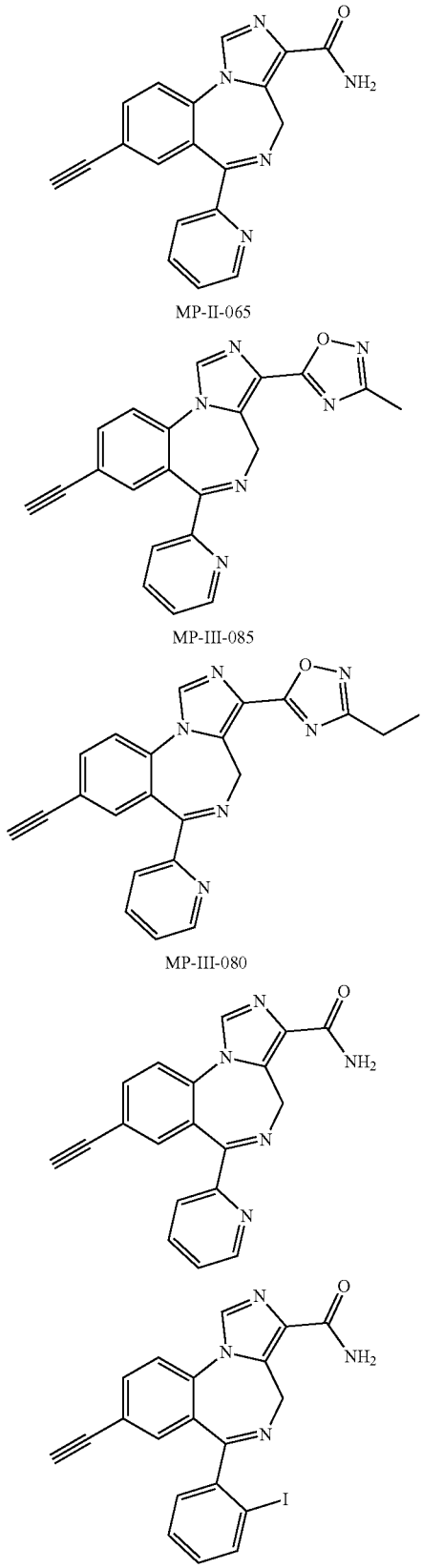
MP-II-065
MP-III-085
MP-III-080
-continued
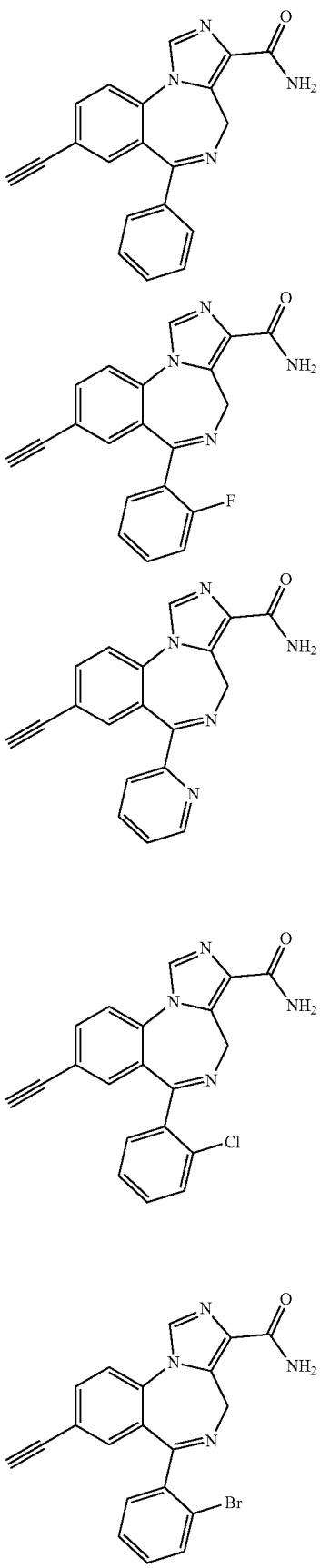

-continued
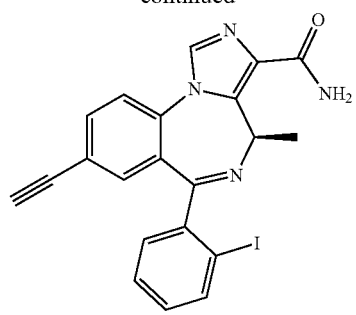
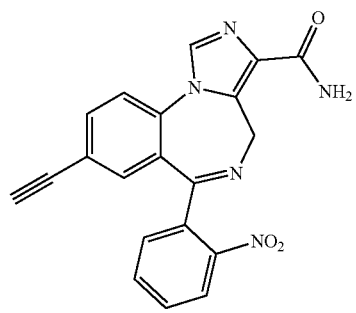
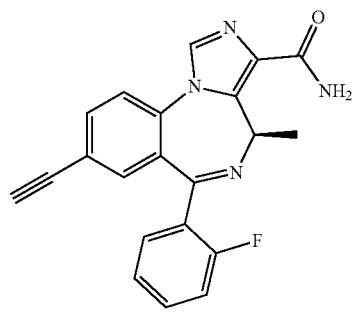
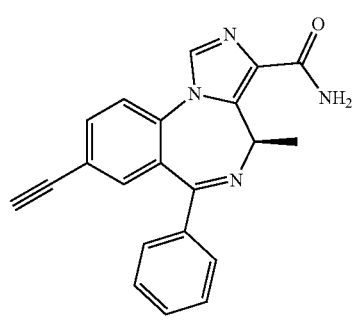
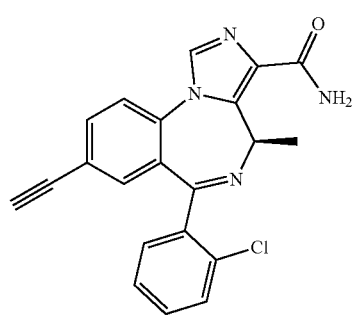
-continued
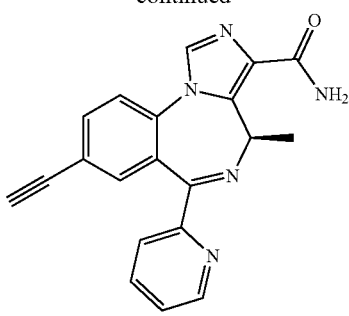
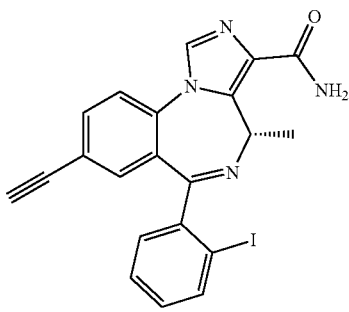
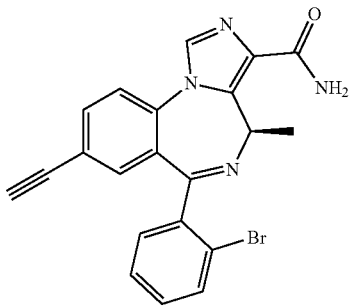
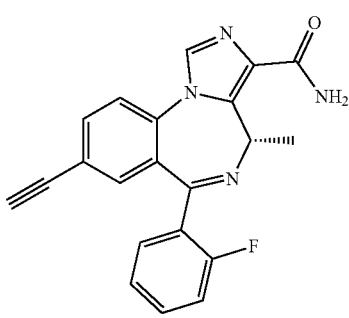

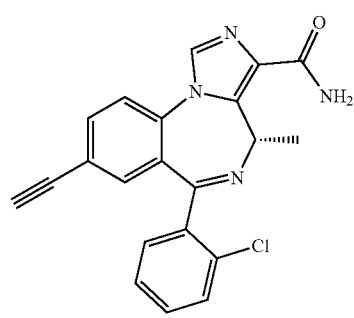
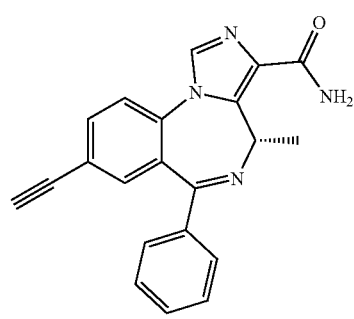
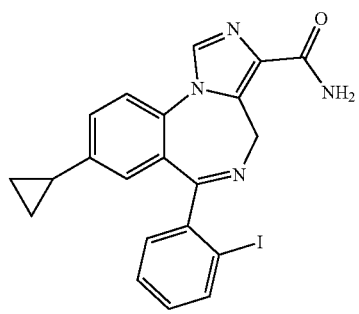
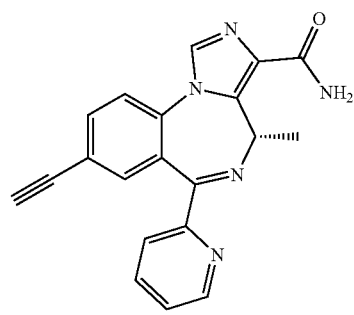
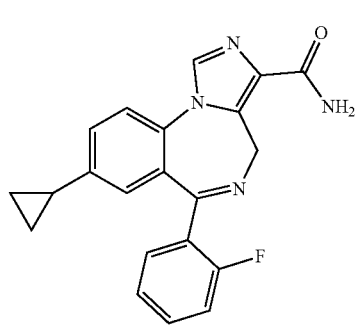
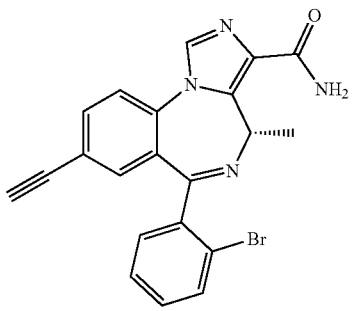
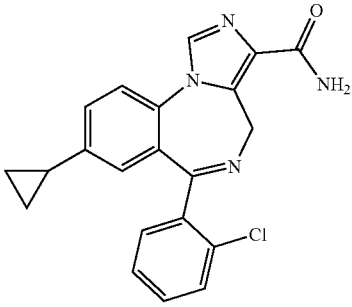
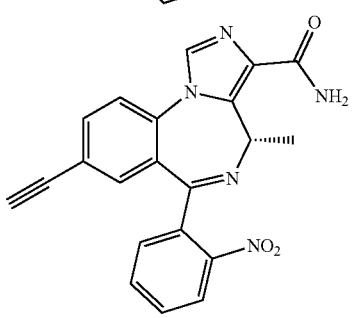
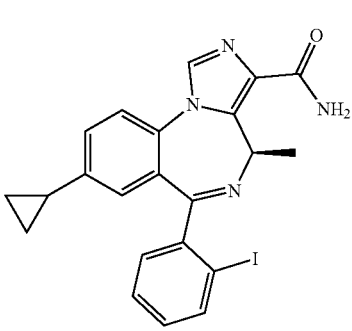
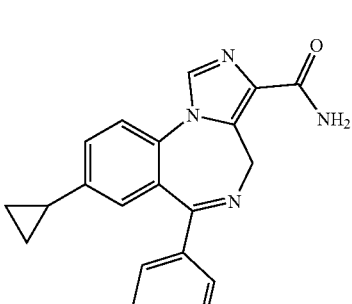

-continued
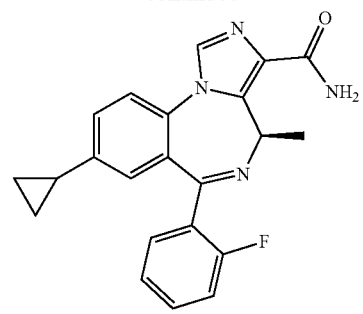
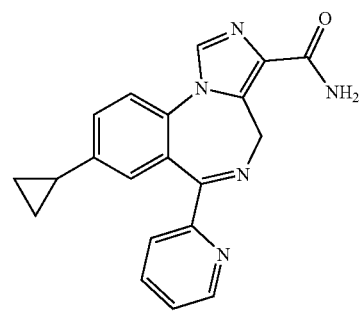
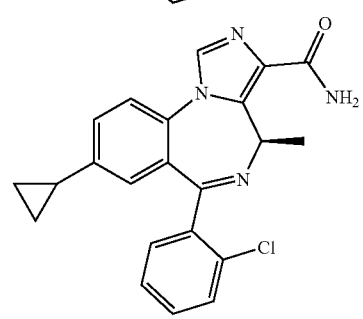
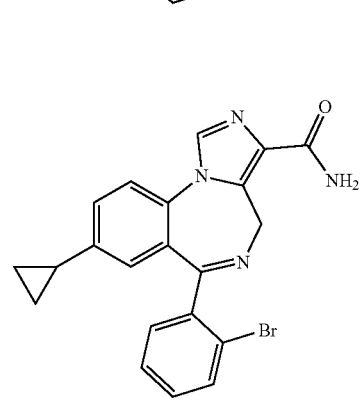
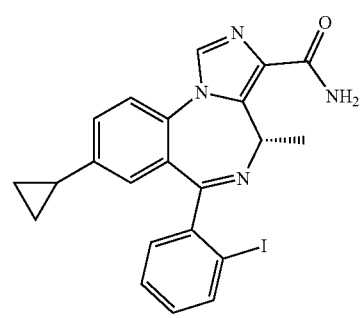
-continued
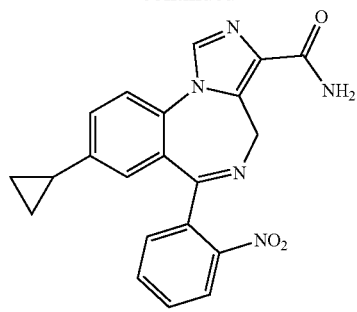
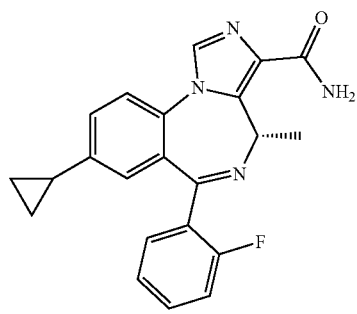
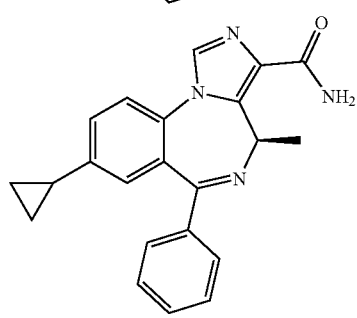
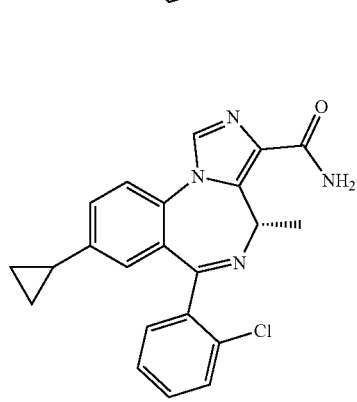
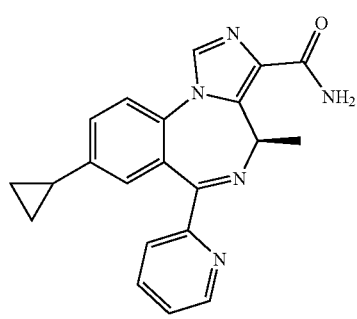

27
-continued
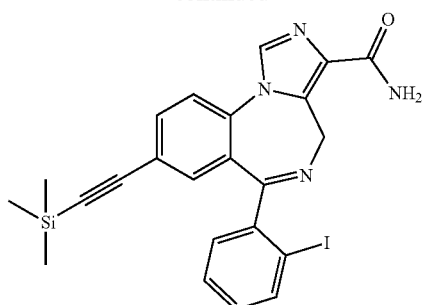
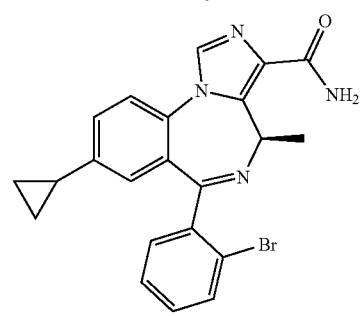
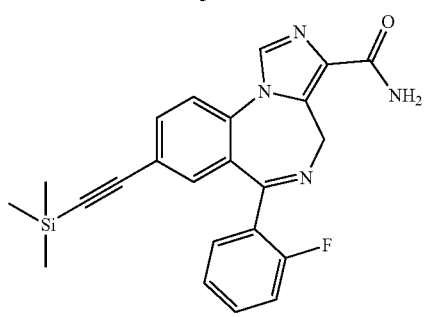
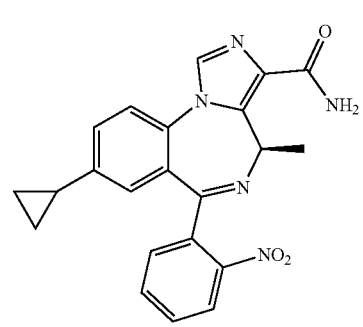
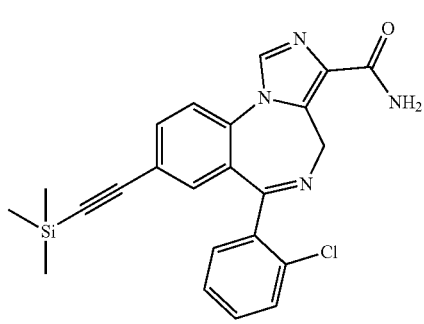
28
-continued
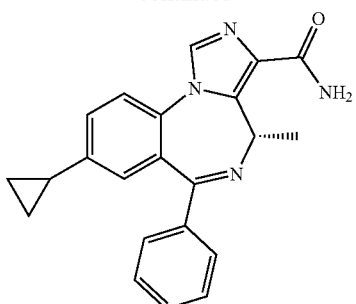
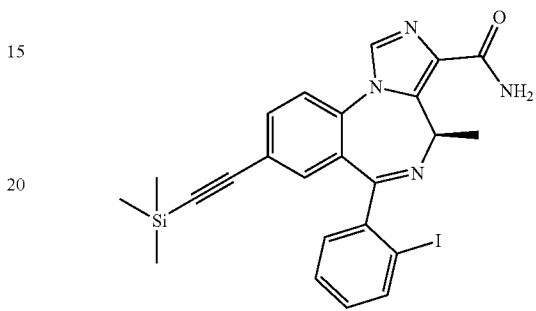
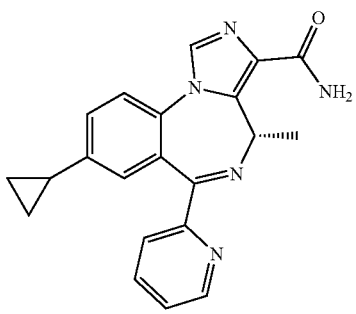
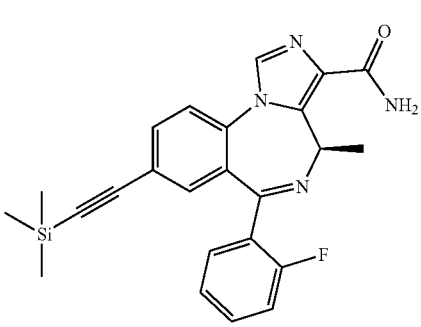
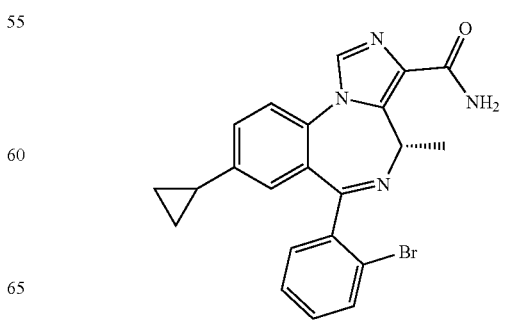

29
-continued
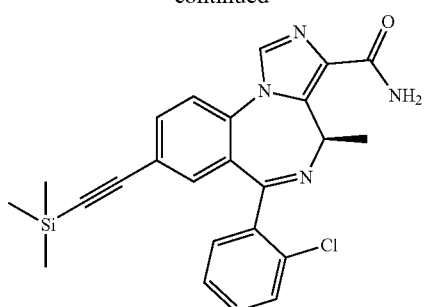
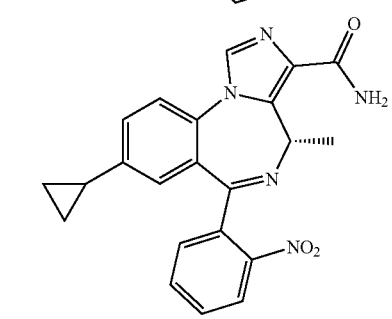
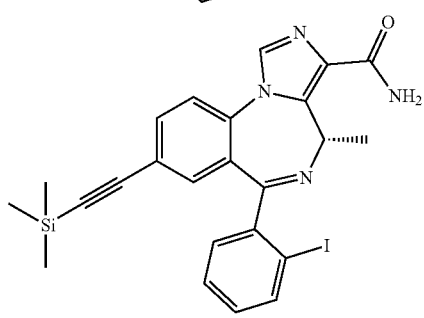
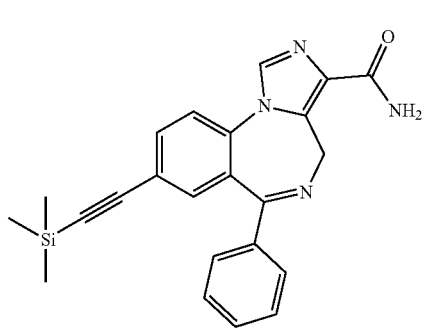
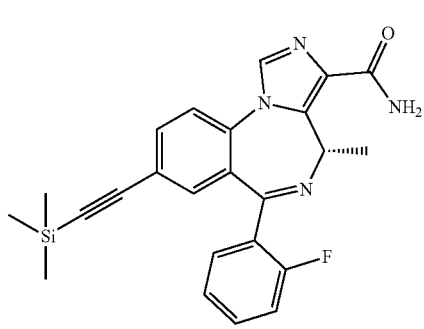
30
-continued
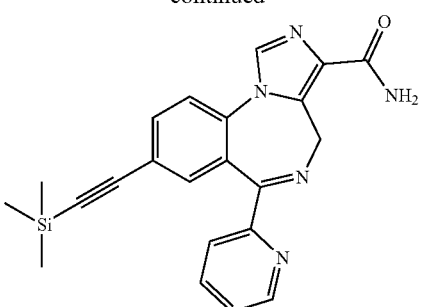
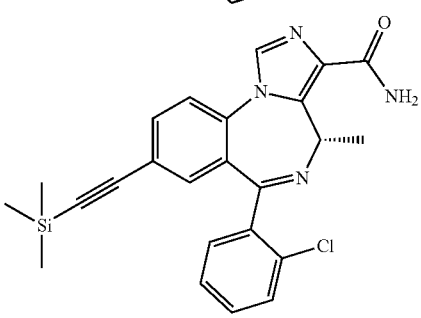
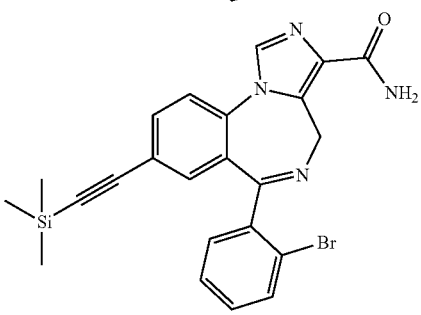
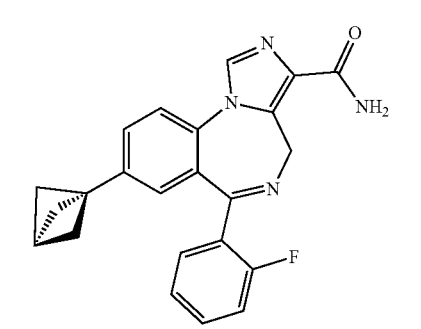
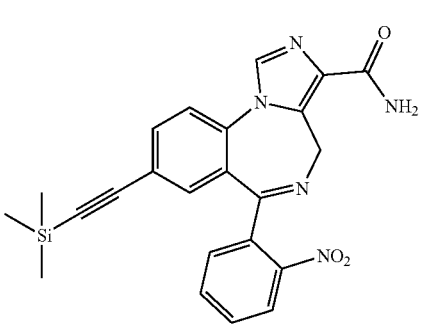

31
-continued
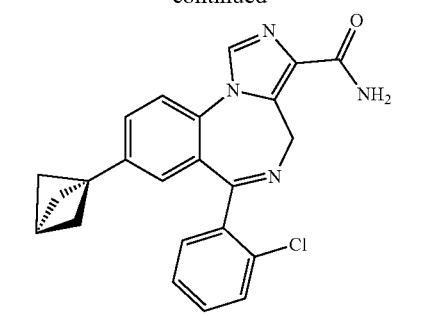
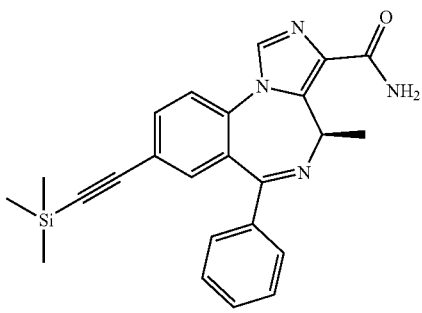
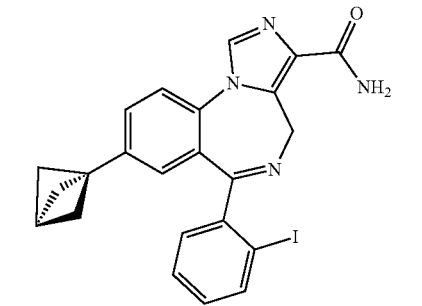
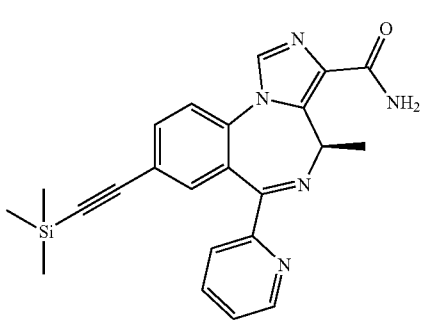
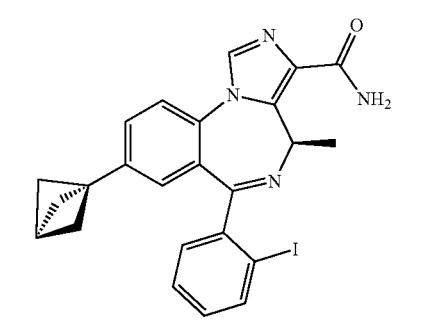
32
-continued
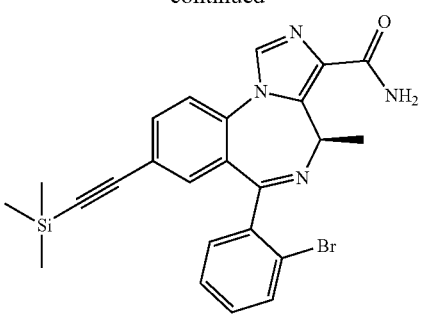
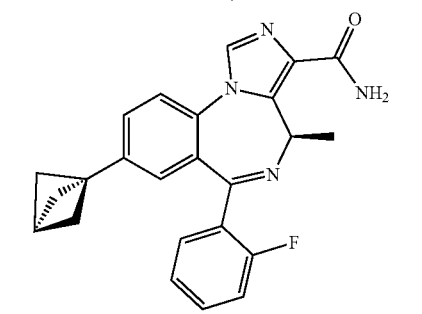
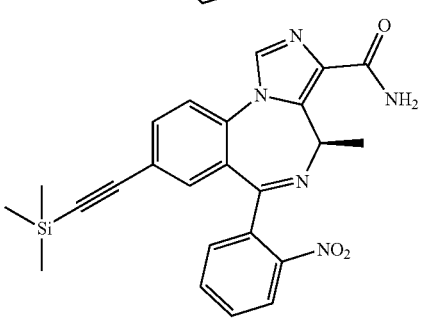
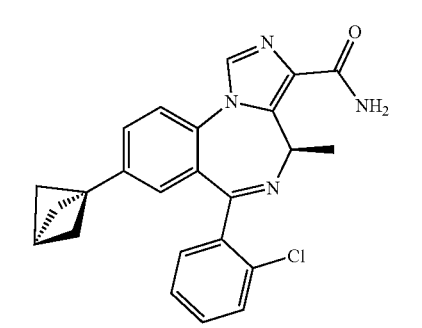
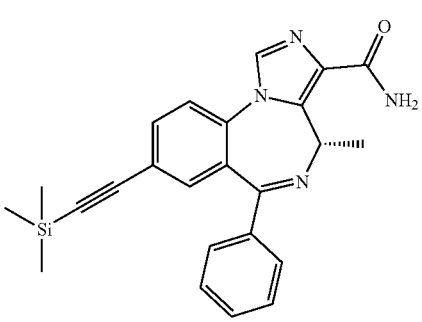

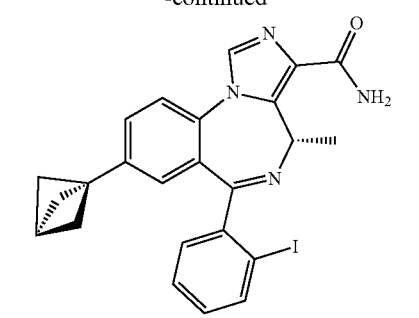
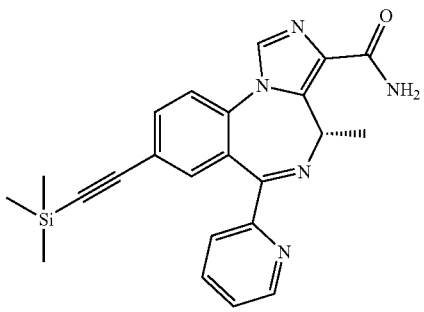
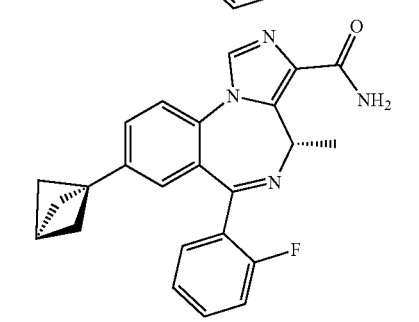
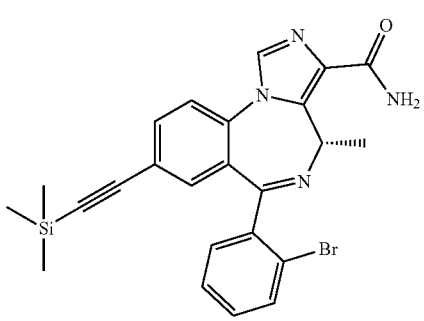
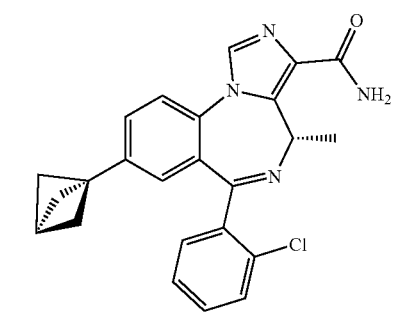
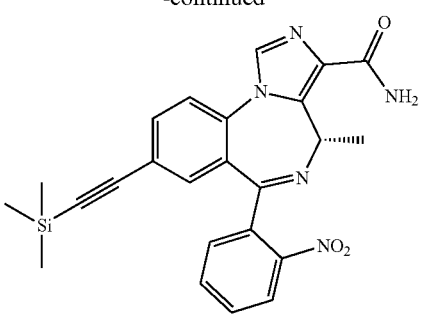
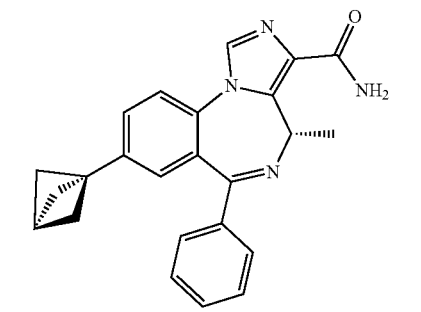
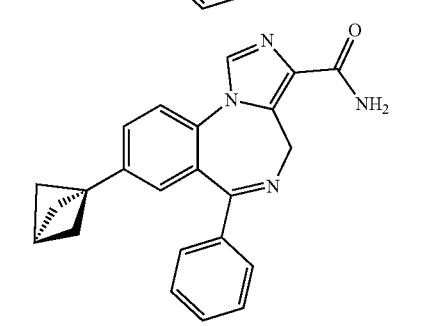
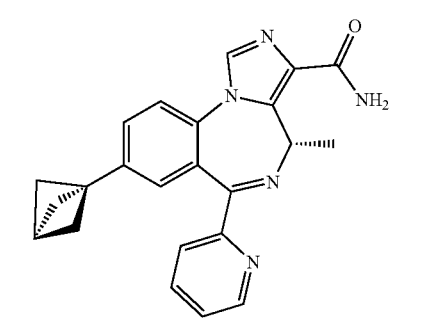
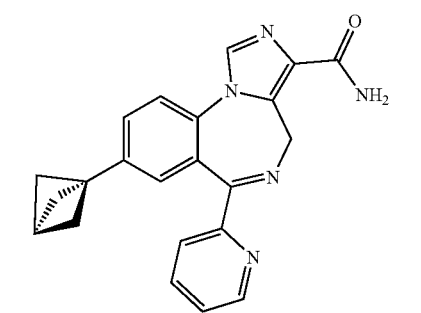

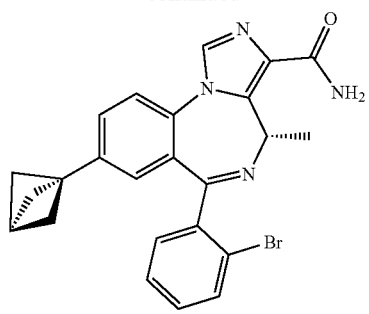
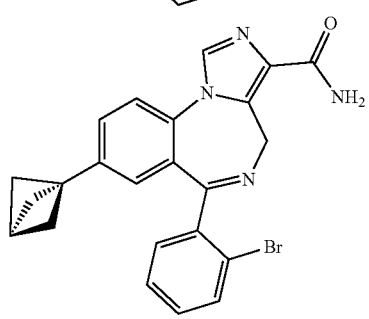
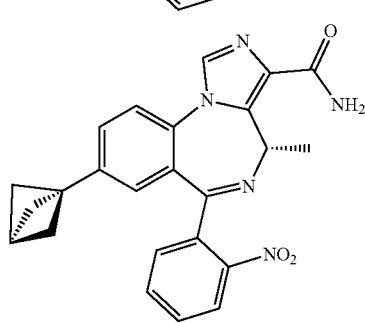
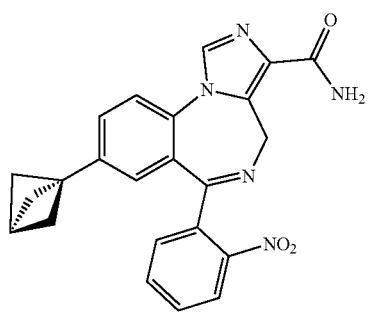
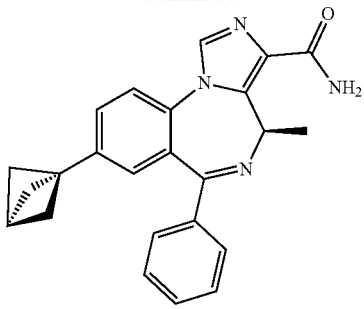
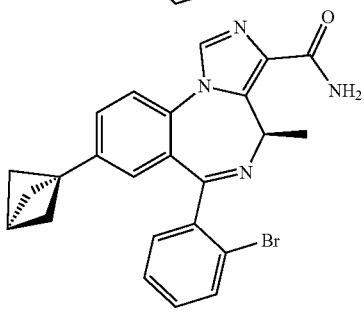
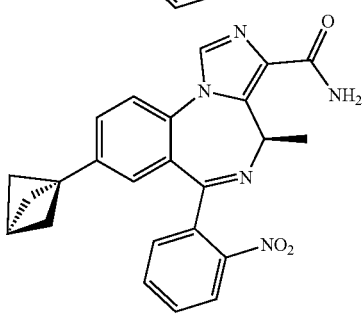
Compounds may further include the following, wherein X is CH, CF, CCl, or N; $R^4$ is H or $CH_3$; and $R^5$ is H or $CH_3$:
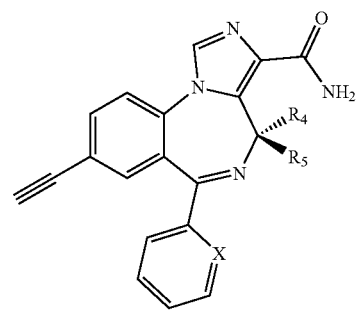
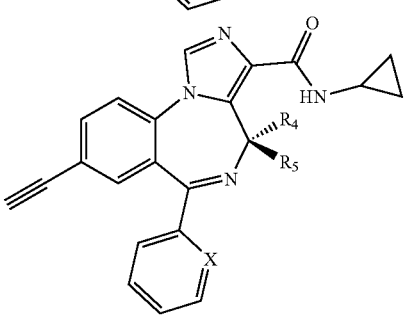

37
-continued
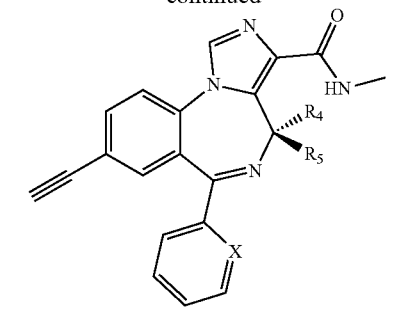
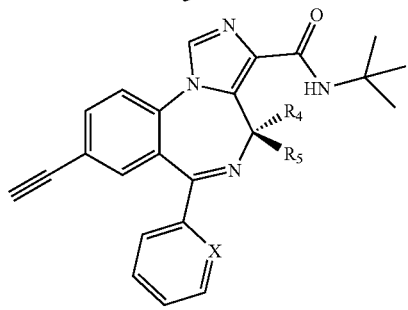
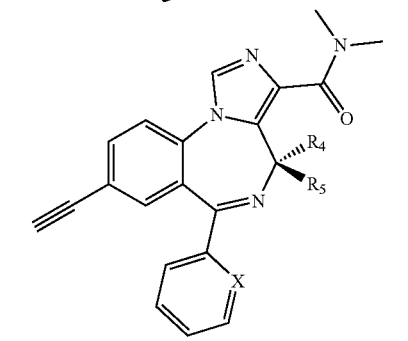
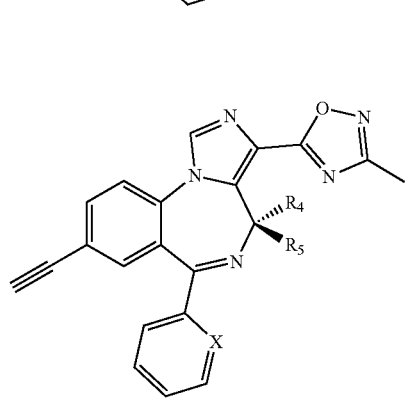
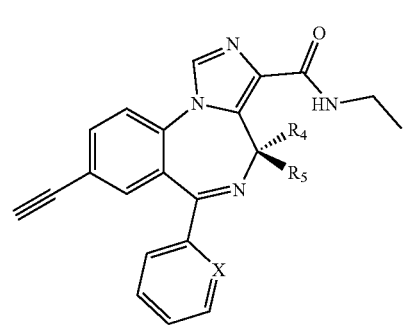
38
-continued
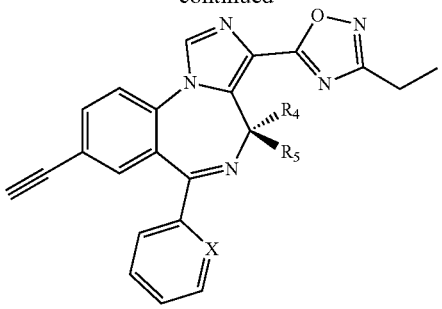
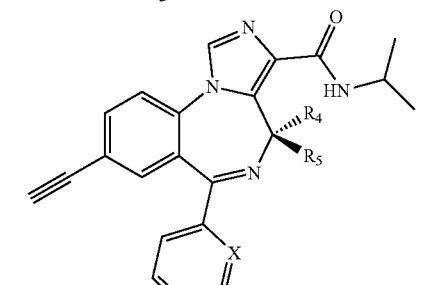
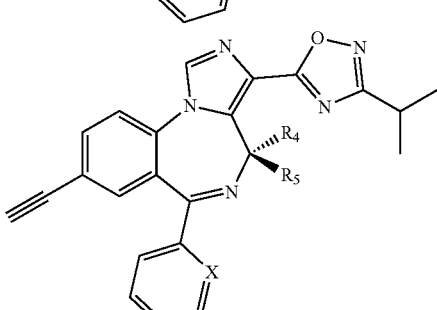
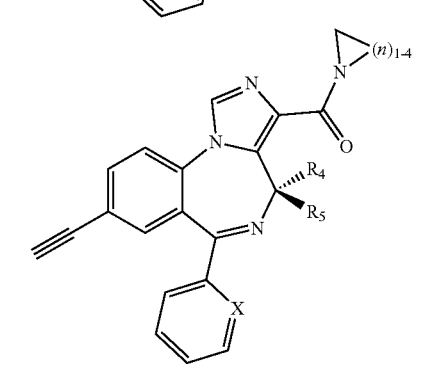
Compounds may further include the following:
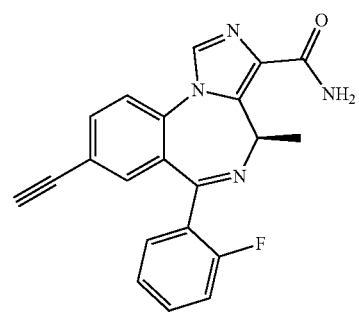
MP-III-019.B -continued

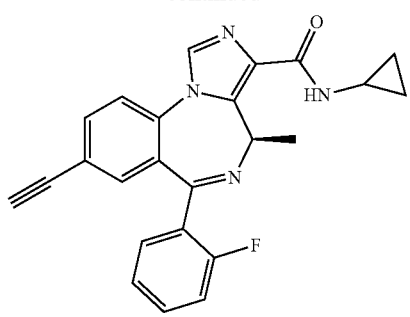

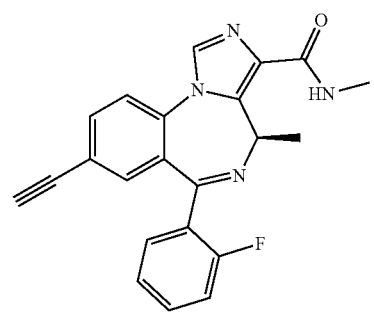

MP-III-022

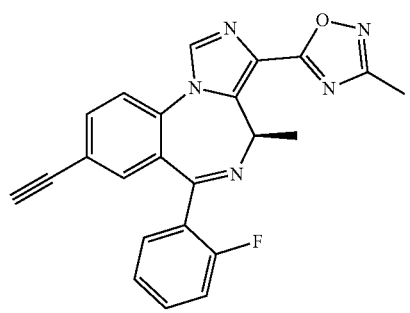

MP-IV-004

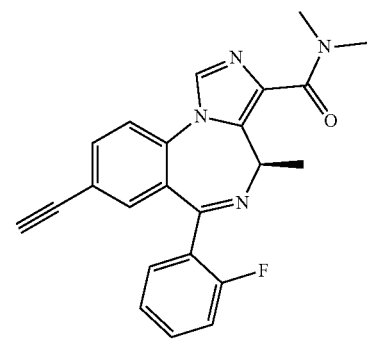

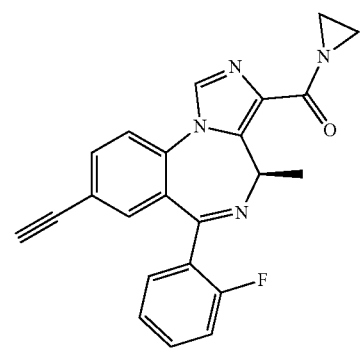

-continued

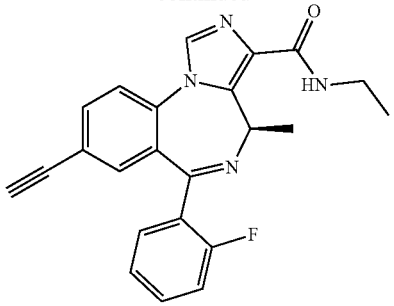

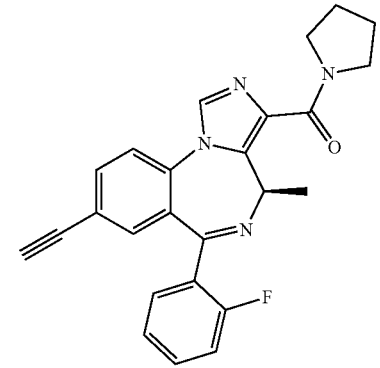

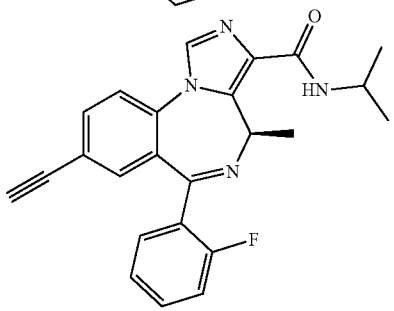

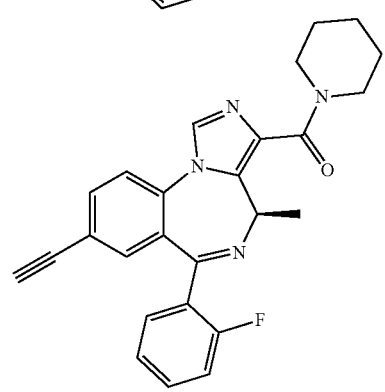

For compounds of formula (I), (II), (III), (IV), (V), and (VI), groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Compounds of formula (I), (II), (III), (IV), (V), and (VI) include compounds that differ only in the presence of one or more isotopically enriched atoms. For example, compounds may have the present structures except for the replacement of hydrogen by deuterium or tritium, or the replacement of a carbon by a $^{13}C$- or $^{14}C$-enriched carbon.

A compound of formula (I), (II), (III), (IV), (V), or (VI) can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds. Suitable pharmaceutically acceptable salts of the compounds of this disclosure include acid addition salts which may, for example, be formed by mixing a solution of the compound according to the disclosure with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. Furthermore, where the compounds of the disclosure carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In addition to salt forms, the present disclosure may also provide compounds of formula (I), (II), (III), (IV), (V), or (VI) that are in a prodrug form. Prodrugs of the compounds are those compounds that readily undergo chemical changes under physiological conditions to provide the compounds. Prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Compounds of formula (I), (II), (III), (IV), (V), and (VI) can be, for example, an enantiomerically enriched isomer of a stereoisomer described herein. Enantiomer, as used herein, refers to either of a pair of chemical compounds whose molecular structures have a mirror-image relationship to each other. For example, a compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

A preparation of a compound of formula (I), (II), (III), (IV), (V), or (VI) may be enriched for an isomer of the compound having a selected stereochemistry, e.g., R or S, corresponding to a selected stereocenter. For example, the compound may have a purity corresponding to a compound having a selected stereochemistry of a selected stereocenter of at least about 60%, 65%, 70%, 75%, 80%, 85%, 90%, 95%, 96%, 97%, 98%, or 99%. A compound can, for example, include a preparation of a compound disclosed herein that is enriched for a structure or structures having a selected stereochemistry, e.g., R or S, at a selected stereocenter.

In some embodiments, a preparation of a compound of formula (I), (II), (III), (IV), (V), or (VI) may be enriched for isomers (subject isomers) which are diastereomers of the compound. Diastereomer, as used herein, refers to a stereoisomer of a compound having two or more chiral centers that is not a mirror image of another stereoisomer of the same compound. For example, the compound may have a purity corresponding to a compound having a selected diastereomer of at least about 60%, 65%, 70%, 75%, 80%, 85%, 90%, 95%, 96%, 97%, 98%, or 99%.

When no specific indication is made of the configuration at a given stereocenter in a compound, any one of the configurations or a mixture of configurations is intended.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound of formula (I), (II), (III), (IV), (V), or (VI) can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

Synthesis of Compounds

Compounds of formula (I), (II) (III), (IV), (V), and (VI) may be synthesized from commercially available starting materials. Exemplary syntheses are illustrated below in the Examples.

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Evaluation of Compounds

Compounds may be analyzed using a number of methods, including ex vivo and in vivo methods.

For example, the $GABA_A$ subunit selectivity of compounds can be evaluated using competitive binding assays. Such assays have been previously described (Choudhary et al. *Mol Pharmacol.* 1992, 42, 627-33; Savić et al. *Progress in Neuro-Psychopharmacology & Biological Psychiatry*, 2010, 34, 376-386). The assays involve the use of a radiolabeled compound known to bind to $GABA_A$ receptors, such as [$^3$H]flunitrazepam. Membrane proteins can be harvested and incubated with the radiolabeled compound, and non-specific binding can be evaluated by comparing binding of the radiolabeled compound to another, non-labeled compound (e.g., diazepam). Bound radioactivity can be quantified by liquid scintillation counting. Membrane protein concentrations can be determined using commercially available assay kits (e.g., from Bio-Rad, Hercules, Calif.).

Compounds can also be evaluated in electrophysiological assays in Xenopus oocytes, or in transfected cell lines. Compounds can be pre-applied before the addition of GABA, which can then be co-applied with the compounds until a peak response is observed. Between applications, oocytes or transfected cell lines can be washed to ensure full recovery from desensitization. For current measurements of the GABA response magnitude (Fisher et al. *Mol Pharmacol,* 1997, 52, 714-724), the oocytes or transfected cells can be impaled with microelectrodes, and recordings performed using voltage clamps.

Compounds described herein may be $GABA_A$ receptor ligands which exhibit antidepressant, anxiolytic or pro-cognitive activities due to increased agonist efficacy at $GABA_A/\alpha5$ and/or $GABA_A/\alpha2$, $GABA_A/\alpha3$ or $GABA_A/\alpha_{2/3}$ receptors. The compounds may possess at least 2-fold, suitably at least 5-fold, and advantageously at least a 10-fold, selective efficacy for $GABA_A/\alpha5$ receptors relative to the $GABA_A/\alpha1$ receptors. However, compounds which are not selective in terms of their agonist efficacy for the $GABA_A/\alpha5$ receptors are also encompassed within the scope of the present disclosure. Such compounds will desirably exhibit functional selectivity by demonstrating pro-cognitive and/or antidepressant activity with decreased sedative-hypnotic/muscle relaxant/ataxic activity due to decreased efficacy at $GABA_A/\alpha1$ receptors.

GABAergic receptor subtype selective compounds which are ligands of the GABAA receptors acting as agonists or partial agonists or positive allosteric modulator (PAM) are referred to hereinafter as "$GABA_A$ receptor agonists" or "$GABA_A$ receptor partial agonists" or "agonists" or "partial agonists" or "PAM". In particular these are compounds that are ligands of the benzodiazepine (BZ) binding site of the $GABA_A$ receptors, and hence acting as BZ site agonists, partial agonists or PAMs. Such ligands also include compounds acting at the GABA site or at modulatory sites other than the benzodiazepine site of $GABA_A$ receptors.

GABAergic receptor subtype selective compounds act as agonists, partial agonists or PAM by selectively or preferentially activating the $GABA_A/\alpha5$ receptors, as compared to the $GABA_A/\alpha_1$ receptors. A selective or preferential therapeutic agent has less binding affinity or efficacy to the $GABA_A/\alpha_1$ receptors compared to the $GABA_A/\alpha_5$, $GABA_A/\alpha_2$ or $GABA_A/\alpha_3$ receptors. Alternatively, the agent binds with a comparable affinity to $GABA_A/\alpha_5$, $GABA_A/\alpha_1$, $GABA_A/\alpha_2$, and $GABA_A/\alpha_3$ receptors but exerts preferential efficacy of the $GABA_{A/\alpha5}$ receptor activation compared to the $GABA_A/\alpha1$ receptors. Alternatively, a selective agent can also have greater or lesser binding affinity to $GABA_A/\alpha_2$ and $GABA_A/\alpha_3$ receptors relative to $GABA_A/\alpha_5$. The Bz/GABA agonists act at the benzodiazepine site of the respective $GABA_A$ receptors but are not restricted to this drug binding domain in its receptor interactions.

Pharmacokinetic properties of the GABA receptor subtype specific compounds are assessed measuring compound content in plasma and brain (Piantadosi et al. *Front Pharmacol,* 2016, 7, 446) following intra peritoneal, per esophagus and intravenous administration. Mice and rats receive the different compounds at different doses. Serial brain and plasma concentrations are obtained at different times and LC/MS/MS is used to measure the concentration of each compound in each sample. Using this assay, the $C_{max}$, $T_{max}$, $AUC_{0-12}$, $AUC_{0-\infty}$, $T_{1/2}$ and $\beta$ are measured for each compound in each tissue, each route of administration for both species. Compounds with optimal pharmacokinetic properties are considered for potential therapeutic intervention.

Metabolic availability of the GABA receptor subtype specific compounds are assessed by measuring the rate of degradation of the compound using human and mouse liver microsomal assay. Liver microsomes are incubated with each compound and half-life, intrinsic clearance and metabolic rates are measured. Compounds with optimal metabolic parameters are considered for potential therapeutic intervention.

Cell toxicity and viability can be evaluated in in vitro conditions. Human cells (HEPG2 and/or HEK293 cell lines from liver and kidney, respectively) are incubated with the compounds and the cell viability assay is performed to determine toxicity of the compounds. Compounds with a $LD_{50}$ superior to 100 µM are considered to have no toxic effect on cell viability.

Other methods for evaluating compounds are known to those skilled in the art. For evaluating potential to improve cognitive functions, numerous behavioral tests exist in rodents and other mammals, including but not limited to tests for attention, visual and auditory processing, motor function, short term and working memory, learning and memory processes for multiple cognitive dimensions (procedural, declarative, spatial/reference memory etc.).

Declarative and procedural cognitive functions can be evaluated using various mazes, including the Morris water maze, the radial maze, the Barnes' hole board etc (Gallagher et al, *Behav Neurosci,* 1993, 107, 618-626; Vorhees and Williams, *ILAR J,* 2014, 55, 310-332; Schwabe et al. *Neurosci & Biobehavioral review,* 2010, 34, 584-591). These paradigms test learning and memory abilities, and are used to identify efficacy of compounds in improving learning and memory capacities of animals to refer to their environment to solve a challenge. Animals are trained to learn the task and to recall the information during a retrieval/probe test. Methods in the field for testing potential pro-cognitive properties of compounds include administration of the compounds during the learning and/or the recall phases of the tests. Compounds that reduce the latency to succeed and/or the number of errors in the task during the learning and/or the recall phases are considered to have potential pro-cognitive actions.

Other tests measuring cognitive functions include discrimination task between familiar and novel objects/subjects. These tests include but are not limited to variation of the novel object recognition test, place recognition test, the social novelty discrimination, three chamber test, etc. (Morici et al, *Behav Brain Research,* 2015, 292, 241-251; Millan and Bales, *Neurosci & Biobehavioral Reviews,* 2013, 37, 2166-2180). The concept of these tests is to assess the ability of the animal to discriminate between a familiar and a novel element in its environment. Compounds that increase the time interacting with the novel element are considered to have pro-cognitive properties.

Short-term and working memory functions can also be assessed using different tasks employing Morris water maze, Y-Maze or T-Maze apparatuses or variations (Lalonde, *Neurosci & Biobehavioral Reviews,* 2002, 26, 91-104). Briefly, these tests are based on the ability of the animals to keep information for a short period of time, in order to recall the information shortly after the acquisition. Efficient processes of working memory require irrelevant information to be "erased" to allow the acquisition of new relevant information. For example, short-term working memory can be assessed by exploiting the innate tendency of the animals to explore a new environment and rely on their propensity to spontaneously alternate when repetitively given the choice to visit two different arms of the apparatus. Following multiple trials, the number of errors can increase because of a load of interference. The load of interference can be modulated by variation of the delay between trials, with long inter-trial intervals increasing the load of interference indexed as an increase in the number of errors. Stress paradigms, normal aging or other models of neuropsychiatric or neurodegenerative disorders can be used to reduce cognitive performance in these tests. This would be characterized by an increase in the number of errors (i.e. increasing errors in water maze tasks, or a performance around the chance level of 50% in alternation tasks). Compounds that reverse these deficits are considered to have pro-cognitive actions.

For evaluating antidepressant potential of compounds, numerous tests exist in rodents and other mammals to assess emotionality, including but not limited to tests for anxiety-, behavioral despair-, helplessness- or anhedonia-like behavioral responses.

Per standard methods in the field, forced swim test and tail suspension test (Castagne et al. *Curr Protoc Neurosci*, 2011, Chapter 8) are predominantly used to screen antidepressant action in rodents but are also employed as behavioral measures of despair in response to stress. Briefly rodents are acutely or sub-chronically injected for testing potential antidepressant compounds. Rodents are placed in an inescapable situation (in a tank of water or hanged by the tail) and a count of the immobile time is measured as an index of resignation to a state of despair. Compounds that reduced immobility in these tests are considered to have potential antidepressant actions.

Other methods of evaluating antidepressant actions include behavioral reactivity to aversive stimuli such as learned helplessness test or fear conditioning (Cryan and Mombereau, *Molecular Psychiatry*, 2004, 9, 326; Phillips and LeDoux, Behavioral Neuroscience, 1992, 106, 274-285). Both tests rely on the ability of the animals to cope to an adverse conditioned and non-conditioned stimulus. Foot shocks are applied to the animals and the behavioral response produced is used as an index for potential antidepressant properties of the compounds. Compounds that decrease the number and/or latency to escape the foot shock in the learned helplessness test, as well as the time spent freezing in the fear conditioning paradigm are considered to have potential antidepressant actions.

Potential antidepressant activity of the compounds can also be evaluated for their properties to reverse anhedonia-like behaviors observed in animal models exhibiting altered emotionality. For example, the novelty induced hypophagia, the sucrose preference or consumption, or the cookie tests can be employed to assess anhedonia in rodent. Anhedonia is characterized by a decrease in seeking pleasant experiences including but not limited to palatable solution or food (Willner, *Neuropsychobiology*, 2005, 52, 90-110; Nollet et al. *Curr Protoc Neurosci*, 2013, Chapter 5). Compounds that increase the seeking of pleasurable experience are considered to have potential antidepressant actions.

Other methods for evaluating compounds are known to those skilled in the art. Anxiety symptoms are often co-morbid and difficult to separate from the mood spectrum observed in depression or AD. For example, an assessment of anxiolytic effects of compounds can be accomplished objectively and quantitatively with operant-based conflict procedures, as described in Fischer et al. Neuropharmacology 59 (2010) 612-618. Briefly, behavior which is positively reinforced can be suppressed in these procedures by response-contingent administration of a noxious stimulus such as mild electric shock. If a compound has an anxiolytic effect it increases the rates of responding that are normally suppressed by response-contingent delivery of shock. The strength of conflict procedures is their predictive validity with respect to expected therapeutic effects in humans.

Potential anxiolytic activity and locomotor activity can be evaluated in a home-cage like apparatus. Animals with high level of anxiety have a propensity to spend more time hidden in their shelter, limiting their exploratory behaviors. The same setting can be used with the application of a light challenge. Anxious animals continue avoiding the lit zone even after the end of the light challenge (Pham et al. *J Neurosci Methods*, 2009, 178, 323-326). Compounds that increase the exploration and limit this avoidance behavior in these type of test are considered to have potential antidepressant/anxiolytic actions.

Anxiolytic activity can also be evaluated in the light/dark box test by a method developed by Crawley (*Neurosci Biobehav Rev* 1985, 9, 37-44). The light/dark box is a simple noninvasive test for anxiolytic activity. Compounds that increased the latency to enter the dark box and/or increase the time spent in the lit box are considered to have an anxiolytic action.

Potential anxiolytic activity can be measured in the elevated plus maze and the open-field tests (Bailey and Crawley, Methods of Behavior Analysis in Neuroscience, 2009, $2^{nd}$ Edition). In both tests, a conflict is created between the animal's natural tendency to explore and its innate fear of predator threat in an exposed environment. Rodents are placed in the center of the maze/field under a bright light condition. The number of entries as well as the time spent in the exposed areas (open arms/center of the arena) are recorded. Compounds that increase these parameters without decreasing the exploratory behavior are considered to have anxiolytic actions.

Other methods to assess anxiolytic properties of compounds may employ tests that rely on the conflict between the drive for food or sweetened solution and the fear of being placed in a novel environment. In these tests, the latency to approach and to feed in the novelty suppressed feeding or the cookie tests as well as the latency to drink the condensed milk in the novelty induced hypophagia are outcome measures (Nollet et al. *Curr Protoc Neurosci*, 2013, Chapter 5). Compounds that decrease theses parameters are considered to have potential anxiolytic properties.

The marble burying assay (Deacon, *Nat Protocols*, 2006, 1, 122; Kinsey et al., *Pharmacol Biochem Behav* 2011, 98, 21) is another anxiolytic test. Mice or rats are placed in a cage with marbles on top of bedding material which they can dig to bury the marbles. The rodents are then timed and the number of marbles buried is counted. A reduction in marble burying compared to control is considered an anxiolytic effect.

Cognition, depression, anxiety and other behavioral dimensions associated with disorders can be evaluated under normal baseline conditions or using rodent models of the conditions or symptoms. Examples of such models include the unpredictable chronic mild stress, the chronic restraint stress and the social defeat paradigm. For instance, "impaired cognition" and "depressive-like" states can be induced in rodents using a prolonged protocol of unpredictable mild stressors over several weeks. Mild stressors are typically but not exclusively applied in a random manner to provide an unpredictable environment. Mild stressors may include but not limited to changes in light cycles, changes in cage bedding, switching cages, exposure to predator odor, to noise or bright light, social stressor, exposure to aggressive mice. Rodents exposed to these paradigms typically display altered cognitive functions and increased depression- and anxiety-related behaviors and can be assessed by various behavioral tests including but not limited to the ones described herein. Compounds that reverse deficits in these tests can be considered for therapeutic indication.

Cognition, depression, anxiety, and other behavioral dimensions associated with these disorders can be evaluated in rodent models where genetic engineering has been used to induce a cellular or molecular pathology that causes behavioral or physiological changes associated with the disorders. For example, the acute inhibition of SST GABA neurons using a chemogenetic approach induces elevated behavioral emotionality (Soumier and Sibille, *Neuropsychopharmacology*, 2014, 39:9, 2252-62), furthermore, compounds that reduce emotionality can be considered for therapeutic indication.

Deficits in cognitive function associated with neurodegenerative disorders can also be evaluated in the multiple rodent models that have been developed using genetic manipulations to induce pathologies observed in the human brain, such as increased beta-amyloid plaques and/or neurofibrillary tangles. For instance, the TgCRND8 murine model of AD expresses a mutant human bAPP transgene TgCRND8 mice and displays spatial learning deficits at 3 months of age that are accompanied by both increasing levels of Amyloid beta plaques and neurofibrillary tangles in the brain (Janus et al, Nature, 2000, 408:979-982). Data suggests that compounds that reverse or improve cognitive symptoms in these models would be effective in normal or disease related loss of cognition or pathological conditions.

For evaluation of potential to treat schizophrenia, compounds may be tested using a mouse model as described in Gill et al. *Neuropsychopharmacology* 2011, 36: 1903-1911. This mouse model of schizophrenia arises from a development disturbance induced by the administration of a DNA-methylating agent, methylazoxymethanol acetate (MAM), to pregnant dams on gestational day 17. The MAM-treated offspring display structural and behavioral abnormalities, consistent with those observed in human patients with schizophrenia. Antagonism or genetic deletion of the $\alpha 5 GABA_A$ receptor ($\alpha 5 GABA_A$ R) leads to behaviors that resemble some of the behavioral abnormalities seen in schizophrenia, including prepulse inhibition to startle and impaired latent inhibition. The MAM model can be used to show the effectiveness of a benzodiazepine-positive allosteric modulator (PAM) compound selective for the $\alpha 5$ subunit of the $GABA_A R$. In Gill et al., the pathological increase in tonic dopamine transmission in the brain was reversed, and behavioral sensitivity to psychostimulants observed in MAM rats was reduced. The data suggests that such compounds would be effective in alleviating dopamine-mediated psychosis.

Measures of the global locomotion can also be used to assess potential sedative effect of the tested compounds. The mouse is placed in a home-cage like arena and distance travelled is monitored for 30-60 minutes (Tang et al. Behavioral Brain Research, 2002, 136, 555-569). Compounds that induce drastic reduction in the distance travelled are considered having sedative or undesirable side effects.

Measures of spatial and motor coordination can also be assessed to assess the sedative-hypnotic/muscle relaxant/ataxic activity of compounds. The sensorimotor rotarod test is typically used for these assessments (Voss et al. *European Journal of Pharmacology*, 2003, 482, 215-222). This test is carried out 10, 30 and 60 minutes after injection of the test compound. Mice or rats are tested on a rotating rod (rotarod) at 15 rpm for maximum 3 min and the time of fall is recorded. Falling before the 3 minutes period of testing would be indicative of any locomotor coordination impairment induced by the compound.

Such compounds will desirably exhibit functional selectivity by demonstrating pro-cognitive and/or antidepressant activity with decreased sedative-hypnotic/muscle relaxant/ataxic activity due to decreased efficacy at $GABA_A/\alpha 1$ receptors.

Compounds activating GABA-A receptors as we well compounds selective for $GABA_A$ receptor subunits often display anti-epileptic activity, due to their general suppression of neural activity. Accordingly anti-epileptic properties of the compounds can be tested for the ability to suppress seizures in several standard rat and mouse models of epilepsy, as described in U.S. Patent Application Publication No. US 2011/0261711. Anticonvulsant activity of compounds can be compared to diazepam. The standard models incorporated into anticonvulsant screening include the maximal electroshock test (MES), the subcutaneous Metrazol test (scMet), and evaluations of toxicity (TOX). The data for each condition can be presented as a ratio of either the number of animals protected or toxic (loss of locomotor activity) over the number of animals tested at a given time point and dose.

The MES is a model for generalized tonic-clonic seizures and provides an indication of a compound's ability to prevent seizure spread when all neuronal circuits in the brain are maximally active. These seizures are highly reproducible and are electrophysiologically consistent with human seizures. For all tests based on MES convulsions, 60 Hz of alternating current (50 mA in mice, 150 in rats) is delivered for by corneal electrodes which have been primed with an electrolyte solution containing an anesthetic agent (0.5% tetracaine HCL). For Test 1, mice are tested at various intervals following doses of 30, 100 and 300 mg/kg of test compound given by ip injection of a volume of 0.01 mL/g. In Test 2, rats are tested after a dose of 30 mg/kg (po) in a volume of 0.04 mL/g. Test 3 uses varying doses administered via i.p. injection, again in a volume of 0.04 ml/g. An animal is considered "protected" from MES-induced seizures upon abolition of the hindlimb tonic extensor component of the seizure (Swinyard, E. A., et al. in Antiepileptic Drugs, Levy, R. H. M., et al., Eds.; Raven Press: New York, 1989; pp 85-102; White, H. S., et al., Ital J Neurol Sci. 1995a, 16, 73-7; White, H. S., et al., in Antiepileptic Drugs, Levy, R. H. M., Meldrum, B. S., Eds.; Raven Press: New York, pp 99-110, 1995b).

Subcutaneous injection of the convulsant Metrazol produces clonic seizures in laboratory animals. The scMet test detects the ability of a test compound to raise the seizure threshold of an animal and thus protect it from exhibiting a clonic seizure. Animals can pretreated with various doses of the test compound (in a similar manner to the MES test, although a dose of 50 mg/kg (po) is the standard for Test 2 scMet). At the previously determined TPE of the test compound, the dose of Metrazol which will induce convulsions in 97% of animals ($CD_{97}$: 85 mg/kg mice) is injected into a loose fold of skin in the midline of the neck. The animals can be placed in isolation cages to minimize stress (Swinyard et al. J. Physiol. 1961, 132, 97-0.102) and observed for the next 30 minutes for the presence or absence of a seizure. An episode of clonic spasms, approximately 3-5 seconds, of the fore and/or hindlimbs, jaws, or vibrissae is taken as the endpoint. Animals which do not meet this criterion are considered protected.

To further characterize the anticonvulsant activity of compounds, a hippocampus kindling screen can be performed. This screen is a useful adjunct to the traditional MES and scMet tests for identification of a substance potential utility for treating complex partial seizures.

Benzodiazepines can be highly effective drugs in certain treatment paradigms. They are routinely employed for emergency situations such as status epilepticus and other acute conditions. But their use in chronic convulsant diseases has been limited due to side effects such as sedation and with high doses respiratory depression, hypotension and other effects. Further it has long been purported that chronic administration of this class of drugs can lead to tolerance to the anticonvulsant effects. This has limited their utility as first line treatment for chronic anticonvulsant conditions. Discovery of a potent BDZ with a decreased side effect profile and efficacy over extended treatment periods would be highly desirable.

Compositions and Routes of Administration

In another aspect, the disclosure provides pharmaceutical compositions comprising one or more compounds of this disclosure in association with a pharmaceutically acceptable carrier. Such compositions may be in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that compounds may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present disclosure, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present disclosure. Typical unit dosage forms contain from 1 to 100 mg, for example, 1, 2, 5, 10, 25, 50, or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present disclosure may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Suitable dosage level is about 0.01 to 250 mg/kg per day, about 0.05 to 100 mg/kg per day, or about 0.05 to 5 mg/kg per day. The compounds may be administered on a regimen of 1 to 4 times per day, or on a continuous basis via, for example, the use of a transdermal patch.

Pharmaceutical compositions for enteral administration, such as nasal, buccal, rectal or, especially, oral administration, and for parenteral administration, such as intravenous, intramuscular, subcutaneous, peridural, epidural or intrathecal administration, are suitable. The pharmaceutical compositions comprise from approximately 1% to approximately 95% active ingredient, or from approximately 20% to approximately 90% active ingredient.

For parenteral administration including intracoronary, intracerebrovascular, or peripheral vascular injection/infusion preference is given to the use of solutions of the subunit selective $GABA_A$ receptor agonist, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal application is also considered, for example using a transdermal patch, which allows administration over an extended period of time, e.g. from one to twenty days.

Methods of Treatment

Further provided herein are methods of treating a disorder or condition. Further provided are methods of cognitive and mood remediation in neurological disorders.

The disorder may be selected from Alzheimer's Disease (AD), dementia, Traumatic Brain Injury (TBI), cerebrovascular disease, anesthesia, post-traumatic stress disorder (PTSD), depression such as major depression and persistent depressive disorder and bipolar depression, schizophrenia, alcoholism, addiction, anxiety disorder, epilepsy, neuropathic pain, autism spectrum disorder, or a combination thereof.

Anxiety disorder is divided into generalized anxiety disorder, phobic disorder, and panic disorder; each has its own characteristics and symptoms and they require different treatment. Particular examples of anxiety disorders include generalized anxiety disorder, panic disorder, phobias such as agoraphobia, social anxiety disorder, obsessive-compulsive disorder, post-traumatic stress disorder, separation anxiety and childhood anxiety disorders.

There are many different epilepsy syndromes, each presenting with its own unique combination of seizure type, typical age of onset, EEG findings, treatment, and prognosis. Exemplary epilepsy syndromes include, e.g., Benign centrotemporal lobe epilepsy of childhood, Benign occipital epilepsy of childhood (BOEC), Autosomal dominant nocturnal frontal lobe epilepsy (ADNFLE), Primary reading epilepsy, Childhood absence epilepsy (CEA), Juvenile absence epilepsy, Juvenile myoclonic epilepsy (JME), Symptomatic localization-related epilepsies, Temporal lobe epilepsy (TLE), Frontal lobe epilepsy, Rasmussen's encephalitis, West syndrome, Dravet's syndrome, Progressive myoclonic epilepsies, and Lennox-Gastaut syndrome (LGS). Genetic, congenital, and developmental conditions are often associated with epilepsy among younger patients. Tumors might be a cause for patients over age 40. Head trauma and central nervous system infections may cause epilepsy at any age.

Schizophrenia is a mental disorder characterized by a breakdown of thought processes and by poor emotional responsiveness. Particular types of schizophrenia include paranoid type, disorganized type, catatonic type, undifferentiated type, residual type, post-schizophrenic depression and simple schizophrenia.

Autism spectrum disorder encompasses a range of phenotypes expressed during neurodevelopment, characterized by persistent deficits in social communication and interaction across various contexts.

The treatment can also be directed at a symptom dimension (e.g. cognition, mood) across disorders, from neuropsychiatric (e.g., depression, schizophrenia) to neurodegenerative (e.g. AD) disorders, consistent with a dimensional perspective of underlying brain pathologies.

The methods may include administering to a subject in need thereof a compound or composition as described herein.

The following non-limiting examples are intended to be purely illustrative of some aspects and embodiments, and show specific experiments that were carried out in accordance with the disclosure.

EXAMPLES

Example 1: Synthesis of MP-III-022 and MP-III-023

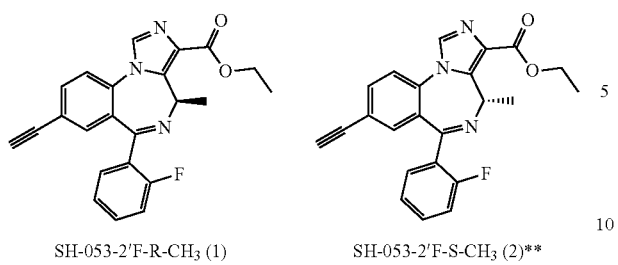

SH-053-2'F-R-CH₃ (1)          SH-053-2'F-S-CH₃ (2)**

Reagents and Conditions: a) D-Boc-alanine, DCC, CH₂Cl₂, 0° C. to r.t., 87%; b) CH₂Cl₂, HCl (g), 0° C. to r.t.; c) methanol/water, pH 8.5 (1 M NaOH), r.t., 75% over two steps; d) THF, K-t-BuO, ClPO(OEt)₂, CNCH₂CO₂Et, -78° C. to r.t., 78%; d) Pd(PPh₃)₂(OAc)₂, TMS-acetylene, Et₃N, CH₃CN, reflux, 12 h., 91%; e) TBAF, THF, water, -78° C., 95%
**Compound 2 synthesized with comparable yields using L-Boc-alanine in step a.

Scheme 2. Synthesis of MP-III-022.

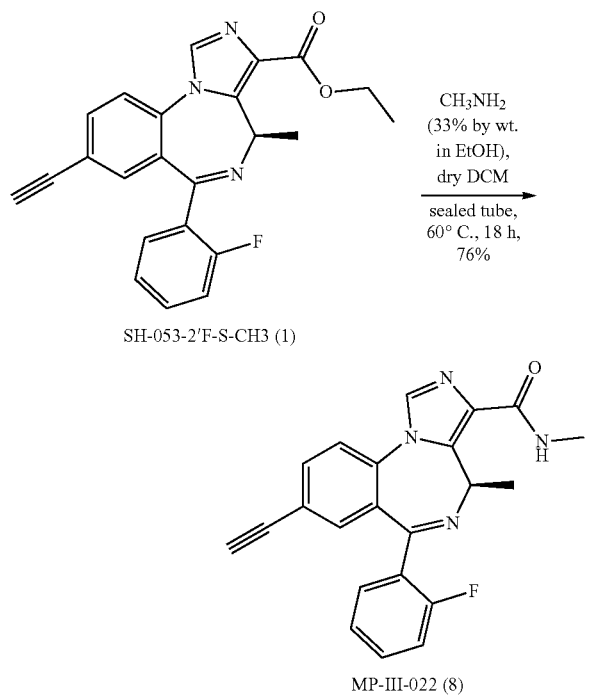

SH-053-2'F-S-CH3 (1)

MP-III-022 (8)

Scheme 3. Synthesis of MP-III-023.

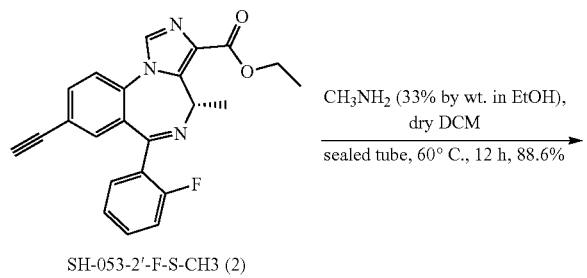

SH-053-2'-F-S-CH3 (2)

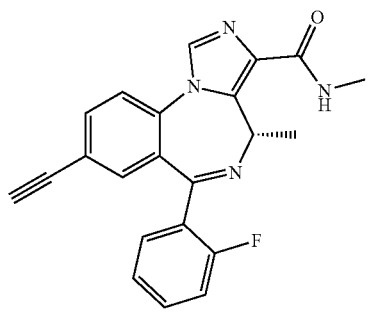

MP-III-023 (9)

(S)-8-ethynyl-6-(2-fluorophenyl)-N,4-dimethyl-4H-benzo[f]imidazo[1,5-a][1,4]diazepine-3-carboxamide MP-III-023 (9)

The ethyl ester SH-053-2'F—S—CH₃ (2) (2.0 g, 5.16 mmol) was dissolved in dry DCM (10 mL), which was added to a sealed vessel fitted with a septum at 0° C. and methyl amine (20 mL; 33% by wt. solution in EtOH) was added. The vessel was sealed with a screw-cap and stirred at 60° C. for 12 hours. The solution was then cooled to r.t. and the methyl amine, DCM and ethanol were removed under reduced pressure. The residue which resulted was purified by a wash column (silica gel, EtOAc and 1% MeOH) to afford pure amide 9 as a white powder (1.7 g, 4.56 mmol, 88.6%); ¹H NMR (500 MHz, CDCl₃) δ 7.84 (s, 1H), 7.80-7.57 (m, 2H), 7.54 (d, J=8.3 Hz, 1H), 7.50-7.41 (m, 2H), 7.27 (t, J=7.4 Hz, 1H), 7.17 (br s, 1H), 7.04 (t, J=9.3 Hz, 1H), 6.91 (q, J=7.3 Hz, 1H), 3.16 (s, 1H), 2.96 (d, J=5.0 Hz, 3H), 1.28 (d, J=6.6 Hz, 3H); HRMS (LCMS-IT-TOF) Calc. for C22H17FN4O (M+H)+373.1459, found 373.1453.

Example 2: Synthesis of GL-II-31

Scheme 4. Synthesis of GL-II-31.

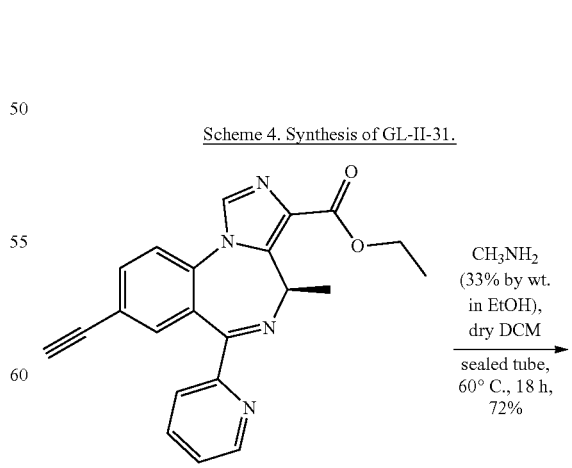

GL-II-19-2'N-R-CH3 (10)

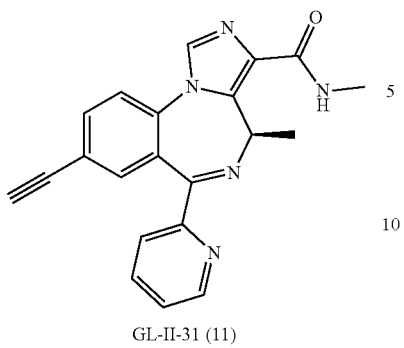

GL-II-31 (11)

(R)-8-ethynyl-N,4-dimethyl-6-(pyridin-2-yl)-4H-benzo[f]imidazo[1,5-a][1,4]diazepine-3-carboxamide GL-II-31 (11)

The ethyl ester GL-II-19-2'N—R—CH₃ (10) (1.7 g, 4.59 mmol) was dissolved in dry DCM (15 mL), which was added to a sealed vessel fitted with a septum at 0° C. and methyl amine (25 mL; 33% by wt. solution in EtOH) was added. The vessel was sealed with a screw-cap and stirred at 60° C. for 18 hours. The solution was then cooled to r.t. and the methyl amine, DCM and ethanol were removed under reduced pressure. Add 5 mL DCM to the crude, the mixture was stirred at 35° C. for 5 min, then pure product was filtered off. The filtrate was further purified by a flash column chromatography (silica gel, 7:3 EtOAc and Hexane) to afford additional portion of pure amide 11 as a white powder (1.2 g, 3.37 mmol, 72%); $^1$H NMR (500 MHz, CDCl₃) δ 8.57 (d, J=4.3 Hz, 1H), 8.08 (d, J=7.7 Hz, 1H), 7.84-7.68 (m, 3H), 7.52-7.41 (m, 2H), 7.37 (t, J=5.8 Hz, 1H), 7.17 (br s, 1H), 6.91 (q, J=7.4 Hz, 1H), 3.14 (s, 1H), 2.97 (d, J=4.9 Hz, 3H), 1.28 (d, J=7.2 Hz, 3H); $^{13}$C NMR (75 MHz, MeOD) δ 165.47, 163.87, 157.41, 148.30, 138.74, 137.34, 135.81, 135.57, 135.25, 135.17, 134.26, 131.06, 127.84, 124.84, 124.22, 122.43, 121.10, 81.43, 79.66, 25.56, 14.45; HRMS (LCMS-IT-TOF) Calc. for C₂₁H₁₇N₅O (M+H)⁺356.1506, found 356.1504.

Example 3. Synthesis of RV-II-04

Scheme 5. Synthesis of RV-II-04.

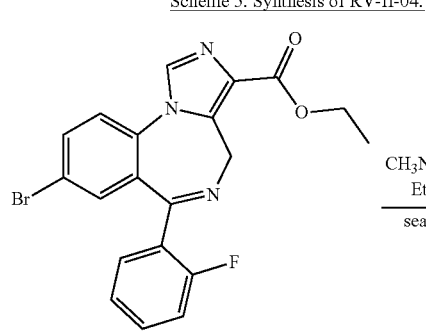

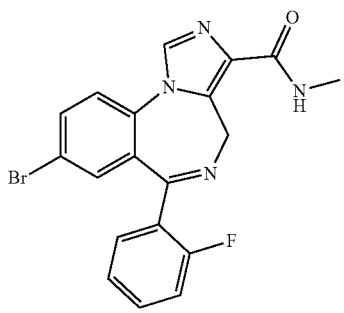

RV-II-04 (13)

The ethyl ester 12 (2.0 g, 4.67 mmol) was dissolved in dry DCM (10 mL), which was added to a sealed vessel fitted with a septum at 0° C. and methyl amine (20 mL; 33% by wt. solution in EtOH) was added. The vessel was sealed with a screw-cap and stirred at 60° C. for 15 hours. The solution was then cooled to r.t. and the methyl amine, DCM and ethanol were removed under reduced pressure. The residue which resulted was purified by a wash column (silica gel, 7:3 EtOAc and Hexane) to afford pure amide 13 as a yellow powder (1.35 g, 3.26 mmol, 70%); 1H NMR (500 MHz, CDCl3) δ 7.85 (s, 1H), 7.78 (dd, J=8.5 Hz, 1.9 Hz, 1H), 7.73 (td, J=7.7 Hz, 1.5 Hz, 1H), 7.50-7.43 (m, 3H), 7.28 (t, J=7.6 Hz, 1H), 7.12 (br s, 1H), 7.04 (t, J=9.4 Hz, 1H), 6.33 (br s, 1H), 4.13 (br s, 1H), 2.99 (d, J=4.9 Hz, 3H); HPLC-MS (ESI): m/z 413.15 (M+H)⁺.

Example 4. Synthesis of MP-II-065

Scheme 6. Synthesis of MP-II-065.

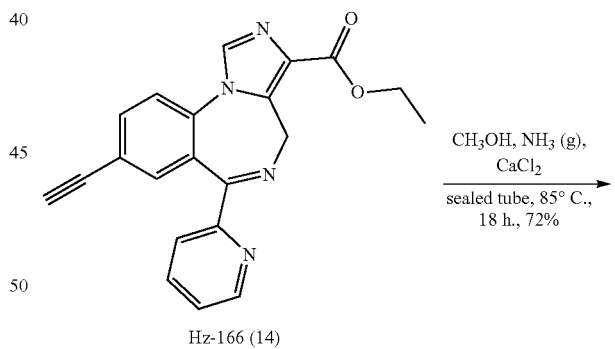

Hz-166 (14)

MP-II-065 (15)

8-ethynyl-6-(pyridin-2-yl)-4H-benzo[f]imidazo[1,5-a][1,4]diazepine-3-carboxamide MP-II-065 (15)

The ethyl ester 14 (1 g, 2.81 mmol) and calcium chloride (311 mg, 2.81 mmol) were placed inside a sealable vessel with a stir bar. Methanol (dry, 20 mL) was added and a septum was placed to seal the vessel. In a separate flask, ammonia (g) was bubbled into methanol (dry, 20 mL) until saturated, about 10 minutes. The ammonia-methanol solution was added to the vessel containing 14 and the vessel was sealed with a screw cap. The reaction mixed was heated and stirred at 85° C. for 18 hours. The reaction was allowed to cool and the methanol was removed under reduced pressure. The solid which remained was dissolved in ethyl acetate and filtered to remove the calcium chloride. The filtrate was washed with brine, dried ($Na_2SO_4$) and solvent removed under reduced pressure. The residue that remained was purified using a flash column chromatography (EtOAc with 1% methanol and 1% trimethylamine) to afford pure 15 as a white solid (661 mg, 2.02 mmol, 72%); $^1$H NMR (300 MHz, $CDCl_3$) δ 8.57 (d, J=4.6 Hz, 1H), 8.14 (d, J=8.0 Hz, 1H), 7.84 (s, 2H), 7.81-7.73 (m, 1H), 7.61-7.51 (m, 2H), 7.42-7.32 (m, 1H), 7.01 (s, 1H), 6.26 (s, 1H), 5.38 (s, 1H), 4.13 (s, 1H), 3.17 (s, 1H); $^{13}$C NMR (75 MHz, $CDCl_3$) δ 167.38, 164.71, 156.59, 148.59, 136.87, 136.52, 136.32, 135.53, 135.14, 133.29, 131.01, 127.14, 124.72, 124.04, 122.76, 121.07, 81.77, 79.35, 44.80; HPLC-MS (ESI): m/z 328.12 (M+H)$^+$.

Example 5. General Synthetic Route to Carboxamides

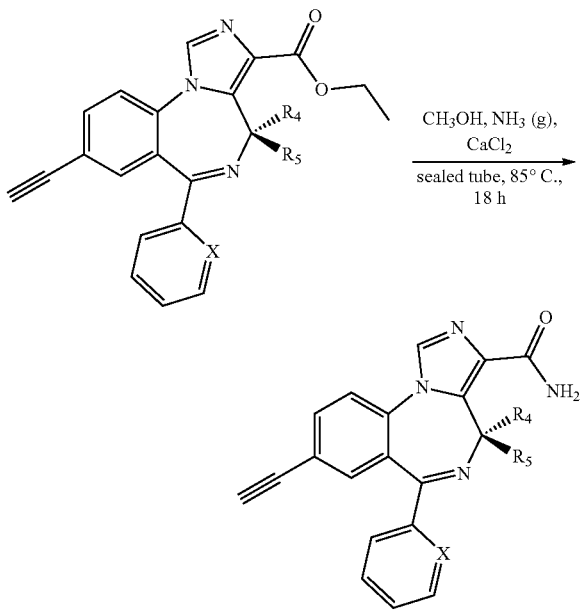

Scheme 7. General synthetic route to carboxamides.

Example 6. General Synthetic Route to Amides

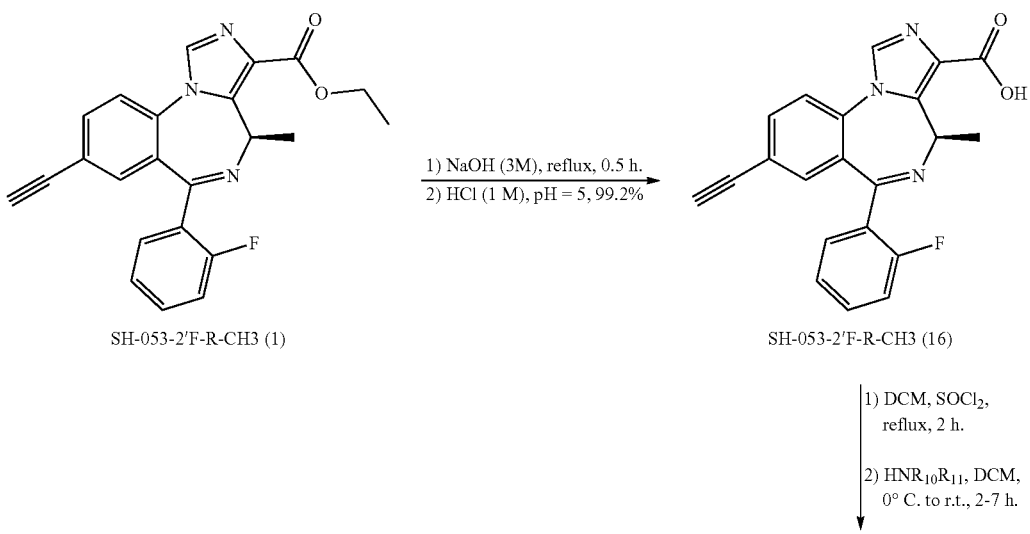

Scheme 8. General synthetic route to amides.

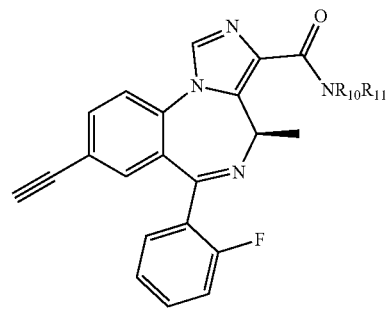

| | | |
|---|---|---|
| $R_{10} = CH_3$; | $R_{11} = CH_3$ | GL-II-73 (17), 70% |
| $R_{10} = H$; | $R_{11} = CH_2CH_3$ | GL-II-74 (18), 78% |
| $R_{10} = H$; | $R_{11} = CH_2CH(CH_3)_2$ | GL-II-75 (19), 82% |
| $R_{10} = CH_2CH_2$; | $R_{11} = CH_2CH_2$ | GL-II-76 (20), 80% |

(R)-8-ethynyl-6-(2-fluorophenyl)-4-methyl-4H-benzo[f]imidazo[1,5-a][1,4]diazepine-3-carboxylic acid SH-053-2'F—R—CH₃-acid (16)

The ethyl ester SH-053-2'F—R—CH₃ (1) (20.0 g, 51.6 mmol) was dissolved 500 mL of EtOH, after which solid NaOH (16.6 g, 413 mmol) was added to the solution. This reaction mixture was heated to 55° C. for 0.5 hour and the EtOH was removed under reduced pressure. The remaining aq. solution was stirred at 0° C. for 10 min and then aq. HCl (1M) was added dropwise to the solution until the pH was 5 (pH paper). A pale white precipitate which formed, was left in the solution for 10 min and was then collected by filtration, washed with cold water and the aq. layer also allowed to stand at r.t. for 10 hours to yield additional acid. The combined solids were dried in a vacuum oven at 80° C. for 7 hours to get pure acid 16 as a white powder (18.4 g, 51.2 mmol, 99.2%); $^1$H NMR (300 MHz, DMSO-d$^6$): δ 8.42 (s, 1H), 7.94 (d, J=8.4 Hz, 1H), 7.82 (d, J=8.2 Hz, 1H), 7.56 (dt, J=7.8 Hz, 6.5 Hz, 2H), 7.33 (t, J=7.4 Hz, 1H), 7.22 (t, J=9.3 Hz, 2H), 6.53 (d, J=7.1 Hz, 1H), 2.51 (s, 1H), 1.16 (d, J=6.8 Hz, 3H); $^{13}$C NMR (75 MHz, DMSO-d$^6$): δ 164.76, 162.81, 158.19, 140.57, 136.57, 135.54, 134.74, 133.18, 132.65, 131.88, 129.88, 129.35, 125.17, 123.98, 121.09, 116.53, 116.25, 83.42, 82.01, 49.79, 15.08; HRMS (LCMS-IT-TOF) Calc. for $C_{21}H_{14}FN_3O_2(M+H)^+$ 360.1143, found 360.1140.

General Procedure for Other Amides

A mixture of the acid (SH-053-2'F—R—CH₃-acid 16 or its enantiomer 21) (2 g, 5.56 mmol), thionyl chloride (55.6 mmol) and dry DCM 50 mL was put into an oven dried round bottom flask under argon. This suspension was allowed to reflux at 60° C. for 2 hours under argon. The absence of the starting material was confirmed by TLC (silica gel). The organic solvent and excess thionyl chloride were evaporated under reduced pressure which was repeated 5 times with dry DCM. The yellow residue obtained was dissolved in dry DCM and cooled to 0° C. for 10 min under argon. Then appropriate amine (11.12 mmol), followed by Et₃N (5.56 mmol) was added to the reaction mixture at 0° C. and the mixture was then allowed to warm to r.t. and stirred for approximately 7 hours. After the completion of the reaction the solvent was removed under reduced pressure. The residue was treated with ice cold water and extracted with DCM. The combined organic layer was washed with brine (20 mL). The solvent was removed under reduced pressure and the residue was purified by column chromatography to yield the corresponding pure amides.

Example 7. Synthesis of GL-II-73

(R)-8-ethynyl-6-(2-fluorophenyl)-N,N,4-trimethyl-4H-benzo[f]imidazo[1,5-a][1,4]diazepine-3-carboxam GL-II-73 (17)

17 was prepared from 16 following the general procedure with dry dimethylamine as the nucleophile. The crude residue was purified by a column chromatography (silica gel, EtOAc and 1% MeOH) to yield pure dimethyl amide 17 as a light yellow powder (1.5 g, 3.9 mmol, 70%); $^1$H NMR (300 MHz, CDCl₃): δ 7.94 (s, 1H), 7.7 (d, J=8.4 Hz, 1H), 7.76 (t, J=6.9 Hz, 1H), 7.54-7.42 (m, 3H), 7.26 (t, J=7.4 Hz, 1H), 7.04 (t, J=9.4 Hz, 1H), 4.33 (q, J=6.9 Hz, 1H), 3.15 (s, 1H), 3.12 (s, 3H), 3.00 (s, 3H), 1.93 (d, J=6.9 Hz, 3H); HRMS (LCMS-IT-TOF) Calc. for $C_{23}H_{19}FN_4O$ (M+H)$^+$ 387.1616, found 387.1626.

Example 8. Synthesis of GL-II-74

(R)—N-ethyl-8-ethynyl-6-(2-fluorophenyl)-4-methyl-4H-benzo[f]imidazo[1,5-a][1,4]diazepine-3-carboxamide GL-II-74 (18)

18 was prepared from 16 following the general procedure with dry ethylamine as the nucleophile. The crude residue was purified by a column chromatography (silica gel, 6:4 EtOAc and Hexane) to yield pure ethyl amide 18 as a white powder (1.6 g, 4.3 mmol, 78%); $^1$H NMR (300 MHz, CDCl₃): δ 7.82 (s, 1H), 7.69-7.60 (m, 2H), 7.54 (d, J=8.3 Hz, 1H), 7.45-7.40 (m, 2H), 7.26 (t, J=7.4 Hz, 1H), 7.16 (br s, 1H), 7.04 (t, J=9.2 Hz, 1H), 6.93 (q, J=7.4 Hz, 1H), 3.49-3.39 (m, 2H), 3.14 (s, 1H), 1.27-1.20 (m, 6H); $^{13}$C NMR (75 MHz, CDCl₃) δ 162.81, 162.51, 158.47, 138.81, 134.96, 134.71, 133.90, 133.37, 131.84, 131.37, 129.78, 124.46, 124.42, 122.04, 121.38, 116.20, 115.92, 81.55, 79.52, 49.89, 33.70, 15.02; HRMS (LCMS-IT-TOF) Calc. for $C_{23}H_{19}FN_4O$ (M+H)$^+$ 387.1616, found 387.1618.

Example 9. Synthesis of GL-II-75

(R)—N-cyclopropyl-8-ethynyl-6-(2-fluorophenyl)-4-methyl-4H-benzo[f]imidazo[1,5-a][1,4]diazepine-3-carboxamide GL-II-75 (19)

19 was prepared from 16 following the general procedure with dry cyclopropylamine as the nucleophile. The crude residue was purified by a column chromatography (silica gel, 5:5 EtOAc and Hexane) to yield pure cyclopropyl amide 19 as a white powder (1.8 g, 4.5 mmol, 82%); $^1$H NMR (300 MHz, CDCl$_3$): δ 7.80 (s, 1H), 7.68-7.61 (m, 2H), 7.53 (d, J=8.4 Hz, 1H), 7.45-7.40 (m, 2H), 7.28-7.21 (m, 2H), 7.03 (t, J=9.3 Hz, 1H), 6.90 (q, J=7.4 Hz, 1H), 3.15 (s, 1H), 2.86-2.80 (m, 1H), 1.27 (d, J=6.7 Hz, 3H), 0.83-0.79 (m, 2H), 0.63-0.57 (m, 2H); $^{13}$C NMR (75 MHz, CDCl$_3$) δ 164.02, 162.82, 158.47, 138.91, 134.97, 134.65, 133.89, 133.37, 131.86, 131.58, 131.36, 129.78, 124.47, 122.04, 121.42, 116.20, 115.92, 81.53, 79.55, 49.88, 22.10, 14.99, 6.54, 6.50; HRMS (LCMS-IT-TOF) Calc. for C$_{24}$H$_{19}$FN$_4$O (M+H)$^+$399.1616, found 399.1621.

Example 10. Synthesis of GL-II-76

(R)-(8-ethynyl-6-(2-fluorophenyl)-4-methyl-4H-benzo[f]imidazo[1,5-a][1,4]diazepin-3-yl)(pyrrolidin-1-yl)methanone GL-II-76 (20)

20 was prepared from 16 following the general procedure with dry pyrrolidine as the nucleophile. The crude residue was purified by a column chromatography (silica gel, 6:4 EtOAc and Hexane) to yield pure product 20 as a white powder (1.8 g, 4.4 mmol, 80%); $^1$H NMR (300 MHz, CDCl$_3$): δ 7.90 (s, 1H), 7.70-7.59 (m, 2H), 7.51 (d, J=8.4 Hz, 1H), 7.46-7.40 (m, 2H), 7.26 (t, J=7.4 Hz, 1H), 7.04 (t, J=9.3 Hz, 1H), 4.34 (q, J=6.4 Hz, 1H), 3.74-3.41 (m, 4H), 3.14 (s, 1H), 1.96-1.88 (m, 4H), 1.27 (d, J=6.5 Hz, 3H); HRMS (LCMS-IT-TOF) Calc. for C$_{25}$H$_{21}$FN$_4$O (M+H)$^+$413.1772, found 413.1772.

Example 11. Synthesis of GL-I-54

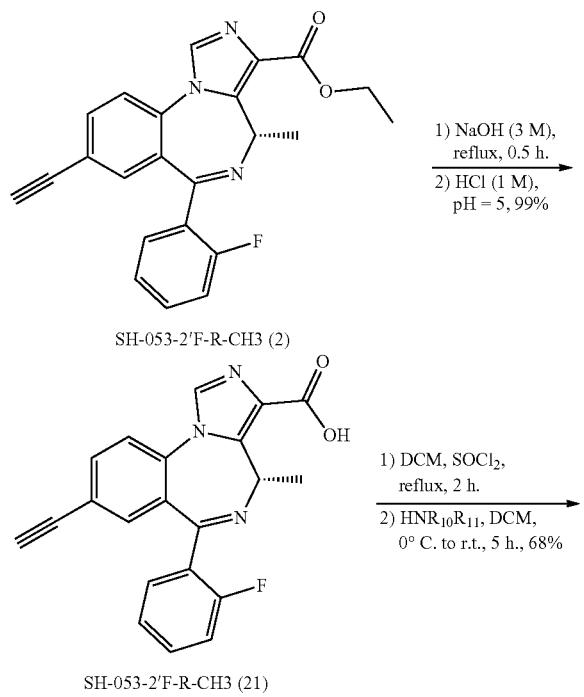

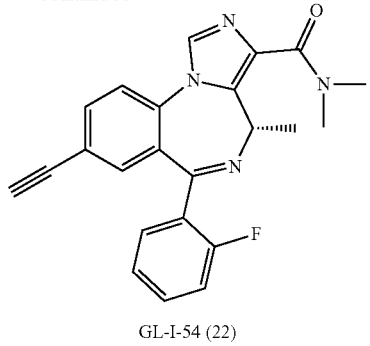

GL-I-54 (22)

(S)-8-ethynyl-6-(2-fluorophenyl)-4-methyl-4H-benzo[f]imidazo[1,5-a][1,4]diazepine-3-carboxylic acid SH-053-2'F—S-CH3-acid (21)

The ethyl ester SH-053-2'F—S—CH3 (2) (5.0 g, 12.91 mmol) was dissolved 200 mL of EtOH, after which solid NaOH (4.1 g, 103.25 mmol) was added to the solution. This reaction mixture was heated to 55° C. for 0.5 hour and the EtOH was removed under reduced pressure. The remaining aq. solution was stirred at 0° C. for 10 min and then aq. HCl (1M) was added dropwise to the solution until the pH was 5 (pH paper). A pale white precipitate which formed, was left in the solution for 10 min and was then collected by filtration, washed with cold water and the aq. layer also allowed to stand at r.t. for 10 hours to yield additional acid. The combined solids were dried in a vacuum oven at 80° C. for 7 hours to get pure acid 21 as a white powder (4.6 g, 12.7 mmol, 99%); $^1$H NMR (300 MHz, DMSO-d$^6$): δ 8.35 (s, 1H), 7.93 (d, J=8.1 Hz, 1H), 7.80 (d, J=8.1 Hz, 1H), 7.56-7.55 (m, 3H), 7.34 (t, J=7.3 Hz, 1H), 7.24-7.18 (m, 2H), 6.62 (d, J=7.1 Hz, 1H), 4.35 (s, 1H), 1.14 (d, J=6.5 Hz, 3H); $^{13}$C NMR (75 MHz, DMSO-d$^6$): δ 164.88, 162.90, 158.28, 140.79, 136.78, 135.65, 134.83, 133.22, 132.43, 131.77, 129.82, 129.45, 125.21, 123.97, 121.12, 116.64, 116.25, 83.43, 82.11, 49.65, 15.11; HRMS (LCMS-IT-TOF) Calc. for C$_{21}$H$_{14}$FN$_3$O$_2$(M+H)$^+$360.1143, found 360.1148.

(S)-8-ethynyl-6-(2-fluorophenyl)-N,N,4-trimethyl-4H-benzo[f]imidazo[1,5-a][1,4]diazepine-3-carboxamide GL-I-54 (22)

22 was prepared from 21 following the general procedure with dry dimethylamine as the nucleophile. The crude residue was purified by a column chromatography (silica gel, EtOAc and 1% MeOH) to yield pure dimethyl amide 22 as a light yellow powder (1.4 g, 3.8 mmol, 68%); $^1$H NMR (500 MHz, CDCl$_3$): δ 7.93 (s, 1H), 7.73 (d, J=8.4 Hz, 1H), 7.65 (t, J=6.8 Hz, 1H), 7.56-7.42 (m, 3H), 7.27 (t, J=7.4 Hz, 1H), 7.05 (t, J=9.4 Hz, 1H), 4.33 (q, J=6.8 Hz, 1H), 3.15 (s, 1H), 3.13 (s, 3H), 3.01 (s, 3H), 1.94 (d, J=6.8 Hz, 3H); HRMS (LCMS-IT-TOF) Calc. for C$_{23}$H$_{19}$FN$_4$O (M+H)$^+$ 387.1616, found 387.1624.

Example 12. General Synthetic Route to Oxadiazoles

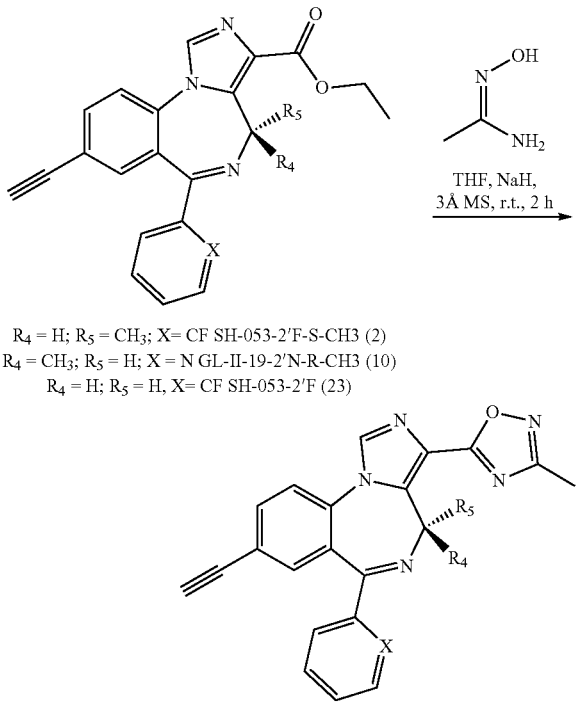

Scheme 10. General synthetic route to oxadiazoles.

R₄ = H; R₅ = CH₃; X= CF SH-053-2'F-S-CH3 (2)
R₄ = CH₃; R₅ = H; X = N GL-II-19-2'N-R-CH3 (10)
R₄ = H; R₅ = H, X= CF SH-053-2'F (23)

R₄ = H; R₅ = CH₃; X= CF GL-I-65 (24), 74%
R₄ = CH₃; R₅ = H; X = N GL-II-33 (25), 77%
R₄ = H; R₅ = H; X = CF GL-III-23 (26), 52%

General Procedure for Oxadiazoles

The ethyl ester (2 or 10 or 23) was dissolved in dry THF at r.t. under argon. In a separate flask which contained 3Å molecular sieves, the oximes, were dissolved in dry THF under argon and treated with sodium hydride (60% dispersion in mineral oil). The mixture, which resulted, was stirred for 15 min at which point the solution containing the ethyl ester was added. The reaction mixture, which resulted, was stirred at r.t. for 2 hours or until the starting material was consumed as indicated by TLC (silica gel). The reaction mixture was quenched with a saturated aq. NaHCO₃ solution. Water was then added and the product was extracted with EtOAc. The organic layers were combined, washed with brine, dried (Na₂SO₄) and the solvent was removed under reduced pressure. The solid which resulted was purified by flash chromatography (silica gel) to afford the pure corresponding oxadiazole.

Example 13. Synthesis of GL-I-65

(S)-5-(8-ethynyl-6-(2-fluorophenyl)-4-methyl-4H-benzo[f]imidazo[1,5-a][1,4]diazepin-3-yl)-3-methyl-1,2,4-oxadiazole GL-I-65 (24)

24 was prepared from 2 (1.64 g, 4.23 mmol) following the general procedure with oxime (627 mg, 8.46 mmol) and sodium hydride (60% dispersion in mineral oil) (254 mg, 6.34 mmol) in 100 mL dry THF. The crude residue was purified by a column chromatography (silica gel, 5:5 EtOAc and Hexane) to yield pure product 24 as a white powder (1.24 g, 3.12 mmol, 74%); ¹H NMR (500 MHz, CDCl₃): δ 8.02 (s, 1H), 7.77 (d, J=8.5 Hz, 1H), 7.63-7.60 (m, 2H), 7.51-7.45 (m, 2H), 7.28 (t, J=7.5 Hz, 1H), 7.07 (t, J=9.6 Hz, 1H), 6.77 (q, J=7.1 Hz, 1H), 3.18 (s, 1H), 2.47 (s, 3H), 1.36 (d, J=7.3 Hz, 3H); HRMS (LCMS-IT-TOF) Calc. for C₂₃H₁₆FN₅O (M+H)⁺398.1412, found 398.1419.

Example 14. Synthesis of GL-II-33

(R)-5-(8-ethynyl-4-methyl-6-(pyridin-2-yl)-4H-benzo[f]imidazo[1,5-a][1,4]diazepin-3-yl)-3-methyl-1,2,4-oxadiazole GL-II-33 (25)

25 was prepared from 10 (2 g, 5.4 mmol) following the general procedure with oxime (800 mg, 10.8 mmol) and sodium hydride (60% dispersion in mineral oil) (324 mg, 8.1 mmol) in 100 mL dry THF. The crude residue was purified by a column chromatography (silica gel, EtOAc) to yield pure product 25 as a white powder (1.58 g, 4.15 mmol, 77%); ¹H NMR (500 MHz, CDCl₃): δ 8.59 (d, J=4.5 Hz, 1H), 8.04-8.02 (m, 2H), 7.85-7.74 (m, 2H), 7.62 (d, J=8.4 Hz, 1H), 7.49 (br s, 1H), 7.40 (t, J=6.1 Hz, 1H), 6.75 (q, J=7.5 Hz, 1H), 3.18 (s, 1H), 2.48 (s, 3H), 1.36 (d, J=7.5 Hz, 3H); ¹³C NMR (75 MHz, CDCl₃) δ 170.81, 167.42, 165.35, 157.45, 148.60, 139.28, 136.90, 136.45, 136.01, 135.77, 135.54, 135.19, 127.95, 124.68, 124.03, 122.37, 121.21, 81.61, 79.61, 49.97, 14.67, 11.66; HRMS (LCMS-IT-TOF) Calc. for C₂₂H₁₆N₆O (M+H)⁺381.1458, found 381.1461.

Example 15. Synthesis of GL-III-23

5-(8-ethynyl-6-(2-fluorophenyl)-4H-benzo[f]imidazo[1,5-a][1,4]diazepin-3-yl)-3-methyl-1,2,4-oxadiazole GL-III-23 (26)

26 was prepared from 23 (3.0 g, 8.03 mmol) following the general procedure with oxime (1.2 g, 16.06 mmol) and sodium hydride (60% dispersion in mineral oil) (482 mg, 12.04 mmol) in 100 mL dry THF. The crude residue was purified by a column chromatography (silica gel, 7:3 EtOAc and Hexane) to yield pure product 26 as a white powder (1.6 g, 4.17 mmol, 52%); ¹H NMR (500 MHz, CDCl₃): δ 8.11 (s, 1H), 7.80 (d, J=8.6 Hz, 1H), 7.69 (t, J=7.5 Hz, 1H), 7.64 (d, J=8.6 Hz, 1H), 7.51 (br s, 1H), 7.49 (q, J=6.4 Hz, 1H), 7.28 (t, J=7.5 Hz, 1H), 7.06 (t, J=9.1 Hz, 1H), 6.19 (br s, 1H), 4.52 (br s, 1H), 3.19 (s, 1H), 2.48 (s, 3H); HRMS (LCMS-IT-TOF) Calc. for C22H14FN5O (M+H)+384.1255, found 384.1273.

Example 16. Synthesis of GL-II 54

Scheme 11. Synthesis of GL-II-54.

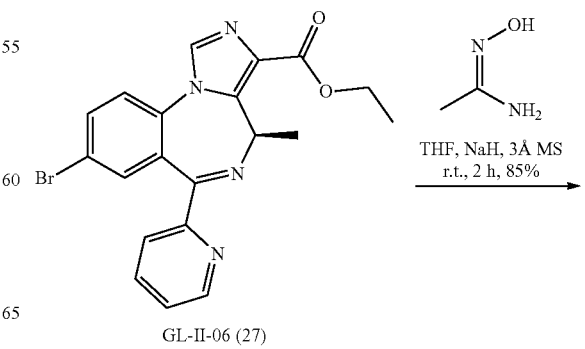

GL-II-06 (27)

-continued

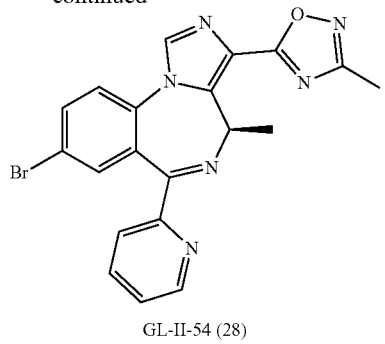

GL-II-54 (28)

(R)-5-(8-bromo-4-methyl-6-(pyridin-2-yl)-4H-benzo[f]imidazo[1,5-a][1,4]diazepin-3-yl)-3-methyl-1,2,4-oxadiazole GL-II-54 (28)

28 was prepared from 27 (2.0 g, 4.7 mmol) following the general procedure with oxime (1.3 g, 17.5 mmol) and sodium hydride (60% dispersion in mineral oil) (282 mg, 7.1 mmol) in 100 mL dry THF. The crude residue was purified by a column chromatography (silica gel, EtOAc and 1% MeOH) to yield pure product 28 as a white powder (1.7 g, 3.9 mmol, 85%); $^1$H NMR (500 MHz, CDCl$_3$): δ 8.59 (d, J=4.5 Hz, 1H), 8.06 (d, J=7.6 Hz, 1H), 8.00 (s, 1H), 7.85-7.77 (m, 2H), 7.53-7.51 (m, 2H), 7.40 (t, J=6.3 Hz, 1H), 6.76 (q, J=6.7 Hz, 1H), 2.49 (s, 3H), 1.37 (d, J=7.6 Hz, 3H); HRMS (LCMS-IT-TOF) Calc. for $C_{20}H_{15}BrN_6O$ (M+H)$^+$ 435.0564, found 435.0557.

Example 17. Y-Maze Alternation Task

Young Animals and Chronic Stress Procedure:
C57/B16 mice, males and females were ordered from Jackson Laboratories at 8 weeks old and were kept in normal housing conditions (12 h light ON cycle starting at 7 am/water and food ad libitum) for one week. During this week, animals were single housed and handled to reduce the anxiety-like response toward the experimenter. To induce a working memory deficit, mice were subjected to a chronic restraint stress protocol (CRS). They were placed in a 50 ml Falcon® tube, twice a day, for 1 hour during their diurnal cycle. The time of occurrence of the stress was randomized every day to avoid predictability. CRS was not applied on testing days. Y-maze test occurred 15 hours minimum after the last stressor.

Young Versus Old Animals Testing:
C57/B16 male mice males were ordered from Jackson Laboratories at 10 months-old and were kept in normal housing conditions (12 h light ON cycle starting at 7 am/water and food ad libitum) until they reached the age of 18 months. A younger cohort of 8 week old animals was used as controls for the experiment. Before testing animals were handled to reduce the anxiety-like response toward the experimenter. Normal aging induced-working memory deficits were assessed using the Y-maze test as described below.

Protocol:
Mice were first habituated to the Y-maze apparatus and distal cues during 2 consecutive days over a 10 min free exploration session (one session per day). The next day, animals performed a training session consisting in seven successive trials separated by a 30 s inter-trial interval (ITI); during this training session, mice were familiarized with the experimental procedure (opening and closing of the doors and confinement into the goal arms). For each trial, mice remained in the start-box for a 30 s ITI. Then, the door was opened and the mouse was allowed to enter freely one of the two goal arms; the chosen arm was closed and the choice was recorded. After a 30 s confinement period into the chosen arm, the mouse was removed and brought back to the start-box for a second trial identical to the first one and this procedure was repeated over the series of trials.

The same general procedure used in the training session was implemented 24 h later, except that the ITI was lengthened to 90 s. For this experiment, animals were acutely injected i.p. with vehicle or αPAM, 30 minutes before the beginning of the test. To dissociate memory deficits from an eventual progressive loss of motivation to alternate over the series, an 8th trial was added to the series which was separated from the 7th trial by a shorter ITI (5 s). All animals failing to alternate at the 8th trial were excluded. The mean alternation rate was calculated and was expressed in percentage (number of alternation done by the animal/total number of alternation possible×100)±SEM. The percentage of alternation during the entire task is considered as an index of working memory performance (50% of being a random alternation rate). Factorial ANOVA was applied to the data to reveal differences between groups. If the ANOVA was significant for group effect (p<0.05), Scheffe post-hoc analysis were conducted to identify which groups are different from each other.

Drug Preparation and Administration:
All drugs were diluted in a vehicle solution containing 85% $H_2O$, 14% propylene glycol (Sigma Aldrich) and 1% Tween 80 (Sigma Aldrich). Working solutions were prepared at a concentration of 10 mg/mL and administered i.p. adjusted to the body weight of each animal. Doses used were either 1, 5, 10 or 20 mg/kg. For all Y maze experiments, animals were acutely injected i.p. with vehicle or αPAM, 30 minutes before the beginning of the test.

Figure 3:
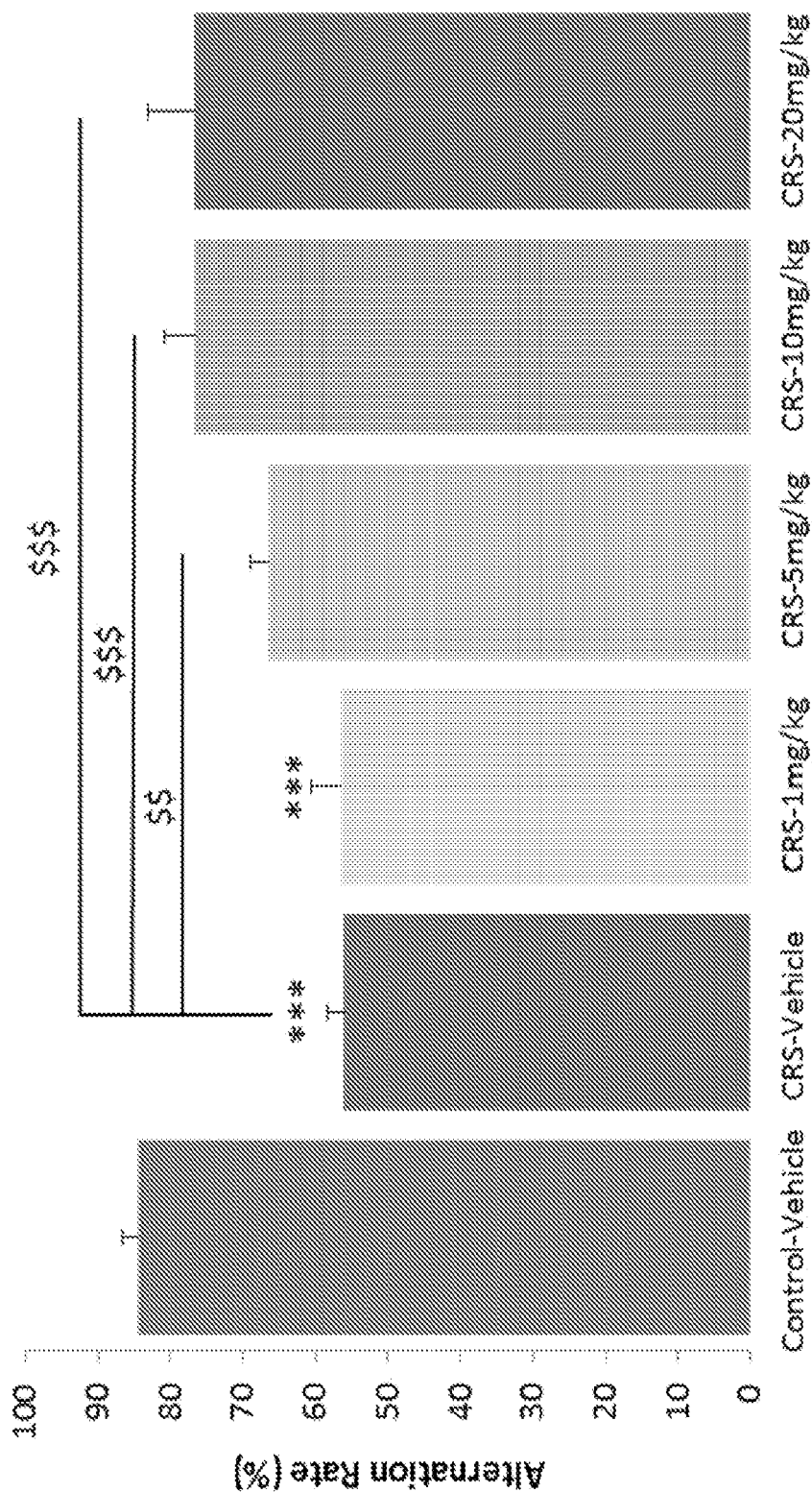
FIG. 3 shows the effects of GL-II-73 on percent alternation rate in the Y-maze spatial alternation task assessing working memory in mice. Chronic restraint stress (CRS) paradigm was used to induce a working memory deficit in young (2-3 month-old) animals. The animals were injected with GL-II-73 (0, 1, 5, 10 or 20 mg/kg) i.p. 30 minutes before testing. Number of animals tested: Control-Veh: 28, CRS-Veh: 30, CRS-1 mg/kg: 5, CRS-5 mg/kg: 17, CRS-10 mg/kg: 15 and CRS-20 mg/kg: 5. ANOVA revealed statistical significance on the overall effect of the treatment. Differences between groups were detected using the PLSD post-hoc test ***p<0.001 compared to the "Control-Vehicle" group/$$p<0.01 and $$$p<0.001 compared to the "CRS-Vehicle" group).

Results of the Y-Maze alternation task after treatment with GL-II-73:
Data (FIG. 3) showed a significant difference between groups (ANOVA: F(5,94)=17.5; p<0.0001). Fisher's PLSD post hoc analysis showed that CRS induced significant reduction of working memory in this test ***p<0.001 when compared to control-vehicle group. This effect was reversed by administration of GL-II-73 (30 min before test). Our results demonstrate that GL-11-73 has a pro-cognitive effect at 5 mg/kg (p<0.01) and at 10 and 20 mg/kg (ps<0.001) compared to the CRS-Vehicle group. These results suggest a potential indication of this compound to reverse cognitive deficits.

Figure 4:
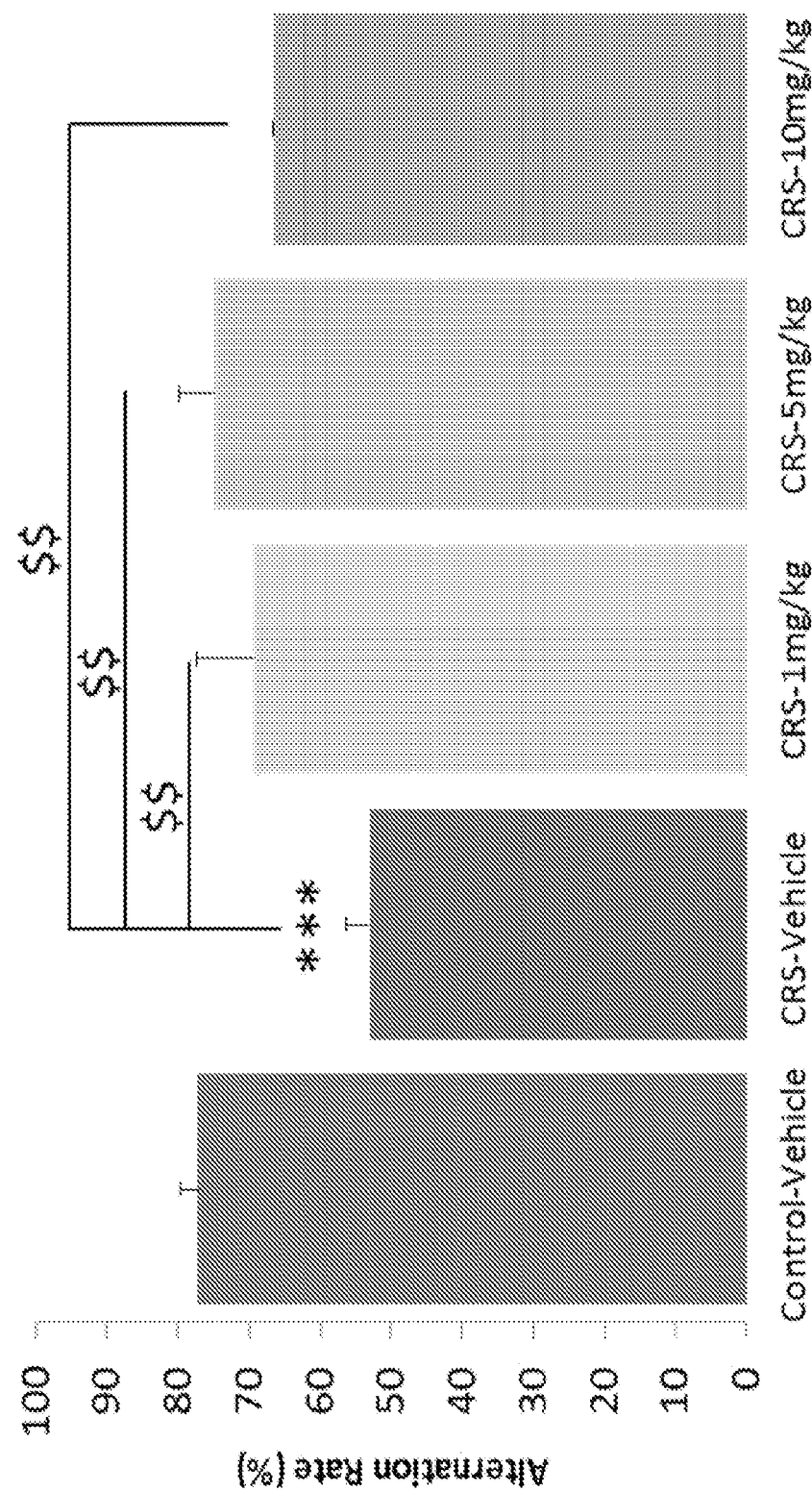
FIG. 4 shows the effects of GL-II-75 on percent alternation rate in the Y-maze spatial alternation task assessing working memory in mice. Mice subjected to CRS were injected with GL-II-75 (0, 1, 5, 10 mg/kg) i.p. 30 minutes before testing. Number of animals tested (n): n=(4-11)/group. ANOVA revealed statistical significance on the overall effect of stress and significant reversal of CRS-induced impairment in working memory in animal groups administered with GL-II-75 at 1, 5 and 10 mg/kg. Differences between groups were tested using the PLSD post-hoc test (***p<0.001 compared to the "Control-Vehicle" group and $$p<0.01 compared to the "CRS-Vehicle" group).

Results of the Y-Maze Alternation Task after Treatment with GL-II-75:
Data analysis (FIG. 4) showed a significant difference between groups (ANOVA: F(4,30)=6.3; p=0.0008). Fisher's PLSD post hoc analysis revealed that CRS-induced deficits in this memory task are reversible by administration of GL-II-75 30 min before the test. GL-II-75 has a significant pro-cognitive effect at 1, 5 and 10 mg/kg (p<0.05, compared to the Control-Vehicle group). These results suggest a potential indication of this compound to reverse cognitive deficits.

Figure 5:
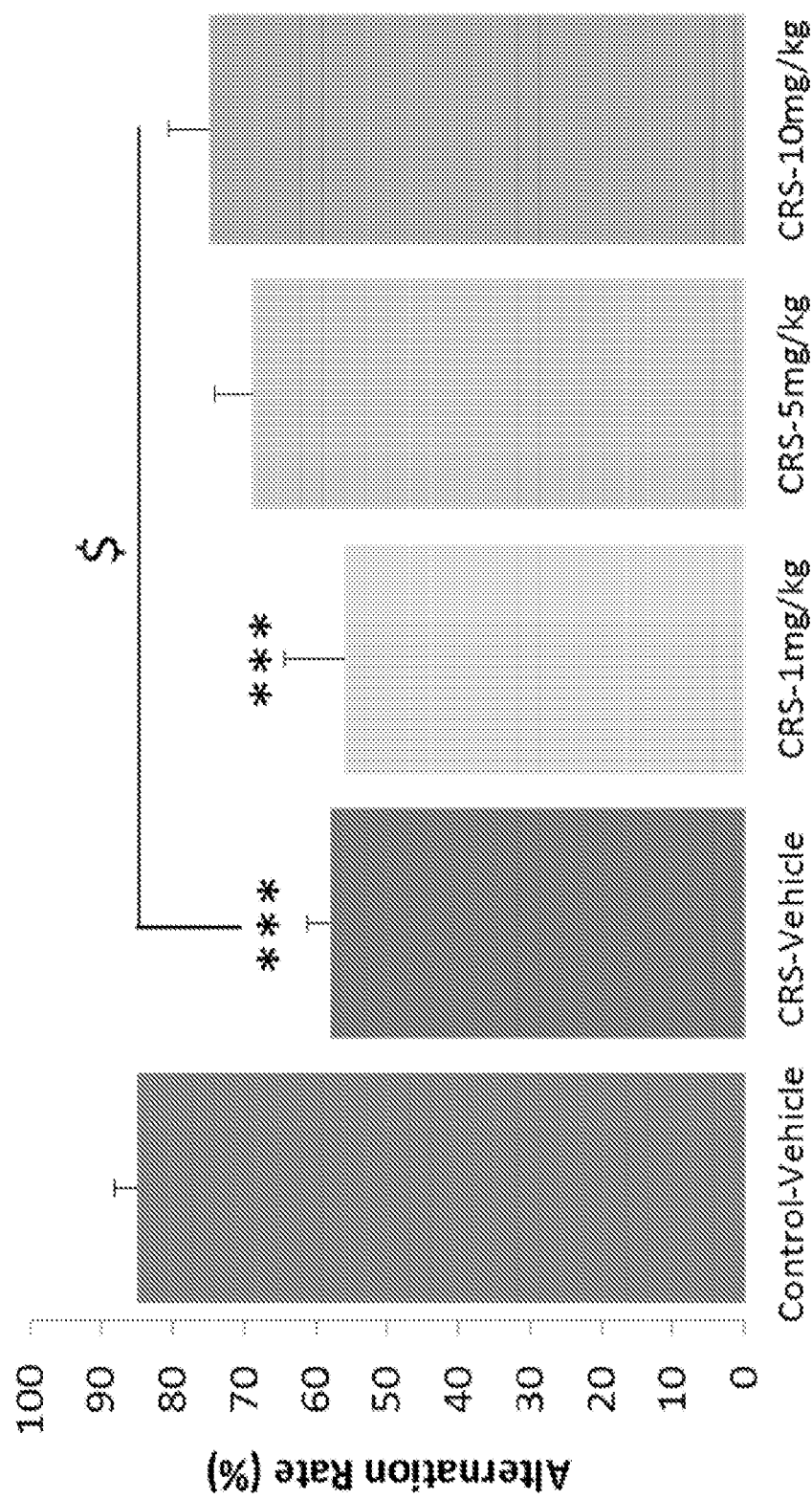
FIG. 5 shows the effects of GL-I-54 on percent alternation rate in the Y-maze spatial alternation task assessing working memory in mice. Mice subjected to CRS were injected with GL-I-54 (0, 1, 5, 10 mg/kg) i.p. 30 minutes before testing. Number of animals tested (n): n=(6-9)/group. ANOVA revealed statistical significance on the overall effect of stress and significant reversal of CRS-induced impairment in working memory in animal groups administered with GL-I-54 at 10 mg/kg. Differences between groups were tested using the PLSD post-hoc test (***p<0.001 compared to the "Control-Vehicle" group and $p<0.05 compared to the "CRS-Vehicle" group).

Data Results of the Y-Maze alternation task after treatment with GL-I-54: analysis (FIG. 5) showed a significant difference between groups (ANOVA: F(4,29)=6.6; p=0.0006). Fisher's PLSD post hoc analysis revealed decreased performance in CRS-veh animals (p<0.001) as well as in CRS animals administered with 1 mg/kg of GL-I-54 (p<0.001). GL-I-54 injected at 10 mg/kg had a significant pro-cognitive effect revealed by Fisher's PLSD post hoc test (p<0.05). These results suggest a potential indication of this compound to reverse cognitive deficits.

Figure 6:
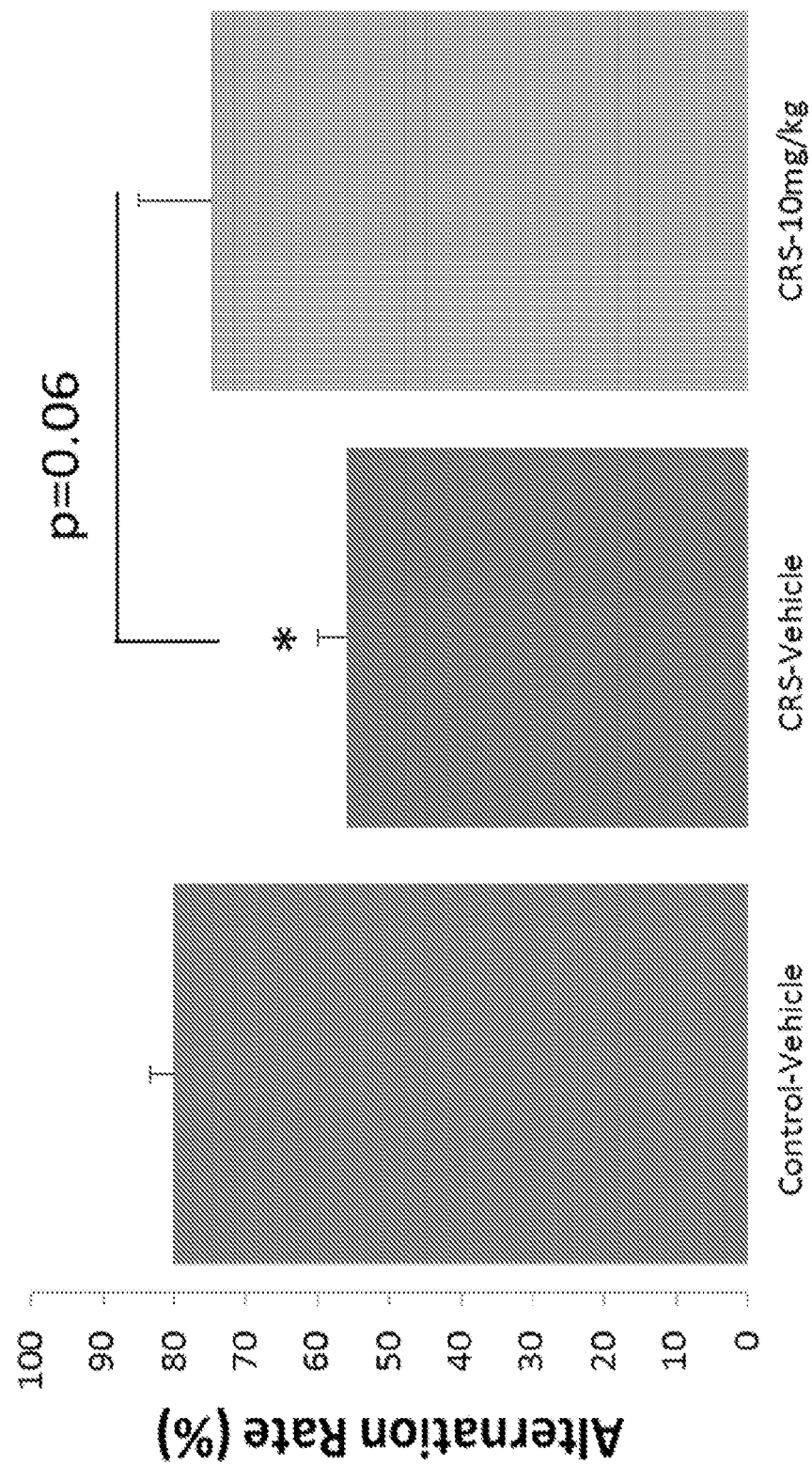
FIG. 6 shows the effects of GL-II-33 on percent alternation rate in the Y-maze spatial alternation task assessing working memory in mice. Mice subjected to CRS were injected with GL-II-33 (10 mg/kg, i.p., 30 minutes before testing). Number of animals tested (n): n=(4-5)/group. ANOVA revealed statistical significance on the overall effect of stress and a trend in the reversal of CRS-induced impairment in working memory in animal groups administered with GL-II-33 at 10 mg/kg. Differences between groups were tested using the PLSD post-hoc test (*p<0.05 compared to the "Control-Vehicle" group).

Results of the Y-Maze Alternation Task after Treatment with GL-II-33:

Data analysis (FIG. 6) demonstrated significant differences between groups (ANOVA: $F(2,11)=4.2$; $p=0.0439$).

Figure 10:
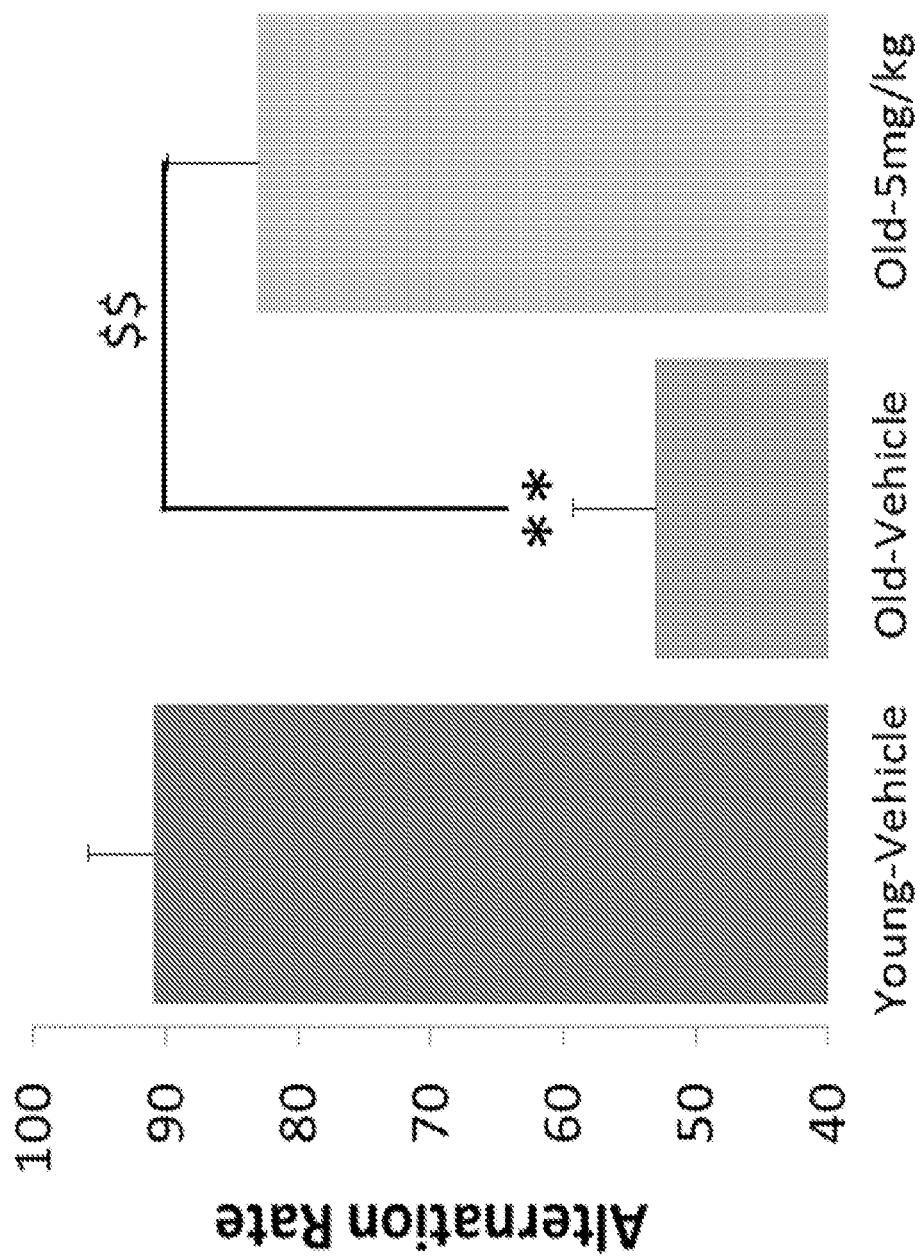
FIG. 10 shows the effects of GL-II-75 on percent alternation rate in the Y-maze spatial alternation task assessing working memory in old mice. 18 months-old mice subjected were injected with GL-II-75 (5 mg/kg, i.p) or vehicle 30 minutes before testing. Number of animals tested (n): n=6/group. ANOVA revealed statistical significance on the overall effect of age and significant reversal of age-induced impairment in working memory in animals administered with GL-II-75 at 5 mg/kg. Differences between groups were tested using the PLSD post-hoc test (**p<0.01 compared to the "Young-Vehicle" group and $$p<0.01 compared to the "Old-Vehicle" group).
Figure 11A:
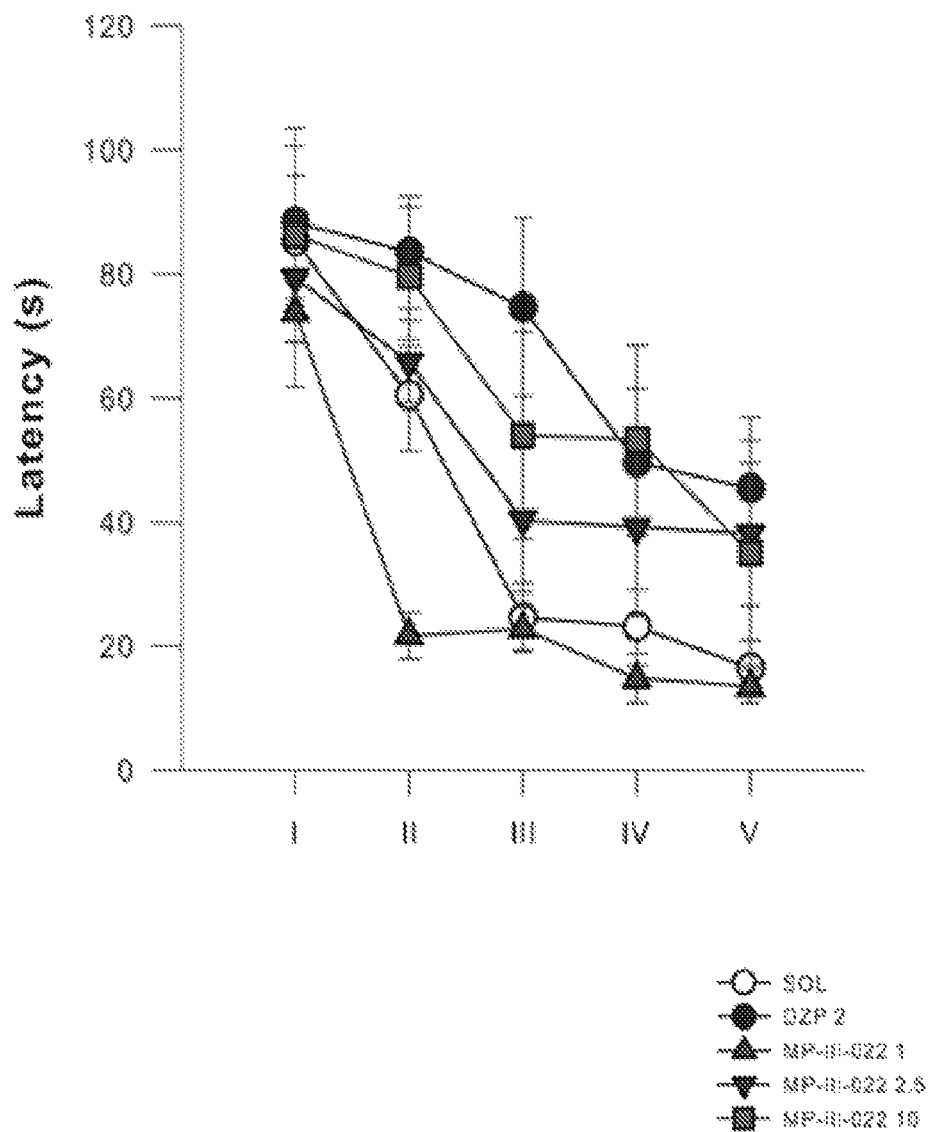
FIG. 11 shows the effects of diazepam 2 mg/kg and MP-III-022 1, 2 and 10 mg/kg on (a) latency to platform, (b) total distance, (c) distance in the peripheral ring (%) and (d)
Figure 11B:
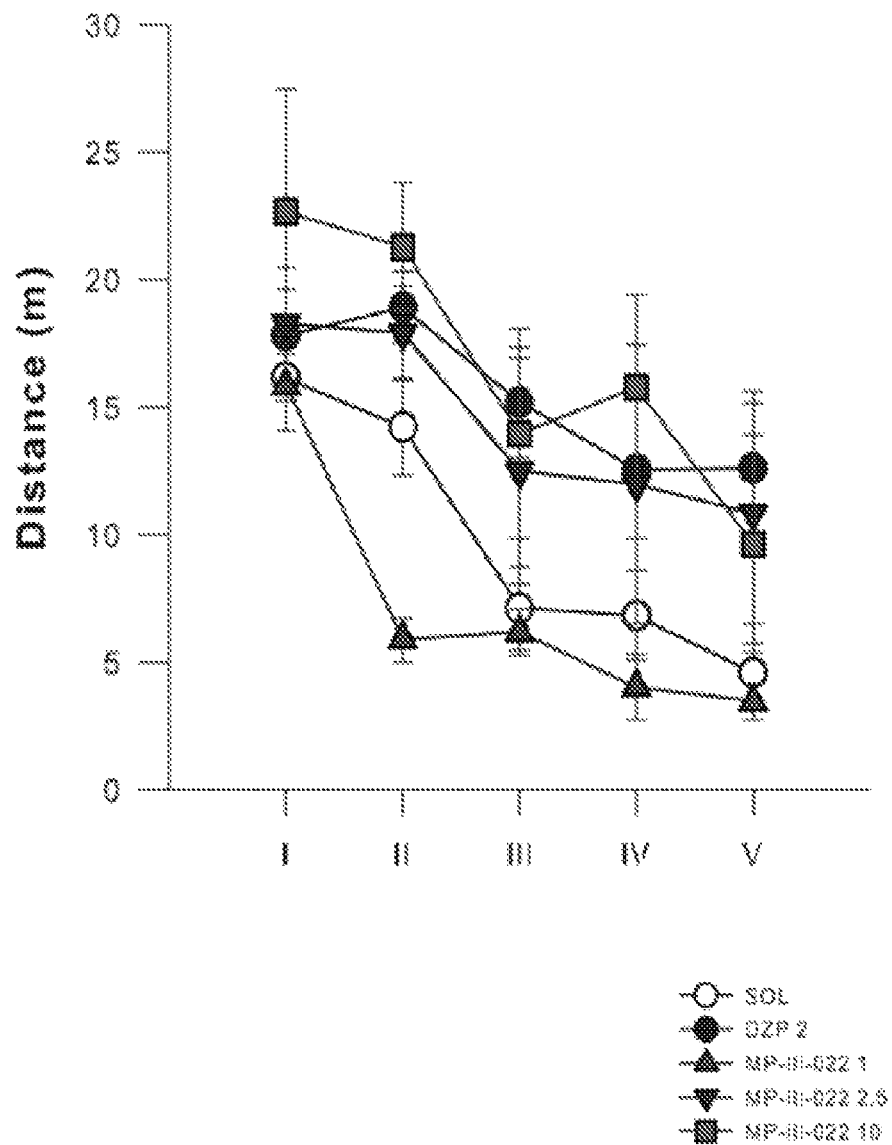
Figure 11C:
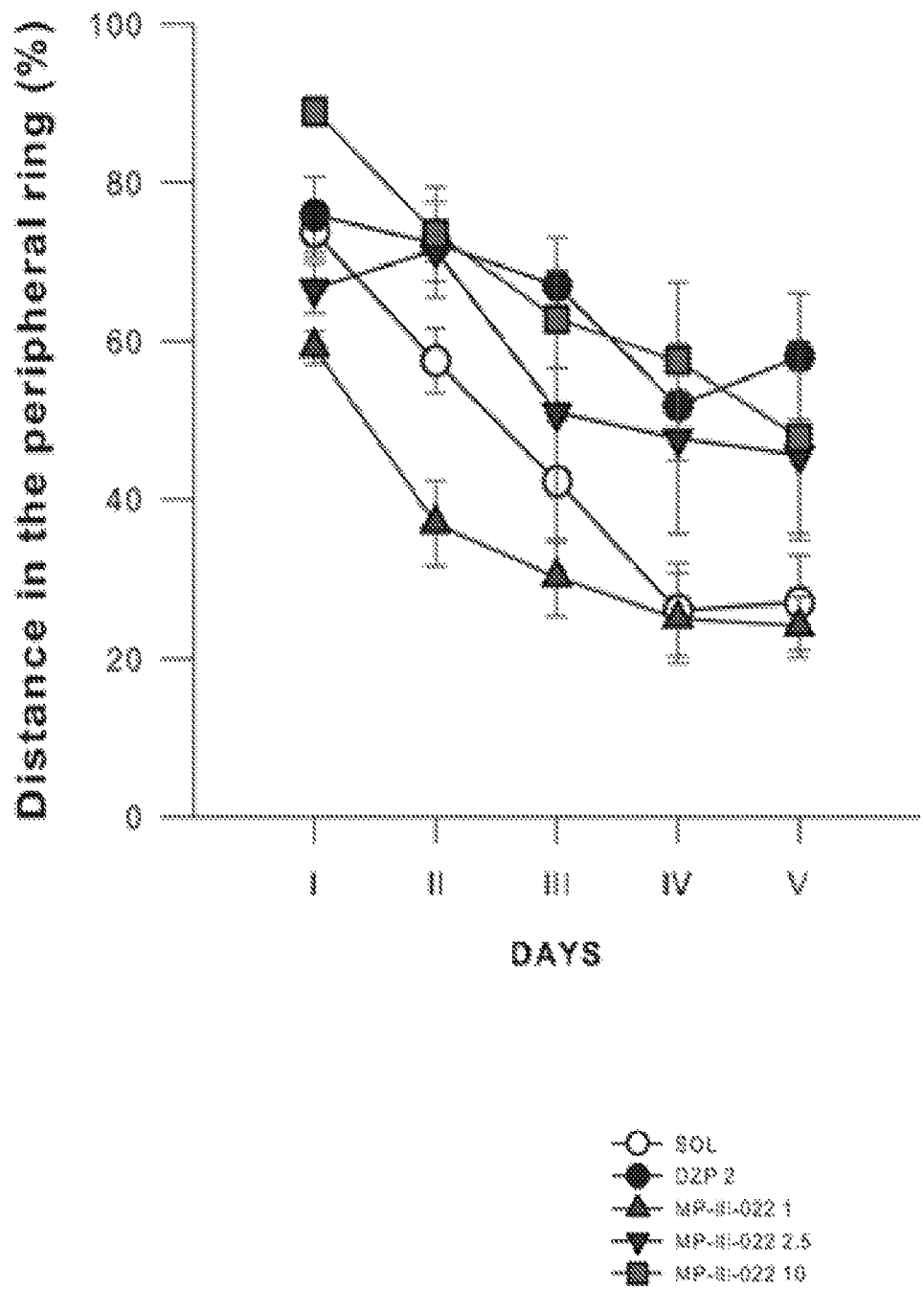
Figure 11D:
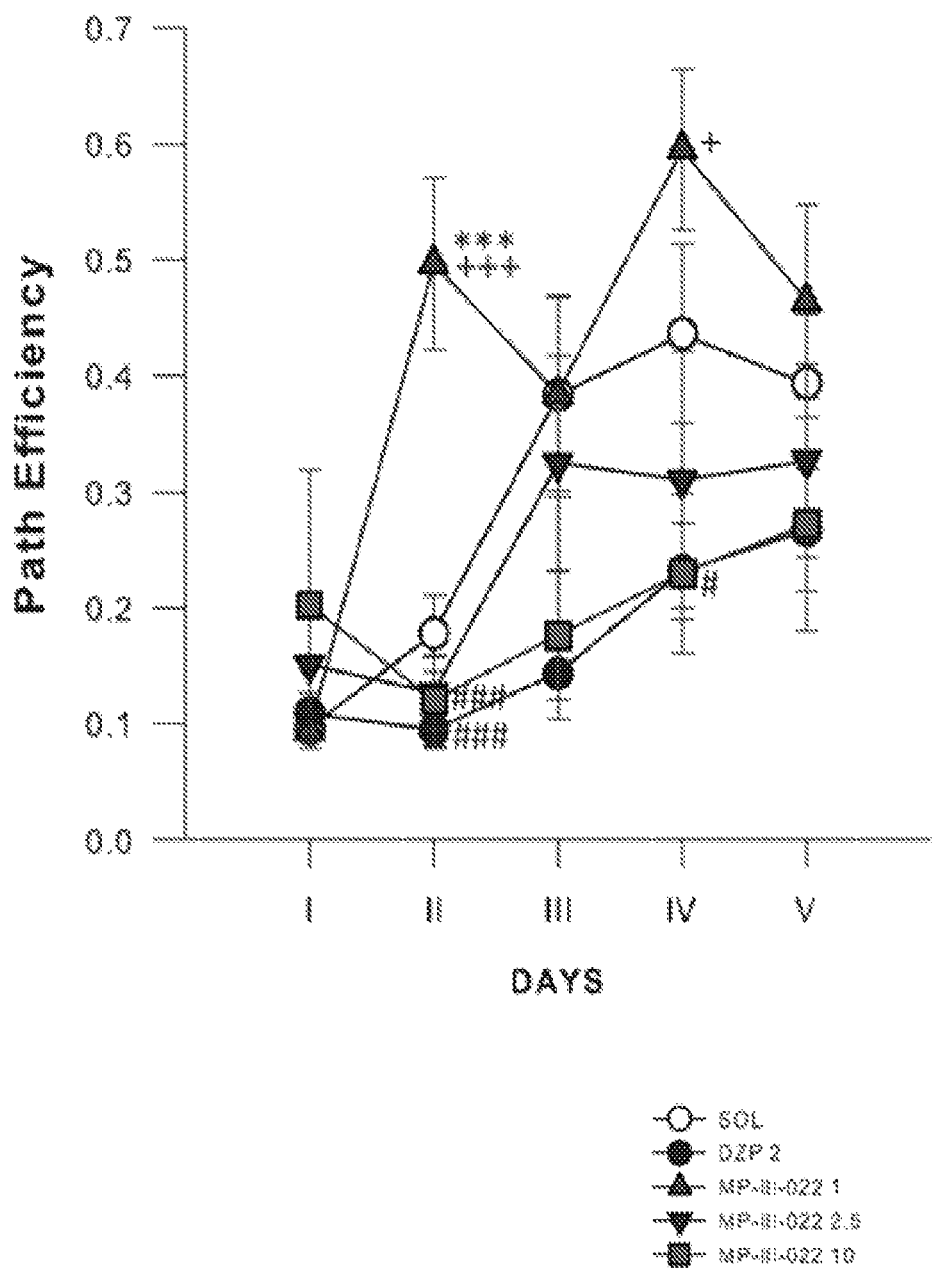

Data analysis (FIG. 10) demonstrated a significant difference between groups (ANOVA: $F(2,10)=11.57$; $p=0.0025$). Fisher's PLSD post hoc analysis revealed that administration of GL-II-75 has a significant pro-cognitive effect in aged animals at 5 mg/kg (p<0.01, compared to the Old-Vehicle group). These results suggest a potential indication of this compound to reverse cognitive deficits.

TABLE 1

Y-MAZE ALTERNATION TASK

|  | MP-III-022 | MP-III-023 | GL-II-74 | GL-II-76 | GL-II-31 | GL-III-23 | GL-II-54 | RV-II-04 |
|---|---|---|---|---|---|---|---|---|
| Genus Specific Changes |  |  | AMIDE |  |  | OXADIAZOLE | AMIDE Br in R1 (sedation) | OXADIAZOLE Br in R1 (sedation) |
| Dose | 5 mg/kg | 5 mg/kg | 1-5-10 mg/kg | 10 mg/kg | 10 mg/kg | 10 mg/kg | 10 mg/kg | 5 mg/kg |
| N (mice) | 4 | 4 |  | 6 | 5 | 5 | 4 | 4 |
| Alternation rate (%) | 45.5% | 62.5% | <58.3% | 47.2% | 56.6% | 56.6% | 66.66% | 54.1% |
| p-value compared to Ctrl-Veh | <0.001 | 0.023 | <0.06 | 0.04 | 0.027 | 0.0079 | 0.57 | 0.02 |
| p-value compared to CRS-Veh | 0.23 | 0.73 | >0.69 | .16 | 0.59 | 0.96 | 0.56 | 0.82 |

Fisher's PLSD post hoc analysis revealed decreased performance in CRS-veh animals (p<0.05) and increase in alternation rate after GL-II-33 10 mg/kg not significant from control-vehicle group. Although GL-II-33 mouse group was not statistically different from CRS-vehicle mouse group, a trend was detected when using the Fisher's PLSD post hoc test (p=0.06). These results suggest a potential indication of this compound to reverse cognitive deficits.

Figure 7:
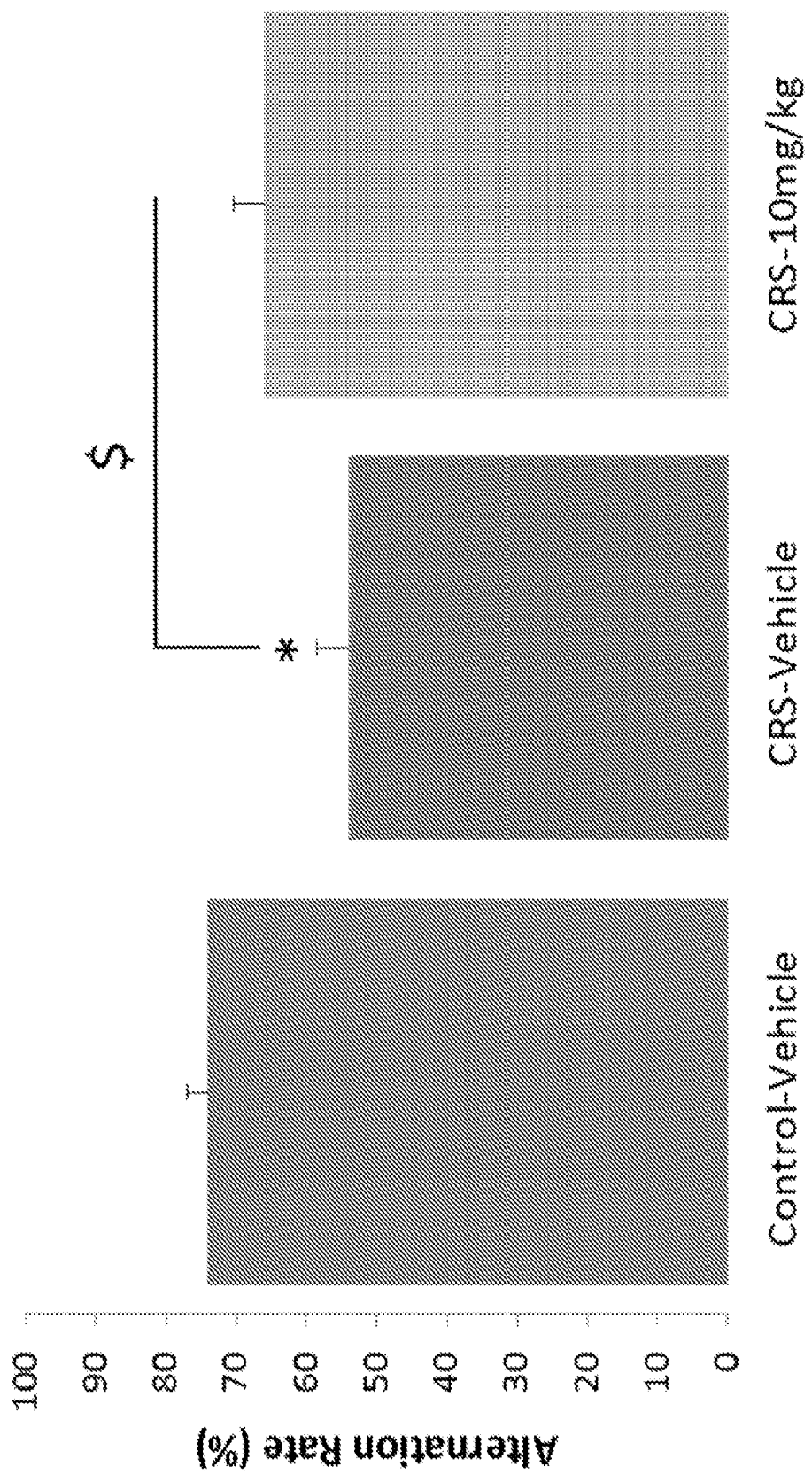
FIG. 7 shows the effects of GL-I-65 on percent alternation rate in the Y-maze spatial alternation task assessing working memory in mice. Mice subjected to CRS were injected with GL-II-65 (10 mg/kg, i.p., 30 minutes before testing). Number of animals tested (n): n=(9-11)/group. ANOVA revealed statistical significance on the overall effect of stress and significant reversal of CRS-induced impairment in working memory in animal groups administered with GL-I-65 at 10 mg/kg. Differences between groups were tested using the PLSD post-hoc test (*p<0.05 compared to the "Control-Vehicle" group, and $p<0.05 compared to "CRS-Vehicle" group).

Results of the Y-Maze Alternation Task after Treatment with GL-I-65:

Data analysis (FIG. 7) showed significant differences between groups (ANOVA: $F(2,28)=5.38$; $p=0.0105$). Fisher's PLSD post hoc analysis revealed decreased performance in CRS-veh animals (p<0.05) and increase in alternation rate after GL-I-65 10 mgkg not significant from control-vehicle group and statistically significant from CRS-vehicle group (p<0.05). These results suggest a potential indication of this compound to reverse cognitive deficits.

Figure 8:
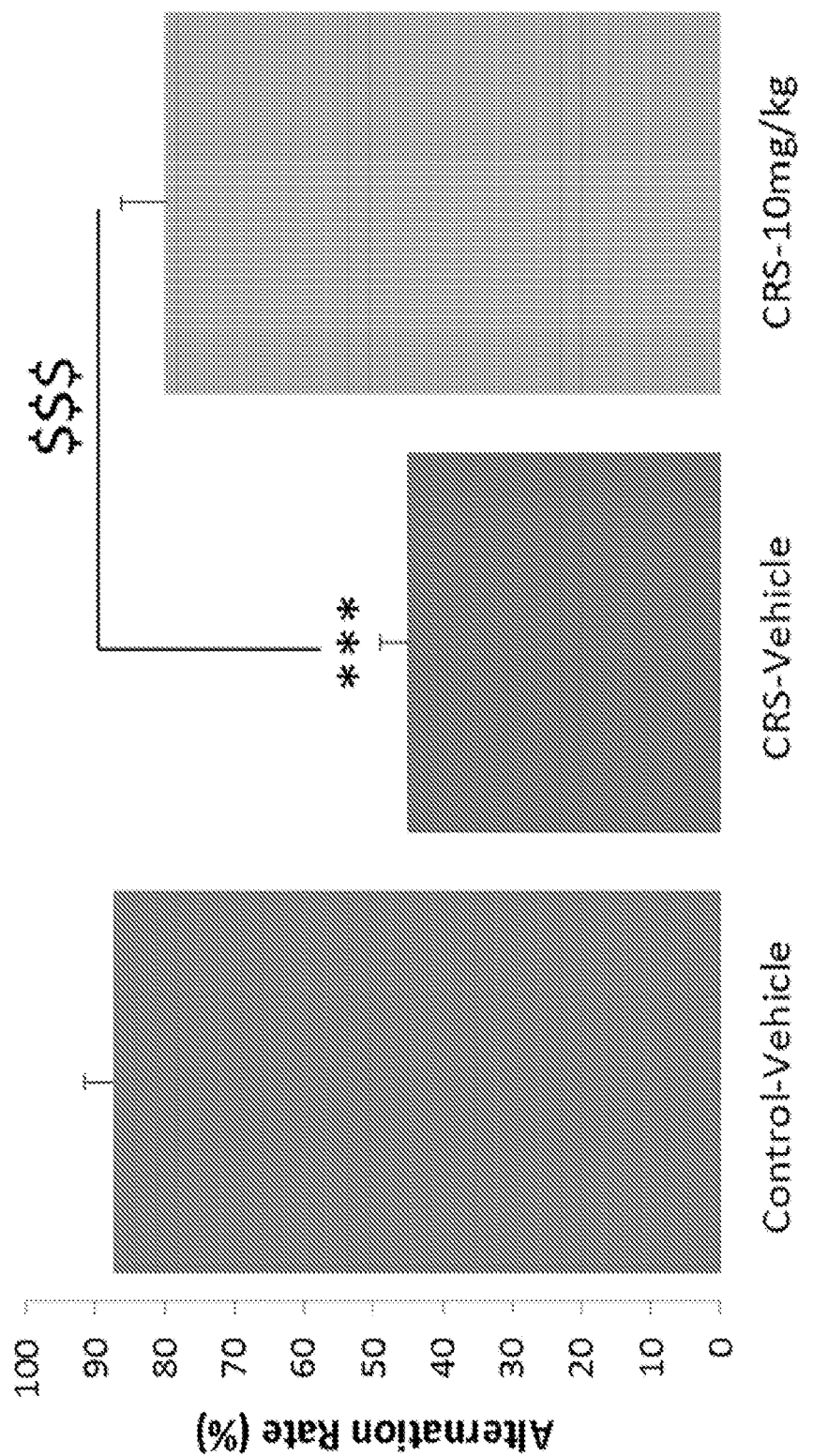
FIG. 8 shows the effects of racemic mix (GL-II-73/GL-I-54) on percent alternation rate in the Y-maze spatial alternation task assessing working memory in mice. Mice subjected to CRS were injected with the racemic mix solution (10 mg/kg, ip. 5 mg/kg each enantiomer, 30 minutes before testing) or vehicle. Number of animals tested (n): n=(4-5)/group. ANOVA revealed statistical significance on the overall effect of stress and significant reversal of CRS-induced impairment in working memory in animal groups administered with the racemic mix. Differences between groups were tested using the PLSD post-hoc test (***p<0.001 compared to the "Control-Vehicle" group/ $$$p<0.001 compared to the "CRS-Vehicle" group).

Results of the Y-Maze Alternation Task after Treatment with a Racemic Mixture of GL-II-73 and GL-I-54:

Data analysis (FIG. 8) demonstrated significant differences between groups (ANOVA: $F(2,10)=16.82$; $p=0.0006$). Fisher's PLSD post hoc analysis revealed a significant decreased performance in CRS-veh animals (p<0.001). Administration of the racemic mix (GL-II-73/GL-I-54) induced a reversal of the cognitive impairment induce by CRS (p<0.001). These results suggest a potential indication of these compounds to reverse cognitive deficits.

Figure 9:
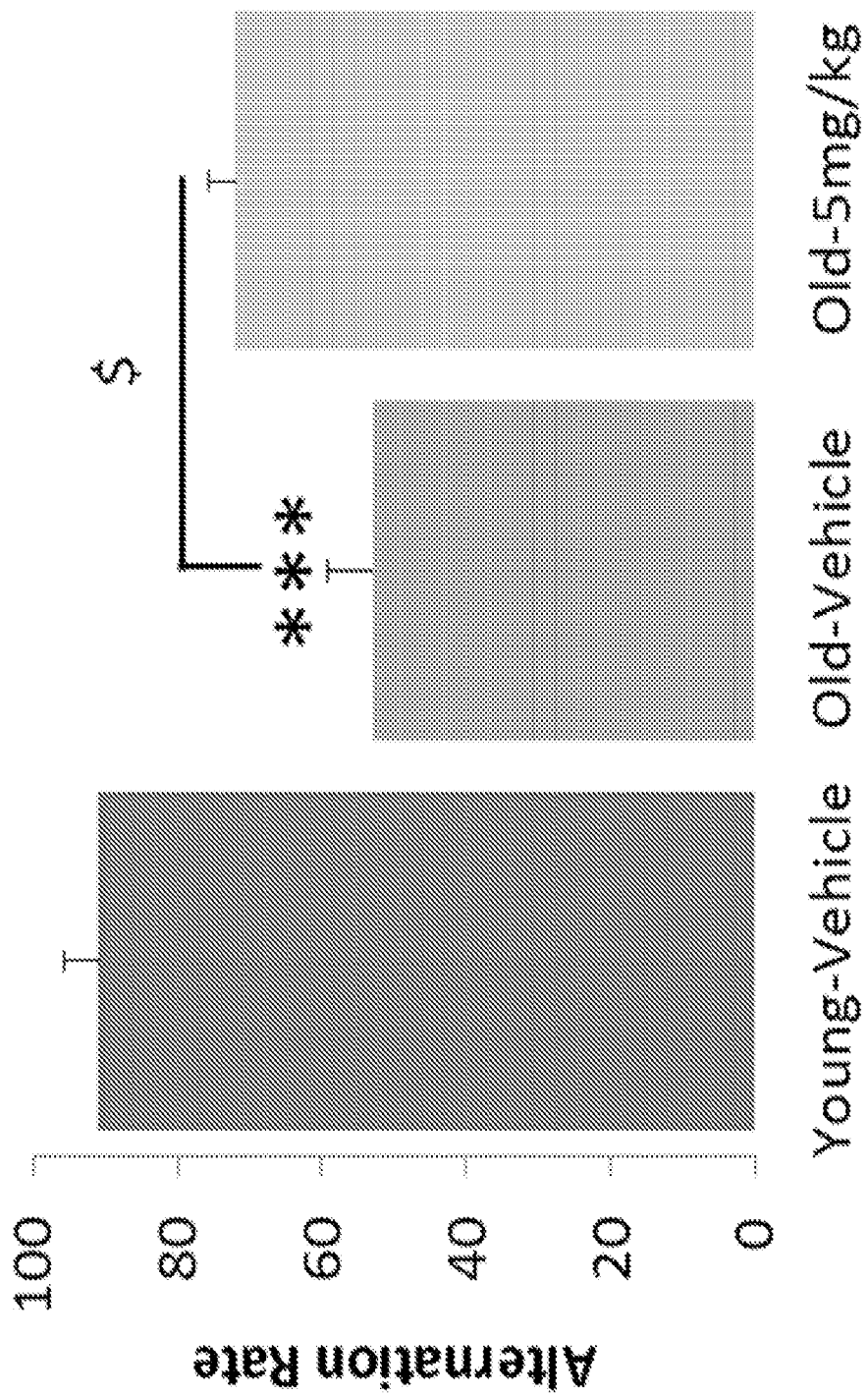
FIG. 9 shows the effects of GL-II-73 on percent alternation rate in the Y-maze spatial alternation task assessing working memory in old mice. 18 months-old mice subjected were injected with GL-II-73 (5 mg/kg, i.p) or vehicle 30 minutes before testing. Number of animals tested (n): n=6/group. ANOVA revealed statistical significance on the overall effect of age and significant reversal of age-induced impairment in working memory in animals administered with GL-II-73 at 5 mg/kg. Differences between groups were tested using the PLSD post-hoc test (***p<0.001 compared to the "Young-Vehicle" group and $p<0.05 compared to the "Old-Vehicle" group).

Results of the Y-Maze Alternation Task in Aqed Animals after Treatment with GL-II-73:

Data analysis (FIG. 9) showed a significant difference between groups (ANOVA: $F(2,12)=13.79$; $p=0.0008$). Fisher's PLSD post hoc analysis revealed that administration of GL-II-73 has a significant pro-cognitive effect in aged animals at 5 mg/kg (p<0.05, compared to the Old-Vehicle group). These results suggest a potential indication of this compound to reverse cognitive deficits.

Results of the Y-Maze Alternation Task in Aqed Animals after Treatment with GL-II-75:

Example 18. Effects of Alpha PAMs in Other Cognitive Tests

Procedure for the Morris Water Maze Assay:

The potential of MP-III-022 to affect cognitive performance of rats was assessed in 2 well-validated behavioral models. First, Morris water maze experiments were performed in a 2 m diameter circular pool filled to a height of 30 cm with water at $22\pm1°$ C. The escape platform (15 cm×10 cm) was submerged 2 cm below the water surface. All experimental details were as described in Savic et al. (Int. J. Neuropsychopharmacol. 2009, 12, 1179-1193). On each of the five consecutive days rats were given one swimming block, consisting of four trials. For each trial the rat was placed in the water at one of four pseudo-randomly determined starting positions. Once the rat has found and mounted the escape platform it was permitted to remain on the platform for 15 s. The rat was guided to the platform by the experimenter if it failed to locate it within 120 s. During the acquisition phase, treatments were applied once daily before the swimming block. On the sixth day, rats were given a treatment-free probe test (60 s) without the platform. The probe test was started from the novel, most distant location. Dependent variables chosen for tracking during the acquisition trials were: escape latency (s), total distance traveled (m), path efficiency (the ratio of the shortest possible path length to actual path length), % of distance swam in the peripheral annulus and mean speed (m/s). The selected parameters in the probe test were the distance swam in the target zone (s) and % of the distance swam in the peripheral annulus. We tested the effects of 1, 2.5 and 10 mg/kg MP-III-022 and 2 mg/kg diazepam as control drug. The doses of MP-III-022 were selected so that they elicit a mild, moderate and strong positive modulation of α5GABAARs, respectively, in accordance with the analysis of thorough pharmacokinetic and electrophysiological data presented in Stamenic et al. (Eur. J. Pharmacol. 2016, 791, 433-443). The data from the acquisition days in the Morris water maze were averaged for each rat (total data/total number of trials per day) and analyzed using two-way ANOVA with repeated measures (factors: Treatment and Days) with Days as the repeated measure. In the case of significant interaction, separate one-way ANOVAs were conducted to assess the influence of treatment within individual levels of factor Days. The data from the probe test were assessed using one-way ANOVA.

Procedure for the Social Novelty Discrimination (SND) Assay:

The SND test compares the social investigation times of an adult rat with a familiar and a novel juvenile rat. Testing consisted of two consecutive juvenile presentations periods to an adult subject: period 1 (P1) and period 2 (P2). At the beginning of P1, one juvenile was placed into the adult home cage and the time spent by the adult investigating the juvenile (anogenital sniffing, licking, close pursuing and pawing) was recorded manually for 5 min. During P2, the same juvenile and a second, novel juvenile were placed in the cage together with the adult, and the times spent by the adult investigating each juvenile were measured independently for 3 min. A different pair of juvenile rats was presented to each adult tested. Manual scoring was conducted in a blinded manner. SND was deliberately impaired in control rats by the parametric manipulation applied, as there was 30 min delay between P1 and P2, and their SND was expected to be low. The influence of MP-III-022 (1, 2.5 or 10 mg/kg) on the thus induced impairment in SND was examined. There were five groups of rats which received one of the following treatments 20 min before P1: solvent, 1.5 mg/kg diazepam and 1, 2.5 and 10 mg/kg MP-III-022. The amount of time investigating familiar (Tf) and novel (Tn) juvenile during P2 was manually scored, and discrimination indexes (Tn−Tf/Tn+Tf) was calculated. Total exploration time during P1 and P2 was also manually recorded.

Results of the Morris Water Maze Assay:

The results of the five-day acquisition phase of the water maze test are presented in FIG. 11. As summarized in TABLE 2, significant effects of factors Treatment and Days were observed for all parameters measured. Our results demonstrated that at the highest dose selective for α5GABAARs (10 mg/kg, according to Stamenic et al., 2016), MP-III-022 elicited spatial learning incapacitation indistinguishable from that induced by diazepam 2 mg/kg used as a positive control. This is the first result which directly demonstrates that water maze impairments characteristic for benzodiazepines are achievable through positive modulation of α5GABAARs solely. The affected receptors are most probably located in the hippocampus, bearing in mind that the water maze is commonly seen as a hippocampal-dependent cognitive task. As the two-way repeated measures ANOVA for mean speed was not statistically significant for factor Treatment (F(4,27)=1.112, p=0.317), any sensorimotor disturbances during acquisition sessions can be excluded. Notably, the post hoc tests revealed that the group treated with 1 mg/kg MP-III-022 differed from both, 2 mg/kg diazepam and 10 mg/kg MP-III-022 group for all parameters: the animals receiving 1 mg/kg MP-III-022 had shorter escape latencies, shorter distances, swam less distance in the peripheral ring and had higher path efficiencies. Moreover, post hoc analysis after one-way ANOVA on Day II revealed that rats treated with 1 mg/kg MP-III-022 had higher path efficiencies compared to the control and all other treatment groups (Day II, FIG. 5d), suggesting that a slight level of selective modulation, associated with the lowest dose of MP-III-022, tended to make rats faster to acquire the task. TABLE 2. The effects of 2 mg/kg DZP and 1, 2.5 and 10 mg/kg MP-III-022 administration on the rat's behavior in the MWM. Two-way repeated measures ANOVA and overall post hoc results for latency to platform (s), total distance (m), distance swam in the peripheral annulus (%) and path efficiency. SOL=solvent; DZP=diazepam; MP=MP-III-022; ns=not significant.

TABLE 2

| Factor | Latency (s) | Total distance (m) | Distance in the peripheral ring (%) | Path efficiency |
|---|---|---|---|---|
| Treatment: F(4, 27) p | 3.962 0.012 | 4.946 0.004 | 6.994 <0.001 | 6.445 <0.001 |
| Days: F(4, 108) p | 43.761 <0.001 | 22.438 <0.001 | 37.268 <0.001 | 19.000 <0.001 |
| Interaction: F(16, 108) p | 1.527 0.103 | 1.135 0.333 | 1.460 0.128 | 2.074 0.014 |
| SNK post hoc for Treatment | | | | |
| SOL vs. 2 mg/kg DZP | ns | 0.086 | 0.018 | 0.086 |
| SOL vs. 1 mg/kg MP | ns | ns | ns | 0.052 |
| SOL vs. 2.5 mg/kg MP | ns | 0.099 | ns | ns |
| SOL vs. 10 mg/kg MP | ns | 0.038 | 0.030 | 0.077 |
| 2 mg/kg DZP vs. 1 mg/kg MP | 0.017 | 0.019 | 0.001 | 0.001 |
| 2 mg/kg DZP vs. 2.5 mg/kg MP | ns | ns | ns | ns |
| 2 mg/kg DZP vs. 10 mg/kg MP | ns | ns | ns | ns |
| 1 mg/kg MP vs. 2.5 mg/kg MP | ns | 0.036 | 0.018 | 0.022 |
| 1 mg/kg MP vs. 10 mg/kg MP | 0.026 | 0.007 | 0.002 | 0.002 |

Figure 12A:
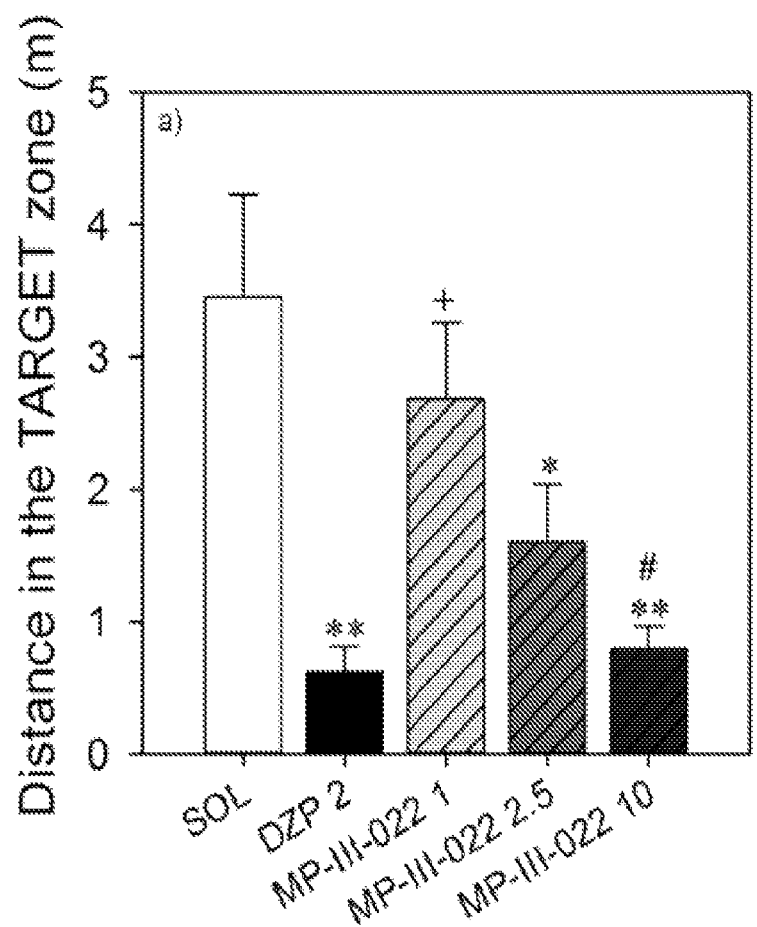
Figure 12B:
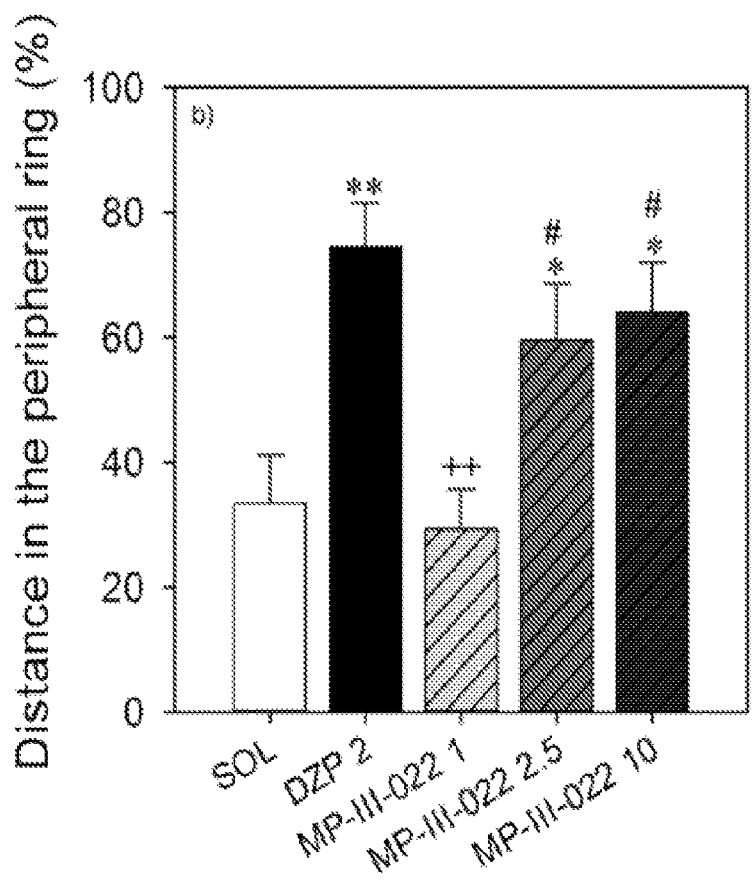

One-way ANOVA applied on results from the probe test revealed a significant influence of treatment on both parameters analyzed: the distance swam in the target region (F(4,27)=6.26, p=0.001; FIG. 12a), and the percent of distance swam in the peripheral ring (F(4,27)=6.84, p<0.001; FIG. 12b). Although high doses of MP-III-022 mimic the cognitive disruption effect of diazepam on spatial learning and memory, 1 mg/kg of MP-III-022 induce a significant improvement in spatial learning and memory processes, confirming that α5 modulation may have pro-cognitive effects.

Results of the Social Novelty Discrimination Assay:

The effects of 1.5 mg/kg diazepam and 1, 2.5 and 10 mg/kg MP-III-022 on the rats' behavior in the social novelty discrimination procedure are presented in FIG. 13. One-sample t-test for discrimination indices revealed significant differences from zero (i.e. chance level) only for the 10 mg/kg MP-III-022 group (t (7)=2.446; p=0.023, FIG. 25a). Similarly, paired t-test revealed significance of time spent in exploring the familiar and the novel juvenile rat during P2, showing that only the 10 mg/kg MP-III-022 group spent significantly more time in exploring the new rat (t(7)=−2.921, p=0.022, FIG. 25b). The same statistical analysis on exploration time revealed a statistical trend in rats treated with 2.5 mg/kg diazepam (t(7)=−2.076, p=0.077). The finding of facilitation of social novelty discrimination by selective potentiation of α5GABAARs is novel and suggests that MP-III-022 has pro-cognitive effects. Altogether, the results of the two assays suggest that a strong selective potentiation of α5GABAARs (three times the level elicited by low concentrations of GABA, as assessed in Stamenic et al., 2016) can induce both a facilitatingaction on social recognition, and an enhancedspatial learning and memory.

Example 19. Forced Swim Test

Procedure for the Forced Swim Test Assay (FST)

Animals:

C57B1/6 male mice were ordered from Jackson Laboratories at 8 weeks-old and were group housed (4-5 mice/cage) under normal housing conditions (12 h light ON cycle starting at 7 am/water and food ad libitum) for one week. During this week, animals were handled in order to habituate them to the experimenter and to reduce their anxiety-like response during behavioral testing.

Drug Preparation and Administration:

All drugs were diluted in a vehicle solution containing 85% $H_2O$, 14% propylene glycol (Sigma Aldrich) and 1% Tween 80 (Sigma Aldrich). Working solutions were prepared at a concentration of 20 mg/mL and administered i.p. adjusted to the body weight of each animal. Doses used were either 1, 5 or 10 mg/kg. For all FST experiments, animals were injected i.p. with vehicle or αPAM.

Protocol:

Mice were tested in the forced swim test (FST) (measure of despair-like behavior used for the assessment of antidepressant efficacy). Animals were sub-chronically injected three times (24, 20 and 1 hour before testing) as per standard methods in the field for testing potential antidepressant compounds.

One hour after the last injection, mice were placed in an inescapable transparent tank filled with water (25 cm, 25-26° C.), where they are unable to touch the bottom and unable to jump out of the tank. Animal were recorded for a period of 6 minutes and a manual count of the immobile time in the tank was measured for the 2-6 minutes period by an experimenter blinded to the mouse treatment history. Immobility is defined as the minimum amount of movement to stay afloat. Compounds that reduced immobility in the FST are considered to have potential antidepressant actions.

Results of the Forced Swim Test after Treatment with GL-II-73: Data (FIG. 14) showed a trend towards difference between groups (ANOVA $F(3,34)=8.189$; $p=0.0614$). Furthermore, post hoc analysis identified that GL-II-73 10 mg/kg significantly decreased the immobility as compared to vehicle group $*p<0.05$. These results suggest a potential indication of this compound as antidepressant.

Results of the Forced Swim Test after Treatment with GL-II-74:

Data (FIG. 15) showed a significant difference between groups (ANOVA $F(3,43)=7.122$; $p<0.001$). Furthermore, post hoc analysis identified that GL-II-74 at 5 and 10 mg/kg significantly decreased the immobility as compared to vehicle group $*p<0.05$. These results suggest a potential indication of this compound as antidepressant.

Results of the Forced Swim Test after Treatment with GL-II-75:

Data (FIG. 16) showed a significant difference between groups (ANOVA $F(3,44)=6.427$ $p<0.01$). Furthermore, post hoc analysis identified that GL-II-75 at 5 and 10 mg/kg significantly decreased the immobility as compared to vehicle group $*p<0.05$ and $***p<0.001$. These results suggest a potential indication of this compound as antidepressant.

Results of the Forced Swim Test after Treatment with MP-III-022:

T-test analysis revealed a significant decrease in immobility time of MP-III-022 (10 mg/kg) as compared to vehicle (t-test, $*p<0.05$). (FIG. 17). These results suggest a potential indication of this compound as antidepressant.

Results of the Forced Swim Test after Treatment with GL-I-54:

T-test analysis revealed a significant decrease in immobility time of GL-I-54 (5 mg/kg) as compared to vehicle (t-test, $***p<0.001$). (FIG. 18). These results suggest a potential indication of this compound as antidepressant.

Results of the Forced Swim Test after Treatment with GL-II-54:

T-test analysis revealed a significant decrease in immobility time of GL-II-54 (10 mg/kg) as compared to vehicle (t-test, $*p<0.05$). (FIG. 19). These results suggest a potential indication of this compound as antidepressant.

TABLE 3

OTHER RESULTS FOR FORCED SWIM TEST

|  | GL-II-31 | GL-III-23 | GL-II-33 | GL-I-65 |
|---|---|---|---|---|
| Genus | AMIDE | | OXADIAZOLE | |
| Dose | 10 mg/kg | 10 mg/kg | 10 mg/kg | 10 mg/kg |
| N (mice) | 10 | 10 | 10 | 10 |
| p-value compared to Veh | p > 0.1 | p > 0.1 | p > 0.1 | p > 0.1 |

Example 20: Locomotor Activity

Home cage locomotor activity changes for GL-II-73, GL-II-74, GL-II-75 and MP-III-022 was quantified to assess the animal's movement, in dim light condition and to detect potential sedative effects of the different compounds. Mice were placed in a clean cage, similar to their home-cage (28.2×17.1 cm), without bedding and lid to allow video recording from the top. Tacking was performed and distance travelled (30 min session) was analyzed using ANY-Maze™ tracking software (version 499z) to assess the locomotor activity in a home-cage environment. Animals received a single dose of compound or vehicle solution 1 hour before testing.

Drug preparation and administration: All drugs were diluted in a vehicle solution containing 85% H2O, 14% propylene glycol (Sigma Aldrich) and 1% Tween 80 (Sigma Aldrich). Working solutions were prepared at a concentration of 20 mg/mL and administered i.p. adjusted to the body weight of each animal. Doses used were either 1, 5 or 10 mg/kg. For all locomotor activity experiments, animals were acutely injected i.p. with vehicle or αPAM, 1 hour before the beginning of the test.

Results of Locomotor Activity after Treatment with GL-II-73:

Data analysis demonstrated significant differences between groups (ANOVA: $F(3,36)=3.8$; $p=0.016$). Fisher's PLSD analysis revealed no significant effect of GL-II-73 at 1 mg/kg and a significant increase in locomotion at 5 and 10 mg/kg ($p<0.05$ and $p<0.001$ respectively) compared to the Vehicle group. (FIG. 20). These results suggest no sedation effect of the compound.

Results of Locomotor Activity after Treatment with GL-II-74:

Data analysis demonstrated significant differences between groups (ANOVA: $F(3,34)=3.18$; $p=0.0381$). Fisher's PLSD post hoc analysis revealed no significant effect of GL-II-74 at low doses (1 or 5 mg/kg) and a significant increase in locomotion at 10 mg/kg ($p<0.01$) compared to the Vehicle group. (FIG. 21) These results suggest no sedation effect of the compound.

Results of Locomotor Activity after Treatment with GL-II-75:

Data analysis demonstrated significant differences between groups (ANOVA: $F(3,36)=7.038$; $p=0.0008$). Fisher's PLSD post hoc analysis revealed no significant effect of GL-II-75 at 5 mg/kg and a significant increase in locomotion at 1 and 10 mg/kg ($p<0.05$ and $p<0.001$ respectively) compared to the Vehicle group. (FIG. 22). These results suggest no sedation effect of the compound.

Figure 24B:
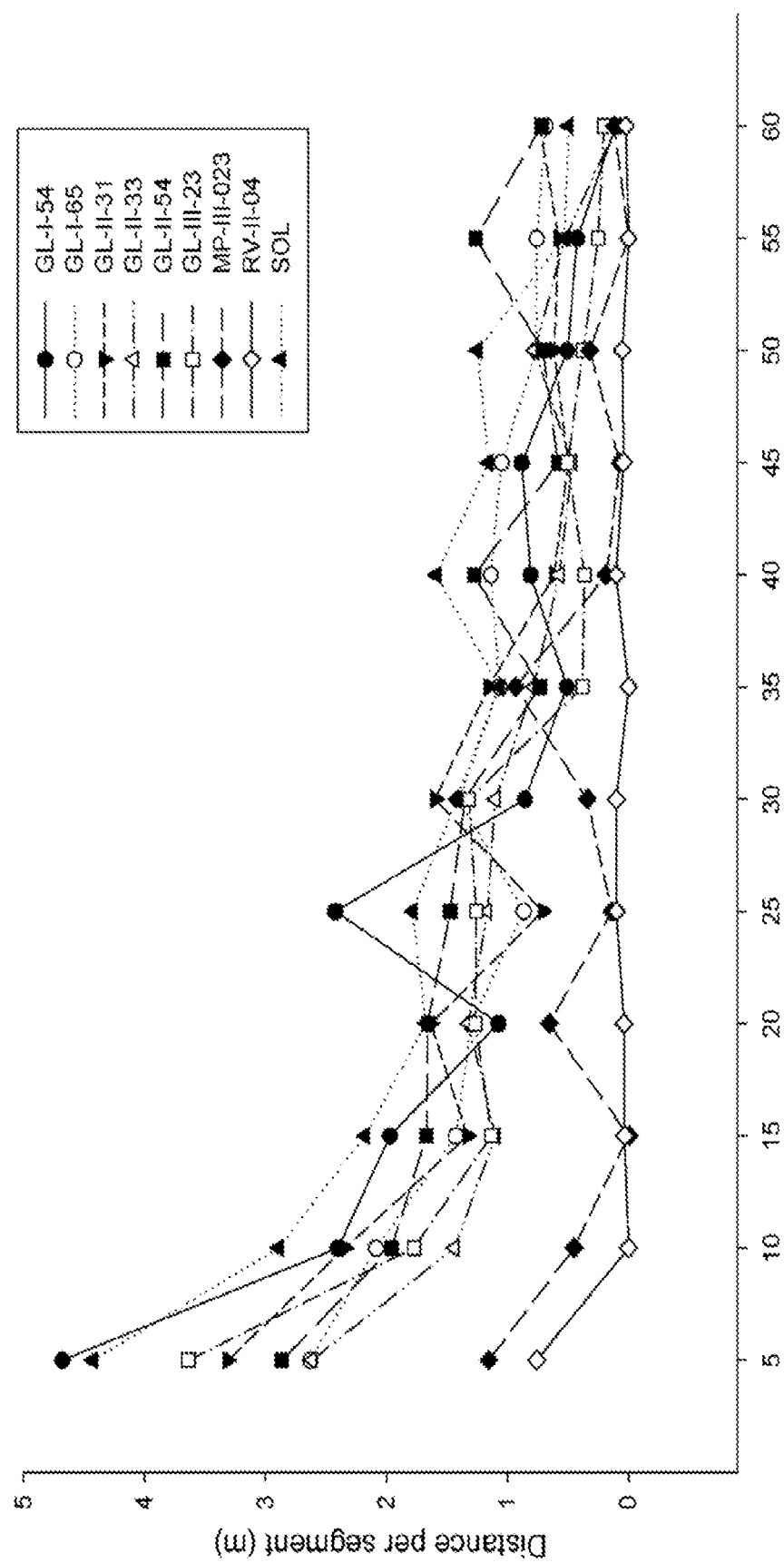

Results of Locomotor Activity after Treatment with MP-III-022:

Data analysis showed no significant difference between MP-III-022 and vehicle groups ($p=0.52$). (FIG. 23). These results suggest no sedation effect of the compound. Procedure for the assessment of locomotor activity changes induced by additional ligands in rats. The influence of RV-II-04, GL-II-31, MP-III-023, GL-I-54, GL-III-23, GL-II-33, GL-II-54 and GL-I-65, all dosed at 10 mg/kg, on spontaneous locomotor activity was assessed in experimentally naïve adult male Wistar rats weighing 350-400 g (n=48). The test was performed in the apparatus consisting of four white and opaque Plexiglas chambers (40×25×35 cm) under dim red light (20 lux). Digital camera mounted above the apparatus recorded the animal activity, which was tracked and analyzed using ANY-maze Video Tracking System software (Stoelting Co, Wood Dale, Ill., USA). The ligands were dissolved/suspended with the aid of sonication in the solvent (SOL) containing 85% distilled water, 14% propylene glycol and 1% Tween 80. The 10 mg/kg dose of each of ligands or SOL were applied i.p. in the 10 ml/kg volume and a single rat was immediately placed in the center of the chamber. The activity was tracked for a total of 60 min. Chambers were cleaned with diluted ethanol after every trial. Statistical analysis (one-way ANOVA and post hoc SNK tests where applicable) was performed in SigmaPlot 11 software (Systat, USA). Results for locomotor activity assessment after treatment with additionnal ligands: the overall distances that rats traveled during 60 min of recording are presented in FIG. 24a, while FIG. 24b shows distances traveled in 5-min bins. The ANOVA revealed significant differences in overall distance traveled during 60 min ($F(8,40)=4.71$, $P<0.001$). According to the post hoc test, MP-III-023, and especially RV-II-04 induced a profound sedation. A two-way repeated measures ANOVA of 5-min interval distances revealed a significant effect of all factors (Treatment: $F(8,440)=4.71$, $P<0.001$; Time: $F(11,440)=45.88$, $P<0.001$; Interaction: $F(88,440)=1.96$, $P<0.001$). It was demonstrated that MP-III-023, and especially RV-II-04 induced sedation during nearly the whole period of recording.

Example 21: Locomotor Coordination

Procedure:

Female Swiss Webster mice (10 weeks of age) from Charles River Laboratory, WIL, MA were used for the experiments. The animals were housed under specific pathogen-free conditions, under standard conditions of humidity, temperature and a controlled 12 h light and dark cycle and had free access to food and water. The sensorimotor rotarod test was carried out 10, 30 and 60 minutes after the injection. Mice were tested on a rotarod at 15 rpm for maximum 3 min and the time of fall was recorded. Falling before the 3 minutes period of testing assesses of locomotor coordination impairment induced by the compound.

Drug Preparation and Administration:

Mice (N=10/group) received a single administration via oral gavage of test compound (40 mg/kg), diazepam (5 mg/kg), or vehicle (2% polyethylene glycol, 2.5% hydroxypropylmethyl cellulose solution).

Results of Locomotor Coordination Assessment:

Most of the compounds, including the diazepam positive control (5 mg/kg), showed sensorimotor steadiness at 10 minutes, followed by 30 and 60 minutes. The compounds that caused the most severe motor impairment were RV-II-04, MP-III-023, and GL-I-54. These results suggest sedative effect of these 3 compounds. Compounds in this series that exhibited no sensorimotor impairment are GL-II-31, GL-II-33, GL-II-54, GL-I-65, GL-II-73, GL-II-74, and GL-II-76. (FIG. 25). These results suggest no sedation effect of these compounds.

Example 22: Electrophysioloqy

Procedure:

Transfection of Mammalian Cells and Electrophysiological Recordings. Full-length cDNAs for $GABA_A$ receptor subtypes (generously provided by Dr. Robert Macdonald, Vanderbilt University and Dr. David Weiss, University of Texas Health Science Center, San Antonio, Tex.) in mammalian expression vectors were transfected into the human embryonic kidney cell line HEK-293T (GenHunter, Nashville, Tenn.) (Chestnut et al, 1996, J. Immunol. Methods 193, 17-27). All subtypes were rat clones except for α2, which was a human clone. Cells were maintained in Dulbecco's modified Eagle's medium (DMEM) plus 10% fetal bovine serum, 100 IU/mL penicillin, and 100 µg/mL streptomycin.

HEK-293T cells were transiently transfected using calcium phosphate precipitation. Plasmids encoding $GABA_A$ receptor subtype cDNAs were added to the cells in 1:1:1 ratios (α:β:γ) of 2 µg each.31 For identification of positively transfected cells, 1 µg of the plasmid pHook-1 (Invitrogen Life Technologies, Grand Island N.Y.) containing cDNA encoding the surface antibody sFv was also transfected into the cells.11 Following a 4-6 h incubation at 3% CO2, the cells were treated with a 15% glycerol solution in BBS buffer (50 mM BES(N,N-bis[2-hydroxyethyl]-2-aminoethanesulfonic acid), 280 mM NaCl, 1.5 mM Na2HPO4) for 30 s. The selection procedure for pHook expression was performed 18-52 h later. The cells were passaged and mixed for 30-60 min with 3-5 µL of magnetic beads coated with antigen for the pHook antibody (approximately 6×105 beads).11 Bead-coated cells were isolated using a magnetic stand. The selected cells were resuspended into supplemented DMEM, plated onto glass coverslips treated with poly L-lysine and collagen, and used for recordings the next day.

Cells were patch-clamped at −50 mV in the whole-cell recording configuration. The bath solution consisted of (in mM): 142 NaCl, 8.1 KCl, 6 MgCl2, 1 CaCl2), and 10 HEPES (4-(2-hydroxyethyl)-1-piperazineethanesulfonic acid) with pH=7.4 and osmolarity adjusted to 295-305 mOsm. Recording electrodes were filled with a solution of (in mM) 153 KCl, 1 MgCl2, 5 K-EGTA (ethylene glycol-bis(β-aminoethyl ether N,N,N'N'-tetraacetate), and 10 HEPES with pH=7.4 and osmolarity adjusted to 295-305 mOsm. GABA was diluted into the bath solution from freshly made or frozen stocks in water. Compounds were dissolved in DMSO and diluted into bath solution with the highest DMSO level applied to cells of 0.01%. Patch pipettes were pulled from borosilicate glass (World Precision Instruments, Sarasota, Fla.) on a two-stage puller (Narishige, Japan) to a resistance of 5-10 MΩ. Solutions containing GABA or GABA+ compounds were applied to cells for 5 s. using a 3-barrelled solution delivery device controlled by a computer-driven stepper motor (SF-77B, Harvard Apparatus, Holliston, Mass., open tip exchange time of <50 ms). There was a continuous flow of external solution through the chamber. Currents were recorded with an Axon 200B (Foster City, Calif.) patch clamp amplifier.

Whole-cell currents were analyzed using the programs Clampfit (pClamp9 suite, Axon Instruments, Foster City, Calif.) and Prism (Graphpad, San Diego, Calif.). Concentration-response data was fit with a four-parameter logistic equation (current=[minimum current+(maximum current−minimum current)]/1+(10(logEC50−log[modulator])n) where n represents the Hill number. All fits were made to normalized data with current expressed as a percentage of the response to GABA alone for each cell.

Results of electrophysiological assay: Exposure to GL-II-73, GL-II-74, GL-II-75 and GL-II-76 at 1 µM concentration induced an increased in the percent of response to GABA in cells transfected with the alpha 5 subunit. GL-II-73, 74 and 75 had the greatest response (FIG. 26) suggesting that these compounds have high affinity to α5 subunit.

Example 23: Pharmacokinetic of the α-PAM Compounds in Mice and Rats

Procedure:

The concentration-time profile of MP-III-022 in rat plasma and brain after intraperitoneal (i.p.) administration of the 2.5 mg/kg dose, with the calculated pharmacokinetic parameters, as well plasma and brain concentrations after i.p. administration of a wide range of doses (1, 2.5, 10, 15 and 20 mg/kg), have been already presented in Stamenic et al. (Eur. J. Pharmacol. 2016, 791, 433-443). The data demonstrated an excellent systemic and brain exposure to MP-III-022 after a single dose, though with a rather short terminal elimination half-life in Wistar rats (t1/2 of 35 min and 70 min for plasma and brain, respectively).

The pharmacokinetic properties of 12 other synthesized compounds: GL-II-73, GL-II-74, GL-II-75, GL-II-76, RV-II-04, GL-II-31, MP-III-023, GL-I-54, GL-III-23, GL-II-33, GL-11-54 and GL-I-65 were tested in adult male Wistar rats (Military farm, Belgrade, Serbia) and C57/BL6 mice (Military Medical Academy, Serbia). Kinetic behavior of GL-II-73, GL-II-74, GL-II-75 and GL-II-76 was first assessed by cassette dosing (White and Manitpisitkul, Drug Met. Disp. 2001, 29, 957-66; Cai et al., Bioanalysis 2013, 5, 1691-701) of all four ligands by oral gavage or i.p. injection at either 1 mg/kg or 10 mg/kg in both, mice and rats, sacrificed either 20 min or 2 h post-dosing. Such a pilot study, with two of each: dose, route, time and species (three animals per time point), enabled us to measure concentrations of ligands in plasma, liver and brain tissue and assess their potential to interact with each other. The estimated relative ratios of compounds at both doses suggested that the ligands were not prone to interaction, which was confirmed by further testing of GL-II-73, GL-II-74 and GL-II-75 applied as single treatments. GL-II-76 was not subjected to any further pharmacokinetic studies as its brain concentrations were suboptimal for putative use as a CNS-active drug. Just as an example, the measured plasma, liver and brain concentrations of GL-II-76 in mice sacrificed 20 min after i.p. dosing at 10 mg/kg were 604.87±198.00 ng/ml, 4360.25±1568,01 ng/g and 204.45±100.85 ng/g, respectively; other data from this pilot experiment are not presented.

Thus, in the second series of experiments, GL-II-73, GL-II-74 and GL-II-75 at the dose of 3 mg/kg were singly administered by oral gavage or intravenous (i.v.) injection in rats, and also at 10 mg/kg by i.p. injection in mice; the obtained plasma or brain concentration—time curves are presented in FIG. 28-30. In the third series of experiments, presented in FIG. 31-34, ligands RV-II-04, GL-II-31, MP-III-023 and GL-I-54 were dosed at 3 mg/kg as a cassette via each of three routes (oral gavage, i.v. and i.p. injection) in both, mice and rats. The fourth series of experiments was analogous to the previous one, and assessed pharmacokinetic profiles of GL-III-23, GL-II-33, GL-II-54 and GL-I-65 in mice and rats, as presented in FIG. 35-38. All values represent total concentration in plasma (ng/mL) or brain (ng/g).

Rats or mice in the second through fourth series of experiments were divided in five groups of animals; each group contained three animals and corresponded to predetermined time intervals (5, 20, 60, 180 or 240, and 720 min). Dosage form of the compound was prepared by diluting it in the solvent containing 85% distilled water, 14% propylene glycol and 1% Tween 80 with the aid of sonication. The blood samples were collected in heparinized syringes via cardiac puncture of rats anesthetized with ketamine and xylazine mixture dosed i.p. at 90 mg/kg+16 mg/kg (10% Ketamidor, Richter Pharma Ag, Austria, and Xylased, 20 mg/ml, Bioveta, A. S., Czech Republic) and centrifuged at 800 rcf for 10 min to obtain plasma. The animals were decapitated and brains were weighed, homogenized in 5 ml (rats) or 1.25 ml (mice) of methanol and centrifuged at 6000 rcf for 20 min. To determine the concentration of the ligand in plasma and supernatants of brain tissue homogenates, it was extracted from these samples by solid phase extraction, using Oasis HLB cartridges (Waters Corporation, Milford, Mass.). The used procedure of sample preparation and determination of ligands for the benzodiazepine binding site by ultraperformance liquid chromatography-tandem mass spectrometry (UPLC-MS/MS) with Thermo Scientific Accela 600 UPLC system connected to a Thermo Scientific TSQ Quantum Access MAX triple quadrupole mass spectrometer (Thermo Fisher Scientific, San Jose, Calif.), equipped with electrospray ionization (ESI) source, has been described in detail in literature (e.g. Obradovic et al., Brain Res. 2014, 1554, 36-48).

Non-compartmental pharmacokinetic analysis was performed using PK Functions for Microsoft Excel software (by Joel Usansky, Atul Desai, and Diane Tang-Liuwere), while graphs were constructed in commercial statistical software Sigma Plot 11 (Systat Software Inc., USA). Brain-to-plasma partition coefficient was calculated as follows: Kp=AUCO−∞, brain/AUCO−∞, plasma, where AUCO−∞ stands for area under the concentration versus time curve from zero to infinity. Oral bioavailability (F) was calculated using the equation:

$$F = \frac{D_{IV} \times AUC_{PO}}{D_{PO} \times AUC_{IV}},$$

where DIV and DPO represent intravenous and oral doses, and AUCIV and AUCPO are AUCO−∞ after intravenous and oral administration of the compound, respectively.

Results of the pharmacokinetic parameters in mice and rats obtained for novel ligands: GL-II-73, GL-II-74, GL-II-75, RV-II-04, GL-II-31, MP-III-023, GL-I-54, GL-III-23, GL-11-33, GL-II-54 and GL-I-65, are presented in FIG. 27.

Considering in parallel the respective concentration-time profiles (FIG. 28-38), it can be concluded that the potential of examined ligands for systemic exposure, as evidenced by AUC and Cmax values in plasma, is generally quite high, irrespective of the route of administration. Moreover, and of crucial importance for any in vivo studies, all 11 ligands are also brain-penetrant at the exception of GI-II-76. The calculated Kp values after i.p. administration in mice, rounded to the second decimal place, were: 0.30 for GL-II-73, 1.06 for GL-II-74, 0.80 for GL-II-75, 1.15 for RV-II-04, 0.33 for GL-II-31, 1.15 for MP-III-023, 0.19 for GL-I-54, 2.37 for GL-III-23, 1.46 for GL-II-33, 1.17 for GL-II-54 and 1.29 for GL-I-65. In general terms, the values of this parameter close to or greater than unity indicate excellent brain targeting of the ligand. To ease comparison between the concentrations obtained in vivo and those used in vitro, it is illustrative to express the kinetic results in molar besides the weight concentrations. After i.p. dosing at 3 mg/kg, ligands GL-II-31, GL-II-33 and GL-I-65 reached moderate to high submicromolar concentrations, ligands GL-I-54 and GL-II-54 reached high submicromolar to low micromolar values, while ligands RV-II-04, MP-III-023 and GL-III-23 reached micromolar concentrations in mouse brain tissue; after a 10 mg/kg dose, GL-II-73, GL-II-74 and GL-II-75 were in the micromolar range of brain concentrations. Similarly, moderate to high submicromolar or micromolar values were measured in rat brain tissue as well.

Example 24: Human and Mouse Liver Microsomal—Methods

Human and mouse liver microsomes were obtained fom BD Gentest.
Procedure:
Each evaluation included six independent assays carried out three at a time, on two different days
1. Preparation of solutions:
a. 1 mM test compound in DMSO.
b. 5 µM Verapamil in Acetonitrile as internal standard (ISTD) (store on ice).
2. For a total volume of Microsomal Assay Mixture (MAM) 390 µL, sufficient for seven time points, combine the following
a. 282 µL of 18.2 mΩ of water.
b. 80 µL of 0.5 M potassium phosphate buffer (pH 7.4)
c. 20 µL of NADPH A. (Corning life sciences, Cat #451220)
d. 4 µL of NADPH B. (Corning life sciences, Cat #451200)
e. 4 µL of test compound.
3. Sonicate MAM for 5 min and meanwhile thaw microsomes (20 mg/mL) (BD Gentest, Cat #452156) on ice.
4. Aliquot 100 µL of ice cold ISTD into 7 separate 1.5 mL conical vials and label them the time points for 0, 10, 20, 40, 60, 90, and 120 min.
5. Arrange the timer. Microsomes (Final concentration of 0.5 mg/mL) should be added to all time points except the zero time point.
6. Add 50 µL of the MAM solution to the conical vial labelled as zero time point. Place the remaining MAM solution in the incubator (37° C.) for 5 min and initiate the reaction with addition of microsomes (8.8 µL) and record the time.
7. At the end of each time interval remove 50 µL and add 100 µL to ISTD in conical vial, sonicate for 10 sec and spin down at 10,000 rpm for 5 minutes.
8. Take 100 µL of supernatant and transfer to Spin-X HPLC filter tubes (Corning Incorporated, Cat #8169) and centrifuge at 13,000 rpm for 5 minutes and take 5 µL from this solution and dilute in 495 µL of LCMS grade methanol (Fischer scientific, CAS #67-56-1) in an 2 mL glass auto sampler vial (Microsolv, Cat #95025-WCV)
9. The samples are analyzed by LCMS-8040. (Shimadzu)
Calculation: From the peak area, calculate the following $$\text{Peak area Ration} = \frac{\text{Peak area of test compound}}{\text{Peak area of internal standart (Verapamil)}}$$

$$\% \text{ remaining at time } T = \frac{\text{Peak area ratio at particular time } T}{\text{Peak area ratio at zero time point}} * 100$$

(T=0, 10, 20, 30, 40, 50, 60, and 120 min)
The compounds are tested for the metabolic stability in the Human and Mouse Liver microsomes at 10 µM concentration. The half-life and percent remaining of the compound at the end of two hours are presented in the following table.

TABLE 4

Human and mouse liver microsome stability assay.

| Compound Name | Genus | Half-life (min) (HumanLM) | % left after 2 hr. (Human LM) | Half-life (min) (MouseLM) | % left after 2 hr. (MouseLM) |
|---|---|---|---|---|---|
| GL-II-73 | AMIDE | 755 ± 243 | 92.4 ± 0.2 (1 h) | 309 ± 36 | 86.6 ± 0.2 (1 h) |
| GL-II-74 | | 751 ± 214 | 92.0 ± 0.2 (1 h) | 69 ± 3 | 56.5 ± 0.3 (1 h) |
| GL-II-75 | | 712 ± 165 | 93.4 ± 0.2 (1 h) | 239 ± 22 | 83.5 ± 0.2 (1 h) |
| GL-II-76 | | 154 ± 5 | 75 ± 0.1 (1 h) | 23 ± 1 | 18.6 ± 0.3 (1 h) |
| MP-III-022 | | 141 ± 18 | 69.4 ± 0.4 (1 h) | 164 ± 10 | 76.6 ± 0.2 |
| RV-II-04 | | 595 ± 157 | 80.2 ± 0.4 | 302 ± 33 | 73.7 ± 0.3 |
| GL-II-31 | | 1870 ± 765 | 92.0 ± 0.3 | 1840 ± 590 | 93.2 ± 0.2 |
| MP-III-023 | | 1790 ± 40 | 91.6 ± 0.4 | 846 ± 5 | 84.6 ± 0.2 |
| GL-I-54 | | 100 ± 4.5 | 36.4 ± 2.0 | 53 ± 10 | 15.0 ± 3.0 |
| GL-III-23 | OXADIAZOLE | 504.2 ± 77 | 82.0 ± 0.3 | 1324 ± 316 | 92.0 ± 0.2 |
| GL-II-33 | | 2586 ± 1106 | 95.3 ± 0.2 | 500 ± 66 | 82.0 ± 0.3 |
| GL-II-54 | | 404 ± 61 | 76.0 ± 0.2 | 2331 ± 1112 | 93.6 ± 0.2 |
| GL-I-65 | | 866 ± 213 | 86.4 ± 0.3 | 443 ± 67 | 81.0 ± 0.4 |

Pharmacokinetics in human or mouse liver microsome (HLM and MLM respectively). The half-life is expressed in minutes and the remaining quantity of compounds after 1 or 2 hours is expressed in %.

Results of the Metabolic Assay:

In human liver microsomes GL-II-31, MP-III-023, GL-II-33, GL-II-73, GL-II-74 and GL-II-75 are the most stable among the investigated compounds. More than 90% of each compound remained after one or two hours, respectively. The comparison of MP-III-022 and MP-III-023 showed that the S-enantiomer (MP-III-023) was more stable than R-enantiomer MP-III-022. The opposite relationship was observed for GL-II-73 (R-enantiomer), which was more stable than S-enantiomer GL-I-54. All other compounds were stable in the presence of HLM with more than 70% remaining after one or two hours except GL-I-54.

In mouse liver microsomes, GL-II-31, GL-III-23 and GL-II-54 are the most stable compounds with more than 90% remaining after 2 hours. Regarding the stability of the enantiomers, GL-II-73 was more stable than GL-I-54 in the mouse liver microsomes (81.6% vs 15.0%), and MP-III-023 was more stable than MP-III-022 (84.6% vs 76.6%). All the other compounds were stable in the presence of HLM with more than 70% remaining after one or two hours except GL-II-74, GL-II-76 and GL-I-54.

In both human and mouse liver microsomes, all oxadiazoles were stable with more than 80% remaining after two hours. After two hours, 95.3% remained of GL-II-33 in the presence of human liver microsomes. In the presence of mouse liver microsomes, more than 90% remained of GL-III-23 and GL-II-54 after two hours. The compounds with moderate to high stability are considered for therapeutic indication.

Example 25: Cytotoxicity Assay

Cell Line Culture and Procedure:

Human liver hepatocellular carcinoma (HEPG2) and human embryonic kidney 293 (HEK293) cell lines were purchased (ATCC) and cultured in 75 cm2 flasks (CellStar). Cells were grown in DMEM/High Glucose (Hyclone, #SH3024301) media to which non-essential amino acids (Hyclone, #SH30238.01), 10 mM HEPES (Hyclone, #SH302237.01), 5×106 units of penicillin and streptomycin (Hyclone, #SV30010), and 10% of heat inactivated fetal bovine serum (Gibco, #10082147) were added. Cells were harvested using 0.05% Trypsin (Hyclone, #SH3023601), washed with PBS, and dispensed into sterile white, optical bottom 384-well plates (NUNC, #142762). After three hours, small molecule solutions were transferred with a Tecan Freedom EVO liquid handling system equipped with a 100 nL pin tool (V&P Scientific). The controls (E)-10-(bromotriphenylphosphoranyl)decyl 4-(4-(tert-butyl)phenyl)-4-oxobut-2-enoate (400 µM in DMSO, positive control) and DMSO (negative control). The cells were incubated for 48 hours followed by the addition of CellTiter-Glo™, a luminescence-based cell viability assay (Promega, Madison, Wis.). All luminescence readings were performed on a Tecan Infinite M1000 plate reader. The assay was carried out in quadruplet with three independent runs. The data was normalized to the controls and analyzed by nonlinear regression (GraphPad Prism).

TABLE 5

| | CYTOTOXICITY ASSAY | | |
|---|---|---|---|
| S.NO. | COMPOUND CODE | HEK293 $LD_{50}$ (µM) | HEPG2 $LD_{50}$ (µM) |
| 1. | MP-III-022 | >100 | >200 |
| 2. | MP-III-023 | >200 | >200 |
| 3. | GL-II-31 | >400 | >400 |
| 4. | RV-II-04 | >200 | >200 |
| 5. | GL-I-54 | >400 | >400 |
| 6. | GL-II-73 | >200 | >400 |
| 7. | GL-II-76 | >100 | >400 |
| 8. | GL-II-33 | >400 | >400 |
| 9. | GL-II-54 | >400 | >400 |
| 10. | GL-III-23 | >100 | >100 |

Results of the cytotoxicity assay demonstrate that the compounds tested are not toxic to the respective cell line in varying high concentrations.

Example 26: Pharmacodynamic Assessment of Oxadiazoles

The anxiolytic-like effects of MP-III-080 and MP-III-085 were evaluated in mice using a marble burying assay. At 10 mg/kg, oxadiazole MP-III-080 produced a significant reduction in marble burying as compared to vehicle. At 30 mg/kg MP-III-085 and MP-III-080 significantly decreased marble-burying. Mice treated with 30 mg/kg of MP-III-080, however, showed weak signs of sedation. To evaluate the potential for anti-anxiety versus motor side effects of these compounds, a motorsensory study using mice on a rotating rod (rotarod) was carried out with the same mice as studied for marble-burying. Male, NIH Swiss Webster mice (n=10) were injected i.p. with either vehicle or a test compound (10 or 30 mg/kg) 30 min prior to testing.

Various features and advantages of the disclosure are set forth in the following claims.

What is claimed is:
1. A compound selected from the group consisting of:

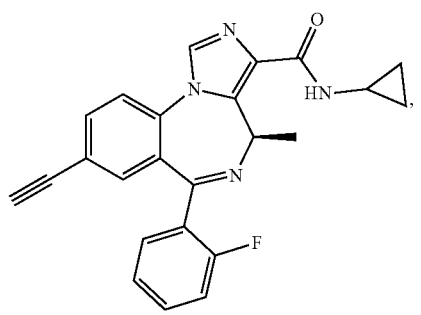

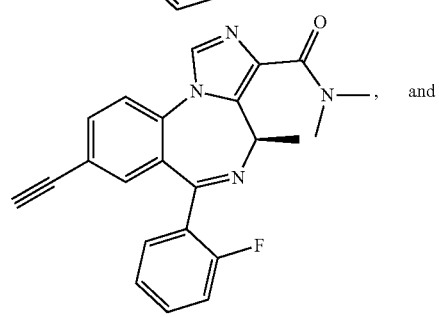

and

-continued

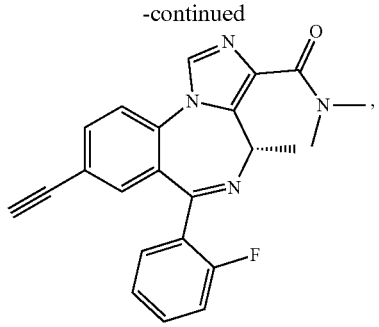

or a pharmaceutically acceptable salt thereof.

2. The compound of claim 1 that is

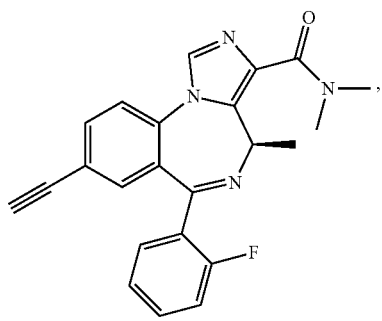 [SMILES: C#Cc1ccc2c(c1)C(c1ccccc1F)=N[C@H](C)c1c(C(=O)N(C)C)ncn1-2]

or a pharmaceutically acceptable salt thereof.

3. The compound of claim 1 that is

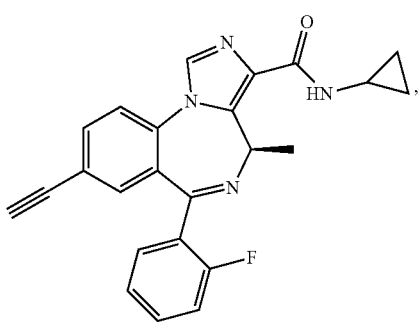 [SMILES: C#Cc1ccc2c(c1)C(c1ccccc1F)=N[C@H](C)c1c(C(=O)NC3CC3)ncn1-2]

or a pharmaceutically acceptable salt thereof.

4. The compound of claim 1 that is

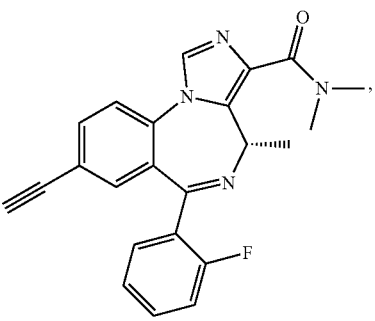 [SMILES: C#Cc1ccc2c(c1)C(c1ccccc1F)=N[C@@H](C)c1c(C(=O)N(C)C)ncn1-2]

or a pharmaceutically acceptable salt thereof.

5. A pharmaceutical composition comprising the compound according to claim 2, or a pharmaceutically acceptable salt thereof, and a pharmaceutically acceptable excipient.

6. A pharmaceutical composition comprising the compound according to claim 3, or a pharmaceutically acceptable salt thereof, and a pharmaceutically acceptable excipient.

7. A pharmaceutical composition comprising the compound according to claim 4, or a pharmaceutically acceptable salt thereof, and a pharmaceutically acceptable excipient.

* * * * *